US008841275B2

(12) United States Patent
Du et al.

(10) Patent No.: US 8,841,275 B2
(45) Date of Patent: Sep. 23, 2014

(54) 2'-SPIRO-NUCLEOSIDES AND DERIVATIVES THEREOF USEFUL FOR TREATING HEPATITIS C VIRUS AND DENGUE VIRUS INFECTIONS

(75) Inventors: Jinfa Du, New Hope, PA (US); Michael Joseph Sofia, Doylestown, PA (US)

(73) Assignee: Gilead Pharmasset LLC, Foster City, CA (US)

( * ) Notice: Subject to any disclaimer, the term of this patent is extended or adjusted under 35 U.S.C. 154(b) by 101 days.

(21) Appl. No.: 13/307,256

(22) Filed: Nov. 30, 2011

(65) Prior Publication Data

US 2012/0142626 A1 Jun. 7, 2012

Related U.S. Application Data

(60) Provisional application No. 61/417,946, filed on Nov. 30, 2010.

(51) Int. Cl.
*A01N 43/04* (2006.01)
*A61K 31/70* (2006.01)

(52) U.S. Cl.
USPC .......... 514/45; 514/42; 514/43; 514/46; 514/47; 536/27.1; 536/27.11; 536/27.13

(58) Field of Classification Search
None
See application file for complete search history.

(56) References Cited

U.S. PATENT DOCUMENTS

| | | |
|---|---|---|
| 3,798,209 A | 3/1974 | Witkowski |
| 3,852,267 A | 12/1974 | Meyer |
| 3,994,974 A | 11/1976 | Murakami |
| RE29,835 E | 11/1978 | Witkowski |
| 4,797,285 A | 1/1989 | Barenholz |
| 4,814,477 A | 3/1989 | Wijnberg |
| 4,957,924 A | 9/1990 | Beauchamp |
| 5,013,556 A | 5/1991 | Woodle |
| 5,026,687 A | 6/1991 | Yarchoan |
| 5,077,056 A | 12/1991 | Bally |
| 5,077,057 A | 12/1991 | Szoka |
| 5,091,188 A | 2/1992 | Haynes |
| 5,118,820 A | 6/1992 | Hertel |
| 5,145,684 A | 9/1992 | Liversidge |
| 5,149,794 A | 9/1992 | Yatvin |
| 5,154,930 A | 10/1992 | Popescu |
| 5,157,027 A | 10/1992 | Biller |
| 5,192,549 A | 3/1993 | Barenolz |
| 5,194,654 A | 3/1993 | Hostetler |
| 5,213,804 A | 5/1993 | Martin |
| 5,223,263 A | 6/1993 | Hostetler |
| 5,225,212 A | 7/1993 | Martin |
| 5,256,641 A | 10/1993 | Yatvin |
| 5,256,798 A | 10/1993 | Chou |
| 5,277,914 A | 1/1994 | Szoka |
| 5,316,771 A | 5/1994 | Barenholz |
| 5,372,808 A | 12/1994 | Blatt |
| 5,376,380 A | 12/1994 | Kikuchi |
| 5,405,598 A | 4/1995 | Schinazi |
| 5,411,947 A | 5/1995 | Hostetler |
| 5,420,266 A | 5/1995 | Britton |
| 5,426,183 A | 6/1995 | Kjell |
| 5,453,499 A | 9/1995 | Chou |
| 5,462,724 A | 10/1995 | Schinazi |
| 5,463,092 A | 10/1995 | Hostetler |
| 5,496,546 A | 3/1996 | Wang |
| 5,538,865 A | 7/1996 | Reyes |
| 5,543,389 A | 8/1996 | Yatvin |
| 5,543,390 A | 8/1996 | Yatvin |
| 5,543,391 A | 8/1996 | Yatvin |
| 5,549,910 A | 8/1996 | Szoka |
| 5,554,728 A | 9/1996 | Basava |
| 5,567,434 A | 10/1996 | Szoka |
| 5,610,054 A | 3/1997 | Draper |
| 5,633,358 A | 5/1997 | Gruetzke |
| 5,633,388 A | 5/1997 | Diana |
| 5,676,942 A | 10/1997 | Testa |
| 5,695,784 A | 12/1997 | Pollinger |
| 5,703,058 A | 12/1997 | Schinazi |
| 5,711,944 A | 1/1998 | Gilbert |
| 5,725,859 A | 3/1998 | Omer |
| 5,736,155 A | 4/1998 | Bally |
| 5,738,845 A | 4/1998 | Imakawa |
| 5,738,846 A | 4/1998 | Greenwald |
| 5,747,646 A | 5/1998 | Hakimi |
| 5,767,097 A | 6/1998 | Tam |
| 5,792,834 A | 8/1998 | Hakimi |
| 5,827,533 A | 10/1998 | Needham |

(Continued)

FOREIGN PATENT DOCUMENTS

| | | |
|---|---|---|
| CN | 1079473 | 12/1993 |
| CN | 101108870 | 1/2008 |

(Continued)

OTHER PUBLICATIONS

Abraham, et al., "Synthesis and Biological Activity of Aromatic Amino Acid Phosphoramidates of 5-Fluoro-2'-deoxyuridine and 1-Beta-Arabinofuranosylcytosine: Evidence of Phosphoramidase Activity," J. Med. Chem., (1996), 39:4569-4575.

Abraham, et al., "Synthesis, Biological Activity and Decomposition Studies of Amino Acid Phosphomonoester Amidates of Acyclovir" Nucleosides, Nucleotides and Nucleic Acids, (1997), 16(10):2079-2092.

Aquaro, et al., "Activities of Masked 2',3'-Dideoxynucleoside Monophosphate Derivatives against Human Immunodeficiency Virus in Resting Macrophages," Antimicrobial Agents and Chemotherapy, (2000), 44(1):173-177.

ASIF, Pharmacokinetics of the Antiviral Agent B-D-2'-Deoxy-2'-Fluoro-2'-C-Methylcytidine in Rhesus Monkeys, Antimicrobial Agents and Chemotherapy, vol. 51, No. 8, (2007), 2877-2882.

Balzarini, et al., "Mechanism of anti-HIV action of masked alaninyl d4t-MP derivatives," PNAS, (1996), 93:7295-7299.

Banker, G.S., "Modern Pharmaceutics, 3ed.", Marcel Dekker, New York, (1996), 451 and 596.

(Continued)

*Primary Examiner* — Patrick Lewis

(74) *Attorney, Agent, or Firm* — Sheppard, Mullin, Richter & Hampton LLP

(57) ABSTRACT

Disclosed herein are 2'-spiro-nucleosides and derivatives thereof useful for treating a subject infected by hepatitis C virus or dengue virus.

57 Claims, No Drawings

(56) References Cited

U.S. PATENT DOCUMENTS

| | | |
|---|---|---|
| 5,830,455 A | 11/1998 | Valtuena |
| 5,830,905 A | 11/1998 | Diana |
| 5,834,594 A | 11/1998 | Hakimi |
| 5,837,257 A | 11/1998 | Tsai |
| 5,846,964 A | 12/1998 | Ozeki |
| 5,849,696 A | 12/1998 | Chretien |
| 5,869,253 A | 2/1999 | Draper |
| 5,882,679 A | 3/1999 | Needham |
| 5,891,468 A | 4/1999 | Martin |
| 5,891,874 A | 4/1999 | Colacino |
| 5,905,070 A | 5/1999 | Schinazi |
| 5,908,621 A | 6/1999 | Glue |
| 5,922,757 A | 7/1999 | Chojkier |
| 5,928,636 A | 7/1999 | Alber |
| 5,942,223 A | 8/1999 | Bazer |
| 5,980,884 A | 11/1999 | Blatt |
| 5,990,276 A | 11/1999 | Zhang |
| 6,004,933 A | 12/1999 | Spruce |
| 6,034,134 A | 3/2000 | Gold |
| 6,043,077 A | 3/2000 | Barber |
| 6,056,961 A | 5/2000 | Lavie |
| 6,060,080 A | 5/2000 | Kikuchi |
| 6,090,932 A | 7/2000 | McGee |
| 6,130,326 A | 10/2000 | Ramasamy |
| 6,132,763 A | 10/2000 | Fisher |
| 6,143,321 A | 11/2000 | Needham |
| 6,156,501 A | 12/2000 | McGall |
| 6,180,134 B1 | 1/2001 | Zalipsky |
| 6,200,598 B1 | 3/2001 | Needham |
| 6,214,375 B1 | 4/2001 | Modi |
| 6,224,903 B1 | 5/2001 | Martin |
| 6,232,300 B1 | 5/2001 | Schinazi |
| 6,239,159 B1 | 5/2001 | Brown |
| 6,267,985 B1 | 7/2001 | Chen |
| 6,294,192 B1 | 9/2001 | Patel |
| 6,296,870 B1 | 10/2001 | Needham |
| 6,348,587 B1 | 2/2002 | Schinazi |
| 6,372,883 B1 | 4/2002 | Attwood |
| 6,383,471 B1 | 5/2002 | Chen |
| 6,391,859 B1 | 5/2002 | Schinazi |
| 6,395,300 B1 | 5/2002 | Straub |
| 6,410,531 B1 | 6/2002 | Llinas-Brunet |
| 6,420,380 B2 | 7/2002 | Llinas-Brunet |
| 6,455,513 B1 | 9/2002 | McGuigan |
| 6,455,690 B1 | 9/2002 | Tam |
| 6,475,985 B1 | 11/2002 | Wagner |
| 6,479,463 B1 | 11/2002 | Wang |
| 6,495,677 B1 | 12/2002 | Ramasamy |
| 6,509,320 B1 | 1/2003 | Wang |
| 6,534,523 B1 | 3/2003 | Llimas-Brunet et al. |
| 6,552,183 B1 | 4/2003 | Ramasamy |
| 6,555,677 B2 | 4/2003 | Petrillo |
| 6,569,463 B2 | 5/2003 | Patel |
| 6,573,248 B2 | 6/2003 | Ramasamy |
| 6,635,278 B1 | 10/2003 | Dahl |
| 6,642,206 B2 | 11/2003 | Ramasamy |
| 6,645,528 B1 | 11/2003 | Straub |
| 6,653,455 B1 | 11/2003 | Johdo |
| 6,660,721 B2 | 12/2003 | Devos |
| 6,677,314 B2 | 1/2004 | Klecker |
| 6,677,315 B2 | 1/2004 | Klecker |
| 6,680,068 B2 | 1/2004 | Campbell |
| 6,680,303 B2 | 1/2004 | Schinazi |
| 6,682,715 B2 | 1/2004 | Klecker |
| 6,683,045 B2 | 1/2004 | Klecker |
| 6,703,374 B1 | 3/2004 | Klecker |
| 6,726,925 B1 | 4/2004 | Needham |
| 6,753,309 B2 | 6/2004 | Klecker |
| 6,777,395 B2 | 8/2004 | Bhat |
| 6,784,166 B2 | 8/2004 | Devos |
| 6,787,305 B1 | 9/2004 | Li |
| 6,787,526 B1 | 9/2004 | Bryant |
| 6,812,219 B2 | 11/2004 | LaColla |
| 6,815,542 B2 | 11/2004 | Hong |
| 6,846,810 B2 | 1/2005 | Martin |
| 6,897,201 B2 | 5/2005 | Boyer |
| 6,908,924 B2 | 6/2005 | Watanabe |
| 6,911,424 B2 | 6/2005 | Schinazi |
| 6,914,054 B2 | 7/2005 | Sommadossi |
| 6,923,988 B2 | 8/2005 | Patel |
| 6,932,983 B1 | 8/2005 | Straub |
| 6,962,991 B2 | 11/2005 | Dempcy |
| 6,977,257 B2 | 12/2005 | Parab |
| 7,018,985 B1 | 3/2006 | Boyer |
| 7,018,989 B2 | 3/2006 | McGuigan |
| 7,060,294 B2 | 6/2006 | Batra |
| 7,060,689 B2 | 6/2006 | Goins |
| 7,070,801 B2 | 7/2006 | Yamazaki |
| 7,081,449 B2 | 7/2006 | Pietrzkowski |
| 7,105,493 B2 | 9/2006 | Sommadossi |
| 7,105,499 B2 | 9/2006 | Carroll |
| 7,125,855 B2 | 10/2006 | Bhat |
| 7,148,206 B2 | 12/2006 | Sommadossi |
| 7,163,929 B2 | 1/2007 | Sommadossi |
| 7,202,224 B2 | 4/2007 | Eldrup |
| 7,217,523 B2 | 5/2007 | Wagner |
| 7,268,119 B2 | 9/2007 | Cook |
| 7,307,065 B2 | 12/2007 | Schinazi |
| 7,323,453 B2 | 1/2008 | Olsen |
| 7,365,057 B2 | 4/2008 | LaColla |
| 7,390,791 B2 | 6/2008 | Becker |
| 7,429,572 B2 | 9/2008 | Clark |
| 7,462,608 B2 | 12/2008 | Chen |
| 7,601,820 B2 | 10/2009 | Wang |
| 7,608,597 B2 | 10/2009 | Sommadossi |
| 7,608,600 B2 | 10/2009 | Storer |
| 7,635,689 B2 | 12/2009 | LaColla |
| 7,754,699 B2 | 7/2010 | Chun |
| 7,879,815 B2 | 2/2011 | MacCoss |
| 7,964,580 B2 | 6/2011 | Sofia |
| 8,173,621 B2 | 5/2012 | Du |
| 8,334,270 B2 | 12/2012 | Sofia |
| 8,481,510 B2 * | 7/2013 | Jonckers et al. ............. 514/50 |
| 2001/0034440 A1 | 10/2001 | Shepard |
| 2002/0058635 A1 | 5/2002 | Averett |
| 2002/0142050 A1 | 10/2002 | Straub |
| 2002/0198173 A1 | 12/2002 | Schinazi |
| 2003/0050229 A1 | 3/2003 | Sommadossi |
| 2003/0060400 A1 | 3/2003 | LaColla et al. |
| 2003/0120071 A1 | 6/2003 | McGuigan |
| 2003/0144502 A1 | 7/2003 | Pietrzkowski |
| 2003/0153744 A1 | 8/2003 | Mekouar |
| 2003/0187018 A1 | 10/2003 | Llinas-Brunet |
| 2004/0006007 A1 | 1/2004 | Gosselin |
| 2004/0014108 A1 | 1/2004 | Eldrup |
| 2004/0023240 A1 | 2/2004 | Marliere |
| 2004/0023901 A1 | 2/2004 | Cook |
| 2004/0038993 A1 | 2/2004 | Shipps |
| 2004/0059104 A1 | 3/2004 | Cook |
| 2004/0063622 A1 | 4/2004 | Sommadossi |
| 2004/0067901 A1 | 4/2004 | Bhat |
| 2004/0072788 A1 | 4/2004 | Bhat |
| 2004/0097461 A1 | 5/2004 | Sommadossi |
| 2004/0097462 A1 | 5/2004 | Sommadossi |
| 2004/0101535 A1 | 5/2004 | Sommadossi |
| 2004/0102414 A1 | 5/2004 | Sommadossi |
| 2004/0110717 A1 | 6/2004 | Carroll |
| 2004/0142980 A1 | 7/2004 | Finzel |
| 2004/0167140 A1 | 8/2004 | Schinazi |
| 2004/0191824 A1 | 9/2004 | Dempcy |
| 2004/0214844 A1 | 10/2004 | Otto |
| 2004/0224917 A1 | 11/2004 | Dahl |
| 2004/0229839 A1 | 11/2004 | Babu |
| 2004/0229840 A1 | 11/2004 | Bhat |
| 2004/0248892 A1 | 12/2004 | Wang |
| 2004/0254141 A1 | 12/2004 | Schinazi |
| 2004/0259934 A1 | 12/2004 | Olsen |
| 2004/0265969 A1 | 12/2004 | Li |
| 2004/0266996 A1 | 12/2004 | Rabi |
| 2005/0009737 A1 | 1/2005 | Clark |
| 2005/0020825 A1 | 1/2005 | Storer |
| 2005/0026853 A1 | 2/2005 | Mekouar |
| 2005/0031588 A1 | 2/2005 | Sommadossi |
| 2005/0048116 A1 | 3/2005 | Straub |

(56) References Cited

U.S. PATENT DOCUMENTS

| | | |
|---|---|---|
| 2005/0058710 A1 | 3/2005 | Straub |
| 2005/0075309 A1 | 4/2005 | Storer |
| 2005/0080034 A1 | 4/2005 | Standring |
| 2005/0090432 A1 | 4/2005 | McPhee |
| 2005/0090660 A1 | 4/2005 | Watanabe |
| 2005/0119189 A1 | 6/2005 | Cottrell |
| 2005/0124532 A1 | 6/2005 | Sommadossi |
| 2005/0130931 A1 | 6/2005 | Boyer |
| 2005/0137161 A1 | 6/2005 | Sommadossi |
| 2005/0148534 A1 | 7/2005 | Castellino |
| 2005/0154056 A1 | 7/2005 | Yang |
| 2005/0164960 A1 | 7/2005 | Olsen |
| 2005/0215513 A1 | 9/2005 | Boojamra |
| 2005/0215614 A1 | 9/2005 | Singh |
| 2005/0227947 A1 | 10/2005 | Chan |
| 2005/0228013 A1 | 10/2005 | Thurkauf |
| 2005/0261237 A1 | 11/2005 | Boojamra |
| 2005/0267018 A1 | 12/2005 | Blatt |
| 2006/0003951 A1 | 1/2006 | Mekouar |
| 2006/0014943 A1 | 1/2006 | Dempcy |
| 2006/0034937 A1 | 2/2006 | Patel |
| 2006/0035866 A1 | 2/2006 | Cannizzaro |
| 2006/0040890 A1 | 2/2006 | Martin |
| 2006/0040927 A1 | 2/2006 | Blake |
| 2006/0040944 A1 | 2/2006 | Gosselin |
| 2006/0057196 A1 | 3/2006 | Hussain |
| 2006/0079478 A1 | 4/2006 | Boojamra |
| 2006/0100166 A1 | 5/2006 | De Koning |
| 2006/0110727 A9 | 5/2006 | McGall |
| 2006/0122146 A1 | 6/2006 | Chun |
| 2006/0122154 A1 | 6/2006 | Olsen |
| 2006/0142238 A1 | 6/2006 | McGuigan |
| 2006/0166964 A1 | 7/2006 | Hudyma |
| 2006/0188570 A1 | 8/2006 | Batra |
| 2006/0194749 A1 | 8/2006 | Keicher |
| 2006/0199783 A1 | 9/2006 | Wang |
| 2006/0234962 A1 | 10/2006 | Olsen |
| 2006/0241064 A1 | 10/2006 | Roberts |
| 2006/0241071 A1 | 10/2006 | Grinstaff |
| 2006/0252715 A1 | 11/2006 | Keicher |
| 2006/0264389 A1 | 11/2006 | Bhat |
| 2006/0264404 A1 | 11/2006 | Boojamra |
| 2006/0276511 A1 | 12/2006 | Serrano-Wu |
| 2006/0287300 A1 | 12/2006 | Klein |
| 2006/0293306 A1 | 12/2006 | Beaulieu |
| 2007/0015905 A1 | 1/2007 | LaColla |
| 2007/0026073 A1 | 2/2007 | Doney |
| 2007/0037735 A1 | 2/2007 | Gosselin |
| 2007/0037773 A1 | 2/2007 | Sommadossi |
| 2007/0042939 A1 | 2/2007 | LaColla |
| 2007/0042988 A1 | 2/2007 | Klumpp |
| 2007/0042990 A1 | 2/2007 | Gosselin |
| 2007/0049754 A1 | 3/2007 | Boojamra |
| 2007/0054842 A1 | 3/2007 | Blatt |
| 2007/0059360 A1 | 3/2007 | Jaiswal |
| 2007/0060498 A1 | 3/2007 | Gosselin |
| 2007/0060541 A1 | 3/2007 | Gosselin |
| 2007/0077295 A1 | 4/2007 | Dahl |
| 2007/0087960 A1 | 4/2007 | Storer |
| 2007/0099902 A1 | 5/2007 | Dahl |
| 2007/0155731 A1 | 7/2007 | Butora |
| 2007/0197463 A1 | 8/2007 | Chun |
| 2007/0225249 A1 | 9/2007 | Shi |
| 2007/0265222 A1 | 11/2007 | MacCoss |
| 2007/0265262 A1 | 11/2007 | Schmitz |
| 2007/0275912 A1 | 11/2007 | Bhat |
| 2007/0275947 A1 | 11/2007 | Bergstrom |
| 2008/0014228 A1 | 1/2008 | Darmuzey |
| 2008/0021047 A1 | 1/2008 | Butora |
| 2008/0139802 A1 | 6/2008 | Axt |
| 2008/0182863 A1 | 7/2008 | Simmen |
| 2008/0200423 A1 | 8/2008 | Cook |
| 2008/0280850 A1 | 11/2008 | Sommadossi |
| 2009/0004138 A1 | 1/2009 | Francom |
| 2009/0105302 A1 | 4/2009 | Simmen |
| 2009/0131460 A1 | 5/2009 | Simmen |
| 2009/0137521 A1 | 5/2009 | Hamilton |
| 2009/0156595 A1 | 6/2009 | Raboisson |
| 2009/0176732 A1 | 7/2009 | Beigelman |
| 2009/0233879 A1 | 9/2009 | Reddy |
| 2009/0280084 A1 | 11/2009 | Schinazi |
| 2009/0281140 A1 | 11/2009 | Simmen |
| 2009/0281141 A1 | 11/2009 | Simmen |
| 2009/0306007 A1 | 12/2009 | Wagner |
| 2010/0022468 A1 | 1/2010 | Meppen |
| 2010/0029008 A1 | 2/2010 | Rojas et al. |
| 2010/0035835 A1 | 2/2010 | Narjes |
| 2010/0081628 A1 | 4/2010 | Du |
| 2010/0120855 A1 | 5/2010 | Simmen |
| 2010/0137576 A1 | 6/2010 | Stec |
| 2010/0152128 A1 | 6/2010 | Attenni |
| 2010/0173863 A1 | 7/2010 | Schinazi |
| 2010/0227801 A1 | 9/2010 | Hopkins |
| 2010/0279973 A1 | 11/2010 | Chun |
| 2010/0286083 A1 | 11/2010 | Bao |
| 2010/0298257 A1 | 11/2010 | Ross |
| 2010/0316594 A1 | 12/2010 | Sommadossi |
| 2011/0015146 A1 | 1/2011 | Sofia |
| 2011/0124592 A1 | 5/2011 | McGuigan |
| 2011/0130440 A1 | 6/2011 | Manoharan |
| 2011/0229438 A1 | 9/2011 | Dragovich |
| 2011/0257121 A1 | 10/2011 | Chang |
| 2011/0257122 A1 | 10/2011 | Sofia |
| 2012/0142626 A1 | 6/2012 | Du |
| 2012/0258928 A1 | 10/2012 | Du |
| 2013/0029929 A1 | 1/2013 | Sofia |

FOREIGN PATENT DOCUMENTS

| | | |
|---|---|---|
| DE | 19914474 | 10/1999 |
| EP | 180276 | 5/1986 |
| EP | 0350287 | 1/1990 |
| EP | 0524579 | 1/1993 |
| EP | 1828217 | 9/2007 |
| EP | 1881001 | 1/2008 |
| EP | 2097430 | 9/2009 |
| EP | 2124555 | 12/2009 |
| EP | 2207786 | 7/2010 |
| JP | 5238939 | 9/1993 |
| WO | WO89/02733 | 4/1989 |
| WO | WO90/00555 | 1/1990 |
| WO | WO91/16920 | 11/1991 |
| WO | WO91/18914 | 12/1991 |
| WO | WO91/19721 | 12/1991 |
| WO | WO93/00910 | 1/1993 |
| WO | WO94/26273 | 11/1994 |
| WO | WO95/13090 | 5/1995 |
| WO | WO95/24185 | 9/1995 |
| WO | WO96/15132 | 5/1996 |
| WO | WO96/32403 | 10/1996 |
| WO | WO97/12033 | 4/1997 |
| WO | WO97/36554 | 10/1997 |
| WO | WO98/16184 | 4/1998 |
| WO | WO98/17679 | 4/1998 |
| WO | WO98/22496 | 5/1998 |
| WO | WO99/07734 | 2/1999 |
| WO | WO99/15194 | 4/1999 |
| WO | WO99/32139 | 7/1999 |
| WO | WO99/32140 | 7/1999 |
| WO | WO99/43691 | 9/1999 |
| WO | WO99/59621 | 11/1999 |
| WO | WO99/64016 | 12/1999 |
| WO | WO00/06529 | 2/2000 |
| WO | WO00/09531 | 2/2000 |
| WO | WO00/37110 | 6/2000 |
| WO | WO01/09121 | 2/2001 |
| WO | WO01/32153 | 5/2001 |
| WO | WO01/60315 | 8/2001 |
| WO | WO01/79246 | 10/2001 |
| WO | WO01/81359 | 11/2001 |
| WO | WO01/90121 | 11/2001 |
| WO | WO01/91737 | 12/2001 |
| WO | WO01/92282 | 12/2001 |
| WO | WO01/96353 | 12/2001 |

(56) References Cited

FOREIGN PATENT DOCUMENTS

| | | |
|---|---|---|
| WO | WO02/08187 | 1/2002 |
| WO | WO02/08198 | 1/2002 |
| WO | WO02/08251 | 1/2002 |
| WO | WO02/08256 | 1/2002 |
| WO | WO02/18404 | 3/2002 |
| WO | WO02/32414 | 4/2002 |
| WO | WO02/32920 | 4/2002 |
| WO | WO02/48116 | 6/2002 |
| WO | WO02/48157 | 6/2002 |
| WO | WO02/48165 | 6/2002 |
| WO | WO02/48172 | 6/2002 |
| WO | WO02/057287 | 7/2002 |
| WO | WO02/057425 | 7/2002 |
| WO | WO02/060926 | 8/2002 |
| WO | WO02/100415 | 12/2002 |
| WO | WO03/000713 | 1/2003 |
| WO | WO03/006490 | 1/2003 |
| WO | WO03/010141 | 2/2003 |
| WO | WO03/011877 | 2/2003 |
| WO | WO03/024461 | 3/2003 |
| WO | WO03/026589 | 4/2003 |
| WO | WO03/037895 | 5/2003 |
| WO | WO03/051899 | 6/2003 |
| WO | WO03/053989 | 7/2003 |
| WO | WO03/061576 | 7/2003 |
| WO | WO03/062256 | 7/2003 |
| WO | WO03/064456 | 8/2003 |
| WO | WO03/068244 | 8/2003 |
| WO | WO03/101993 | 12/2003 |
| WO | WO03/104250 | 12/2003 |
| WO | WO03/105770 | 12/2003 |
| WO | WO03/106477 | 12/2003 |
| WO | WO04/000858 | 12/2003 |
| WO | WO2004/000858 | 12/2003 |
| WO | WO2004/002422 | 1/2004 |
| WO | WO2004/002940 | 1/2004 |
| WO | WO2004/002944 | 1/2004 |
| WO | WO2004/002977 | 1/2004 |
| WO | WO2004/002999 | 1/2004 |
| WO | WO2004/003000 | 1/2004 |
| WO | WO2004/003138 | 1/2004 |
| WO | WO2004/007512 | 1/2004 |
| WO | WO2004/009020 | 1/2004 |
| WO | WO2004/009610 | 1/2004 |
| WO | WO2004/011478 | 2/2004 |
| WO | WO2004/014313 | 2/2004 |
| WO | WO2004/014852 | 2/2004 |
| WO | WO2004/035571 | 4/2004 |
| WO | WO2004/041201 | 5/2004 |
| WO | WO2004/046331 | 6/2004 |
| WO | WO2004/065367 | 8/2004 |
| WO | WO2004/080466 | 9/2004 |
| WO | WO2004/094452 | 11/2004 |
| WO | WO2004/096210 | 11/2004 |
| WO | WO2004/096234 | 11/2004 |
| WO | WO2004/096235 | 11/2004 |
| WO | WO2004/096286 | 11/2004 |
| WO | WO2004/106356 | 12/2004 |
| WO | WO2005/002626 | 1/2005 |
| WO | WO2005/003147 | 1/2005 |
| WO | WO2005/007810 | 1/2005 |
| WO | WO2005/009418 | 2/2005 |
| WO | WO2005/012327 | 2/2005 |
| WO | WO2005/020884 | 3/2005 |
| WO | WO2005/021568 | 3/2005 |
| WO | WO2005/028502 | 3/2005 |
| WO | WO2005/037214 | 4/2005 |
| WO | WO2005/067900 | 7/2005 |
| WO | WO2005/072361 | 8/2005 |
| WO | WO2005/082144 | 9/2005 |
| WO | WO2005/087788 | 9/2005 |
| WO | WO2005/095403 | 10/2005 |
| WO | WO2005/103045 | 11/2005 |
| WO | WO2005/123087 | 12/2005 |
| WO | WO2006/000922 | 1/2006 |
| WO | WO2006/012078 | 2/2006 |
| WO | WO2006/012440 | 2/2006 |
| WO | WO2006/020082 | 2/2006 |
| WO | WO2006/029081 | 3/2006 |
| WO | WO2006/031725 | 3/2006 |
| WO | WO2006/035061 | 4/2006 |
| WO | WO2006/037028 | 4/2006 |
| WO | WO2006/063149 | 6/2006 |
| WO | WO2006/063717 | 6/2006 |
| WO | WO2006/065335 | 6/2006 |
| WO | WO2006/065590 | 6/2006 |
| WO | WO2006/093801 | 9/2006 |
| WO | WO2006/094347 | 9/2006 |
| WO | WO2006/100310 | 9/2006 |
| WO | WO2006/119347 | 11/2006 |
| WO | WO2006/120251 | 11/2006 |
| WO | WO2006/120252 | 11/2006 |
| WO | WO2006/121820 | 11/2006 |
| WO | WO2007/002602 | 1/2007 |
| WO | WO2007/014920 | 2/2007 |
| WO | WO2007/014921 | 2/2007 |
| WO | WO2007/014922 | 2/2007 |
| WO | WO2007/014925 | 2/2007 |
| WO | WO2007/014926 | 2/2007 |
| WO | WO2007/015824 | 2/2007 |
| WO | WO2007/020193 | 2/2007 |
| WO | WO2007/027248 | 3/2007 |
| WO | WO2007/039142 | 4/2007 |
| WO | WO2007/039145 | 4/2007 |
| WO | WO2007/065829 | 6/2007 |
| WO | WO2007/070556 | 6/2007 |
| WO | WO2007/076034 | 7/2007 |
| WO | WO2007/088148 | 8/2007 |
| WO | WO2007/092000 | 8/2007 |
| WO | WO2007/093901 | 8/2007 |
| WO | WO2007/095269 | 8/2007 |
| WO | WO2008/010921 | 1/2008 |
| WO | WO2008/045419 | 4/2008 |
| WO | WO2008/048128 | 4/2008 |
| WO | WO2008/062206 | 5/2008 |
| WO | WO2008/079206 | 7/2008 |
| WO | WO2008/082601 | 7/2008 |
| WO | WO2008/085508 | 7/2008 |
| WO | WO2008/121634 | 10/2008 |
| WO | WO2008/142055 | 11/2008 |
| WO | WO2009/052287 | 4/2009 |
| WO | WO2009/115893 | 9/2009 |
| WO | WO2009/120878 | 10/2009 |
| WO | WO2009/129120 | 10/2009 |
| WO | WO2010/042834 | 4/2010 |
| WO | WO2010/075517 | 7/2010 |
| WO | WO2010/075549 | 7/2010 |
| WO | WO2010/075554 | 7/2010 |
| WO | WO2010/080878 | 7/2010 |
| WO | WO2010/130726 | 11/2010 |
| WO | WO2011/123668 | 10/2011 |

OTHER PUBLICATIONS

Bartenschlager, et al., "Kinetic and Structural Analyses of Hepatitis C Virus Polyprotein Processing," J. Virol., (1994), 68(8):5045-5055.
Bartenschlager, et al., "Nonstructural Protein 3 of the Hepatitis C Virus Encodes a Serine-Type Proteinase Requried for Cleavage at the NS3/4 and NS4/5 Junctions," J. Virol., (1993), 67(7):3835-3844.
Baschang, et al., Neue Derivate von Thymidin-3',5'-cyclophosphat, Angew. Chem., (1973), 85(1):44-45.
Battaglia, et al., "Combination Therapy with Interferon and Ribavirin in the Treatment of Chronic Hepatitis C Infection," The Annals of Pharmacotherapy, (2000), 34(4):487-494.
Bazan, et al., "Detection of a Trypsin-like Serine Protease Domain in Flaviviruses and Pestiviruses," Virology, (1989), 171:637-639.
Beaulieu, et al., "Inhibitors of the HCV NS5B polymerase: New hope for the treatment of hepatitis C infections," Current Opinion in Investigational Drugs, (2004), 5(8):838-850.
Behrens, et al., "Indentification and properties of the RNA-dependent RNA polymerase of hepatitis C virus," EMBO, (1996), 15(1):12-22.
Berenguer, et al., "Hepatitis C virus in the transplant setting," Antiviral Therapy. Second International Conference on Therapies for

(56) References Cited

OTHER PUBLICATIONS

Viral Hepatitis, (1998), 3(3):125-136.
Beres, et al., "Synthesis and Antitumor and Antiviral Properties of 5-Alkyl-2'-deoxyuridines, 3',5'-Cyclic Monophosphates, and Neutral Cyclic Triesters," J. Med. Chem., (1986), 29(4):494-499.
Beres, et al., Synthesis and Antitumor and Antiviral Properties of 5-Halo- and 5-(Trifluoromethyl)-2'-deoxyuridine 3',5'-Cyclic Monophosphates and Neutral Triesters, J. Med. Chem., (1986), 29: 1243-1249.
Bhat, et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003, Savannah, GA).
Broeders, et al., "A 400- and 600-MHz 1H NMR Conformational Study on Nucleoside Cyclic 3',5'Pv-TBP Systems. Conformational Transmission Induces Diequatorial Orientation of the 3',5'-Dioxaphosphorinane Ring in a Nonchair Conformation," J. Am. Chem. Soc., (1990), 112:7475-7482.
Broeders, et al., 2'-O-Methyl-cis-adenosine 3',5'-cyclic methyl monophosphate, a new model system for cAMP. Aspects of structure and reactivity, Can J. Chem., (1993), 71:855-863.
Byrn, et al., "Pharmaceutical Solids: A Strategic Approach to Regulatory Considerations", Pharmaceutical Research, (1995), 12(7): 945-954.
Byrn, et al., "Hydrates and Solvates," Solid State Chemistry of Drugs, 2d Chapter 11, (2003), 233-247.
Calisher, et al., "Antigenic Relationships between Flaviviruses as Determined by Cross-neutralization Tests with Polyclonal Antisera," J. Gen. Virol., (1989), 70:37-43.
Carroll, et al., "Nucleoside Analog Inhibitors of Hepatitis C Virus Replication," Infectious Disorders—Drug Targets, (2006), 6:17-29.
Chang, et al., "Amino Acid Phosphoramidate Monoesters of 3'-Azido-3'-deoxythymidine: Relationship between Antiviral Potency and Intracellular Metabolism" Journal of Medicinal Chemistry, 2001, 44, 223-231.
Chang, et al. Discovery of PSI-353661, a Novel Purine Nucleotide Prodrug for the Treatment of HCV Infection. ACS Medicinal Chemistry Letters (2011), 2(2), 130-135.
Chapman, et al., "Purification of PMPA amidate prodrugs by SMB chromatography and x-ray crystallography of the diastereomerically pure GS-7340," Nucleosides, Nucleotides and Nucleic Acids, (2001), 20(4-7):1085-1090.
Chapman, et al.,"Practical synthesis, separation, and stereochemical assignment of the PMPA pro-drug GS-7340," Nucleosides, Nucleotides and Nucleic Acids, (2001), 20(4-7):621-628.
Chawla, et al., "Challenges in Polymorphism of Pharmaceuticals", CRIPS, (2004), 5(1): 9-12.
Chen, et al., "In Vivo Pharmacokinetics and Metabolism of Anti-Human Immunodeficiency Virus Agent D4t-5'-[P-Bromophenyl Methoxyalaninyl Phosphate] (Sampidine) In Mice," Drug Metabolism and Disposition, (2001), 29(7):1035-1041.
Chen, et al., "Metabolism of Stavudine-5'-[P-Bromophenyl Methoxyalaninyl Phosphate], Stampidine, In Mice, Dogs, and Cats," Drug Metabolism and Disposition, (2002), 30(12):1523-1531.
Chou, et al., "Evidence that Human Histidine Triad Nucleotide Binding Protein 3 (Hint3) is a Distinct Branch of the Histidine Triad (HIT) Super family," J. Mol. Biol., (2007), 373:978-989.
Chou, et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, (2007), 4(2):208-217.
Chu, et al., "Isolation and Structure of SCH 351633: A Novel Hepatitis C Virus (HCV) NS3 Protease Inhibitor from the Fungus *Penicillium griseofulvum*," Bioorganic & Medicinal Chemistry Letters, (1999), 9:1949-1952.
Chu, et al., "Structure of Sch 68631: A New Hepatitis C virus Proteinase Inhibitor from *Streptomyces* sp." Tetrahedron Letters, (1996), 37(40): 7229-7232.

Cihlar, et al., "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, (2008), 52(2):655-665.
Clark, et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, (2005), 48(17):5504-5508.
Congiatu, et al., "Molecular Modelling Studies on the Binding of Some Protides to the Putative Human Phosphoramidase Hint1," Nucleosides, Nucleotides and Nucleic Acids, (2007), 26(8):1121-1124.
Congiatu, et al., "Naphthyl Phosphoramidate Derivatives of BVdU as Potential Anticancer Agents: Design, Synthesis and Biological Evaluation," Nucleosides, Nucleotides, and Nucleic Acids, (2005), 24(5-7):485-489.
Curley, et al., "Synthesis and anti-HIV evaluation of some phosphoramidate derivatives of AZT: studies on the effect of chain elongation on biological activity," Antiviral Research, (1990), 14:345-356.
Davis, G.L., "Current Therapy for Chronic Hepatitis C," Gastroenterology, (2000), 118:S104-S114.
D'Cruz, et al., "Stampidine: a selective oculo-genital microbicide," Journal of Antimicrobial Chemotherapy, (2005), 56:10-19.
De Lombaert, et al., "N-Phosphonomethyl Dipeptides and Their Phosphonate Prodrugs, a New Generation of Neutral Endopeptidase (NEP, EC 3.4.24.11) Inhibitors," J. Med. Chem., (1994), 37(4):498-511.
Drontle, et al., "Designing a Pronucleotide Stratagem: Lessons from Amino Acid Phosphoramidates of Anticancer and Antiviral Pyrimidines," MiniReviews in Medicinal Chemistry, (2004), 4:409-419.
Eckart, et al., "The hepatitus C virus encodes a serine protease involved in processing of the putative nonstructural proteins from the viral polyprotein precursor," Biochem. Biophys. Res. Comm., (1993), 192(2):399-406.
Edmundson, et al., "Cyclic Organophosphorus Compounds. Part 23. Configurational Assignments in the 4-Phenyl-1,3,2λ-dioxaphosphorinane Series. X-Ray Molecular Structure of cis-2-Benzylamino-4-phenyl-1,3,2-dioxaphosphorinane," J. Chem. Res. Synop., (1989), 122-123.
Egron, et al., "S-Acyl-2-thioethyl Phosphoramidate Diester Derivatives as Mononucleotide Prodrugs." J. Med. Chem., (2003), 46:4564-4571.
Eisenberg, et al., "Metabolism of GS-7340, A novel phenyl monophosphoramidate intracellular prodrug of PMPA, in blood," Nucleosides, Nucleotides & Nucleic Acids, (2001), 20(4-7):1091-1098.
Eldrup, A., "Structure Activity Relationship of 2' Modified Nucleosides for Inhibition of Hepatitis C Virus," (Oral Session V: Hepatitis C Virus, Flavaviruses), 16th International Conference on Antiviral Research, Abstract No. 119, p. A75 (Apr. 27-May 1, 2003, Savannah, GA).
Eldrup, A., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).
Engels, et al., "Synthese und Eigenschaften von Uridin-3',5'-cyclophosphat-estern," Chem. Ber., (1977), 110(6):2019-2027 (with English Abstract).
Failla, et al., "Both NS3 and NS4A are required for proteolytic processing of hepatitus C virus nonstructural protein," J. Virol., (1994), 68:3753-3760.
Farquhar, et al., "Synthesis and Biological Evaluation of Neutral Derivatives of 5-Fluoro-2'-deoxyuridine 5'-Phosphate," J. Med. Chem., (1983), 26(8):1153-1158.
Farquhar. et al., "Synthesis of Biological Evaluation of 9-[5'-(2-0xo-I,3,2-oxazaphosphorinan-2-yl)-Beta-D-arabinosylladenine and 9-[5'-(2-0xo-I,3,2-dioxaphosphorinan-2-yl)-Beta-D-arabinosyl]adenine: Potential Neutral Precursors of 9-[Beta-D-Arabinofuranosyl]adenine 5'-Monophosphate," J. Med. Chem., (1985), 28(9):1358-1361.

(56) References Cited

OTHER PUBLICATIONS

Fields, et al., "Virology," Editors: Fields, B. N., Knipe, D. M., and Howley, P. M., Lippincott-Raven Publishers, Philadelphia, PA, (1996), Chapter 31:931-959.
Final International Report and Written Opinion of PCT/US2009/069475 mailed May 10, 2010.
Freed, et al., "Evidence for acyloxymethyl esters of pyrimidine 5'-deoxyribonucleotides as extracellular sources of active 5'-deoxyribonucleotides in cultured cells," Biochemical Pharmacology, (1989), 38(9):3193-3198.
Goekjian, et al., "Synthesis of Fluorinated Macrocyclic Bis(indoyl)maleimides as Potential 19F NMR Probes for Protein Kinase C," J. Org. Chem., (1999), 64(12):4238-4246.
Gorbalenya, et al., "A conserved NTP-motif in putive helicases," Nature, (1988), 333:22.
Gorbalenya, et al., "N-termianl domains of putative helicases of flavi-and pestiviruses may be serine proteases," Nucleic Acid Res., (1989), 17(10):3889-3897.
Grakoui, et al., "A second hepatitus C virus-encoded proteinase," Proc. Natl. Acad. Sci., (1993), 90:10583-10587.
Grakoui, et al., "Characterization of the Hepatitis C Virus-Encoded Serine Proteinase: Determination of Proteinase-Dependent Polyprotein Cleavage Sites," J. Virol., (1993), 67(5):2832-2843.
Griffith, et al., "HCV Anti-viral Agents," Annual Reports in Medicinal Chemistry, (2004), 39:223-237.
Gromova, et al., "Optical rotatory dispersion and circular dichroism of mono- and oligonucleotide-amino acids (amidates)," Biochim. Biophys. Acta, (1971), 240:1-11.
Guillory, J.K., et al., "Polymorphism in Pharmaceutical Solids" (1999); 183-226.
Gunic, et al., "6-Hydrazinopurine 2'-methyl ribonucleosides and their 5'-monophosphate prodrugs as potent hepatitis C virus inhibitors," Bioorg. & Med. Chem. Letters, (2007), 17(9):2456-2458.
Gunic, et al., Cyclic monophosphate prodrugs of base-modified 2'-C-methyl ribonucleosides as potent inhibitors of hepatitis C virus RNA replication, Biorganic & Medicinal Chemistry Letters, (2007), 17:2452-2455.
Haleblian, "Characterization of Habits and Crystalline Modification of Solids and Their Pharmaceutical Applications", J. Pharm. Sci., (1975), 64(8):1269-1288.
Halstead, S.B., "Pathogenesis of Dengue: Challenges to Molecular Biology," Science, (1988), 239:476-481.
Halstead, S.B., "Selective Primary Health Care: Strategies for Control of Disease in the Developing World XI. Dengue," Rev. Infect. Dis., (1984), 6(2):251-264.
Harris, et al., "Synthesis and antiviral evaluation of phosphoramidate derivatives of (E)-5-(2-bromovinyl)-2'-deoxyuridine," Antiviral Chemistry & Chemotherapy, (2002), 12:293-300.
Hernandez, et al., "Synthesis of Highly Functionalized Chiral Nitriles by Radical Fragmentation of Beta-Hydroxy Azides. Convenient Transformation of Aldononitriles into 1,4- and 1,5-Iminoalditols," J. Org. Chem., (2004), 69(24):8437-8444.
Hertel, et al., "Synthesis of 2-Deoxy-2,2-difluoro-D-ribose and 2-Deoxy-2,2-difluoro-D-ribofuranosyl Nucleosides," J. Org. Chem., (1988), 53:2406-2409.
Hijikata, et al., "Two Distinct Proteinase Activites Required for the Processing of a Putative Nonstructural Precursor Protein of Hepatitis C Virus," J. Virol., (1993), 67(8):4665-4675.
Hooz, et al., "A rapid, mild procedure for the preparation of alkyl chlorides and bromides," Can. J. Chem., (1968), 46:86-87.
Hostetler, et al., "Greatly Enhanced Inhibition of Human Immunodeficiency Virus Type 1 Replication in CEM and HT4-6C by 3'-Deoxythymidine Diphosphate Dimyristoylglycerol, a Lipid Prodrug of 3'-Deoxythymidine," Antimicrob. Agents Chemother., (1992), 36(9):2025-2029.
Hostetler, et al., "Synthesis and Antiretroviral Activity of Phospholipid Analogs of Azidothymidine and Other Antiviral Nucleosides," J. Biol. Chem., (1990), 265(11):6112-6117.

Howes et al., "The Regiospecific One-Pot Phosphorylation of Either the 5'- or 2'-Hydroxyl in 3'-Deoxycytidines Without Protection: Critical Role of the Base" Nucleosides, Nucleotides, and Nucleic Acids, 2003, 22 (5-8), 687-689.
Hunston, et al., "Synthesis and Biological Properties of Some Cyclic Phosphotriesters Derived from 2'-Deoxy-5-fluorouridine," J. Med. Chem., (1984), 27(4):440-444.
International Preliminary Examination Report of PCT/EP2006/069060, mailed Nov. 5, 2008.
International Preliminary Examination Report of PCT/US2004/012472, issued Dec. 1, 2005.
International Preliminary Examination Report of PCT/US2005/025916, issued Jan. 23, 2007.
International Preliminary Examination Report of PCT/US2005/032406, issued Mar. 10, 2009.
International Preliminary Examination Report of PCT/US2008/058183, issued Apr. 7, 2010.
International Search Report and Written Opinion from related International Application No. PCT/US2004/012472 (WO2005/003147), mailed Dec. 30, 2004.
International Search Report and Written Opinion from related International Application No. PCT/US05/25916, mailed Jun. 15, 2006.
International Search Report and Written Opinion from related International Application No. PCT/EP2006/069060 (WO2007/065829), mailed Jan. 30, 2007.
International Search Report and Written Opinion from related International Application No. PCT/US2005/032406 (W02006/031725), mailed May 8, 2008.
International Search Report and Written Opinion from related International Application No. PCT/US2008/058183 (WO2008/121634), mailed Mar. 31, 2010.
International Search Report and Written Opinion from related International Application No. PCT/US2009/046619 (WO2009/152095), mailed Sep. 23, 2010.
International Search Report & Written Opinion from related International Application No. PCT/US2010/035641, mailed Sep. 28, 2010.
International Search Report and Written Opinion of PCT/US2011/030767 (WO2011/123672), mailed Oct. 2, 2012.
Invitation to Pay Additional Fees & Partial International Search Report of PCT/US2010/035641, mailed Jul. 23, 2010.
Ishii, et al., Expression of Hepatitis C Virus NS5B Protein: Characterization of Its RNA Polymerase Activity and RNA Binding, Hepatology, (1999), 29:1227-1235.
Iyer, et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)" J. Med. Chem., (2000), 43:2266-2274.
Jin, et al., "Expression, Isolation, and Characterization of the Hepatitis C Virus ATPase/RNA Helicase," Arch. Biochem. Biophys., (1995), 323(1):47-53.
Jones, R., "Minireview: Nucleotide Prodrugs," Antiviral Research, vol. 27, pp. 1-17 (1995).
Juodka, et al., "Oligonucleotides and nucleotide-peptides. XXXIV. Synthesis and some properties of complex nucleotidyl (oligonucleotidyl)-P—N)-amino acids (peptides) and their ethyl esters," J. Carbohydrates, Nucleosides, Nucleotides, (1979), 6(4):333-357.
Juodka, et al., "Oligonucleotides and nucleotide-peptides. XXXV. Some properties of nucleotidyl-(5'→N)-amino acids esters differing in amino acid and nucleotide components," J. Carbohydrates, Nucleosides, Nucleotides, (1981), 8(1):19-39.
Juodka, et al., "Oligonucleotides and nucleotide-peptides. XXXVII. On the mechanism of hydrolysis of uridyly1-(5'→N)-amino acids. Intramolecular catalysis by the α-carboxyl group of amino acids," J. Carbohydrates, Nucleosides, Nucleotides, (1981), 8(6):519-535.
Khamnei et al., "Neighboring Group Catalysis in the Design of Nucleotide Prodrugs," J. Med. Chem., (1996), 39:4109-4115.
Kim, et al., "C-Terminal domain of the hepatitis C virus NS3 protein contains an RNA helicse activity," Biochem. Biophys. Res. Comm., (1995), 215(1):160-166.
Kim, et al., "Monitoring the Intracellular Metabolism of Nucleoside Phosphoramidate Pronucleotides by 31P MR," Nucleosides, Nucleotides and Nucleic Acids, (2004), 23(1):483-493.

(56) References Cited

OTHER PUBLICATIONS

Koonin, et al., "Evolution and Taxonomy of Positive-Strand RNA Viruses: Implications of Comparative Analysis of Amino Acid Sequences," Crir. Rev. Biochem. Molec. Biol., (1993), 28(5):375-430.
Kotra, et al., "Structure-Activity Relationships of 2'-Deoxy-2',2'-difluoro-L-erythro-pentofuranosyl Nucleosides," J. Med. Chem., (1997), 40:3635-3644.
Kryuchkov, et al., "Influence of Solvent on the Strength of Cyclic Oxygen-Containing Phosphorus Acids," Bulletin of the Academy of Sciences of the USSR. Division of Chemical Science, (1987), 36(6 Part 1):1145-1148.
Kucera, et al., "Novel Membrane-Interactive Ether Lipid Analogs That Inhibit Infectious HIV-1 Production and Induce Defective Virus Formation," AIDS Research and Human Retroviruses, (1990), 6(4):491-501.
Lackey, et al., "Enzyme-catalyzed therapeutic agent (ECTA) design: activation of the antitumor ECTA compound NB1011 by thymidylate synthase," Biochemical Pharmacology, (2001), 61:179-189.
Lee, et al., "Selective Intracellular Activation of a Novel Prodrug of the Human Immunodeficiency Virus Reverse Transcriptase Inhibitor Tenofovir Leads to Preferential Distribution and Accumulation in Lymphatic Tissue," Antimicrobial Agents and Chemotherapy, (2005), 49(5):1898-1906.
Lehsten, et al., "An Improved Procedure for the Synthesis of Nucleoside Phosphoramidates," Organic Process Research and Development, (2002), 6:819-822.
Li, et al., "Synthesis of the Phosphoramidite Derivative of 2'-Deoxy-2'-C-Beta-methylcytidine", J. Org. Chem., (2003), 68:6799-6802.
Lochmann, et al., "Biochemical Properties of Hepatitis C Virus NS5B RNA-Dependent RNA Polymerase and Identification of Amino Acid Sequence Motifs Essential for Enzymatic Activity," J. Virol., (1997), 71(11):8416-8428.
Lohmann, et al., Biochemical and Kinetic Analyses of NS5B RNA-Dependent RNA Polymerase of the Hepatitis C Virus, Virology, (1998), 249:108-118.
Lopez Aparicio, et al., "Synthesis of Saccharinic Acid Derivatives, Branched-Chain Sugars, Part VII," Carbohydrate Research, (1984), 129:99-109.
Ma, "Characterization of the Metabolic Activation of Hepatitis C Virus Nucleoside Inhibitor B-D-2'-Deoxy-2-Fluro-2'-C-Methylcytidine (PSI-6130) and Identification of a Novel Active 5'-Triphosphate Species," The Journal of Biological Chemistry, vol. 282, No. 41, 29812-29820, Oct. 12, 2007.
McGuigan et al., "Application of Phosphoramidate Pronucleotides Technology to Abacavir Leads to a Significant Enhancement of Antiviral Potency" Journal of Medicinal Chemistry, 2005, 48, 3504-3515.
McGuigan et al., "Application of Phosphoramidate ProTide Technology Significantly Improves Antiviral Potency of Carbocyclic Adenosine Derivatives" Journal of Medicinal Chemistry, 2006, 49, 7215-7226.
McGuigan et al., "Aryl phosphate derivatives of AZT retain activity against HIV1 in cell lines which are resistant to the action of AZT" Antiviral Research, 1992, 17, 311-321.
McGuigan et al., "Aryl Phosphoramidate Derivatives of d4T Have Improved Anti-HIV Efficacy in Tissue Culture and May Act by the Generation of a Novel Intracellular Metabolite" Journal of Medicinal Chemistry, 1996, 39, 1748-1753.
McGuigan, et al., "Synthesis, anti-human immunodeficiency virus activity and esterase lability of some novel carboxylic ester-modified phosphoramidate derivatives of stavudine (d4T)," Antiviral Chemistry & Chemotherapy, (1998), 9:473-479.
McGuigan et al., "Synthesis and evaluation of some novel phosphoramidate derivatives of 3'-azido-3'-deoxythymidine (AZT) as anti-HIV compounds" Antiviral Chemistry and Chemotherapy, 1990, 1(2), 107-113.
McGuigan et al., "Anti-cancer ProTides: tuning the activity of BVDU phosphoramidates related to thymectacin", Biorg. Med. Chem. (2005) 13: 3219-3227.

McIntee, et al., "Amino Acid Phosphoramidate Nucleosides: Potential ADEPT/GDEPT Substrates," Biorg. & Med. Chem. Lett., (2001), 11:2803-2805.
McIntee, et al., "Probing the Mechanism of Action and Decomposition of Amino Acid Phosphomonoester Amidates of Antiviral Nucleoside Prodrugs," J. Med. Chem., (1997), 40:3323-3331.
Meire, et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, (1997), 7(2):99-104.
Meyers, et al., "Moelcular Characterization of Pestiviruses," Advances in Virus Research, (1996), 47:53-118.
Mitchell, et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, (1992), 18:2345-2353.
Moennig, et al., "The Pestiviruses," Adv. Vir. Res., (1992), 41:53-98.
Monath, et al., "Effect of recombinant human granulocyte-macrophage colony-stimulating factor on chemotherapy-induced myelosuppression," New Eng. J. Med, (1988), 319(10):641-643.
Morissette, et al., "High-throughput crystallization: polymorphs, salts, co-crystals and solvates of pharmaceutical solids," Adv. Drug Delivery Rev., (2004), 56:275-300.
Murakami, et al., "Mechanism of Activation of β-D-2'-Deoxy-2'Fluoro-2'-C-Methylcytidine and Inhibition of Hepatitis C Virus NS5B RNA Polymerase," Antimicrobial Agents & Chemotherapy, (2007), 51(2):503-509.
Murakami, et al., "The Mechanism of Action of β-D-2'-Deoxy-2'Fluoro-2'-C-Methylcytidine Involves a Second Metabolic Pathway Leading to β-D-2'-Deoxy-2'Fluoro-2'-C-Methyluridine 5'-Triphosphate, a Potent Inhibitor of the Hepatitis C Virus RNA-Dependent RNA Polymerase," Antimicrobial Agents and Chemotherapy, (2008), 52(2):458-464.
Neidlein, et al., "Mild preparation of 1-benzyloxyiminoalkylphosphonic dichlorides: Aplication to the synthesis of cyclic phosphonic diesters and cyclic monoester amides," Heterocycles, (1993), 35(2):1185-1203.
Nelson, et al., "The Question fo Chair-Twist Equilibria for the Phosphate Rings of Nucleoside Cyclic 3',5'-Monophosphates. 1H NMR and X-ray Crystallographic Study of the Diastereomers of Thymidine Phenyl Cyclic 3',5'-Monophosphate," J. Am. Chem. Soc., (1987), 109(13):4058-4064.
Ni, et al., "Progress and development of small molecule HCV antivirals," Current Opinion in Drug Discovery and Development, (2004), 7(4):446-459.
Nifantyev, et al., "Synthesis and Structure of Some Stable Phospholane-Phospholanes," Phosphorus, Sulfur, and Silicon (1996), 113:1-13.
Novak, et al., "Chiroptical Properties of 2-Methyl-1,4-Lactones; Revised Absolute Configuration of 2-Deoxy-2-C-Methyl-erythro-D-Pentono-1,4-Lactones," Collection of Czechoslovak Chemical Communications, (1974), 39:869-882.
Novak, et al., "Nucleic Acid Components and Their Analogues. CXLIII. Nucleosides Derived From 2-Deoxy-2(R)-C-Methyl-erythro-D-Pentose," Collection of Czechoslovak Chemical Communications, (1971), 36:3670-3677 1971.
Oishi, et al., "Asymetric Dihydroxylation of Chiral Olefins. High Control of Diastereofacial Selection," Tetrahedron Letters, (1993), 34(22):3573-3576.
Olsen, D. et al., "2'-Modified Nucleoside Analogs as Inhibitors of Hepatitis C RNA Replication," (Oral Session V: Hepatitis C Virus, Flaviviruses), 16th International Conference on Antiviral Research, Abstract No. 121, p. A76 (Apr. 27-May 1, 2003, Savannah, GA)).
Otto, "Evaluation of Nucleoside Analogs in the Hepatitis C Virus Replicon System," Framing the Knowledge of Therapeutics for Viral Hepatitis Ed. By RF Schinazi and ER Schiff., 247-261, 2006.
Partial International Search Report of PCT/US2009/069475 (WO/2010/075554) mailed Mar. 5, 2010.
Perrone et al., "Application of the Phosphoramidate ProTide Approach to 4'-Azidouridine Confers Sub-micromolar Potency versus Hepatitis C Virus on an Inactive Nucleoside" J. Med. Chem. 2007, 50(8), 1840-1849.

(56) References Cited

OTHER PUBLICATIONS

Perrone et al., "First Example of Phosphoramidate Approach Applied to a 4'Substituted Purine Nucleoside (4'-Azidoadenosine): Conversion of an Inactive Nucleoside to a Submicromolar Compound versus Hepatitis C Virus" Journal of Medicinal Chemistry, 2007, 50, 5463-5470.
Piantadosi, C., "Synthesis and Evaluation of Novel Ether Lipid Nucleoside Conjugates for Anti-HIV-1 Activity,", J. Med. Chem., vol. 34, No. 4, pp. 1408-1414 (1991).
Pierra, C., "Synthesis and Pharmacokinetics of Valopicitabine (NM283), an Efficient Prodrug of the Potent Anti-HCV Agent 2'-C-Methylcytidine," J. Med. Chem. 2006, 49(22):6614-6620.
Pogam et al., "No Evidence of R7128 Drug Resistance After Up to 4 Weeks Treatment of GT1, 2 and 3 Hepatitis C Virus Infected Individuals", from 44th Annual Meeting of European Association for the Study of the Liver (EASL), Copenhagen, Denmark Apr. 22-Apr. 26, 2009.
Ray, et al., "Intracellular Metabolism of the Nucleotide Prodrug GS-9131, a Potent Anti-Human Immunodeficiency Virus Agent," Antimicrobial Agents and Chemotherapy, (2008), 52(2):648-654.
Reddy, et al. Stereoselective Synthesis of PSI-352938: A β-D-20-Deoxy-20-r-fluoro-20-β-C-methyl-30,50-cyclic Phosphate Nucleotide Prodrug for the Treatment of HCV. Journal of Organic Chemistry (2011), 76(10), 3782-3790.
Remy, et al., "Studies on Fluorinated Pyrimidines. XIV. The Synthesis of Derivatives of 5-Fluoro-2'-deoxyuridine 5'-Phosphate and Related Compounds," J. Org. Chem., (1962), 27:2491-2500.
Response filed Oct. 25, 2010 at the EPO for European patent application No. EP08732818.3.
Ross, et al. Synthesis of Diastereomerically Pure Nucleotide Phosphoramidates. Journal of Organic Chemistry (2011), 76(20), 8311-8319.
Saboulard et al., "Characterization of the Activation Pathway of Phosphoramidate Triester Prodrugs of Stavudine and Zidovudine" American Society for Pharmacology and Experimental Therapeutics, 1999, 56, 693-704.
Schultz et al., "Prodrugs of Biologically Active Phosphate Esters" Bioorganic and Medicinal Chemistry, 2003, 11, 885-898.
Shih, et al., "Preparation and Structure of 2-Dimethylamino-4-phenyl-1,3,2-dioxaphosphorinane-2-oxides," Bull. Inst. Chern., Academia Sinica, (1994), 41:9-16.
Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers" The Journal of Pharmacology and Experimental Therapeutics, 2003, 307(3), 1112-1119.
Siccardi et al., "Stereospecific chemical and enzymatic stability of phosphoramidate triester prodrugs of d4T in vitro" European Journal of Pharmaceutical Sciences, 2004, 22, 25-31.
Siddiqui et al., "Design and Synthesis of Lipophilic Phosphoramidate d4T-MP Prodrugs Expressing High Potency Against HIV in Cell Culture: Structural Determinants for in Vitro Activity and QSAR" Journal of Medicinal Chemistry, 1999, 42, 4122-4128.
Siddiqui et al., "Enhancing the Aqueous Solubility of d4T-based Phosphoramidate Prodrugs" Bioorganic and Medicinal Chemistry Letters, 2000, 10, 381-384.
Smirnov, et al., "A fluorescent study of tryptophan derivatives of oligonucleotides and their helical complexes and polyuridylic acid," FEBS Letters, (1975), 51(1):211-214.
Sofia et al, ".beta.-D-2'-Deoxy-2'-fluoro-2'-C-methyluridine Phosphoramidates: Potent and Selective Inhibitors of HCV RNA Replication", 2nd International Workshop on HCV, Poster #7, 2007.
Sofia et al., ".beta.-D2'-Deoxy-2'-C-methyluridine Phosphoramidates: Potent and Selective Inhibitors of HCV RNA Replication", Postser # P-259, presented at the 14.sup.th International Symposium on Hepatitis C Virus and Related Viruses, Glasgow, Scotland, UK, Sep. 9-13, 2007.

Sofia, M.J., "β-D-2'-Deoxy-2'-fluoro-2'-C-methyluridine Phosphoramidates: Potent and Selective Inhibitors of HCV RNA Replication", 2nd International Workshop on HCV—Resistance and New Compounds, Oct. 31, 2007.
Sofia, et al., "R7128, A Potent and Selective Nucleoside Inhibitor of HCV NS5B Polymerase: An Overview of Clinical Efficacy and Progress Toward Second Generation Inhibitors", From CHI: HCV Drug Discovery 2008, Chicago, IL, Apr. 28, 2008.
Sofia, "Discovery of PSI-352938 and PSI-353661: Purine Nucleotide Prodrugs for the treatment of HCV", First Disclosure Symposium, ACS 240th National Meeting, Boston, MA, Aug. 2010.
Song et al., "Pharmacokinetics of Amino Acid Phosphoramidate Monoesters of Zidovudine in Rats" Antimicrobial Agents and Chemotherapy, 2002, 46(5), 1357-1363.
Starrett, Jr., J., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stella, "Prodrugs as Therapeutics", Expert Opinion Ther. Patents, 2004, 14:3, 277-280.
Stuyver et al., "Inhibition of the Subgenomic Hepatitis C Virus Replicon in Huh-7 Cells by 2'-Deoxy-2'-Fluorocytidine" Antiviral Chemistry & Chemotherapy, 2004, 48(2), 651-654.
Stuyver, "Inhibition of hepatitis C replicon RNA synthesis by B-D-2'-deoxy-2'-fluoro-2'-C-methlcytidine: a specific inhibitor of hepatitis C virus replication," Antiviral Chemistry & Chemotherapy 2006, 17:79-87, 2006.
Stuyver, L., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (Oct. 2003).
Stuyver, L., "Ribonucleoside Analogue that Blocks Replication of Bovine Viral Diarrhea and Hepatitis C Viruses in Culture," Antimicrob. Agents Chemother., vol. 47, No. 1, pp. 244-254 (Jan. 2003).
Sun, et al., "Study on the Chirality of Sulfur in Ethyl (2S, 3R,4R)-4,5-O-lsopropylidene-2,3-sulfiny1-2,3,4,5-tetrahydroxy-pentanoate", Acta Chimica Sinica, 1997, vol. 55, 600-604.
Sun, et al., "The Synthesis of (2s,3R)-Sphingosine from D-Mannitol", Acta Chimica Sinica, 1996, vol. 54, 826-832.
Supplemental European Search Report of European patent appln No. EP 05775359.2 dated Sep. 15, 2010.
Tan, et al., "Hepatitis C Therapeutics: Current Status and Emerging Strategies," Nature Rev. Drug Discov., (2002), 1:867-881.
Tomei, et al., "NS3 Is a Serine Protease Required for Processing of Hepatitis C Virus Polyprotein," J. Viral., (1993), 67(7):4017-4026.
Uckun et al., "In Vivo Pharmacokinetics and Toxicity Profile of the Anti-HIV Agent Stampidine in Dogs and Feline Immunodeficiency Virus-infected Cats" Arzneim.-Forsch./Drug Research 2006, 56(2a), 176-192.
Valette et al., "Decomposition Pathways and in Vitro HIV Inhibitory Effects of IsoddA Pronucleotides: Toward a Rational Approach for Intracellular Delivery of Nucleoside 5'-Monophosphates" Journal of Medicinal Chemistry, 1996, 39, 1981-1990.
Venkatachalam et al., "Synthesis and metabolism of naphthyl substituted phosphoramidate derivatives of stavudine" Bioorganic and Medicinal Chemistry, 2006, 14, 5161-5177.
Venkatachalam et al., Rational Drug Design of Multifunctional Phosphoramidate Substituted Nucleoside Analogs Current Pharmaceutical Design, 2004, 10 (15), 1713-1726.
Wagner et al., "Antiviral Nucleoside Drug Delivery via Amino Acid Phosphoramidates', Nucleosides, Nucleotides and Nucleic Acids" Nucleosides, Nucleotides and nucleic Acids, 1999, 18(4), 913-918.
Walker, et al., "Promising candidates for the treatment of chronic hepatitis C," Exp. Opin. Investig. Drugs, (2003), 12(8):1269-1280.
Warrener, et al., "Pestivirus NS3 (p80) Protein Possesses RNA Helicse Activity," J. Viral., (1995), 69(3):1720-1726.
Wiskerchen, et al,. "Pestivirus Gene Expression: Protein p80 of Bovine Viral Diarrhea Virus Is a Proteinase Involved in Polyprotein Processing," Virology, (1991), 184:341-350.
Wolff, M.E., "Burger's Medicinal Chemistry and Drug Discovery, 5ed, Part I", John Wiley & Sons, (1995), 975-977.

(56) References Cited

OTHER PUBLICATIONS

Wu, et al., "Synthesis and Biological Activity of a Gemcitabine Phosphoramidate Prodrug," J. Med. Chem., (2007), 50:3743-3746.

Wu, et al., "Targeting NS5B RNA-Dependent RNA Polymerase for Anti-HCV Chemotherapy," Current Drug Targets-Infectious Disorders, (2003), 3:207-219.

Xu, et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., (1997), 71(7):5312-5322.

Yuan, et al., "Expression, Purification, and Partial Characterization of HCV RNA Polymerase," Biochem. Biophys. Res. Comm., (1997), 232:231-235.

Yuodka, et al., "Oligonucleotides and polynucleotides. XXVI. Synthesis of esters of nucleotidyl- and oligonucleotidyl-(5'→N)-(amino acid)s and peptides," translated from Bioorganicheskaya Khimiya, (1976), 2(11):1513-1519.

Zhong, et al., "Identification and Characterization of an RNA-Dependent RNA Polymerase Activity within the Nonstructural Protein 5B Region of Bovine Viral Diarrhea Virus," J. Viral., (1998), 72(11):9365-9369.

Zon, G., "4 Cyclophosphoamide Analogues," Progress in Medicinal Chemistry, vol. 19, pp. 205-246 (1982).

Babu BR, et al. 2'-Spiro ribo- and arabinonucleosides: synthesis, molecular modelling and incorporation into oligodeoxynucleotides. Org Biomol Chem. Oct. 21, 2003;1(20):3514-26.

International Search Report and Written Opinion from related PCT application No. PCT/US2011/062643 (WO2012/075140), mailed May 10, 2012.

* cited by examiner

2'-SPIRO-NUCLEOSIDES AND DERIVATIVES THEREOF USEFUL FOR TREATING HEPATITIS C VIRUS AND DENGUE VIRUS INFECTIONS

PRIORITY

Priority is claimed to U.S. provisional patent application 61/417,946, filed on Nov. 30, 2010.

FIELD OF THE INVENTION

Disclosed herein are 2'-spiro-nucleosides and derivatives thereof useful for treating hepatitis C virus and dengue virus infections.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. According to the U.S. Center for Disease Control, there are an estimated 4.5 million infected people in the United States alone. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29:1227-1235; V. Lohmann, et al, *Virology*, 1998, 249:108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Dengue viral infections are problematic in the tropical and subtropical regions of the word. Shi et al. Top. Med. Chem. (2001) 7:243-276. The dengue virus (DENV) is transmitted to humans by certain mosquitoes, and it is has been estimated that up to about 50 million infections occur each year. Parkinson et al. Future Med. Chem. (2010) 2(7): 1181-1203. At the present, there are no specific treatments for dengue viral infections. Fagundes et al. Drug Development Research (2011) 72:480-500. DENV is comprised of ten proteins that includes three structural proteins (C, prM, and E) and seven non-structural proteins (NS1, NS2A, NS2B, NS3, NS4A, NS4B, and NS5). Of these ten proteins, only NS3 and NS5 are known to possess enzymatic activity. A desirable drug substance is one that interferes with the action or function of any one of these ten viral proteins.

Flaviviridae Viruses

The Flaviviridae family of viruses comprises at least three distinct genera: pestiviruses, which cause disease in cattle and pigs; flavivruses, which are the primary cause of diseases such as dengue fever and yellow fever; and hepaciviruses, whose sole member is HCV. The flavivirus genus includes more than 68 members separated into groups on the basis of serological relatedness (Calisher et al, *J. Gen. Virol,* 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.,* 1984, 6, 251-264; Halstead, S. B., *Science,* 239:476-481, 1988; Monath, T. P., *New Eng. J. Med,* 1988, 319, 64 1-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al, *Nature*, 1988, 333, 22; Bazan and Fletterick *Virology*, 1989, 171, 637-639; Gorbalenya et al, *Nucleic Acid Res.*, 1989, 17, 3889-3897). Similarly, the NS5B proteins of pestiviruses and hepaciviruses have the motifs characteristic of RNA-directed RNA polymerases (Koonin, E. V. and Dolja, V. V., *Crir. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology*, 1991, 184, 341-350; Bartenschlager et al, *J. Virol.* 1993, 67, 3835-3844; Eckart et al. *Biochem. Biophys. Res. Comm.* 1993, 192, 399-406; Grakoui et al, *J. Virol.* 1993, 67, 2832-2843; Grakoui et al, *Proc. Natl. Acad Sci. USA* 1993, 90, 10583-10587; Hijikata et al, *J. Virol.* 1993, 67, 4665-4675; Tome et al, *J. Virol*, 1993, 67, 4017-4026). The NS4A protein, in both cases, acts as a cofactor with the NS3 serine protease (Bartenschlager et al, *J. Virol.* 1994, 68, 5045-5055; Failla et al, *J. Virol.* 1994, 68, 3753-3760; Xu et al, *J. Virol*, 1997, 71:53 12-5322). The NS3 protein of both viruses also functions as a helicase (Kim et al, *Biochem. Biophys. Res. Comm.*, 1995, 215, 160-166; Jin and Peterson, *Arch. Biochem. Biophys.*, 1995, 323, 47-53; Warrener and Collett, *J. Virol.* 1995, 69, 1720-1726). Finally, the NS5B proteins of pestiviruses and hepaciviruses have the predicted RNA-directed RNA polymerases activity (Behrens et al, *EMBO*, 1996, 15, 12-22; Lechmann et al, *J. Virol*, 1997, 71, 8416-8428; Yuan et al, *Biochem. Biophys. Res. Comm.* 1997, 232, 231-235; Hagedorn, PCT WO 97/12033; Zhong et al, *J. Virol*, 1998, 72, 9365-9369).

A number of potential molecular targets for drug development of direct acting antivirals as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al, *Nature Rev. Drug Discov.*, 2002, 1, 867-881; Walker, M. P. et al., *Exp. Opin. Investigational Drugs*, 2003, 12, 1269-1280; Ni, Z-J., et al., *Current Opinion in Drug Discovery and Development*, 2004, 7, 446-459; Beaulieu, P. L., et al., *Current Opinion in Investigational Drugs*, 2004, 5, 838-850; Wu, J., et al., *Current Drug Targets-Infectious Disorders*, 2003, 3, 207-219; Griffith, R. C., et al, *Annual Reports in Medicinal Chemistry*, 2004, 39, 223-237; Carrol, S., et al., *Infectious Disorders-Drug Targets*, 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C, et al, *J. Med. Chem.*, 1996, 39, 1748-1753; Valette, G., et al, *J. Med. Chem.*, 1996, 39, 1981-1990; Balzarini, J., et al, *Proc. National Acad Sci USA*, 1996, 93, 7295-7299; Siddiqui, A. Q., et al, *J. Med. Chem.*, 1999, 42, 4122-4128; Eisenberg, E. J., et al., *Nucleosides, Nucleotides and Nucleic Acids*, 2001, 20, 1091-1098; Lee, W. A., et al, *Antimicrobial Agents and Chemotherapy*, 2005, 49, 1898); US 2006/0241064; and WO 2007/095269.

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties prodrugs of nucleosides have been employed. Additional phosphate-containing prodrugs are also known: C. Schultz, Biorg. & Med. Chem. (2003) 11:885-898; C. McGuigan et al, Bioorg. & Med. Chem. Lett. (1994) 4(3): 427-430; C. Meier, Synlett (1998) 233-242; R. J. Jones et al, Antiviral Research (1995) 27:1-17; G. J. Friis et al, Eur. J. Pharm. Sci. (1996) 4:49-59; C. Meier Mini Reviews in Medicinal Chemistry (2002) 2(3): 219-234; C. Perigaud et al., Advances in Antiviral Drug Design; DeClerq E., Ed.; Vol. 2; JAI Press, London, 1996. However, there is no general agreement as to which phosphate-containing prodrug provides for the best activity.

In an effort to improve treatment of HCV or DENV, it remains of vital interest to identify compounds capable of inhibiting the action of NS5B polymerase of HCV or of inhibiting the action or function of a particular DENV protein.

SUMMARY

Disclosed herein is a compound or its stereoisomer or its salt or its metabolite or its deuteride thereof represented by formula I:

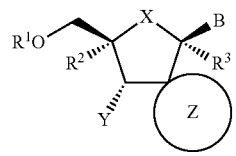

wherein
1) $R^1$ is selected from among
   a) hydrogen,
   b) —P(O)(OH)$_2$, c) —P(O)(O(CH$_2$)$_{1-3}$OC(O)O(C$_{1-6}$alkyl))$_2$,
d) —P(O)(O(CH$_2$)$_{1-3}$OC(O)(alkyl))$_2$,
e) —P(O)(O(CH$_2$)$_{1-3}$SC(O)(alkyl))$_2$,
f) —P(O)(O(CH$_2$)$_{1-3}$OCH$_2$(aryl))$_2$,
g) —P(O)(O(CH$_2$)$_{1-3}$SCH$_2$(aryl))$_2$,
h) —P*(O)(OR$^{1a}$)(NHCHR$^{1b}$C(O)OR$^{1c}$),
where
R$^{1a}$ is
  i) hydrogen,
  ii) alkyl,
  iii) cycloalkyl, or
  iv) aryl,
R$^{1b}$ is
  i) hydrogen,
  ii) C$_{1-6}$alkyl,
  iii) cycloalkyl,
  iv) alkaryl, or
  v) alk(heteroaryl), and
R$^{1c}$ is
  i) hydrogen,
  ii) alkyl,
  iii) cycloalkyl, or
  iv) alkaryl,
i) —P*(O)(NH(alkaryl)(O(CH$_2$)$_{1-3}$SC(O)(alkyl)),
j) a 1,3,2-dioxaphosphinane-2-oxide,
k) a 4H-benzo[d][1,3,2]dioxaphosphinine-2-oxide,
l) —P*(O)(OR$^{1c}$)~, when Y is —O~, where R$^{1c}$ is defined above,
m) —P(O)(OH)—O—P(O)(OH)$_2$,
n) —P(O)(OH)—O—P(O)(OH)—O—P(O)(OH)$_2$,
o) an acyl,
p) a C$_{1-6}$-alkylene-oxy-acyl, and
q) a —C(O)—O-alkyl;
2) R$^2$ is selected from among
  a) hydrogen,
  b) fluoro,
  c) azido,
  d) cyano,
  e) a C$_{1-6}$alkyl,
  f) a vinyl, and
  g) an ethynyl;
3) R$^3$ is selected from among
  a) hydrogen,
  b) methyl, and
  c) cyano,
4) Y is selected from among
  a) hydrogen,
  b) fluoro,
  c) —OH,
  d) —O~, when R$^1$ is —P(O)(OR$^{1c}$)~, where R$^{1c}$ is defined above,
  e) —O(acyl),
  f) O(C$_{1-6}$-alkylene-oxy-acyl),
  g) —O—C(O)—O-alkyl,
  h) —NH$_2$,
  i) —NH(acyl),
  j) —NH—C(O)—O-alkyl, and
  k) azido;
5) X is selected from among
  a) —O—,
  b) —S—,
  c) —NH—,
  d) —CH$_2$,
  e) >C=CH$_2$, and
  f) —NH—C(O)—O-alkyl;

6)  is a four- or five-membered ring selected from among radicals a-o represented by the following structures

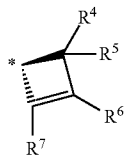

a

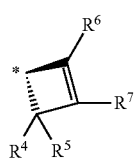

b

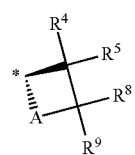

c

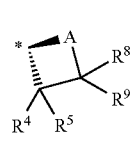

d

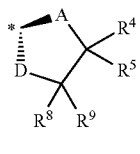

e

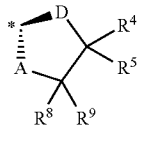

f

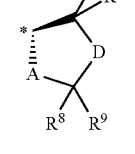

g

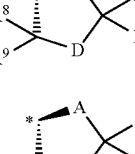

h

i

-continued

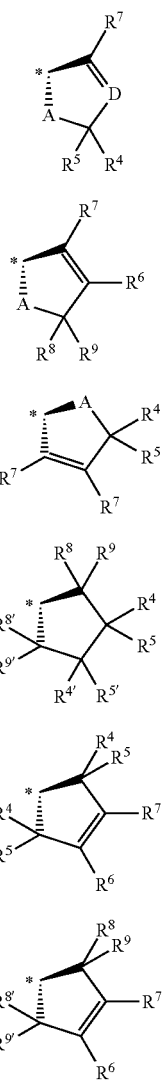

j k l m n o where * represents the point of attachment to the 2'-carbon and where
  a) A is selected from among
    i) —O—,
    ii) —S—,
    iii) —S(O)—,
    iv) —S(O)$_2$—, and
    v) —NH—,
  b) D is selected from among
    i) —O—
    ii) —S— except for rings i and j,
    iii) —S(O)— except for rings i and j,
    iv) —S(O)$_2$— except for rings i and j, and
    v) —NH— except for rings i and j,
    vi) —N—,
    vii) a methylene except for rings i and j,
    viii) a methine, and
    ix) a vinylidene except for rings i and j,
  c) $R^4$, $R^{4'}$, $R^5$, $R^{5'}$, $R^6$, $R^7$, $R^8$, $R^{8'}$, $R^9$, and $R^{9'}$ are independently selected from among
    i) hydrogen,
    ii) halo,
    iii) $C_{1-6}$alkyl,
    iv) hydroxy,
    v) alkoxy,
    vi) cycloalkoxy,
    vii) —O(acyl),
    viii) —O($C_{1-6}$-alkyleneoxyacyl),
    ix) —O—C(O)—O-alkyl,
    x) $C_{1-6}$alkylene-oxy(alkyl),
    xi) alkenyl,
    xii) ethynyl,
    xiii) —NH$_2$,
    xiv) —NH(alkyl),
    xv) —NH(cycloalkyl),
    xvi) heterocyclyl,
    xvii) aryl, and
    xviii) heteroaryl; and
  7) B is selected from among B1, B2, and B3 represented by the following structures:

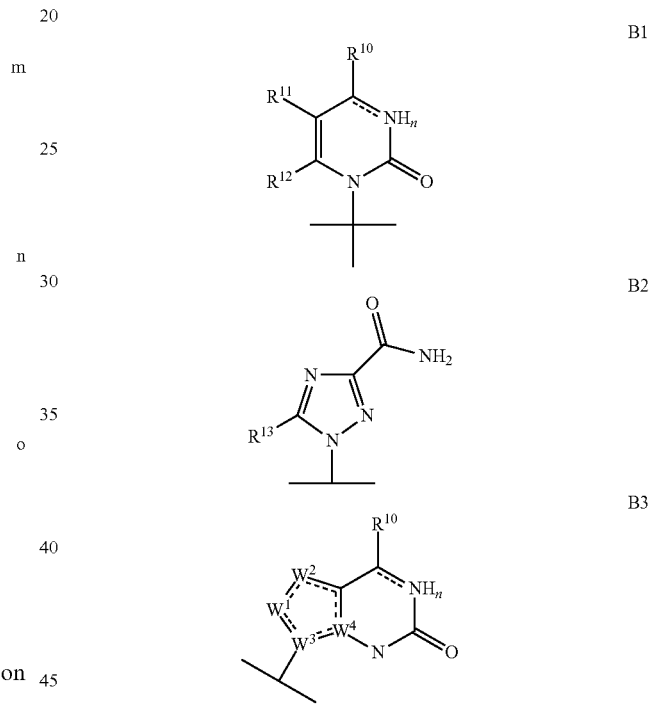

where for B1 n is 0 or 1,
  a) when n is 0, ----- is a double-bond and $R^{10}$ is selected from among
    i) —NH$_2$,
    ii) —NH(alkyl),
    iii) —NH(acyl),
    iv) —NH—C(O)—O-alkyl,
    v) -cycloheteroalkyl,
    vi) -heteroaryl,
    vii) —O(alkyl),
    viii) —O(acyl),
    ix) —O($C_{1-6}$alkylene-oxyacyl), and
    x) —O—C(O)—O-alkyl, or
  b) when n is 1, ----- is a single-bond and $R^{10}$ is selected from among
    i) =O,
    ii) =NH, and
    iii) =N(alkyl), and
  c) independent of the value of n, $R^{11}$ and $R^{12}$ are independently selected from among i) hydrogen,
  ii) halo,
  iii) cyano,
  iv) $C_{1-6}$alkyl,
  v) $C_{2-5}$alkenyl, and
  vi) $C_{2-5}$alkynyl,
where for B2,
  a) $R^{13}$ is selected from among
    i) hydrogen,
    ii) halo,
    iii) cyano,
    iv) —C(O)NH$_2$,
    v) $C_{1-6}$alkyl,
    vi) vinyl, and
    vii) ethynyl,
where for B3 m is 0 or 1, and ---- is a single or double bond
  a) when m is 0, ---- is a double-bond and $R^{16}$ and $R^{17}$ are independently selected from among
    i) hydrogen,
    ii) —NH$_2$,
    iii) —NH(alkyl),
    iv) —NH(acyl),
    iv) —NH—C(O)—O-alkyl,
    v) -cycloheteroalkyl,
    vi) —O(alkyl),
    vii) —O(acyl),
    viii) —O($C_{1-6}$alkyleneoxyacyl), and
    ix) —O—C(O)—O-alkyl,
    x) —S(alkyl), or
  b) when m is 1, ---- is a single-bond
    b1) $R^{16}$ is selected from among
      i) =O,
      ii) =NH, and
      iii) =N(alkyl), and
    b2) $R^{17}$ is selected from among
      i) —NH$_2$,
      ii) —NH(alkyl),
      iii) —NH(acyl),
      iv) —NH—C(O)—O-alkyl, and
      v) -cycloheteroalkyl,
  c) independent of the value of m, each bonding pair, $W^1$ ---- $W^2$, $W^2$ ---- C, C ---- $W^4$, $W^4$ ---- $W^3$, and $W^3$ ---- $W^1$, contained in the five-membered ring comprises a single or a double bond and
    i) $W^1$ is O, S, N, or $CR^{14}$,
    ii) $W^2$ is N or $CR^{15}$,
    iii) $W^3$ is C or N, and
    iv) $W^4$ is C or N
  and where $R^{14}$ and $R^{15}$, if present, are independently selected from among
    i) hydrogen,
    ii) halo,
    iii) cyano,
    iv) —C(O)NH$_2$,
    iv) $C_{1-6}$alkyl,
    vii) vinyl, and
    viii) ethynyl.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "stereoisomer" has its plain and ordinary meaning.

The term "*" denotes the presence of a chiral center. Instances where "*" are not explicitly included in a radical does not necessarily mean that the radical does not contain a chiral center.

The term "P*" means that the phosphorus atom is chiral and that it has a corresponding Cahn-Ingold-Prelog designation of "R" or "S" which have their accepted plain meanings. In some instances, a phosphorus-containing radical does not expressly include an "*" next to the phosphorus atom, e.g., —P(O)(O(CH$_2$)$_{1-3}$OC(O)(alkyl))$_2$, —P(O)(O(CH$_2$)$_{1-3}$SC(O)(alkyl))$_2$, —P(O)(O(CH$_2$)$_{1-3}$OCH$_2$(aryl))$_2$, —P(O)(O(CH$_2$)$_{1-3}$SCH$_2$(aryl))$_2$. In these (and other) instances, it will be understood that chirality at phosphorus will be dictated by the substituent pattern. That is, when the substituents bound to phosphorus are the same, then achirality at phosphorus will exist, but when the substituents bound to the phosphorus are not the same, then chirality at phosphorus will exist.

The term "salts" or "salt thereof" as described herein, refers to a compound comprising a cation and an anion, which can prepared by any process known to one of ordinary skill, e.g., by the protonation of a proton-accepting moiety and/or deprotonation of a proton-donating moiety. Alternatively, the salt can be prepared by a cation/anion metathesis reaction. It should be noted that protonation of the proton-accepting moiety results in the formation of a cationic species in which the charge is balanced by the presence of a anion, whereas deprotonation of the proton-donating moiety results in the formation of an anionic species in which the charge is balanced by the presence of a cation. It is understood that salt formation can occur under synthetic conditions, such as formation of pharmaceutically acceptable salts, or under conditions formed in the body, in which case the corresponding cation or anion is one that is present in the body. Examples of common cations found in the body include, but are not limited to: $H^+$, $Na^+$, $K^+$, $Mg^{2+}$, $Ca^{2+}$, etc. Examples of common anions found in the body include, but are not limited to, $Cl^-$, $HCO_3^-$, $CO_3^{2-}$, $H_2PO_4^-$, $HPO_4^{2-}$, etc.

The phrase "pharmaceutically acceptable salt" means a salt that is pharmaceutically acceptable. It is understood that the term "pharmaceutically acceptable salt" is encompassed by the expression "salt." Examples of pharmaceutically acceptable salts include, but are not limited to acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like. Additional examples of anionic radicals of the pharmaceutically acceptable salt include but are not limited to: acetate, benzenesulfonate, benzoate, bicarbonate, bitartrate, bromide, calcium edetate, camsylate (camphorsulfonate), carbonate, chloride, citrate, edetate, edisylate (1,2-ethanedisulfonate), estolate (lauryl sulfate), esylate (ethanesulfonate), fumarate, gluceptate (glucoheptonate), gluconate, glutamate, glycollylarsanilate (p-glycollamidophenylarsonate), hexylresorcinate, hydrabamine (N,N'-di(dehydroabietyl)ethylenediamine), hydroxynaphthoate, iodide, isethionate (2-hydroxyethanesulfonate), lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, and teoclate (8-chlorotheophyllinate). Basic addition salts formed with the conjugate bases of any of the inorganic acids listed above, wherein the conjugate bases comprise a cationic component selected from among $Li^+$, $Na^+$, $K^+$, $Mg^{2+}$, $Ca^{2+}$, $Al^{3+}$, $NH_gR'''_{4-g}{}^+$, in which $R'''$ is a $C_{1-3}$ alkyl and g is a number selected from among 0, 1, 2, 3, or 4. Additional examples of cationic radicals of the pharmaceutically acceptable salt, include but are not limited to: penzathine, phloroprocaine, pholine, piethanolamine, pthylenediamine, meglumine, and procaine.

The term "metabolite," as described herein, refers to a compound produced in vivo after administration of a compound or its stereoisomer or its salt or its deuteride thereof represented by formula I to a subject in need thereof or as formed in vitro in an assay. Said metabolite may exist as a salt.

The term "deuteride," as described herein, refers to a deuterated analog of the compound represented by formula I where a hydrogen atom is enriched with its 2H-isotope, i.e., deuterium (D). Deuterium substitution can be partial or complete. Partial deuterium substitution means that at least one hydrogen is substituted by at least one deuterium.

The term "halo" or "halogen" as used herein, includes chloro, bromo, iodo and fluoro.

The term "alkyl" refers to an unbranched or branched chain, saturated, monovalent hydrocarbon residue containing 1 to 30 carbon atoms. The term "$C_{1-M}$ alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30.

The term "$C_{1-6}$alkyl" refers to an alkyl containing 1 to 6 carbon atoms. Examples of a $C_{1-6}$ alkyl group include, but are not limited to, methyl, ethyl, n-propyl, t-propyl, n-butyl, i-butyl, s-butyl, t-butyl, n-pentyl, isopentyl, neopentyl, t-pentyl, and hexyl.

The term "$C_{1-6}$-alkylene" refers to an alkylene radical containing 1 to 6 carbon atoms. Examples of a $C_{1-6}$-alkylene include, but are not limited to, a methylene (—CH$_2$—), ethylene (—CH$_2$CH$_2$—), methyl-ethylene (—CH(CH$_3$)CH$_2$—), propylene (—CH$_2$CH$_2$CH$_2$—), methyl-propylene (—CH(CH$_3$)CH$_2$CH$_2$— or —CH$_2$CH(CH$_3$)CH$_2$—), etc. It is understood that a branched $C_{1-6}$-alkylene, such as methyl-ethylene or methyl-propylene, contains a chiral center, in which case the individual stereoisomers are contemplated. It is contemplated that a methylene may be substituted with one or two $C_{1-6}$alkyls.

The term "cycloalkyl" refers to an unsubstituted or substituted carbocycle, in which the carbocycle contains 3 to 10 carbon atoms; preferably 3 to 8 carbon atoms (i.e., a $C_{3-8}$-cycloalkyl); more preferably 3 to 6 carbon atoms (i.e., a $C_{3-6}$-cycloalkyl). In the instance of a substituted carbocycle containing 3 to 10, 3 to 8, or 3 to 6 carbon atoms, the substituents are not to be counted for the carbocycle carbon count. For instance, a cyclohexyl substituted with one or more $C_{1-6}$-alkyl is still, within the meaning contemplated herein, a $C_{3-6}$-cycloalkyl. Examples of a $C_{3-6}$cycloalkyl include, but are not limited to, cyclopropyl, 2-methyl-cyclopropyl, cyclobutyl, 2-methyl-cyclobutyl, cyclopentyl, 2-methyl-cyclopentyl, cyclohexyl, 2-methyl-cyclohexyl, etc.

The term "cycloalkylamino" refers to a unsubstituted or substituted carbocycle comprising an "amino" (—NH—) functional group. The carbocycle contains 3 to 10 carbon atoms; preferably 3 to 8 carbon atoms (i.e., a $C_{3-8}$-cycloalkyl); more preferably 3 to 6-carbon atoms (i.e., a $C_{3-6}$-cycloalkyl). In the instance of a substituted carbocycle containing 3 to 10, 3 to 8, or 3 to 6 carbon atoms, the substituents are not to be counted for the carbocycle carbon count. For instance, a cyclohexyl substituted with one or more $C_{1-6}$-alkyl is still, within the meaning contemplated herein, a $C_{3-6}$-cycloalkyl. Examples of a $C_{3-6}$cycloalkylamino (alternatively referred to as —NH$C_{3-6}$cycloalkyl) include, but are not limited to, cyclopropylamino, 2-methyl-cyclopropylamino, cyclobutylamino, 2-methyl-cyclobutylamino, cyclopentylamino, 2-methyl-cyclopentylamino, cyclohexylamino, 2-methyl-cyclohexylamino, etc. One of ordinary skill will know that said cycloalkylaminos are derived from cycloalkylamines, i.e., cycloalkyls substituted by an amine (—NH$_2$) functional group.

The term "alkoxy" refers to an —O-alkyl group or an —O-cycloalkyl group, wherein alkyl and cycloalkyl are as defined above. Examples of —O-alkyl groups include, but are not limited to, methoxy, ethoxy, n-propyloxy, i-propyloxy, n-butyloxy, i-butyloxy, t-butyloxy, etc. Examples of —O-cycloalkyl groups include, but are not limited to, —O-c-propyl, —O-c-butyl, —O-c-pentyl, —O-c-hexyl, etc.

The term "$C_{1-6}$-alkoxy" refers to an —O—$C_{1-6}$-alkyl group, wherein $C_{1-6}$ alkyl is defined herein.

The term "$C_{3-6}$-cycloalkoxy" refers to an —O—$C_{3-6}$-cycloalkyl group

The term "$C_{1-6}$-alkylene-oxy" refers to an —O—$C_{1-6}$-alkylene group, wherein $C_{1-6}$-alkylene is defined as above. Examples of a $C_{1-6}$-alkylene-oxy include, but are not limited to, methylene-oxy (—CH$_2$O—), ethylene-oxy (—CH$_2$CH$_2$O—), methyl-ethylene-oxy (—CH(CH$_3$)CH$_2$O—), propylene-oxy (—CH$_2$CH$_2$CH$_2$O—), methyl-propylene-oxy (—CH(CH$_3$)CH$_2$CH$_2$O— or —CH$_2$CH(CH$_3$)CH$_2$O—), etc.

The terms "alkaryl" or "alkylaryl" refer to an alkylene group having 1 to 10-carbon atoms with an aryl substituent, such as benzyl. The term "$C_{1-3}$alkaryl" refers to a $C_{1-3}$alkylene group with an aryl substituent. Benzyl is embraced by the term $C_{1-3}$alkaryl.

The term "—O$C_{1-3}$alkaryl" refers a oxygen (—O~) bound to a $C_{1-3}$alkaryl group. Benzyloxy (—OCH$_2$Ph) is embraced by the term —O$C_{1-3}$alkaryl.

The term "aryl," as used herein, and unless otherwise specified, refers to substituted or unsubstituted phenyl (Ph), biphenyl, or naphthyl. The aryl group can be substituted with one or more moieties selected from among alkyl, hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "heteroaryl" refers to an unsubstituted or substituted aromatic heterocycle containing carbon, hydrogen, and at least one of N, O, and S. Examples of heteroaryls include, but are not limited to, a pyrrole, an imidazole, a diazole, a triazole, a tetrazole, a furan, an oxazole, an indole, a thiazole, etc. Additional examples of heteroaryls can be found in T. L. Gilchrist, in "Heterocyclic Chemistry," John Wiley & Sons, 1985. The heteroaryl group can be substituted with one or more moieties selected from among alkyl, hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "heterocycle" or "heterocyclyl" refers to an unsubstituted or substituted radical containing carbon, hydrogen and at least one of N, O, and S. Examples of heterocycles, include, but are not limited to, an aziridine, an azetidine, a pyrrolidine, a piperidine, a piperazine, etc. Additional examples of heterocycles can be found in T. L. Gilchrist, in "Heterocyclic Chemistry," John Wiley & Sons, 1985. The heterocycle can be substituted with one or more moieties selected from among alkyl, hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alk(heteroaryl)" and "alk(heterocyclyl)" refers to a $C_{1-6}$-alkylene group with a heteroaryl and heterocyclyl substituent, respectively.

The term "cycloheteroalkyl" refers to an unsubstituted or substituted heterocycle, in which the heterocycle contains 2 to 9 carbon atoms; preferably 2 to 7 carbon atoms; more preferably 2 to 5 carbon atoms. Examples of cycloheteroalkyls include, but are not limited to, aziridin-1-yl, aziridin-2-yl, N—$C_{1-3}$-alkyl-aziridin-2-yl, azetidinyl, azetidin-1-yl, N—$C_{1-3}$-alkyl-azetidin-m'-yl, pyrrolidin-m'-yl, pyrrolidin-1-yl, N—$C_{1-3}$-alkyl-pyrrolidin-m'-yl, piperidin-m'-yl, piperidin-1-yl, and N—$C_{1-3}$-alkyl-piperidin-m'-yl, where m' is 2, 3, or 4 depending on the cycloheteroalkyl. Specific examples of N—$C_{1-3}$-alkyl-cycloheteroalkyls include, but are not limited to, N-methyl-aziridin-2-yl, N-methyl-azetidin-3-yl, N-methyl-pyrrolidin-3-yl, N-methyl-pyrrolidin-4-yl, N-methyl-piperidin-2-yl, N-methyl-piperidin-3-yl, and N-methyl-piperidin-4-yl. In the instance of $R^{10}$, $R^{16}$, and $R^{17}$, the point of attachment between the cycloheteroalkyl ring carbon and the ring occurs at any one of m'.

The term "acyl" refers to a substituent containing a carbonyl moiety and a non-carbonyl moiety and is meant to include an amino-acyl. The carbonyl moiety contains a double-bond between the carbonyl carbon and a heteroatom, where the heteroatom is selected from among O, N and S. When the heteroatom is N, the N is substituted by a $C_{1-6}$. The non-carbonyl moiety is selected from straight, branched, and cyclic alkyl, which includes, but is not limited to, a straight, branched, or cyclic $C_{1-20}$ alkyl, $C_{1-10}$ alkyl, or a $C_{1-6}$-alkyl; alkoxyalkyl, including methoxymethyl; aralkyl, including benzyl; aryloxyalkyl, such as phenoxymethyl; or aryl, including phenyl optionally substituted with halogen (F, Cl, Br, I), hydroxyl, $C_1$ to $C_4$ alkyl, or $C_1$ to $C_4$ alkoxy, sulfonate esters, such as alkyl or aralkyl sulphonyl, including methanesulfonyl, the mono, di or triphosphate ester, trityl or monomethoxytrityl, substituted benzyl, trialkylsilyl (e.g. dimethyl-t-butylsilyl) or diphenylmethylsilyl. When at least one aryl group is present in the non-carbonyl moiety, it is preferred that the aryl group comprises a phenyl group.

The term "$C_{2-7}$acyl" refers to an acyl group in which the non-carbonyl moiety comprises a $C_{1-6}$alkyl. Examples of a $C_{2-7}$-acyl, include, but are not limited to: —C(O)CH$_3$, —C(O)CH$_2$CH$_3$, —C(O)CH(CH$_3$)$_2$, —C(O)CH(CH$_3$)CH$_2$CH$_3$, —C(O)C(CH$_3$)$_3$, etc.

The term "aminoacyl" includes N,N-unsubstituted, N,N-monosubstituted, and N,N-disubstituted derivatives of naturally occurring and synthetic α, β γ or δ amino acyls, where the amino acyls are derived from amino acids. The amino-nitrogen can be substituted or unsubstituted or exist as a salt thereof. When the amino-nitrogen is substituted, the nitrogen is either mono- or di-substituted, where the substituent bound to the amino-nitrogen is a $C_{1-6}$alkyl or an alkaryl. In the instance of its use for the compound of formula I, it is understood that an appropriate atom (O or N) is bound to the carbonyl carbon of the aminoacyl.

The term "amino acid" includes naturally occurring and synthetic α, β γ or δ-amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutamyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "$C_{1-6}$-alkylene-oxy-acyl" refers to an —O—$C_{1-6}$-alkylene-acyl group, wherein $C_{1-6}$-alkylene and acyl are defined as above. Examples of a $C_{1-6}$-alkylene-oxy-acyl include, but are not limited to, methylene-oxy-acyl (—CH$_2$O—C(O)alkyl), ethylene-oxy-acyl (—CH$_2$CH$_2$O—C(O)alkyl), methyl-ethylene-oxy-acyl (—CH(CH$_3$)CH$_2$O—C(O)alkyl), propylene-oxy-acyl (—CH$_2$CH$_2$CH$_2$O—C(O)alkyl), methyl-propylene-oxy-acyl (—CH(CH$_3$)CH$_2$CH$_2$O—C(O)alkyl or —CH$_2$CH(CH$_3$)CH$_2$O—C(O)alkyl), etc. As the expression "acyl" encompasses "aminoacyl," further contemplated radicals include but are not limited to $C_{1-6}$-alkyl-oxy-aminoacyl, where aminoacyl is defined above.

The term "alkenyl" refers to an unsubstituted or a substituted hydrocarbon chain radical having from 2 to 10 carbon atoms having one or more olefinic double bonds. The term "$C_{2-N}$ alkenyl" refers to an alkenyl comprising 2 to N carbon atoms, where N is an integer having the following values: 3, 4, 5, 6, 7, 8, 9, or 10. For example, the term "$C_{2-10}$alkenyl" refers to an alkenyl comprising 2 to 10 carbon atoms. The term "$C_{2-4}$alkenyl" refers to an alkenyl comprising 2 to 4 carbon atoms. Examples include, but are not limited to, vinyl, 1-propenyl, 2-propenyl (allyl) or 2-butenyl (crotyl). It is understood that the alkenyl or $C_{2-N}$-alkenyl can be substituted with one or more radicals selected from among alkyl, halo, alkoxy, aryloxy, nitro, and cyano.

The term "vinyl," which is embraced by the term "$C_{2-4}$alkenyl," refers to —CR'═CR"R'", where R', R", and R'" are independently selected from among hydrogen, $C_{1-6}$-alkyl, halo, and $C_{1-6}$-alkoxy. Examples of a vinyl include, but are not limited to, ethenyl (—CH═CH$_2$), 2-bromo-ethenyl (—CH═CHBr), etc.

The term "ethynyl," as used herein, refers to —C≡CR', where R' is selected from among hydrogen, $C_{1-6}$-alkyl, halo, and $C_{1-6}$-alkoxide.

The term "methine," as used herein, refers to the radical —CR'=, where R' is selected from among hydrogen, $C_{1-6}$alkyl, halo, and $C_{1-6}$-alkoxide.

The term "vinylidene," as used herein, refers to >C=CRR', where R and R' are independently selected from among hydrogen, $C_{1-6}$-alkyl, halo, and $C_{1-6}$-alkoxide.

The expressions —P(O)(OH)$_2$, —P(O)(OH)—OP(O)(OH)$_2$, and —P(O)(OH)—O—P(O)(OH)—O—P(O)(OH)$_2$, refer to mono-(P$_1$), di-(P$_2$), and tri-(P$_3$) phosphate radicals, respectively.

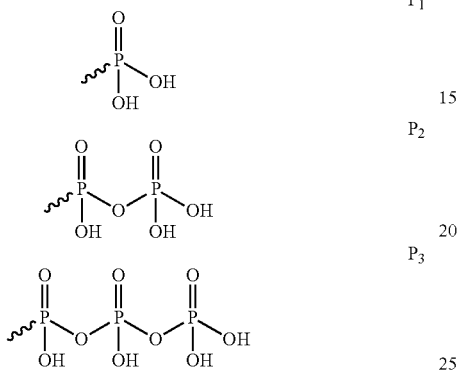

The P$_1$, P$_2$, and P$_3$ phosphate radicals may be introduced at the 5'-OH of a nucleoside compound either by synthetic means in the lab or by enzymatic (or metabolic) means in a cell or biological fluid (either in vivo or in vitro). It is understood that the acidities of the hydroxyl (—OH) substituents vary and that salts of the phosphate radicals are possible.

The term "—P*(O)(OR$^{1a}$)(NHCHR$^{1b}$C(O)OR$^{1c}$)" or "phosphoramidate" as used herein is represented by the following structure:

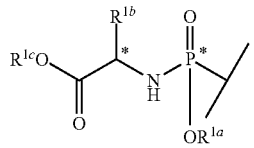

where R$^{1a}$, R$^{1b}$, and R$^{1c}$ are as defined above. Examples of phosphoramidate moieties are described in U.S. Pat. No. 7,964,580. It will be understood that the ~NHCH*(R$^{1b}$)C(O)OR$^{1c}$ fragment can be derived from an amino acid, which is defined above.

Under the Summary, certain definitions related to R$^1$, 1)l), and Y, 4)d), include the expressions "—P*(O)(OR$^{1c}$)~" (see R$^1$, 1)1)) and "—O~" (see Y, 4)d)). It is understood that when R$^1$ is "—P*(O)(OR$^{1c}$)~" and Y is "—O~" or when Y is "—O~" and R$^1$ is "—P(O)(OR$^{1c}$)~", then compound I has the structure shown on the left, where the R$^1$ and Y substituents are identified on the right:

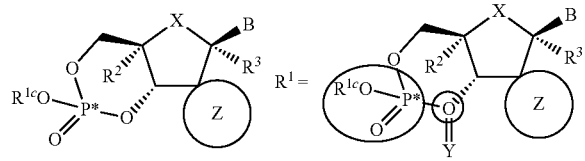

It is understood that use of the expression "cyclophosphate" or "cyclic-phosphate" is meant to embrace the left-hand structure. These expressions likewise have the same meanings when recited as definitions for certain embodiments and aspects of those embodiments.

The term "a 1,3,2-dioxaphosphinane-2-oxide," as used herein is represented by an unsubstituted form (j1) or a substituted form (j2), as represented by the following structures:

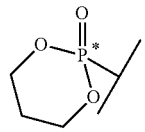

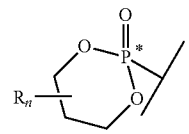

where R$_n$ is selected from among hydroxy, an alkyl, a hydroxyalkyl, an aryloxide, an aryl, such as phenyl, a heteroaryl, such as pyridinyl, where the aryl and the heteroaryl can be substituted by 1-3 substituents independently selected from among an alkyl, an alkoxy, and a halo. A preferred R$_n$ is pyridinyl which can be substituted by 1-3 substituents independently selected from among a $C_{1-6}$alkyl, a $C_{1-6}$-alkoxy, and a halo.

The term "aryloxide," or "aryloxy" as used herein, and unless otherwise specified, refers to substituted or unsubstituted phenoxide (PhO—), p-phenyl-phenoxide (p-Ph-PhO—), or naphthoxide, preferably the term aryloxide refers to substituted or unsubstituted phenoxide. The aryloxide group can be substituted with one or more moieties selected from among hydroxyl, F, Cl, Br, I, —C(O)($C_{1-6}$alkyl), —C(O)O($C_{1-6}$alkyl), amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "4H-benzo[d][1,3,2]dioxaphosphine-2-oxide," as used herein is represented by an unsubstituted form (k1) or a substituted form (k2), as represented by the following structures:

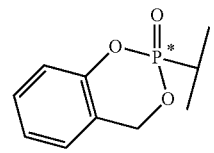

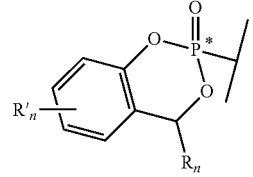

where R$_n$ and R'$_n$, where R$_n$ is hydrogen and one alkyl radical, or two alkyl radicals independent of one another, and R'$_n$ is one, two, or three radicals selected from among alkyl, alkoxy, aryloxy, and halo. Preferably, R'$_n$ is one, two, or three radicals selected from among a $C_{1-6}$alkyl, a $C_{1-6}$, alkoxy, and a halo. More preferably, R'$_n$ is one radical selected from among a $C_{1-6}$-alkyl, a $C_{1-6}$-alkoxy, and a halo.

In the structure B3, as a possible radical for B, the language "each bonding pair, W$^1$ ---- W$^2$, W$^2$ ---- C, C ---- W$^4$, W$^4$ ---- W³, and W³ ---- W¹, contained in the five-membered ring comprises a single or a double bond" is presented above.

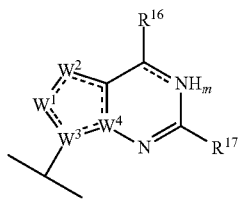
B3

In the event that resolution problems or printing errors might obscure the pictoral representation of B3, it is contemplated that there exists a bonding configuration represented by " ---- " between each one of W¹ ---- W², W² ---- C, C ---- W⁴, W ---- W³, and W³ ---- W¹, within the five-membered ring framework, where " ---- " is understood to be a single- or double-bond. It is not contemplated that all bonding pairs contained in the five-membered ring therein are all double bonds or all single bonds. Rather, it is contemplated that when a certain definitional requirement is selected, then the bonding arrangement of the five-membered ring satisfies Hückel's rule, i.e., the total number of pi-bond and lone-pair electrons for the selected radicals is 6. For example, when $W^1$ is O or S, $W^2$ is $CR^{15}$, $W^3$ is C, and $W^4$ is C (see I-3-12 or I-3-13), then the contemplated structure is:

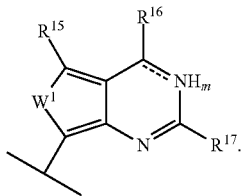

Formula I is recited above. Implicit to formula I is the exclusion of compounds disclosed in B. R. Babu et al. Org. Biomol. Chem. (2003) 1:3514-3526, whether said compounds are explicitly or implicitly disclosed therein. For instance, the compounds identified there as 9b, 14b, 21, and 27, are not contemplated to be within the scope of formula I (as well as formula I-1 presented below)

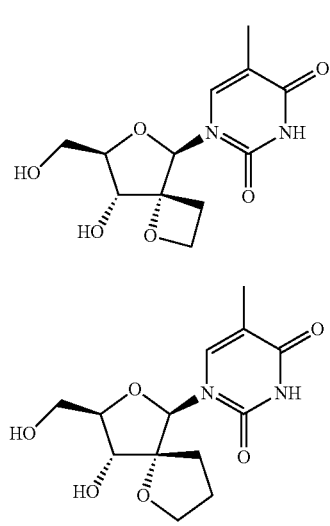

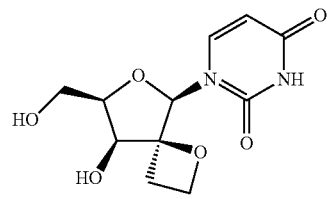

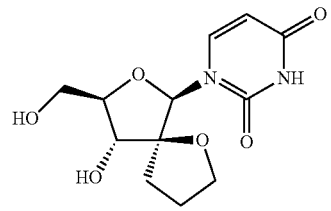

However, these compounds, as well as derivatives embraced by formula I, are contemplated for treating a subject infected by HCV or DENV and are contemplated for compositions useful for treating a subject infected by HCV or DENV, as explained in further detail below. The compound numbering for compounds 9b, 14b, 21, and 27 is as found in Babu et al. It should be noted that compounds 21 and 27 are exemplified herein with the numbering here of 36 and 32, respectively.

The term "effective amount" as used herein means an amount required to reduce symptoms of the disease in a subject.

The term "subject," as used herein means a mammal.

The term "medicament," as used herein means a substance used in a method of treatment and/or prophylaxis of a subject in need thereof.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

As used herein, "treatment" or "treating" is an approach for obtaining beneficial or desired clinical results. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. The term "treatment" of an HCV infection, as used herein, also includes treatment or prophylaxis of a disease or a condition associated with or mediated by HCV infection, or the clinical symptoms thereof.

The term "protecting group" which is derived from a "protecting compound," has its plain and ordinary meaning, i.e., at least one protecting or blocking group is bound to at least one functional group (e.g., —OH, —NH₂, etc.) that allows chemical modification of at least one other functional group. Examples of protecting groups, include, but are not limited to, benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, C(O)O($C_{1-6}$alkyl), C(O)O($C_{1-6}$alkylene) aryl (e.g., —C(O)OCH$_2$Ph), C(O)Oaryl, CH$_2$O—-alkyl, CH$_2$O-aryl, SO$_2$-alkyl, SO$_2$-aryl, a protecting group comprising at least one silicon atom, such as, tert-butyldimethylsilyl, tert-butyldiphenylsilyl, Si($C_{1-6}$alkyl)$_2$OSi($C_{1-6}$alkyl)$_2$OH, such as, —Si($^i$Pr)$_2$OSi($^i$Pr)$_2$OH or ~OSi($^i$Pr)$_2$OSi($^i$Pr)$_2$O~. Additional examples are disclosed in e.g., Protective Groups in Organic Synthesis, 3$^{nd}$ ed. T. W. Greene and P. G. M. Wuts, John Wiley & Sons, New York, N.Y., 1999).

The term "leaving group" ("LG") as used herein, has its plain and ordinary meaning for one of ordinary skill in this art. Examples of leaving groups include, but are not limited to: halogen (Cl, Br, or I); tosylate, mesylate, triflate, acetate, etc.

Embodiments

A first embodiment is directed to a compound or its stereoisomer or its salt or its metabolite or its deuteride thereof represented by formula I-1

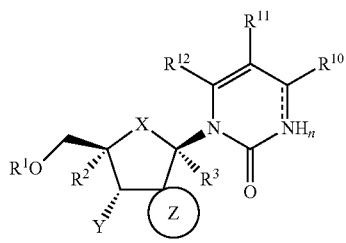

I-1 wherein $R^1$, $R^2$, Y, $R^3$, $\underset{Z}{\bigcirc}$, X, $R^{10}$, $R^{11}$, $R^{12}$, n, and ---- have the meanings described above.

A first aspect of the first embodiment is directed to a compound or its stereoisomer or its salt or its metabolite or its deuteride thereof represented by formula I-1 wherein 1) $R^1$ is selected from among
   a) hydrogen,
   b) —P(O)(OH)$_2$,
   c) —P(O)(O(CH$_2$)$_{1-3}$OC(O)O($C_{1-6}$alkyl))$_2$,
   d) —P(O)(O(CH$_2$)$_{1-3}$OC(O)($C_{1-6}$alkyl))$_2$,
   e) —P(O)(O(CH$_2$)$_{1-3}$SC(O)($C_{1-6}$alkyl))$_2$,
   f) —P(O)(O(CH$_2$)$_{1-3}$OCH$_2$(aryl))$_2$,
   g) —P(O)(O(CH$_2$)$_{1-3}$SCH$_2$(aryl))$_2$,
   h) —P*(O)(OR$^{1a}$)(NHCHR$^{1b}$C(O)OR$^{1c}$),
   wherein
   $R^{1a}$ is
      i) hydrogen,
      ii) $C_{1-6}$-alkyl,
      iii) $C_{3-6}$cycloalkyl, or
      iv) aryl,
   $R^{1b}$ is
      i) hydrogen,
      ii) $C_{1-6}$alkyl,
      iii) $C_{3-6}$cycloalkyl,
      iv) $C_{1-3}$alkaryl, or
      v) alk(heteroaryl), and $R^{1c}$ is
      i) hydrogen,
      ii) $C_{1-6}$alkyl,
      iii) $C_{3-6}$cycloalkyl, or
      vi) $C_{1-3}$alkaryl,
   i) —P*(O)(NH(alkaryl)(O(CH$_2$)$_{1-3}$SC(O)(alkyl)),
   j) a 1,3,2-dioxaphosphinane-2-oxide,
   k) a 4H-benzo[d][1,3,2]dioxaphosphinine-2-oxide,
   l) —P*(O)(OR$^{1c}$)~, when Y is —O~, where $R^{1c}$ is defined above,
   m) —P(O)(OH)—O—P(O)(OH)$_2$,
   n) —P(O)(OH)—O—P(O)(OH)—O—P(O)(OH)$_2$,
   o) a $C_{2-7}$acyl,
   p) an aminoacyl
   q) a $C_{1-6}$-alkylene-oxy-$C_{2-7}$acyl, and
   r) a —C(O)—O—$C_{1-6}$alkyl;
2) $R^2$ is selected from among
   a) hydrogen,
   b) fluoro,
   c) azido, and
   d) cyano;
3) $R^3$ is selected from among
   a) hydrogen,
   b) methyl, and
   c) cyano,
4) Y is selected from among
   a) hydrogen,
   b) fluoro,
   c) —OH,
   d) —O~, when $R^1$ is —P(O)(OR$^{1c}$)~, where $R^{1c}$ is defined above,
   e) —O($C_{2-7}$acyl),
   f) —O(aminoacyl),
   g) —O($C_{1-6}$-alkylene-oxy-acyl),
   h) —O—C(O)—O—$C_{1-6}$alkyl,
   i) —NH$_2$,
   j) —NH($C_{2-7}$acyl),
   k) —NH(aminoacyl),
   l) —NH—C(O)—O—$C_{1-6}$alkyl and
   m) azido;
5) X is selected from among
   a) —O— and
   b) —S—;

6) $\underset{Z}{\bigcirc}$ is a four- or five-membered ring selected from among radicals c, d, e, f, g, and h, represented by the following structures

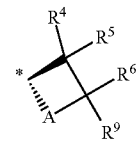

c

d

-continued

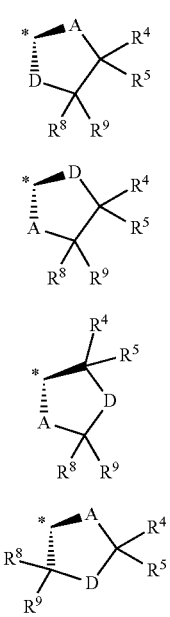

where * represents the point of attachment to the 2'-carbon and where
a) A is selected from among
  i) —O—,
  ii) —S—,
  iii) —S(O)—,
  iv) —S(O)$_2$—, and
  v) —NH—,
b) D is selected from among
  i) —O—,
  ii) —S—,
  iii) —S(O)—,
  iv) —S(O)$_2$—, and
  v) —NH—,
  vi) a methylene, and
  vii) a vinylidene,
c) $R^4$, $R^5$, $R^8$, and $R^9$ are independently selected from among
  i) hydrogen,
  ii) halo,
  iii) $C_{1-6}$alkyl
  iv) hydroxy,
  v) alkoxy,
  vi) cycloalkoxy,
  vii) —O(acyl),
  viii) —O($C_{1-6}$-alkyleneoxyacyl),
  ix) —O—C(O)—O-alkyl,
  x) $C_{1-6}$alkylene-oxy(alkyl),
  xi) alkenyl,
  xii) ethynyl,
  xiii) —NH$_2$,
  xiv) —NH(alkyl),
  xv) —NH(cycloalkyl),
  xvi) heterocyclyl,
  xvii) aryl, and
  xviii) heteroaryl; and
7a) n is 0, ----- is a double-bond and $R^{10}$ is selected from among
  i) —NH$_2$,
  ii) —NH($C_{1-6}$alkyl),
  iii) —NH(acyl),
  iv) —NH—C(O)—O-alkyl,
  v) -cycloheteroalkyl,
  vi) -heteroaryl,
  vii) —O(alkyl),
  viii) —O(acyl),
  ix) —O($C_{1-6}$alkylene-oxyacyl), and
  x) —O—C(O)—O-alkyl, or
7b) n is 1, ----- is a single-bond and $R^{10}$ is selected from among
  i) =O,
  ii) =NH, and
  iii) =N(alkyl); and
7c) independent of the value of n, $R^{11}$ and $R^{12}$ are independently selected from among
  i) hydrogen,
  ii) halo,
  iii) cyano,
  iv) $C_{1-6}$alkyl,
  v) $C_{2-5}$alkenyl, and
  vi) $C_{2-5}$alkynyl.

A second aspect of the first embodiment is directed to a compound or its stereoisomer or its salt or its metabolite or its deuteride thereof represented by formula I-1
wherein
1) $R^1$ is selected from among
  a) hydrogen,
  b) —P(O)(OH)$_2$,
  c) —P(O)(O(CH$_2$)$_{1-3}$OC(O)O($C_{1-6}$alkyl))$_2$,
  d) —P(O)(O(CH$_2$)$_{1-3}$OC(O)($C_{1-6}$alkyl))$_2$,
  e) —P(O)(O(CH$_2$)$_{1-3}$SC(O)($C_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
  wherein
  $R^{1a}$ is
    i) hydrogen,
    ii) $C_{1-6}$alkyl,
    iii) $C_{3-6}$cycloalkyl, or
    iv) aryl,
  $R^{1b}$ is
    i) hydrogen,
    ii) $C_{1-6}$alkyl,
    iii) $C_{3-6}$cycloalkyl,
    iv) $C_{1-3}$alkaryl, or
    v) alk(heteroaryl), and
  $R^{1c}$ is
    i) hydrogen
    ii) $C_{1-6}$alkyl,
    iii) $C_{3-6}$cycloalkyl, or
    iv) $C_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where $R^{1c}$ is defined above,
  m) —P(O)(OH)—O—P(O)(OH)$_2$,
  n) —P(O)(OH)—O—P(O)(OH)—O—P(O)(OH)$_2$,
  o) a $C_{2-7}$acyl,
  p) an aminoacyl,
  q) a $C_{1-6}$-alkylene-oxy-$C_{2-7}$acyl, and
  r) a —C(O)—O—$C_{1-6}$alkyl;
2) $R^2$ is hydrogen;
3) $R^3$ is hydrogen;

4) Y is selected from among
  a) —OH,
  b) —O~, when $R^1$ is —P(O)(OR$^{1c}$)~, where $R^{1c}$ is defined above,
  c) —O(C$_{2-7}$acyl),
  d) —O(aminoacyl),
  e) —O(C$_{1-6}$-alkylene-oxy-acyl), and
  f) —O—C(O)—O—C$_{1-6}$alkyl;
5) X is —O—;
6) 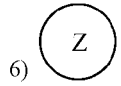 is a four- or five-membered ring selected from among radicals c, d, e, f, g, and h, represented by the following structures c 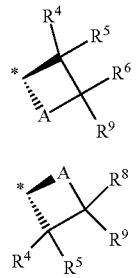

d 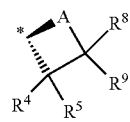

e 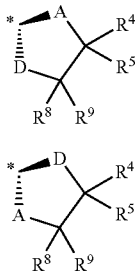

f g 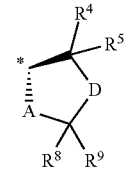

h 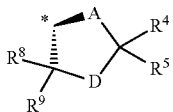

where * represents the point of attachment to the 2'-carbon and where
  a) A is selected from among
    i) —O—,
    ii) —S—,
    iii) —S(O)—,
    iv) —S(O)$_2$—, and
    v) —NH—,
  b) D is selected from among
    i) —O—,
    ii) —S—,
    iii) —S(O)—,
    iv) —S(O)$_2$,
    v) —NH—,
    vi) a methylene, and
    vii) a vinylidene,
  c) $R^4$, $R^5$, $R^8$, and $R^9$ are independently selected from among
    i) hydrogen,
    ii) halo, and
    iii) C$_{1-6}$alkyl; and
7a) n is 0, ---- is a double-bond and $R^{10}$ is selected from among
    i) —NH$_2$,
    ii) —NH(C$_{1-6}$alkyl),
    iii) —NH(C$_{2-7}$acyl), and
    iv) —NH—C(O)—O—C$_{1-6}$alkyl, or
7b) n is 1, ---- is a single-bond and $R^{10}$ is selected from among
    i) =O and
    ii) =N(alkyl), and
7c) independent of the value of n, $R^{11}$ and $R^{12}$ are independently selected from among
    i) hydrogen,
    ii) halo,
    iv) C$_{1-6}$alkyl, and
    v) C$_{2-4}$alkenyl.

A third aspect of the first embodiment is directed to a compound or its stereoisomer or its salt or its metabolite or its deuteride thereof represented by formula I-1
  wherein
  1) $R^1$ is selected from among
    a) hydrogen,
    b) —P(O)(OH)$_2$,
    c) —P(O)(O(CH$_2$)$_{1-3}$OC(O)O(C$_{1-6}$alkyl))$_2$,
    d) —P(O)(O(CH$_2$)$_{1-3}$OC(O)(C$_{1-6}$alkyl))$_2$,
    e) —P(O)(O(CH$_2$)$_{1-3}$SC(O)(C$_{1-6}$alkyl))$_2$,
    f) —P(O)(O(CH$_2$)$_{1-3}$OCH$_2$(aryl))$_2$,
    g) —P(O)(O(CH$_2$)$_{1-3}$SCH$_2$(aryl))$_2$,
    h) —P*(O)(OR$^{1a}$)(NHCHR$^{1b}$C(O)OR$^{1c}$),
    wherein
    $R^{1a}$ is
      i) hydrogen,
      ii) C$_{1-6}$alkyl,
      iii) C$_{3-6}$cycloalkyl, or
      iv) aryl,
    $R^{1b}$ is
      i) hydrogen,
      ii) C$_{1-6}$alkyl,
      iii) C$_{3-6}$cycloalkyl,
      iv) C$_{1-3}$alkaryl, or
      v) alk(heteroaryl), and
    $R^{1c}$ is
      i) hydrogen
      ii) C$_{1-6}$alkyl,
      iii) C$_{3-6}$cycloalkyl, or
      vi) C$_{1-3}$alkaryl,
    i) —P*(O)(NH(alkaryl)(O(CH$_2$)$_{1-3}$SC(O)(alkyl)),
    j) a 1,3,2-dioxaphosphinane-2-oxide,
    k) a 4H-benzo[d][1,3,2]dioxaphosphinine-2-oxide,
    l) —P*(O)(OR$^{1c}$)~, when Y is —O~, where $R^{1c}$ is defined above,
    m) —P(O)(OH)—O—P(O)(OH)$_2$,
    n) —P(O)(OH)—O—P(O)(OH)—O—P(O)(OH)$_2$,
    o) a C$_{2-7}$acyl,
    p) an aminoacyl,
    q) a C$_{1-6}$-alkylene-oxy-C$_{2-7}$acyl, and
    r) a —C(O)—O—C$_{1-6}$alkyl;
2) $R^2$ is hydrogen;
3) $R^3$ is hydrogen;

4) Y is selected from among
 a) —OH,
 b) —O~, when $R^1$ is —P(O)(OR$^{1c}$)~, where $R^{1c}$ is defined above,
 c) —O(C$_{2-7}$acyl),
 d) —O(aminoacyl),
 e) —O(C$_{1-6}$-alkylene-oxy-acyl), and
 f) —O—C(O)—O—C$_{1-6}$alkyl;
5) X is —O—;

6) 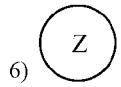 is a four- or five-membered ring selected from among radicals c, d, e, f, g, and h, represented by the following structures

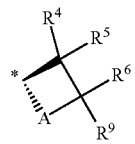 c

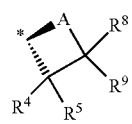 d

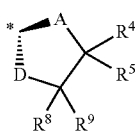 e

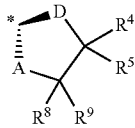 f

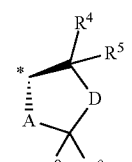 g

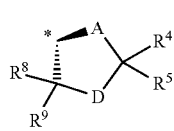 h where * represents the point of attachment to the 2'-carbon and where
 a) A is —O—,
 b) D is —O— or —CH$_2$—,
 c) $R^4$, $R^5$, $R^8$, and $R^9$ are each hydrogen; and
7a) n is 0, ---- is a double-bond and $R^{10}$ is selected from among
 i) —NH$_2$,
 ii) —NH(C$_{1-6}$alkyl),
 iii) —NH(C$_{2-7}$acyl), and
 iv) —NH—C(O)—O—C$_{1-6}$alkyl, or
7b) n is 1, ---- is a single-bond and $R^{10}$ is selected from among
 i) =O and
 ii) =N(alkyl), and 7c) independent of the value of n, $R^{11}$ and $R^{12}$ are independently selected from among
 i) hydrogen,
 ii) halo,
 iv) C$_{1-6}$alkyl, and
 v) C$_{2-4}$alkenyl.

A fourth aspect of the first embodiment is directed to a compound or its stereoisomer or its salt or its metabolite or its deuteride thereof represented by formula I-1
wherein
1) $R^1$ is selected from among
 a) hydrogen,
 b) —P(O)(OH)$_2$,
 c) —P(O)(O(CH$_2$)$_{1-3}$OC(O)O(C$_{1-6}$alkyl))$_2$,
 d) —P(O)(O(CH$_2$)$_{1-3}$OC(O)(C$_{1-6}$alkyl))$_2$,
 e) —P(O)(O(CH$_2$)$_{1-3}$SC(O)(C$_{1-6}$alkyl))$_2$,
 f) —P(O)(O(CH$_2$)$_{1-3}$OCH$_2$(aryl))$_2$,
 g) —P(O)(O(CH$_2$)$_{1-3}$SCH$_2$(aryl))$_2$,
 h) —P*(O)(OR$^{1a}$)(NHCHR$^{1b}$C(O)OR$^{1c}$),
 wherein
 $R^{1a}$ is
  i) hydrogen or
  iv) aryl,
 $R^{1b}$ is
  i) hydrogen or
  ii) C$_{1-6}$alkyl, and
 $R^{1c}$ is
  i) hydrogen
  ii) C$_{1-6}$alkyl,
  iii) C$_{3-6}$cycloalkyl, or
  iv) C$_{1-3}$alkaryl,
 i) —P*(O)(NH(alkaryl)(O(CH$_2$)$_{1-3}$SC(O)(alkyl)),
 j) a 1,3,2-dioxaphosphinane-2-oxide,
 k) a 4H-benzo[d][1,3,2]dioxaphosphinine-2-oxide,
 l) —P*(O)(OR$^{1c}$)~, when Y is —O~, where $R^{1c}$ is defined above,
 m) —P(O)(OH)—O—P(O)(OH)$_2$,
 n) —P(O)(OH)—O—P(O)(OH)—O—P(O)(OH)$_2$,
 o) a C$_{2-7}$acyl,
 p) an aminoacyl,
 q) a C$_{1-6}$-alkylene-oxy-C$_{2-7}$acyl, and
 r) a —C(O)—O—C$_{1-6}$alkyl;
2) $R^2$ is hydrogen;
3) $R^3$ is hydrogen;
4) Y is selected from among
 a) —OH,
 b) —O~, when $R^1$ is —P(O)(OR$^{1c}$)~, where $R^{1c}$ is defined above,
 c) —O(C$_{2-7}$acyl), and
 d) —O(aminoacyl);
5) X is —O—;

6) 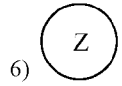 is a four- or five-membered ring selected from among radicals c, d, e, and f represented by the following structures

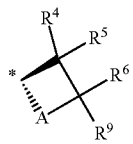 c

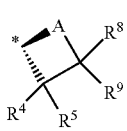
d

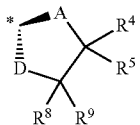
e

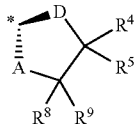
f where * represents the point of attachment to the 2'-carbon and where
  a) A is —O—,
  b) D is —O— or —CH$_2$
  c) $R^4$, $R^5$, $R^8$, and $R^9$ are each hydrogen; and
7a) n is 0, ----- is a double-bond and $R^{10}$ is selected from among
  i) —NH$_2$,
  ii) —NH(C$_{1-6}$alkyl),
  iii) —NH(C$_{2-7}$acyl), and
  iv) —NH—C(O)—O—C$_{1-6}$alkyl, or
7b) n is 1, ----- is a single-bond and $R^{10}$ is selected from among
  i) =O and
  ii) =N(alkyl), and
7c) independent of the value of n, $R^{11}$ and $R^{12}$ are independently selected from among
  i) hydrogen,
  ii) halo,
  iv) C$_{1-6}$alkyl, and
  v) C$_{2-4}$alkenyl.

A second embodiment is directed to a compound or its stereoisomer or its salt or its metabolite or its deuteride thereof represented by formula I-21
wherein

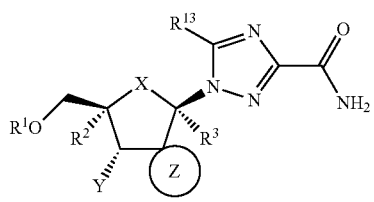
I-2 wherein $R^1$, $R^2$, Y, $R^3$, , and $R^{13}$ have the meanings described above.

A first aspect of the second embodiment is directed to a compound or its stereoisomer or its salt or its metabolite or its deuteride thereof represented by formula I-2 wherein
1) $R^1$ is selected from among
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
wherein
$R^{1a}$ is
  i) hydrogen,
  ii) C$_{1-6}$alkyl,
  iii) C$_{3-6}$cycloalkyl, or
  iv) aryl,
$R^{1b}$ is
  i) hydrogen,
  ii) C$_{1-6}$alkyl,
  iii) C$_{3-6}$cycloalkyl,
  iv) C$_{1-3}$alkaryl, or
  v) alk(heteroaryl), and
$R^{1c}$ is
  i) hydrogen
  ii) C$_{1-6}$alkyl,
  iii) C$_{3-6}$cycloalkyl, or
  iv) C$_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where $R^{1c}$ is defined above,
  m) —P(O)(OH)—O—P(O)(OH)$_2$,
  n) —P(O)(OH)—O—P(O)(OH)—O—P(O)(OH)$_2$,
  o) a C$_{2-7}$acyl,
  p) an aminoacyl,
  q) a C$_{1-6}$-alkylene-oxy-C$_{2-7}$acyl, and
  r) a —C(O)—O—C$_{1-6}$alkyl;
2) $R^2$ is selected from among
  a) hydrogen,
  b) fluoro,
  c) azido, and
  d) cyano;
3) $R^3$ is selected from among
  a) hydrogen,
  b) methyl, and
  c) cyano,
4) Y is selected from among
  a) hydrogen,
  b) fluoro,
  c) —OH,
  d) —O~, when $R^1$ is —P(O)(OR$^{1c}$)~, where $R^{1c}$ is defined above,
  e) —O(C$_{2-7}$acyl),
  f) —O(aminoacyl),
  g) —O(C$_{1-6}$-alkylene-oxy-acyl),
  h) —O—C(O)—O—C$_{1-6}$alkyl,
  i) —NH$_2$,
  j) —NH(C$_{2-7}$acyl),
  k) —NH(aminoacyl),
  l) —NH—C(O)—O—C$_{1-6}$alkyl, and
  m) azido;
5) X is selected from among
  a) —O— and
  b) —S—;
6)  is a four- or five-membered ring selected from among radicals c, d, e, f, g, and h, represented by the following structures

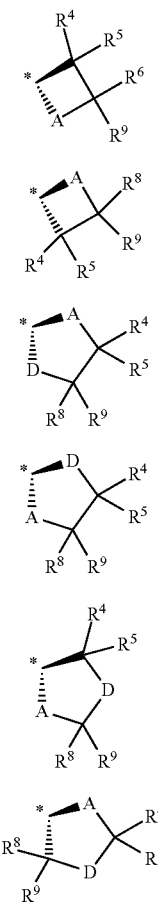

where * represents the point of attachment to the 2'-carbon and where
a) A is selected from among
  i) —O—,
  ii) —S—,
  iii) —S(O)—,
  iv) —S(O)$_2$—, and
  v) —NH—,
b) D is selected from among
  i) —O—,
  ii) —S—,
  iii) —S(O)—,
  iv) —S(O)$_2$—, and
  v) —NH—,
  vi) a methylene, and
  vii) a vinylidene,
c) $R^4$, $R^5$, $R^8$, and $R^9$ are independently selected from among
  i) hydrogen,
  ii) halo,
  iii) $C_{1-6}$alkyl
  iv) hydroxy,
  v) alkoxy,
  vi) cycloalkoxy,
  vii) —O(acyl),
  viii) —O($C_{1-6}$-alkyleneoxyacyl),
  ix) —O—C(O)—O-alkyl,
  x) $C_{1-6}$alkylene-oxy(alkyl),
  xi) alkenyl,
  xii) ethynyl,
  xiii) —NH$_2$,
  xiv) —NH(alkyl),
  xv) —NH(cycloalkyl),
  xvi) heterocyclyl,
  xvii) aryl, and
  xviii) heteroaryl; and
7) $R^{13}$ is hydrogen.

A second aspect of the second embodiment is directed to a compound or its stereoisomer or its salt or its metabolite or its deuteride thereof represented by formula I-2
wherein
1) $R^1$ is selected from among
  a) hydrogen,
  b) —P(O)(OH)$_2$,
  c) —P(O)(O(CH$_2$)$_{1-3}$OC(O)O($C_{1-6}$alkyl))$_2$,
  d) —P(O)(O(CH$_2$)$_{1-3}$OC(O)($C_{1-6}$alkyl))$_2$,
  e) —P(O)(O(CH$_2$)$_{1-3}$SC(O)($C_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
  wherein
  $R^{1a}$ is
    i) hydrogen,
    ii) $C_{1-6}$alkyl,
    iii) $C_{3-6}$cycloalkyl, or
    iv) aryl,
  $R^{1b}$ is
    i) hydrogen,
    ii) $C_{1-6}$alkyl,
    iii) $C_{3-6}$cycloalkyl,
    iv) $C_{1-3}$alkaryl, or
    v) alk(heteroaryl), and
  $R^{1c}$ is
    i) hydrogen,
    ii) $C_{1-6}$alkyl,
    iii) $C_{3-6}$cycloalkyl, or
    iv) $C_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where $R^{1c}$ is defined above,
  m) —P(O)(OH)—O—P(O)(OH)$_2$,
  n) —P(O)(OH)—O—P(O)(OH)—O—P(O)(OH)$_2$,
  o) a $C_{2-7}$acyl,
  p) an aminoacyl,
  q) a $C_{1-6}$-alkylene-oxy-$C_{2-7}$acyl, and
  r) a —C(O)—O—$C_{1-6}$alkyl;
2) $R^2$ is hydrogen;
3) $R^3$ is hydrogen;
4) Y is selected from among
  a) —OH,
  b) —O~, when $R^1$ is —P(O)(OR$^{1c}$)~, where $R^{1c}$ is defined above,
  c) —O($C_{2-7}$acyl),
  d) —O(aminoacyl),
  e) —O($C_{1-6}$-alkylene-oxy-acyl), and
  f) —O—C(O)—O—$C_{1-6}$alkyl;
5) X is —O—;

6) Ⓩ is a four- or five-membered ring selected from among radicals c, d, e, f, g, and h, represented by the following structures

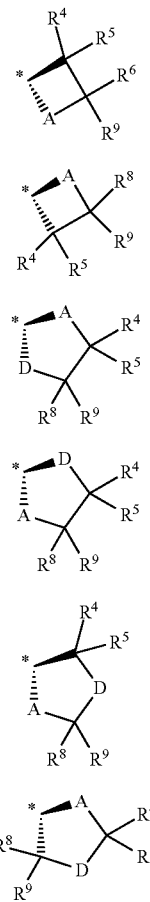

where * represents the point of attachment to the 2'-carbon and where
- a) A is selected from among
  - i) —O—,
  - ii) —S—,
  - iii) —S(O)—,
  - iv) —S(O)$_2$—, and
  - v) —NH—,
- b) D is selected from among
  - i) —O—,
  - ii) —S—,
  - iii) —S(O)—,
  - iv) —S(O)$_2$—, and
  - v) —NH—,
  - vi) a methylene, and
  - vii) a vinylidene,
- c) $R^4$, $R^5$, $R^8$, and $R^9$ are independently selected from among
  - i) hydrogen,
  - ii) halo,
  - iii) $C_{1-6}$alkyl; and
- 7) $R^{13}$ is hydrogen.

A third aspect of the second embodiment is directed to a compound or its stereoisomer or its salt or its metabolite or its deuteride thereof represented by formula I-2
wherein
1) $R^1$ is selected from among
  - a) hydrogen,
  - b) —P(O)(OH)$_2$,
  - c) —P(O)(O(CH$_2$)$_{1-3}$OC(O)O(C$_{1-6}$alkyl))$_2$,
  - d) —P(O)(O(CH$_2$)$_{1-3}$OC(O)(C$_{1-6}$alkyl))$_2$,
  - e) —P(O)(O(CH$_2$)$_{1-3}$SC(O)(C$_{1-6}$alkyl))$_2$,
  - f) —P(O)(O(CH$_2$)$_{1-3}$OCH$_2$(aryl))$_2$,
  - g) —P(O)(O(CH$_2$)$_{1-3}$SCH$_2$(aryl))$_2$,
  - h) —P*(O)(OR$^{1a}$)(NHCHR$^{1b}$C(O)OR$^{1c}$),
wherein
$R^{1a}$ is
  - i) hydrogen,
  - ii) $C_{1-6}$alkyl,
  - iii) $C_{3-6}$cycloalkyl, or
  - iv) aryl,
$R^{1b}$ is
  - i) hydrogen,
  - ii) $C_{1-6}$alkyl,
  - iii) $C_{3-6}$cycloalkyl,
  - iv) $C_{1-3}$alkaryl, or
  - v) alk(heteroaryl), and
$R^{1c}$ is
  - i) hydrogen
  - ii) $C_{1-6}$alkyl,
  - iii) $C_{3-6}$cycloalkyl, or
  - iv) $C_{1-3}$alkaryl,
- i) —P*(O)(NH(alkaryl)(O(CH$_2$)$_{1-3}$SC(O)(alkyl)),
- j) a 1,3,2-dioxaphosphinane-2-oxide,
- k) a 4H-benzo[d][1,3,2]dioxaphosphinine-2-oxide,
- l) —P*(O)(OR$^{1c}$)~, when Y is —O~, where $R^{1c}$ is defined above,
- m) —P(O)(OH)—O—P(O)(OH)$_2$,
- n) —P(O)(OH)—O—P(O)(OH)—O—P(O)(OH)$_2$,
- o) a $C_{2-7}$acyl,
- p) an aminoacyl,
- q) a $C_{1-6}$-alkylene-oxy-$C_{2-7}$acyl, and
- r) a —C(O)—O—$C_{1-6}$alkyl;
2) $R^2$ is hydrogen;
3) $R^3$ is hydrogen;
4) Y is selected from among
  - a) —OH,
  - b) —O~, when $R^1$ is —P(O)(OR$^{1c}$)~, where $R^{1c}$ is defined above,
  - c) —O($C_{2-7}$acyl),
  - d) —O(aminoacyl),
  - e) —O($C_{1-6}$-alkylene-oxy-acyl), and
  - f) —O—C(O)—O—$C_{1-6}$alkyl;
5) X is —O—;

6)  is a four- or five-membered ring selected from among radicals c, d, e, f, g, and h, represented by the following structures

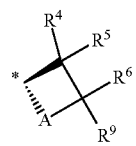

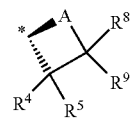

-continued

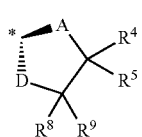
e

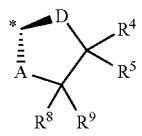
f

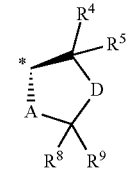
g

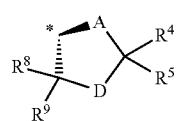
h where * represents the point of attachment to the 2'-carbon and where
a) A is —O—,
b) D is —O— or —CH$_2$—, and
c) R$^4$, R$^5$, R$^8$, and R$^9$ are each hydrogen; and
7) R$^{13}$ is hydrogen.

A fourth aspect of the second embodiment is directed to a compound or its stereoisomer or its salt or its metabolite or its deuteride thereof represented by formula I-2
wherein
1) R$^1$ is selected from among
a) hydrogen,
b) —P(O)(OH)$_2$,
c) —P(O)(O(CH$_2$)$_{1-3}$OC(O)O(C$_{1-6}$alkyl))$_2$,
d) —P(O)(O(CH$_2$)$_{1-3}$OC(O)(C$_{1-6}$alkyl))$_2$,
e) —P(O)(O(CH$_2$)$_{1-3}$SC(O)(C$_{1-6}$alkyl))$_2$,
f) —P(O)(O(CH$_2$)$_{1-3}$OCH$_2$(aryl))$_2$,
g) —P(O)(O(CH$_2$)$_{1-3}$SCH$_2$(aryl))$_2$,
h) —P*(O)(OR$^{1a}$)(NHCHR$^{1b}$C(O)OR$^{1c}$),
wherein
R$^{1a}$ is
 i) hydrogen or
 iv) aryl,
R$^{1b}$ is
 i) hydrogen or
 ii) C$_{1-6}$alkyl, and
R$^{1c}$ is
 i) hydrogen
 ii) C$_{1-6}$alkyl,
 iii) C$_{3-6}$cycloalkyl, or
 iv) C$_{1-3}$alkaryl,
i) —P*(O)(NH(alkaryl)(O(CH$_2$)$_{1-3}$SC(O)(alkyl)),
j) a 1,3,2-dioxaphosphinane-2-oxide,
k) a 4H-benzo[d][1,3,2]dioxaphosphinine-2-oxide,
l) —P*(O)(OR$^{1c}$)~, when Y is —O~, where R$^{1c}$ is defined above,
m) —P(O)(OH)—O—P(O)(OH)$_2$,
n) —P(O)(OH)—O—P(O)(OH)—O—P(O)(OH)$_2$,
o) an C$_{2-7}$acyl,
p) an aminoacyl,
q) a C$_{1-6}$-alkylene-oxy-C$_{2-7}$acyl, and
r) a —C(O)—O—C$_{1-6}$alkyl;
2) R$^2$ is hydrogen;
3) R$^3$ is hydrogen;
4) Y is selected from among
a) —OH,
b) —O~, when R$^1$ is —P(O)(OR$^{1c}$)~, where R$^{1c}$ is defined above,
c) —O(C$_{2-7}$acyl), and
d) —O(aminoacyl);
5) X is —O—;

6)  is a four- or five-membered ring selected from among radicals c, d, e, and f represented by the following structures

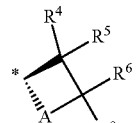
c

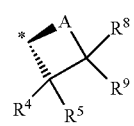
d

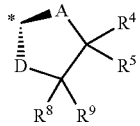
e

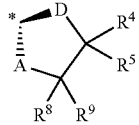
f where * represents the point of attachment to the 2'-carbon and where
a) A is —O—,
b) D is —O— or —CH$_2$—, and
c) R$^4$, R$^5$, R$^8$, and R$^9$ are each hydrogen; and
7) R$^{13}$ is hydrogen.

A third embodiment is directed to a compound or its stereoisomer or its salt or its metabolite or its deuteride thereof represented by formula I-3

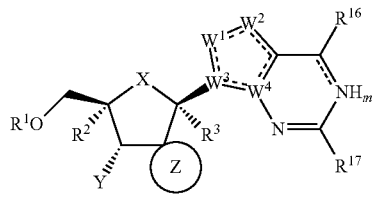
I-3 wherein R$^1$, R$^2$, Y, R$^3$, , X, W$^1$, W$^2$, W$^3$, W$^4$, R$^{16}$, R$^{17}$, m, and ----- have the meanings described above.

A first aspect of the third embodiment is directed to a compound or its stereoisomer or its salt or its metabolite or its deuteride thereof represented by formula I-3
wherein
1) $R^1$ is selected from among
   a) hydrogen,
   b) —P(O)(OH)$_2$,
   c) —P(O)(O(CH$_2$)$_{1-3}$OC(O)O(C$_{1-6}$alkyl))$_2$,
   d) —P(O)(O(CH$_2$)$_{1-3}$OC(O)(C$_{1-6}$alkyl))$_2$,
   e) —P(O)(O(CH$_2$)$_{1-3}$SC(O)(C$_{1-6}$alkyl))$_2$,
   f) —P(O)(O(CH$_2$)$_{1-3}$OCH$_2$(aryl))$_2$,
   g) —P(O)(O(CH$_2$)$_{1-3}$SCH$_2$(aryl))$_2$,
   h) —P*(O)(OR$^{1a}$)(NHCHR$^{1b}$C(O)OR$^{1c}$),
   wherein
   $R^{1a}$ is
      i) hydrogen,
      ii) C$_{1-6}$alkyl,
      iii) C$_{3-6}$cycloalkyl, or
      iv) aryl,
   $R^{1b}$ is
      i) hydrogen,
      ii) C$_{1-6}$alkyl,
      iii) C$_{3-6}$cycloalkyl,
      iv) C$_{1-3}$alkaryl, or
      v) alk(heteroaryl), and
   $R^{1c}$ is
      i) hydrogen
      ii) C$_{1-6}$alkyl,
      iii) C$_{3-6}$cycloalkyl, or
      iv) C$_{1-3}$alkaryl,
   i) —P*(O)(NH(alkaryl))(O(CH$_2$)$_{1-3}$SC(O)(alkyl)),
   j) a 1,3,2-dioxaphosphinane-2-oxide,
   k) a 4H-benzo[d][1,3,2]dioxaphosphinine-2-oxide,
   l) —P*(O)(OR$^{1c}$)~, when Y is —O~ where $R^{1c}$ is defined above,
   m) —P(O)(OH)—O—P(O)(OH)$_2$,
   n) —P(O)(OH)—O—P(O)(OH)—O—P(O)(OH)$_2$,
   o) a C$_{2-7}$acyl,
   p) an aminoacyl,
   q) a C$_{1-6}$-alkylene-oxy-C$_{2-7}$acyl, and
   r) a —C(O)—O—C$_{1-6}$alkyl;
2) $R^2$ is selected from among
   a) hydrogen,
   b) fluoro,
   c) azido, and
   d) cyano;
3) $R^3$ is selected from among
   a) hydrogen,
   b) methyl, and
   c) cyano;
4) Y is selected from among
   a) hydrogen,
   b) fluoro,
   c) —OH,
   d) —O~, when $R^1$ is —P(O)(OR$^{1c}$)~, where $R^{1c}$ is defined above,
   e) —O(C$_{2-7}$acyl),
   f) —O(aminoacyl),
   g) —O(C$_{1-6}$-alkylene-oxy-acyl),
   h) —O—C(O)—O—C$_{1-6}$alkyl,
   I) —NH$_2$,
   j) —NH(C$_{2-7}$acyl),
   k) —NH(aminoacyl),
   l) —NH—C(O)—O—C$_{1-6}$alkyl, and
   m) azido;
5) X is selected from among
   a) —O— and
   b) —S—;

6) 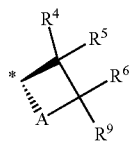 is a four- or five-membered ring selected from among radicals c, d, e, f, g, and h, represented by the following structures

 c

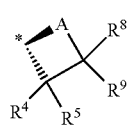 d

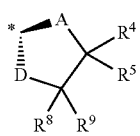 e

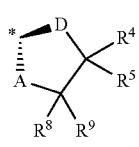 f

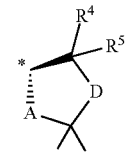 g

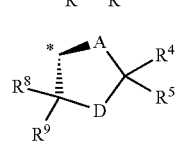 h where * represents the point of attachment to the 2'-carbon and where
   a) A is selected from among
      i) —O—,
      ii) —S—,
      iii) —S(O)—,
      iv) —S(O)$_2$—, and
      v) —NH—,
   b) D is selected from among
      i) —O—,
      ii) —S—,
      iii) —S(O)—,
      iv) —S(O)$_2$—, and
      v) —NH—,
      vi) a methylene, and
      vii) a vinylidene, and
   c) $R^4$, $R^5$, $R^8$, and $R^9$ are independently selected from among
      i) hydrogen,
      ii) halo,
      iii) C$_{1-6}$alkyl
      iv) hydroxy, v) alkoxy,
vi) cycloalkoxy,
vii) —O(acyl),
viii) —O($C_{1-6}$-alkyleneoxyacyl),
ix) —O—C(O)—O-alkyl,
x) $C_{1-6}$alkylene-oxy(alkyl),
xi) alkenyl,
xii) ethynyl,
xiii) —$NH_2$,
xiv) —NH(alkyl),
xv) —NH(cycloalkyl),
xvi) heterocyclyl,
xvii) aryl, and
xviii) heteroaryl; and 7a) m is 0, ---- is a double-bond and $R^{16}$ and $R^{17}$ are independently selected from among
i) hydrogen,
ii) —$NH_2$,
iii) —NH($C_{1-6}$alkyl),
iv) —NH($C_{2-7}$acyl),
iv) —NH—C(O)—O—$C_{1-6}$alkyl,
v) -cycloheteroalkyl,
vi) —O($C_{1-6}$alkyl),
vii) —O($C_{2-7}$acyl),
viii) —O($C_{1-6}$alkyleneoxyacyl),
ix) —O—C(O)—O—$C_{1-6}$alkyl,
x) —S($C_{1-6}$alkyl), and
xi) —O$C_{1-3}$alkaryl, 7b) m is 1, ---- is a single-bond and
b1) $R^{16}$ is selected from among
i) =O,
ii) =NH, and
iii) =N($C_{1-6}$alkyl), and
b2) $R^{17}$ is selected from among
i) —$NH_2$,
ii) —NH($C_{1-6}$alkyl),
iii) —NH($C_{2-7}$acyl),
iv) —NH—C(O)—O—$C_{1-6}$alkyl, and
v) -cycloheteroalkyl, and 7c) independent of the value of m, each bonding pair, $W^1$ ---- $W^2$, $W^2$ ---- C, C ---- $W^4$, $W^4$ ---- $W^3$, and $W^3$ ---- $W^1$, contained in the five-membered ring comprises a single or a double bond and
i) $W^1$ is O, S, N, or $CR^{14}$,
ii) $W^2$ is N or $CR^{15}$,
iii) $W^3$ is C or N, and
iv) $W^4$ is C or N, and
where $R^{14}$ and $R^{15}$, if present, are independently selected from among
i) hydrogen,
ii) halo,
iii) cyano,
iv) —C(O)$NH_2$,
iv) $C_{1-6}$alkyl,
vii) vinyl, and
viii) ethynyl.

A second aspect of the third embodiment is directed to a compound or its stereoisomer or its salt or its metabolite or its deuteride thereof represented by formula I-3
wherein
1) $R^1$ is selected from among
a) hydrogen,
b) —P(O)(OH)$_2$,
c) —P(O)(O($CH_2$)$_{1-3}$OC(O)O($C_{1-6}$alkyl))$_2$,
d) —P(O)(O($CH_2$)$_{1-3}$OC(O)($C_{1-6}$alkyl))$_2$,
e) —P(O)(O($CH_2$)$_{1-3}$SC(O)($C_{1-6}$alkyl))$_2$,
f) —P(O)(O($CH_2$)$_{1-3}$OCH$_2$(aryl))$_2$,
g) —P(O)(O($CH_2$)$_{1-3}$SCH$_2$(aryl))$_2$,
h) —P*(O)(O$R^{1a}$)(NHCHR$^{1b}$C(O)O$R^{1c}$),
wherein
$R^{1a}$ is
i) hydrogen,
ii) $C_{1-6}$alkyl,
iii) $C_{3-6}$cycloalkyl, or
iv) aryl,
$R^{1b}$ is
i) hydrogen,
ii) $C_{1-6}$alkyl,
iii) $C_{3-6}$cycloalkyl,
iv) $C_{1-3}$alkaryl, or
v) alk(heteroaryl), and
$R^{1c}$ is
i) hydrogen,
ii) $C_{1-6}$alkyl,
iii) $C_{3-6}$cycloalkyl, or
iv) $C_{1-3}$alkaryl,
i) —P*(O)(NH(alkaryl)(O($CH_2$)$_{1-3}$SC(O)(alkyl)),
j) a 1,3,2-dioxaphosphinane-2-oxide,
k) a 4H-benzo[d][1,3,2]dioxaphosphinine-2-oxide,
l) —P*(O)(O$R^{1c}$)~, when Y is —O~, where $R^{1c}$ is defined above,
m) —P(O)(OH)—O—P(O)(OH)$_2$,
n) —P(O)(OH)—O—P(O)(OH)—O—P(O)(OH)$_2$,
o) a $C_{2-7}$acyl,
p) an aminoacyl,
q) a $C_{1-6}$-alkylene-oxy-$C_{2-7}$acyl, and
r) a —C(O)—O—$C_{1-6}$alkyl;
2) $R^2$ is hydrogen;
3) $R^3$ is hydrogen;
4) Y is selected from among
a) —OH,
b) —O~, when $R^1$ is —P(O)(O$R^{1c}$)~, where $R^{1c}$ is defined above,
c) —O($C_{2-7}$acyl),
d) —O(aminoacyl),
e) —O($C_{1-6}$-alkylene-oxy-acyl), and
f) —O—C(O)—O—$C_{1-6}$alkyl;
5) X is —O—;

6)  is a four- or five-membered ring selected from among radicals c, d, e, f, g, and h, represented by the following structures

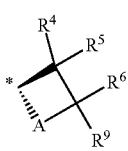
c

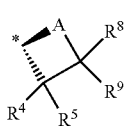
d

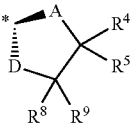
e

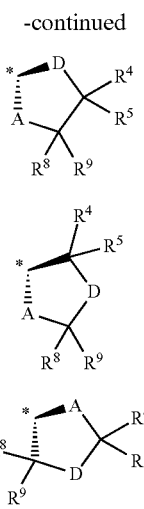

where * represents the point of attachment to the 2'-carbon and where
- a) A is selected from among
  - i) —O—,
  - ii) —S—,
  - iii) —S(O)—,
  - iv) —S(O)$_2$—, and
  - v) —NH—,
- b) D is selected from among
  - i) —O—,
  - ii) —S—,
  - iii) —S(O)—,
  - iv) —S(O)$_2$—, and
  - v) —NH—,
  - vi) a methylene, and
  - vii) a vinylidene, and
- c) $R^4$, $R^5$, $R^8$, and $R^9$ are independently selected from among
  - i) hydrogen,
  - ii) halo,
  - iii) $C_{1-6}$alkyl; and
- 7a) m is 0, ---- is a double-bond and $R^{16}$ and $R^{17}$ are independently selected from among
  - i) hydrogen,
  - ii) —NH$_2$,
  - iii) —NH($C_{1-6}$alkyl),
  - iv) —NH($C_{2-7}$acyl),
  - iv) —NH—C(O)—O—$C_{1-6}$alkyl,
  - v) -cycloheteroalkyl,
  - vi) —O($C_{1-6}$alkyl),
  - vii) —O($C_{2-7}$acyl),
  - viii) —O($C_{1-6}$alkyleneoxyacyl),
  - ix) —O—C(O)—O—$C_{1-6}$alkyl,
  - x) —S($C_{1-6}$alkyl), and
  - xi) —O$C_{1-3}$alkaryl,
- 7b) m is 1, ---- is a single-bond and
  - b1) $R^{16}$ is selected from among
    - i) =O,
    - ii) =NH, and
    - iii) =N($C_{1-6}$alkyl), and
  - b2) $R^{17}$ is selected from among
    - i) —NH$_2$,
    - ii) —NH($C_{1-6}$alkyl),
    - iii) —NH($C_{2-7}$acyl),
    - iv) —NH—C(O)—O—$C_{1-6}$alkyl, and
    - v) -cycloheteroalkyl, and
- 7c) independent of the value of m, each bonding pair, $W^1$ ---- $W^2$, $W^2$ ---- C, C ---- $W^4$, $W^4$ ---- $W^3$, and $W^3$ ---- $W^1$, contained in the five-membered ring comprises a single or a double bond and
  - i) $W^1$ is O, S, N, or $CR^{14}$,
  - ii) $W^2$ is N or $CR^{15}$,
  - iii) $W^3$ is C or N, and
  - iv) $W^4$ is C or N, and
  where $R^{14}$ and $R^{15}$, if present, are independently selected from among
  - i) hydrogen,
  - ii) halo,
  - iii) cyano,
  - iv) —C(O)NH$_2$,
  - iv) $C_{1-6}$alkyl,
  - vii) vinyl, and
  - viii) ethynyl.

A third aspect of the third embodiment is directed to a compound or its stereoisomer or its salt or its metabolite or its deuteride thereof represented by formula I-3 wherein
- 1) $R^1$ is selected from among
  - a) hydrogen,
  - b) —P(O)(OH)$_2$,
  - c) —P(O)(O(CH$_2$)$_{1-3}$OC(O)O($C_{1-6}$alkyl))$_2$,
  - d) —P(O)(O(CH$_2$)$_{1-3}$OC(O)($C_{1-6}$alkyl))$_2$,
  - e) —P(O)(O(CH$_2$)$_{1-3}$SC(O)($C_{1-6}$alkyl))$_2$,
  - f) —P(O)(O(CH$_2$)$_{1-3}$OCH$_2$(aryl))$_2$,
  - g) —P(O)(O(CH$_2$)$_{1-3}$SCH$_2$(aryl))$_2$,
  - h) —P*(O)(OR$^{1a}$)(NHCHR$^{1b}$C(O)OR$^{1c}$),
  wherein
  $R^{1a}$ is
  - i) hydrogen,
  - ii) $C_{1-6}$alkyl,
  - iii) $C_{3-6}$cycloalkyl, or
  - iv) aryl,
  $R^{1b}$ is
  - i) hydrogen,
  - ii) $C_{1-6}$alkyl,
  - iii) $C_{3-6}$cycloalkyl,
  - iv) $C_{1-3}$alkaryl, or
  - v) alk(heteroaryl), and
  $R^{1c}$ is
  - i) hydrogen
  - ii) $C_{1-6}$alkyl,
  - iii) $C_{3-6}$cycloalkyl, or
  - iv) $C_{1-3}$alkaryl,
  - i) —P*(O)(NH(alkaryl)(O(CH$_2$)$_{1-3}$SC(O)(alkyl)),
  - j) a 1,3,2-dioxaphosphinane-2-oxide,
  - k) a 4H-benzo[d][1,3,2]dioxaphosphinine-2-oxide,
  - l) —P*(O)(OR$^{1c}$)~, when Y is —O~ where $R^{1c}$ is defined above,
  - m) —P(O)(OH)—O—P(O)(OH)$_2$,
  - n) —P(O)(OH)—O—P(O)(OH)—O—P(O)(OH)$_2$,
  - o) a $C_{2-7}$acyl,
  - p) an aminoacyl,
  - p) a $C_{1-6}$-alkylene-oxy-$C_{2-7}$acyl, and
  - q) a —C(O)—O—$C_{1-6}$alkyl;
- 2) $R^2$ is hydrogen;
- 3) $R^3$ is hydrogen;
- 4) Y is selected from among
  - a) —OH,
  - b) —O~, when $R^1$ is —P(O)(OR$^{1c}$)~, where $R^{1c}$ is defined above,
  - c) —O($C_{2-7}$acyl),
  - d) —O(aminoacyl),
  - e) —O($C_{1-6}$-alkylene-oxy-acyl), and
  - f) —O—C(O)—O—$C_{1-6}$alkyl;

5) X is —O—;

6) 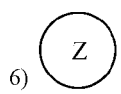 is a four- or five-membered ring selected from among radicals c, d, e, f, g, and h, represented by the following structures

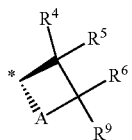 c

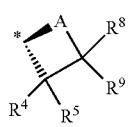 d

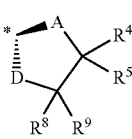 e

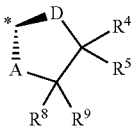 f

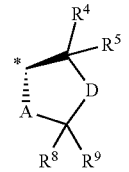 g

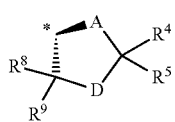 h where * represents the point of attachment to the 2'-carbon and where
  a) A is —O—,
  b) D is —O— or —CH$_1$—,
  c) $R^4$, $R^5$, $R^8$, and $R^9$ are each hydrogen; and
7a) m is 0, ---- is a double-bond and $R^{16}$ and $R^{17}$ are independently selected from among
  i) hydrogen,
  ii) —NH$_2$,
  iii) —NH(C$_{1-6}$alkyl),
  iv) —NH(C$_{2-7}$acyl),
  iv) —NH—C(O)—O—C$_{1-6}$alkyl,
  v) -cycloheteroalkyl,
  vi) —O(C$_{1-6}$alkyl),
  vii) —O(C$_{2-7}$acyl),
  viii) —O(C$_{1-6}$alkyleneoxyacyl),
  ix) —O—C(O)—O—C$_{1-6}$alkyl,
  x) —S(C$_{1-6}$alkyl), and
  xi) —OC$_{1-3}$alkaryl, 7b) m is 1, ---- is a single-bond and
  b1) $R^{16}$ is selected from among
    i) =O,
    ii) =NH, and
    iii) =N(C$_{1-6}$alkyl), and
  b2) $R^{17}$ is selected from among
    i) —NH$_2$,
    ii) —NH(C$_{1-6}$alkyl),
    iii) —NH(C$_{2-7}$acyl),
    iv) —NH—C(O)—O—C$_{1-6}$alkyl, and
    v) -cycloheteroalkyl, and
7c) independent of the value of m, each bonding pair, $W^1$ ---- $W^2$, $W^2$ ---- C, C ---- $W^4$, $W^4$ ---- $W^3$, and $W^3$ ---- $W^1$, contained in the five-membered ring comprises a single or a double bond and
  i) $W^1$ is O, S, N, or CR$^{14}$,
  ii) $W^2$ is N or CR$^{15}$,
  iii) $W^3$ is C or N, and
  iv) $W^4$ is C or N, and
  where $R^{14}$ and $R^{15}$, if present, are independently selected from among
    i) hydrogen,
    ii) halo,
    iii) cyano,
    iv) —C(O)NH$_2$,
    iv) C$_{1-6}$alkyl,
    vii) vinyl, and
    viii) ethynyl.

A fourth aspect of the third embodiment is directed to a compound or its stereoisomer or its salt or its metabolite or its deuteride thereof represented by formula I-3
wherein
1) $R^1$ is selected from among
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
  wherein
  R$^{1a}$ is
    i) hydrogen,
    iv) aryl,
  R$^{1b}$ is
    i) hydrogen or
    ii) C$_{1-6}$alkyl, and
  R$^{1c}$ is
    i) hydrogen
    ii) C$_{1-6}$alkyl,
    iii) C$_{3-6}$cycloalkyl, or
    iv) C$_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where R$^{1c}$ is defined above,
  m) —P(O)(OH)—O—P(O)(OH)$_2$,
  n) —P(O)(OH)—O—P(O)(OH)—O—P(O)(OH)$_2$,
  o) a C$_{2-7}$acyl,
  p) an aminoacyl,
  q) a C$_{1-6}$-alkylene-oxy-C$_{2-7}$acyl, and
  r) a —C(O)—O—C$_{1-6}$alkyl;
2) $R^2$ is hydrogen;
3) $R^3$ is hydrogen;

4) Y is selected from among
a) —OH,
b) —O~, when $R^1$ is —P(O)(OR$^{1c}$)~, where $R^{1c}$ is defined above,
c) —O(C$_{2-7}$acyl), and
d) —O(aminoacyl),
5) X is —O—;

6) 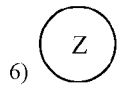 is a four- or five-membered ring selected from among radicals c, d, e, and f, represented by the following structures

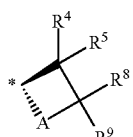 c

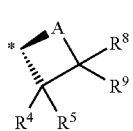 d

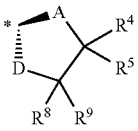 e

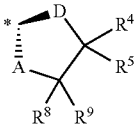 f where * represents the point of attachment to the 2'-carbon and where
a) A is —O—,
b) D is —O— or —CH$_2$—,
c) $R^4$, $R^5$, $R^8$, and $R^9$ are each hydrogen; and
7a) m is 0, ---- is a double-bond and $R^{16}$ and $R^{17}$ are independently selected from among
i) hydrogen,
ii) —NH$_2$,
iii) —NH(C$_{1-6}$alkyl),
iv) —NH(C$_{2-7}$acyl),
iv) —NH—C(O)—O—C$_{1-6}$alkyl,
v) -cycloheteroalkyl,
vi) —O(C$_{1-6}$alkyl),
vii) —O(C$_{2-7}$acyl),
viii) —O(C$_{1-6}$alkyleneoxyacyl),
ix) —O—C(O)—O—C$_{1-6}$alkyl,
x) —S(C$_{1-6}$alkyl), and
xi) —OC$_{1-3}$alkaryl,
7b) m is 1, ---- is a single-bond and
b1) $R^{16}$ is selected from among
i) =O,
ii) =NH, and
iii) =N(C$_{1-6}$alkyl), and
b2) $R^{17}$ is selected from among
i) —NH$_2$,
ii) —NH(C$_{1-6}$alkyl),
iii) —NH(C$_{2-7}$acyl),
iv) —NH—C(O)—O—C$_{1-6}$alkyl, and
v) -cycloheteroalkyl,
7c) independent of the value of m, each bonding pair, $W^1$ ---- $W^2$, $W^2$ ---- C, C ---- $W^4$, $W^4$ ---- $W^3$, and $W^3$ ---- $W^1$, contained in the five-membered ring comprises a single or a double bond and
i) $W^1$ is O, S, N, or CR$^{14}$,
ii) $W^2$ is N or CR$^{15}$,
iii) $W^3$ is C or N, and
iv) $W^4$ is C or N, and
where $R^{14}$ and $R^{15}$, if present, are independently selected from among
i) hydrogen,
ii) halo,
iii) cyano,
iv) —C(O)NH$_2$,
iv) C$_{1-6}$alkyl,
vii) vinyl, and
viii) ethynyl.

A fifth aspect of the third embodiment is directed to a compound or its stereoisomer or its salt or its metabolite or its deuteride thereof represented by formula I-3-1

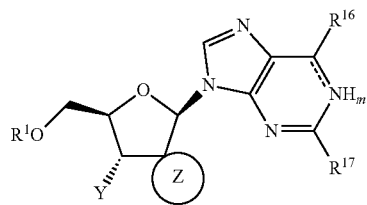 I-3-1 wherein
1) $R^1$ is selected from among:
a) hydrogen,
b) —P(O)(OH)$_2$,
c) —P*(O)(OR$^{1a}$)(NHCHR$^{1b}$C(O)OR$^{1c}$),
wherein
$R^{1a}$ is
i) hydrogen or
ii) aryl,
$R^{1b}$ is
i) hydrogen or
ii) C$_{1-6}$alkyl, and
$R^{1c}$ is
i) hydrogen
ii) C$_{1-6}$alkyl,
iii) C$_{3-6}$cycloalkyl, or
iv) C$_{1-3}$alkaryl,
d) a 1,3,2-dioxaphosphinane-2-oxide,
e) a 4H-benzo[d][1,3,2]dioxaphosphinine-2-oxide,
f) —P*(O)(OR$^{1c}$)~, when Y is —O~, where $R^{1c}$ is defined above,
g) —P(O)(OH)—O—P(O)(OH)$_2$,
h) —P(O)(OH)—O—P(O)(OH)—O—P(O)(OH)$_2$,
i) a C$_{2-7}$acyl, and
j) an aminoacyl; and
2) Y is selected from among
a) —OH,
b) —O~, when $R^1$ is —P(O)(OR$^{1c}$)~, where $R^{1c}$ is defined above,
c) —O(C$_{2-7}$acyl), and
d) —O(aminoacyl); and 3)  is selected from among

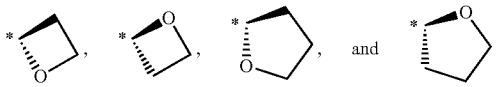

where * represents the point of attachment to the 2'-carbon; and
4a) m is 0, ----- is a double-bond
  4a1) $R^{16}$ is selected from among
    i) —$NH_2$,
    ii) —$NH(C_{1-6}alkyl)$,
    iii) —$NH(C_{2-7}acyl)$,
    iv) -cycloalkylamino,
    v) —$O(C_{1-6}alkyl)$,
    vi) —$O(C_{2-7}acyl)$,
    vii) —$O(C_{1-6}alkyleneoxyacyl)$, and
    viii) —O—C(O)—O—$C_{1-6}alkyl$,
    ix) —$S(C_{1-6}alkyl)$, and
    x) —$OC_{1-3}alkaryl$, and
  4a2) $R^{17}$ is selected from among
    i) hydrogen,
    ii) —$NH_2$, and
    iii) —$NH(C_{1-6}alkyl)$, or
4b) m is 1, ----- is a single-bond
  4b1) $R^{16}$ is =O; and
  4b2) $R^{17}$ is selected from among
    i) —$NH_2$ and
    ii) —$NH(C_{1-6}alkyl)$.

A sixth aspect of the third embodiment is directed to a compound or its stereoisomer or its salt or its metabolite or its deuteride thereof represented by formula I-3-1
wherein
1) $R^1$ is selected from among:
  a) hydrogen,
  b) —$P(O)(OH)_2$,
  c) —$P*(O)(OR^{1a})(NHCHR^{1b}C(O)OR^{1c})$,
  wherein
  $R^{1a}$ is
    i) hydrogen,
    ii) phenyl,
    iii) p-fluorophenyl,
    iv) p-chlorophenyl,
    v) p-bromophenyl, or
    vi) naphthyl,
  $R^{1b}$ is
    i) hydrogen or
    ii) $C_{1-6}alkyl$, and
  $R^{1c}$ is
    i) hydrogen
    ii) $C_{1-6}alkyl$,
    iii) $C_{3-6}cycloalkyl$, or
    iv) $C_{1-3}alkaryl$,
  d) —$P*(O)(OR^{1c})$~, when Y is —O~, where $R^{1c}$ is defined above,
  e) —P(O)(OH)—O—$P(O)(OH)_2$,
  f) —P(O)(OH)—O—P(O)(OH)—O—$P(O)(OH)_2$,
  g) a $C_{2-7}acyl$, and
  h) an aminoacyl; and
2) Y is selected from among
  a) —OH,
  b) —O~, when $R^1$ is —$P(O)(OR^{1c})$~, where $R^{1c}$ is defined above,
  c) —$O(C_{2-7}acyl)$, and
  d) —O(aminoacyl); and 3)  is selected from among

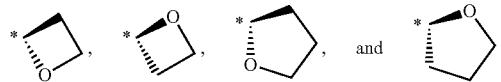

where * represents the point of attachment to the 2'-carbon; and
4a) m is 0, ----- is a double-bond
  4a1) $R^{16}$ is selected from among
    i) —$NH_2$,
    ii) —$NH(C_{1-6}alkyl)$,
    iii) —$NH(C_{2-7}acyl)$,
    iv) -cycloalkylamino,
    v) —$O(C_{1-6}alkyl)$,
    vi) —$O(C_{2-7}acyl)$,
    vii) —$O(C_{1-6}alkyleneoxyacyl)$, and
    viii) —O—C(O)—O—$C_{1-6}alkyl$,
    ix) —$S(C_{1-6}alkyl)$, and
    x) —$OC_{1-3}alkaryl$, and
  4a2) $R^{17}$ is selected from among
    i) hydrogen,
    ii) —$NH_2$ and
    iii) —$NH(C_{1-6}alkyl)$, or
4b) m is 1, ----- is a single-bond
  4b1) $R^{16}$ is =O and
  4b2) $R^{17}$ is selected from among
    i) —$NH_2$ and
    ii) —$NH(C_{1-6}alkyl)$.

A seventh aspect of the third embodiment is directed to a compound or its stereoisomer or its salt or its metabolite or its deuteride thereof represented by formula I-3-1
wherein
1) $R^1$ is selected from among:
  a) hydrogen,
  b) —$P(O)(OH)_2$,
  c) —$P*(O)(OR^{1a})(NHCHR^{1b}C(O)OR^{1c})$,
  wherein
  $R^{1a}$ is
    i) hydrogen,
    ii) phenyl,
    iii) p-fluorophenyl,
    iv) p-chlorophenyl,
    v) p-bromophenyl, or
    vi) naphthyl,
  $R^{1b}$ is
    i) hydrogen or
    ii) $C_{1-6}alkyl$, and
  $R^{1c}$ is
    i) hydrogen
    ii) $C_{1-6}alkyl$,
    iii) $C_{3-6}cycloalkyl$, or
    iv) $C_{1-3}alkaryl$,
  d) —$P*(O)(OR^{1c})$~, when Y is —O~, where $R^{1c}$ is defined above,
  e) —P(O)(OH)—O—$P(O)(OH)_2$,
  f) —P(O)(OH)—O—P(O)(OH)—O—$P(O)(OH)_2$,
  g) a $C_{2-7}acyl$, and
  h) an aminoacyl; and 2) Y is selected from among
   a) —OH,
   b) —O~, when $R^1$ is —P(O)(OR$^{1c}$)~, where $R^{1c}$ is defined above,
   c) —O(C$_{2-7}$acyl), and
   d) —O(aminoacyl); and 3)  is selected from among

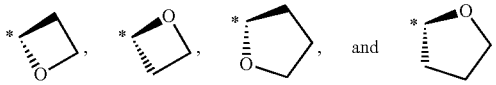

where * represents the point of attachment to the 2'-carbon; and 4a) m is 0, ----- is a double-bond
   4a1) $R^{16}$ is selected from among
      i) —NH$_2$,
      ii) —NH(C$_{1-6}$alkyl),
      iii) —NH(C$_{2-7}$acyl),
      iv) -cycloalkylamino,
      v) —O(C$_{1-6}$alkyl),
      vi) —O(C$_{2-7}$acyl),
      vii) —S(C$_{1-6}$alkyl), and
      viii) —OC$_{1-3}$alkaryl, and
   4a2) $R^{17}$ is selected from among
      i) hydrogen,
      ii) —NH$_2$, and
      iii) —NH(C$_{1-6}$alkyl), or
4b) m is 1, ----- is a single-bond
   4b1) $R^{16}$ is =O and
   4b2) $R^{17}$ is selected from among
      i) —NH$_2$ and
      ii) —NH(C$_{1-6}$alkyl).

An eighth aspect of the third embodiment is directed to a compound or its stereoisomer or its salt or its metabolite or its deuteride thereof represented by formula I-3-1
wherein
1) $R^1$ is selected from among:
   a) hydrogen,
   b) —P(O)(OH)$_2$,
   c) —P*(O)(OR$^{1a}$)(NHCHR$^{1b}$C(O)OR$^{1c}$), wherein
   $R^{1a}$ is
      i) hydrogen,
      ii) phenyl,
      iii) p-fluorophenyl,
      iv) p-chlorophenyl,
      v) p-bromophenyl, or
      vi) naphtyl,
   $R^{1b}$ is
      i) hydrogen or
      ii) C$_{1-6}$alkyl, and
   $R^{1c}$ is
      i) hydrogen
      ii) C$_{1-6}$alkyl,
      iii) C$_{3-6}$cycloalkyl, or
      vi) C$_{1-3}$alkaryl,
   d) —P*(O)(OR$^{1c}$)~, when Y is —O~, where $R^{1c}$ is defined above,
   e) —P(O)(OH)—O—P(O)(OH)$_2$,
   f) —P(O)(OH)—O—P(O)(OH)—O—P(O)(OH)$_2$,
   g) a C$_{2-7}$acyl, and
   h) an aminoacyl; and 2) Y is selected from among
   a) —OH,
   b) —O~, when $R^1$ is —P(O)(OR$^{1c}$)~, where $R^{1c}$ is defined above,
   c) —O(C$_{2-7}$acyl), and
   d) —O(aminoacyl); and 3)  is selected from among

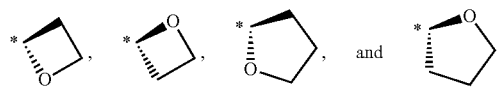

where * represents the point of attachment to the 2'-carbon; and 4a) m is 0, ----- is a double-bond
   4a1) $R^{16}$ is —O(C$_{1-6}$alkyl), —OC$_{1-3}$alkaryl, —S(C$_{1-6}$alkyl), —NH(C$_{1-6}$alkyl), or -cycloalkylamino, and
   4a2) $R^{17}$ is —NH$_2$ or —NH(C$_{1-6}$alkyl), or
   4a3) $R^{16}$ is —NH$_2$, —O(C$_{1-6}$alkyl), —OC$_{1-3}$alkaryl, —S(C$_{1-6}$alkyl), —NH(C$_{1-6}$alkyl), or -cycloalkylamino, and
   4a4) $R^{17}$ is hydrogen, or
4b) m is 1, ----- is a single-bond
   4b1) $R^{16}$ is =O and
   4b2) $R^{17}$ is —NH$_2$ or —NH(C$_{1-6}$alkyl).

A ninth aspect of the third embodiment is directed to a compound or its stereoisomer or its salt or its metabolite or its deuteride thereof represented by formula I-3-2

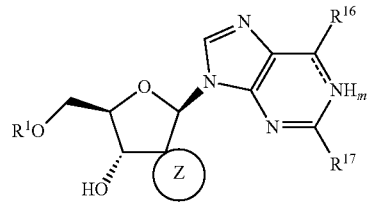

I-3-2 wherein
1) $R^1$ is selected from among:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
      i) hydrogen,
      ii) phenyl,
      iii) p-fluorophenyl,
      iv) p-chlorophenyl,
      v) p-bromophenyl, or
      vi) naphthyl,
   $R^{1b}$ is
      i) hydrogen or
      ii) C$_{1-6}$alkyl, and
   $R^{1c}$ is
      i) hydrogen
      ii) C$_{1-6}$alkyl,
      iii) C$_{3-6}$cycloalkyl, or
      iv) C$_{1-3}$alkaryl,
   d) —P(O)(OH)—O—P(O)(OH)$_2$,
   e) —P(O)(OH)—O—P(O)(OH)—O—P(O)(OH)$_2$, f) a $C_{2-7}$acyl, and
g) an aminoacyl; and 2)  is selected from among

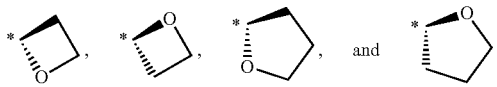

where * represents the point of attachment to the 2'-carbon; and 3a) m is 0, ---- is a double-bond
  3a1) $R^{16}$ is —O($C_{1-6}$alkyl), —O$C_{1-3}$alkaryl, —S($C_{1-6}$alkyl), —NH($C_{1-6}$alkyl), or -cycloalkylamino and
  3a2) $R^{17}$ is —NH$_2$ or —NH($C_{1-6}$alkyl), or
  3a3) $R^{16}$ is —NH$_2$, —O($C_{1-6}$alkyl), —O$C_{1-3}$alkaryl, —S($C_{1-6}$alkyl),
    —NH($C_{1-6}$alkyl), or -cycloalkylamino and
  3a4) $R^{17}$ is hydrogen, or
3b) m is 1, ---- is a single-bond
  3b1) $R^{16}$ is =O and
  3b2) $R^{17}$ is —NH$_2$.

A tenth aspect of the third embodiment is directed to a compound or its stereoisomer or its salt or its metabolite or its deuteride thereof represented by formula I-3-3

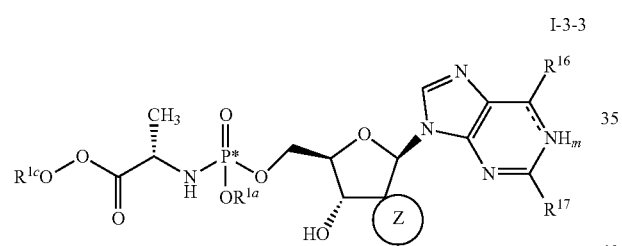

I-3-3 wherein
1) $R^{1a}$ is
  a) hydrogen,
  b) phenyl,
  c) p-fluorophenyl,
  d) p-chlorophenyl,
  e) p-bromophenyl, or
  f) naphthyl, and
2) $R^{1c}$ is
  a) hydrogen
  b) $C_{1-6}$alkyl,
  c) $C_{3-6}$cycloalkyl, or
  d) $C_{1-3}$alkaryl;

3)  is selected from among

where * represents the point of attachment to the 2'-carbon; and 4a) m is 0, ---- is a double-bond
  4a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  4a2) $R^{17}$ is —NH$_2$ or —NH($C_{1-6}$alkyl), or
  4a3) $R^{16}$ is —NH$_2$, —O($C_{1-6}$alkyl), —O$C_{1-3}$alkaryl, —S($C_{1-6}$alkyl), —NH($C_{1-6}$alkyl), or -cycloalkylamino, and
  4a4) $R^{17}$ is hydrogen, or
4b) m is 1, ---- is a single-bond
  4b1) $R^{16}$ is =O and
  4b2) $R^{17}$ is —NH$_2$ or —NH($C_{1-6}$alkyl).

An eleventh aspect of the third embodiment is directed to a compound or its stereoisomer or its salt or its metabolite or its deuteride thereof represented by formula I-3-4

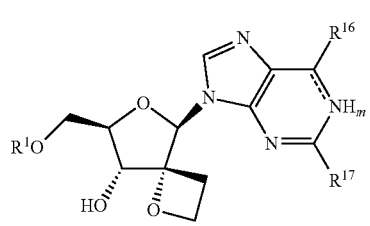

I-3-4 wherein
1) $R^1$ is selected from among:
  a) hydrogen,
  b) —P(O)(OH)$_2$,
  c) —P*(O)(OR$^{1a}$)(NHCHR$^{1b}$C(O)OR$^{1c}$),
  wherein
  $R^{1a}$ is
    i) hydrogen,
    ii) phenyl,
    iii) p-fluorophenyl,
    iv) p-chlorophenyl,
    v) p-bromophenyl, or
    vi) naphthyl,
  $R^{1b}$ is
    i) hydrogen or
    ii) $C_{1-6}$alkyl, and
  $R^{1c}$ is
    i) hydrogen
    ii) $C_{1-6}$alkyl,
    iii) $C_{3-6}$cycloalkyl, or
    iv) $C_{1-3}$alkaryl,
  d) —P(O)(OH)—O—P(O)(OH)$_2$,
  e) —P(O)(OH)—O—P(O)(OH)—O—P(O)(OH)$_2$,
  f) a $C_{2-7}$acyl, and
  g) an aminoacyl; and
2a) m is 0, ---- is a double-bond
  3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  3a2) $R^{17}$ is —NH$_2$ or —NH($C_{1-6}$alkyl), or
  3a3) $R^{16}$ is —NH$_2$, —O($C_{1-6}$alkyl), —O$C_{1-3}$alkaryl, —S($C_{1-6}$alkyl), —NH($C_{1-6}$alkyl), or -cycloalkylamino and
  3a4) $R^{17}$ is hydrogen, or
2b) m is 1, ---- is a single-bond
  3b1) $R^{16}$ is =O and
  3b2) $R^{17}$ is —NH$_2$ or —NH($C_{1-6}$alkyl).

A twelfth aspect of the third embodiment is directed to a compound or its stereoisomer or its salt or its metabolite or its deuteride thereof represented by formula I-3-5

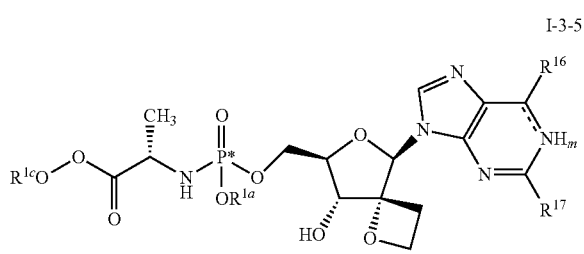

wherein
1) $R^{1a}$ is
   a) hydrogen,
   b) phenyl, or
   c) naphthyl, and
2) $R^{1c}$ is
   a) hydrogen
   b) $C_{1-6}$alkyl,
   c) $C_{3-6}$cycloalkyl, or
   d) $C_{1-3}$alkaryl; and
3a) m is 0, ----- is a double-bond
   3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
   3a2) $R^{17}$ is —$NH_2$ or —NH($C_{1-6}$alkyl), or
   3a3) $R^{16}$ is —$NH_2$, —O($C_{1-6}$alkyl), —O$C_{1-3}$alkaryl, —S($C_{1-6}$alkyl),
      —NH($C_{1-6}$alkyl), or -cycloalkylamino, and
   3a4) $R^{17}$ is hydrogen, or
3b) m is 1, ----- is a single-bond
   3b1) $R^{16}$ is =O and
   3b2) $R^{17}$ is —$NH_2$ or —NH($C_{1-6}$alkyl).

A thirteenth aspect of the third embodiment is directed to a compound or its stereoisomer or its salt or its metabolite or its deuteride thereof represented by formula I-3-5 wherein
1) $R^{1a}$ is
   a) hydrogen,
   b) phenyl, or
   c) naphthyl, and
2) $R^{1c}$ is
   a) hydrogen
   b) $C_{1-6}$alkyl,
   c) $C_{3-6}$cycloalkyl, or
   d) $C_{1-3}$alkaryl; and
3a) m is 0, ----- is a double-bond
   3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
   3a2) $R^{17}$ is —$NH_2$, or
   3a3) $R^{16}$ is —$NH_2$, —O($C_{1-6}$alkyl), —O$C_{1-3}$alkaryl, —NH($C_{1-6}$alkyl), —S($C_{1-6}$alkyl), or -cycloalkylamino, and
   3a4) $R^{17}$ is hydrogen, or
3b) m is 1, ----- is a single-bond
   3b1) $R^{16}$ is =O and
   3b2) $R^{17}$ is —$NH_2$.

A fourteenth aspect of the third embodiment is directed to a compound or its stereoisomer or its salt or its metabolite or its deuteride thereof represented by formula I-3-5
   wherein
1) $R^{1a}$ is
   a) hydrogen,
   b) phenyl, or
   c) naphthyl, and
2) $R^{1c}$ is
   a) hydrogen
   b) $C_{1-6}$alkyl,
   c) $C_{3-6}$cycloalkyl, or
   d) $C_{1-3}$alkaryl; and
3a) m is 0, ----- is a double-bond
   3a1) $R^{16}$ is —O($C_{1-6}$alkyl) or —O$C_{1-3}$alkaryl, and
   3a2) $R^{17}$ is —$NH_2$, or
   3a3) $R^{16}$ is —$NH_2$, and
   3a4) $R^{17}$ is hydrogen, or
3b) m is 1, ----- is a single-bond
   3b1) $R^{16}$ is =O and
   3b2) $R^{17}$ is —$NH_2$.

A fifteenth aspect of the third embodiment is directed to a compound or its salt thereof represented by formula I-3-6

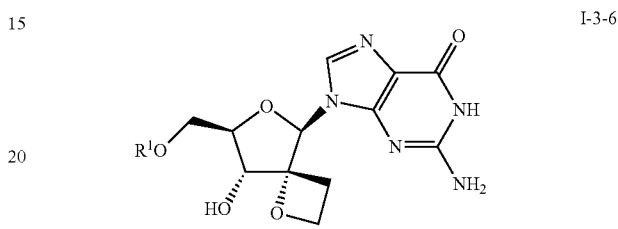

wherein
1) $R^1$ is hydrogen, —P(O)(OH)$_2$, —P(O)(OH)—O—P(O)(OH)$_2$, or —P(O)(OH)—O—P(O)(OH)—O—P(O)(OH)$_2$.

A sixteenth aspect of the third embodiment is directed to a compound or its stereoisomer or its salt or its metabolite or its deuteride thereof represented by formula I-3-7

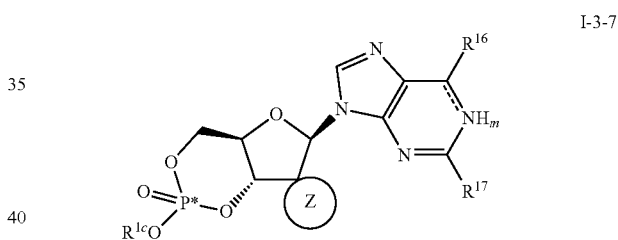

1) $R^{1c}$ is
   a) hydrogen
   b) $C_{1-6}$alkyl,
   c) $C_{3-6}$cycloalkyl, or
   d) $C_{1-3}$alkaryl;

2) Z is selected from among

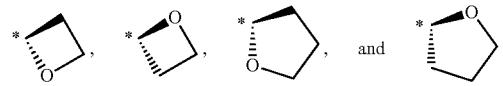

where * represents the point of attachment to the 2'-carbon; and
3a) m is 0, ----- is a double-bond
   3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
   3a2) $R^{17}$ is —$NH_2$, or
   3b1) $R^{16}$ is —$NH_2$, —O($C_{1-6}$alkyl), —O$C_{1-3}$alkaryl, —NH($C_{1-6}$alkyl), —S($C_{1-6}$alkyl), or -cycloalkylamino and
   3b2) $R^{17}$ is hydrogen, or 3b) m is 1, ---- is a single-bond
   3b1) $R^{16}$ is =O and
   3b2) $R^{17}$ is —$NH_2$ or —$NH(C_{1-6}alkyl)$.

A seventeenth aspect of the third embodiment is directed to a compound or its stereoisomer or its salt or its metabolite or its deuteride thereof represented by formula I-3-8

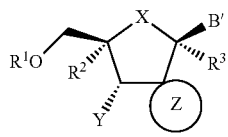
I-3-8 wherein B' is selected from among B5, B6, B7, B8, B9, and B10 represented by the following structures

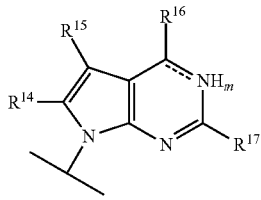
B5

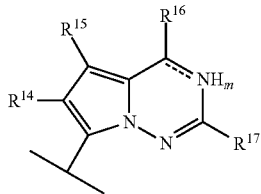
B6

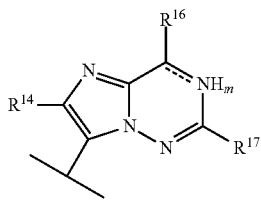
B7

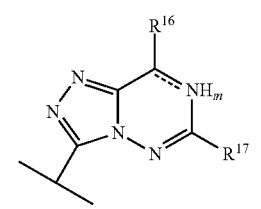
B8

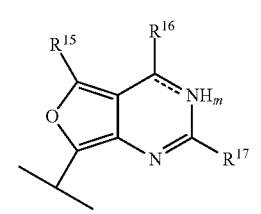
B9

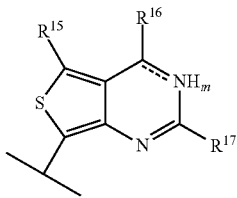
B10 and $R^1$, $R^2$, Y, $R^3$, (Z), X, $R^{14}$, $R^{15}$, $R^{16}$, $R^{17}$, m, and ---- have the meanings described above.

An eighteenth aspect of the third embodiment is directed to a compound or its stereoisomer or its salt or its metabolite or its deuteride thereof represented by formula I-3-8,
wherein
1) $R^1$ is selected from among:
   a) hydrogen,
   b) —$P(O)(OH)_2$,
   c) —$P(O)(O(CH_2)_{1-3}OC(O)O(C_{1-6}alkyl))_2$,
   d) —$P(O)(O(CH_2)_{1-3}OC(O)(C_{1-6}alkyl))_2$,
   e) —$P(O)(O(CH_2)_{1-3}SC(O)(C_{1-6}alkyl))_2$,
   f) —$P(O)(O(CH_2)_{1-3}OCH_2(aryl))_2$,
   g) —$P(O)(O(CH_2)_{1-3}SCH_2(aryl))_2$,
   h) —$P^*(O)(OR^{1a})(NHCHR^{1b}C(O)OR^{1c})$,
   wherein
   $R^{1a}$ is
      i) hydrogen or
      ii) aryl,
   $R^{1b}$ is
      i) hydrogen or
      ii) $C_{1-6}$alkyl, and
   $R^{1c}$ is
      i) hydrogen
      ii) alkyl,
      iii) cycloalkyl, or
      vi) —$C_{1-3}$alkaryl,
   i) —$P^*(O)(NH(alkaryl)(O(CH_2)_{1-3}SC(O)(C_{1-6}alkyl))$,
   j) a 1,3,2-dioxaphosphinane-2-oxide,
   k) a 4H-benzo[d][1,3,2]dioxaphosphinine-2-oxide,
   l) —$P^*(O)(OR^{1c})$~, when Y is —O~, where $R^{1c}$ is defined above,
   m) —$P(O)(OH)$—O—$P(O)(OH)_2$,
   n) —$P(O)(OH)$—O—$P(O)(OH)$—O—$P(O)(OH)_2$,
   o) an $C_{2-7}$acyl,
   p) an aminoacyl,
   q) a $C_{1-6}$-alkylene-oxy-acyl, and
   r) a —C(O)—O—$C_{1-6}$alkyl,
2) $R^2$ is hydrogen;
3) $R^3$ is hydrogen or cyano;
4) Y is selected from among
   a) —OH,
   b) —O~, when $R^1$ is —$P(O)(OR^{1c})$~, where $R^{1c}$ is defined above,
   c) —O(acyl), and
   d) —O($C_{1-6}$-alkylene-oxy$C_{2-7}$acyl);
5) X is —O—;

6)  is selected from among

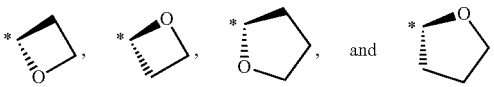

where * represents the point of attachment to the 2'-carbon; and 7a) m is 0, ---- is a double-bond and $R^{16}$ and $R^{17}$ are independently selected from among
  i) hydrogen,
  ii) —$NH_2$,
  iii) —NH(alkyl),
  iv) —NH(acyl),
  iv) —NH—C(O)—O-alkyl,
  v) -cycloheteroalkyl,
  vi) —O(alkyl),
  vii) —O(acyl),
  viii) —O($C_{1-6}$alkyleneoxyacyl),
  ix) —O—C(O)—O-alkyl,
  x) —S($C_{1-6}$alkyl), or
  xi) —O$C_{1-3}$alkaryl, 7b) m is 1, ---- is a single-bond and
  b1) $R^{16}$ is selected from among
    i) =O,
    ii) =NH,
    iii) =N(alkyl), and
  b2) $R^{17}$ is selected from among
    i) —$NH_2$,
    ii) —NH(alkyl),
    iii) —NH(acyl),
    iv) —NH—C(O)—O-alkyl, and
    v) -cycloheteroalkyl,
  7c) independent of the value of m, $R^{14}$ and $R^{15}$, if present, are independently selected from among
    i) hydrogen,
    ii) halo,
    iii) cyano,
    iv) —C(O)$NH_2$,
    iv) $C_{1-6}$alkyl,
    vii) vinyl, and
    viii) ethynyl.

A nineteenth aspect of the third embodiment is directed to a compound or its stereoisomer or its salt or its metabolite or its deuteride thereof represented by formula I-3-8 wherein 1) $R^1$ is selected from among:
  a) hydrogen,
  b) —P(O)(OH)$_2$,
  c) —P(O)(O($CH_2$)$_{1-3}$OC(O)O($C_{1-6}$alkyl))$_2$,
  d) —P(O)(O($CH_2$)$_{1-3}$OC(O)($C_{1-6}$alkyl))$_2$,
  e) —P(O)(O($CH_2$)$_{1-3}$SC(O)($C_{1-6}$alkyl))$_2$,
  f) —P(O)(O($CH_2$)$_{1-3}$O$CH_2$(aryl))$_2$,
  g) —P(O)(O($CH_2$)$_{1-3}$S$CH_2$(aryl))$_2$,
  h) —P*(O)(OR$^{1a}$)(NHCHR$^{1b}$C(O)OR$^{1c}$), wherein
    $R^{1a}$ is
      i) hydrogen or
      ii) aryl,
    $R^{1b}$ is
      i) hydrogen or
      ii) $C_{1-6}$alkyl, and
    $R^{1c}$ is
      i) hydrogen,
      ii) alkyl,
      iii) cycloalkyl, or
      vi) —$C_{1-3}$alkaryl,
  i) —P*(O)(NH(alkaryl)(O($CH_2$)$_{1-3}$SC(O)($C_{1-6}$alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where $R^{1c}$ is defined above,
  m) —P(O)(OH)—O—P(O)(OH)$_2$,
  n) —P(O)(OH)—O—P(O)(OH)—O—P(O)(OH)$_2$,
  o) an $C_{2-7}$acyl,
  p) an aminoacyl,
  q) a $C_{1-6}$-alkylene-oxy-acyl, and
  r) a —C(O)—O—$C_{1-6}$alkyl,
2) $R^2$ is hydrogen;
3) $R^3$ is hydrogen or cyano;
4) Y is selected from among
  a) —OH,
  b) —O~, when $R^1$ is —P(O)(OR$^{1c}$)~, where $R^{1c}$ is defined above,
  c) —O(acyl), and
  d) —O($C_{1-6}$-alkylene-oxy$C_{2-7}$acyl);
5) X is —O—;

6)  is selected from among

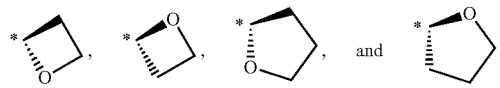

where * represents the point of attachment to the 2'-carbon; and 7a) m is 0, ---- is a double-bond,
  7a1) $R^{16}$ is selected from among
    i) —$NH_2$,
    ii) —NH($C_{1-6}$alkyl),
    iii) —NH($C_{2-7}$acyl),
    iv) —NH—C(O)—O—$C_{1-6}$alkyl,
    v) -cycloheteroalkyl,
    vi) —O($C_{1-6}$alkyl),
    vii) —O($C_{2-7}$acyl),
    viii) —O($C_{1-6}$alkyleneoxyacyl),
    ix) —O—C(O)—O—$C_{1-6}$alkyl,
    x) —S($C_{1-6}$alkyl), and
    xi) —O$C_{1-3}$alkaryl, and
  7a2) $R^{17}$ is selected from among
    i) hydrogen,
    ii) —$NH_2$,
    iii) —NH($C_{1-6}$alkyl),
    iv) —NH($C_{2-7}$acyl), and
    v) —NH—C(O)—O—$C_{1-6}$alkyl, or
7b) m is 1, ---- is a single-bond,
  7b1) $R^{16}$ is =O;
  7b2) $R^{17}$ is selected from among
    i) —$NH_2$,
    ii) —NH($C_{1-6}$alkyl), and
    iii) —NH($C_{2-7}$acyl), and
7c) independent of the value of m, $R^{14}$ and $R^{15}$, if present, are independently selected from among
  i) hydrogen,
  ii) halo,
  iii) cyano, iv) —C(O)NH$_2$,
iv) C$_{1-6}$alkyl,
vii) vinyl, and
viii) ethynyl.

A twentieth aspect of the third embodiment is directed to a compound or its stereoisomer or its salt or its metabolite or its deuteride thereof represented by formula I-3-8 wherein
1) R$^1$ is selected from among:
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
  wherein
  R$^{1a}$ is
    i) hydrogen or
    ii) aryl,
  R$^{1b}$ is
    i) hydrogen or
    ii) C$_{1-6}$alkyl, and
  R$^{1c}$ is
    i) hydrogen
    ii) alkyl,
    iii) cycloalkyl, or
    vi) —C$_{1-3}$alkaryl,
  i) —P*(O)(NH(alkaryl)(O(CH$_2$)$_{1-3}$SC(O)(C$_{1-6}$alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~, where R$^{1c}$ is defined above,
  m) —P(O)(OH)—O—P(O)(OH)$_2$,
  n) —P(O)(OH)—O—P(O)(OH)—O—P(O)(OH)$_2$,
  o) a C$_{2-7}$acyl,
  p) an aminoacyl,
  q) a C$_{1-6}$-alkylene-oxy-acyl, and
  r) a —C(O)—O—C$_{1-6}$alkyl,
2) R$^2$ is hydrogen;
3) R$^3$ is hydrogen or cyano;
4) Y is selected from among
  a) —OH,
  b) —O~, when R$^1$ is —P(O)(OR$^{1c}$)~, where R$^{1c}$ is defined above,
  c) —O(C$_{2-7}$acyl),
  d) —O(aminoacyl), and
  d) —O(C$_{1-6}$-alkylene-oxyC$_{2-7}$acyl);
5) X is —O—;

6) 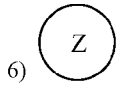 is selected from among

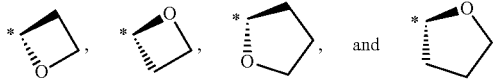

where * represents the point of attachment to the 2'-carbon; and
7a) m is 0, ---- is a double-bond,
  7a1) R$^{16}$ is selected from among
    i) —NH$_2$,
    ii) —NH(C$_{1-6}$alkyl),
    iii) —NH(C$_{2-7}$acyl),
    iv) —O(C$_{1-6}$alkyl),
    v) —O(C$_{2-7}$acyl),
    vi) —O(C$_{1-6}$alkyleneoxyacyl), and
    vii) —O—C(O)—O—C$_{1-6}$alkyl,
    viii) —S(C$_{1-6}$alkyl), and
    ix) —OC$_{1-3}$alkaryl,
  7a2) R$^{17}$ is selected from among
    i) hydrogen,
    ii) —NH$_2$,
    iii) —NH(C$_{1-6}$alkyl),
    iv) —NH(C$_{2-7}$acyl), and
    v) —NH—C(O)—O—C$_{1-6}$alkyl, or
7b) m is 1, ---- is a single-bond,
  7b1) R$^{16}$ is =O;
  7b2) R$^{17}$ is selected from among
    i) —NH$_2$,
    ii) —NH(C$_{1-6}$alkyl), and
    iii) —NH(C$_{2-7}$acyl), and
7c) independent of the value of m, R$^{14}$ and R$^{15}$, if present, are independently selected from among
    i) hydrogen,
    ii) halo,
    iii) cyano,
    iv) —C(O)NH$_2$,
    iv) C$_{1-6}$alkyl,
    vii) vinyl, and
    viii) ethynyl.

A twenty-first aspect of the third embodiment is directed to a compound or its stereoisomer or its salt or its metabolite or its deuteride thereof represented by formula I-3-8 wherein
1) R$^1$ is selected from among:
  a) hydrogen,
  b) —P(O)(OH)$_2$,
  c) —P*(O)(OR$^{1a}$)(NHCHR$^{1b}$C(O)OR$^{1c}$),
  wherein
  R$^{1a}$ is
    i) hydrogen or
    ii) aryl,
  R$^{1b}$ is
    i) hydrogen or
    ii) C$_{1-6}$alkyl, and
  R$^{1c}$ is
    i) hydrogen
    ii) alkyl,
    iii) cycloalkyl, or
    iv) —C$_{1-3}$alkaryl,
  d) a 1,3,2-dioxaphosphinane-2-oxide,
  e) a 4H-benzo[d][1,3,2]dioxaphosphinine-2-oxide,
  f) —P*(O)(OR$^{1c}$)~, when Y is —O~, where R$^{1c}$ is defined above,
  g) —P(O)(OH)—O—P(O)(OH)$_2$,
  h) —P(O)(OH)—O—P(O)(OH)—O—P(O)(OH)$_2$,
  i) a C$_{2-7}$acyl,
  j) an aminoacyl,
  k) a C$_{1-6}$-alkylene-oxy-acyl, and
  l) a —C(O)—O—C$_{1-6}$alkyl,
2) R$^2$ is hydrogen;
3) R$^3$ is hydrogen or cyano;
4) Y is selected from among
  a) —OH,
  b) —O~, when R$^1$ is —P(O)(OR$^{1c}$)~, where R$^{1c}$ is defined above, c) —O(C$_{2-7}$acyl),
  d) —O(aminoacyl), and
  e) —O(C$_{1-6}$-alkylene-oxyC$_{2-7}$acyl);

5) X is —O—;

6)  is selected from among

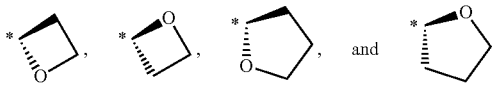, and where * represents the point of attachment to the 2'-carbon; and 7a) m is 0, ----- is a double-bond,
  7a1) $R^{16}$ is selected from among
    i) —$NH_2$,
    ii) —NH($C_{1-6}$alkyl),
    iii) —NH($C_{2-7}$acyl),
    iv) —O($C_{1-6}$alkyl),
    v) —O($C_{2-7}$acyl),
    vi) —O($C_{1-6}$alkyleneoxyacyl), and
    vii) —O—C(O)—O—$C_{1-6}$alkyl,
    viii) —S($C_{1-6}$alkyl), and
    ix) —$OC_{1-3}$alkaryl,
  7a2) $R^{17}$ is selected from among
    i) hydrogen,
    ii) —$NH_2$ and
    iii) —NH($C_{1-6}$alkyl), or
7b) m is 1, ----- is a single-bond,
  7b1) $R^{16}$ is =O;
  7b2) $R^{17}$ is selected from among
    i) —$NH_2$ and
    ii) —NH($C_{1-6}$alkyl) and
7c) independent of the value of m, $R^{14}$ and $R^{15}$, if present, are independently selected from among
  i) hydrogen,
  ii) halo,
  iii) cyano,
  iv) —C(O)$NH_2$,
  iv) $C_{1-6}$alkyl,
  vii) vinyl, and
  viii) ethynyl.

A twenty-second aspect of the third embodiment is directed to a compound or its stereoisomer or its salt or its metabolite or its deuteride thereof represented by formula I-3-9

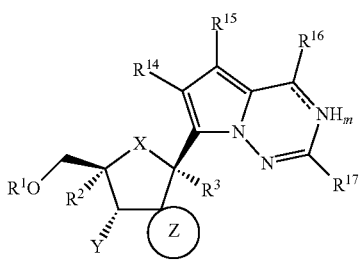

I-3-9 wherein
1) $R^1$ is selected from among:
  a) hydrogen,
  b) —P(O)$(OH)_2$,
  c) —P*(O)($OR^{1a}$)(NHCHR$^{1b}$C(O)$OR^{1c}$), wherein
$R^{1a}$ is
  i) hydrogen or
  ii) aryl,
$R^{1b}$ is
  i) hydrogen or
  ii) $C_{1-6}$alkyl, and
$R^{1c}$ is
  i) hydrogen
  ii) alkyl,
  iii) cycloalkyl, or
  iv) —$C_{1-3}$alkaryl,
d) a 1,3,2-dioxaphosphinane-2-oxide,
e) a 4H-benzo[d][1,3,2]dioxaphosphinine-2-oxide,
f) —P*(O)($OR^{1c}$)~, when Y is —O~, where $R^{1c}$ is defined above,
g) —P(O)(OH)—O—P(O)$(OH)_2$,
h) —P(O)(OH)—O—P(O)(OH)—O—P(O)$(OH)_2$,
i) a $C_{2-7}$acyl,
j) an aminoacyl,
k) a $C_{1-6}$-alkylene-oxy-acyl, and
l) a C(O)—O—$C_{1-6}$alkyl,
2) $R^2$ is hydrogen;
3) $R^3$ is hydrogen or cyano;
4) Y is selected from among
  a) —OH,
  b) —O~, when $R^1$ is —P(O)($OR^{1c}$)~, where $R^{1c}$ is defined above,
  c) —O($C_{2-7}$acyl),
  d) —O(aminoacyl), and
  d) —O($C_{1-6}$-alkylene-oxy$C_{2-7}$acyl);
5) X is —O—;

6)  is selected from among

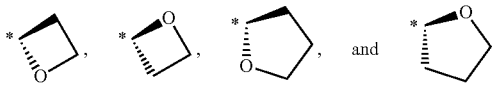, and where * represents the point of attachment to the 2'-carbon; and 7a) m is 0, ----- is a double-bond,
  7a1) $R^{16}$ is selected from among
    i) —$NH_2$,
    ii) —NH($C_{1-6}$alkyl),
    iii) —NH($C_{2-7}$acyl),
    iv) —O($C_{1-6}$alkyl),
    v) —O($C_{2-7}$acyl),
    vi) —O($C_{1-6}$alkyleneoxyacyl), and
    vii) —O—C(O)—O—$C_{1-6}$alkyl,
    viii) —S($C_{1-6}$alkyl),
    ix) —$OC_{1-3}$alkaryl, and
  7a2) $R^{17}$ is selected from among
    i) hydrogen,
    ii) —$NH_2$ and
    iii) —NH($C_{1-6}$alkyl), or
7b) m is 1, ----- is a single-bond,
  7b1) $R^{16}$ is =O; and
  7b2) $R^{17}$ is selected from among
    i) —$NH_2$ and
    ii) —NH($C_{1-6}$alkyl) and
7c) independent of the value of m, $R^{14}$ and $R^{15}$ are independently selected from among
  i) hydrogen,
  ii) halo,
  iii) cyano, iv) —C(O)NH$_2$,
iv) C$_{1-6}$alkyl,
vii) vinyl, and
viii) ethynyl.

A twenty-third aspect of the third embodiment is directed to a compound or its stereoisomer or its salt or its metabolite or its deuteride thereof represented by formula I-3-10

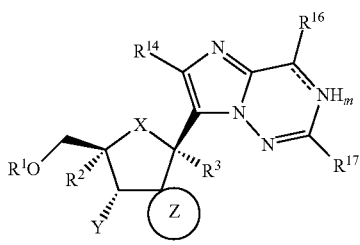

I-3-10 wherein
1) R$^1$ is selected from among:
   a) hydrogen,
   b) —P(O)(OH)$_2$,
   c) —P*(O)(OR$^{1a}$)(NHCHR$^{1b}$C(O)OR$^{1c}$),
   wherein
   R$^{1a}$ is
      i) hydrogen or
      ii) aryl,
   R$^{1b}$ is
      i) hydrogen or
      ii) C$_{1-6}$alkyl, and
   R$^{1c}$ is
      i) hydrogen
      ii) alkyl,
      iii) cycloalkyl, or
      iv) —C$_{1-3}$alkaryl,
   d) a 1,3,2-dioxaphosphinane-2-oxide,
   e) a 4H-benzo[d][1,3,2]dioxaphosphinine-2-oxide,
   f) —P*(O)(OR$^{1c}$)~, when Y is —O~, where R$^{1c}$ is defined above,
   g) —P(O)(OH)—O—P(O)(OH)$_2$,
   h) —P(O)(OH)—O—P(O)(OH)—O—P(O)(OH)$_2$,
   i) a C$_{2-7}$acyl,
   j) an aminoacyl,
   k) a C$_{1-6}$-alkylene-oxy-acyl, and
   l) a —C(O)—O—C$_{1-6}$alkyl,
2) R$^2$ is hydrogen;
3) R$^3$ is hydrogen or cyano;
4) Y is selected from among
   a) —OH,
   b) —O~, when R$^1$ is —P(O)(OR$^{1c}$)~, where R$^{1c}$ is defined above,
   c) —O(C$_{2-7}$acyl),
   d) —O(aminoacyl), and
   e) —O(C$_{1-6}$-alkylene-oxyC$_{2-7}$acyl);
5) X is —O—;

6) 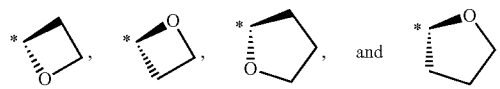 is selected from among

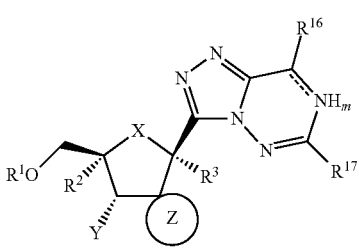

where * represents the point of attachment to the 2'-carbon; and
7a) m is 0, ----- is a double-bond,
   7a1) R$^{16}$ is selected from among
      i) —NH$_2$,
      ii) —NH(C$_{1-6}$alkyl),
      iii) —NH(C$_{2-7}$acyl),
      iv) —O(C$_{1-6}$alkyl),
      v) —O(C$_{2-7}$acyl),
      vi) —O(C$_{1-6}$alkyleneoxyacyl), and
      vii) —O—C(O)—O—C$_{1-6}$alkyl,
      viii) —S(C$_{1-6}$alkyl), and
      ix) —OC$_{1-3}$alkaryl,
   7a2) R$^{17}$ is selected from among
      i) hydrogen,
      ii) —NH$_2$ and
      iii) —NH(C$_{1-6}$alkyl), or
7b) m is 1, ----- is a single-bond,
   7b1) R$^{16}$ is =O;
   7b2) R$^{17}$ is selected from among
      i) —NH$_2$ and
      ii) —NH(C$_{1-6}$alkyl) and
7c) independent of the value of m, R$^{14}$ is selected from among
      i) hydrogen,
      ii) halo,
      iii) cyano,
      iv) —C(O)NH$_2$,
      iv) C$_{1-6}$alkyl,
      vii) vinyl, and
      viii) ethynyl.

A twenty-fourth aspect of the third embodiment is directed to a compound or its stereoisomer or its salt or its metabolite or its deuteride thereof represented by formula I-3-11

I-3-11 wherein
1) R$^1$ is selected from among:
   a) hydrogen,
   b) —P(O)(OH)$_2$,
   c) —P*(O)(OR$^{1a}$)(NHCHR$^{1b}$C(O)OR$^{1c}$),
   wherein
   R$^{1a}$ is
      i) hydrogen or
      ii) aryl, $R^{1b}$ is
  i) hydrogen or
  ii) $C_{1-6}$alkyl, and
$R^{1c}$ is
  i) hydrogen
  ii) alkyl,
  iii) cycloalkyl, or
  iv) —$C_{1-3}$alkaryl,
d) a 1,3,2-dioxaphosphinane-2-oxide,
e) a 4H-benzo[d][1,3,2]dioxaphosphinine-2-oxide,
f) —P*(O)(OR$^{1c}$)~, when Y is —O~, where $R^{1c}$ is defined above,
g) —P(O)(OH)—O—P(O)(OH)$_2$,
h) —P(O)(OH)—O—P(O)(OH)—O—P(O)(OH)$_2$,
i) a $C_{2-7}$acyl,
j) an aminoacyl,
k) a $C_{1-6}$-alkylene-oxy-acyl, and
l) a —C(O)—O—$C_{1-6}$alkyl,
2) $R^2$ is hydrogen;
3) $R^3$ is hydrogen or cyano;
4) Y is selected from among
  a) —OH,
  b) —O~, when $R^1$ is —P(O)(OR$^{1c}$)~, where $R^{1c}$ is defined above,
  c) —O($C_{2-7}$acyl),
  d) —O(aminoacyl), and
  e) —O($C_{1-6}$-alkylene-oxy$C_{2-7}$acyl);
5) X is —O—;
6)  is selected from among

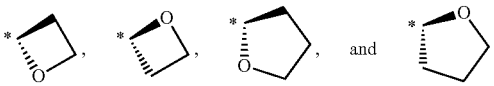

where * represents the point of attachment to the 2'-carbon; and
7a) m is 0, ----- is a double-bond,
  7a1) $R^{16}$ is selected from among
    i) —NH$_2$,
    ii) —NH($C_{1-6}$alkyl),
    iii) —NH($C_{2-7}$acyl),
    iv) —O($C_{1-6}$alkyl),
    v) —O($C_{2-7}$acyl),
    vi) —O($C_{1-6}$alkyleneoxyacyl),
    vii) —O—C(O)—O—$C_{1-6}$alkyl,
    viii) —S($C_{1-6}$alkyl), and
    ix) —O$C_{1-3}$alkaryl, and
  7a2) $R^{17}$ is selected from among
    i) hydrogen,
    ii) —NH$_2$ and
    iii) —NH($C_{1-6}$alkyl), or
7b) m is 1, ----- is a single-bond,
  7b1) $R^{16}$ is =O;
  7b2) $R^{17}$ is selected from among
    i) —NH$_2$ and
    ii) —NH($C_{1-6}$alkyl).

A twenty-fifth aspect of the third embodiment is directed to a compound or its stereoisomer or its salt or its metabolite or its deuteride thereof represented by formula I-3-12

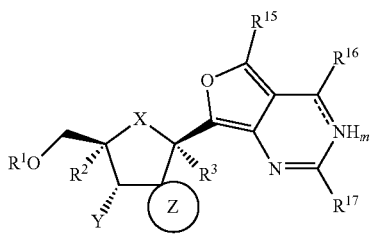

I-3-12 wherein
1) $R^1$ is selected from among:
  a) hydrogen,
  b) —P(O)(OH)$_2$,
  c) —P*(O)(OR$^{1a}$)(NHCHR$^{1b}$C(O)OR$^{1c}$),
  wherein
  $R^{1a}$ is
    i) hydrogen or
    ii) aryl,
  $R^{1b}$ is
    i) hydrogen or
    ii) $C_{1-6}$alkyl, and
  $R^{1c}$ is
    i) hydrogen
    ii) alkyl,
    iii) cycloalkyl, or
    iv) —$C_{1-3}$alkaryl,
  d) a 1,3,2-dioxaphosphinane-2-oxide,
  e) a 4H-benzo[d][1,3,2]dioxaphosphinine-2-oxide,
  f) —P*(O)(OR$^{1c}$)~, when Y is —O~, where $R^{1c}$ is defined above,
  g) —P(O)(OH)—O—P(O)(OH)$_2$,
  h) —P(O)(OH)—O—P(O)(OH)—O—P(O)(OH)$_2$,
  i) a $C_{2-7}$acyl,
  j) an aminoacyl,
  k) a $C_{1-6}$-alkylene-oxy-acyl, and
  l) a —C(O)—O—$C_{1-6}$alkyl,
2) $R^2$ is hydrogen;
3) $R^3$ is hydrogen or cyano;
4) Y is selected from among
  a) —OH,
  b) —O~, when $R^1$ is —P(O)(OR$^{1c}$)~, where $R^{1c}$ is defined above,
  c) —O($C_{2-7}$acyl),
  d) —O(aminoacyl), and
  e) —O($C_{1-6}$-alkylene-oxy$C_{2-7}$acyl);
5) X is —O—;
6)  is selected from among

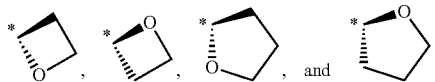

where * represents the point of attachment to the 2'-carbon; and
7a) m is 0, ----- is a double-bond,
  7a1) $R^{16}$ is selected from among
    i) —NH$_2$,
    ii) —NH($C_{1-6}$alkyl),
    iii) —NH($C_{2-7}$acyl),
    iv) —O($C_{1-6}$alkyl), v) —O($C_{2-7}$acyl),
vi) —O($C_{1-6}$alkyleneoxyacyl),
vii) —O—C(O)—O—$C_{1-6}$alkyl,
viii) —S($C_{1-6}$alkyl), and
ix) —O$C_{1-3}$alkaryl,
7a2) $R^{17}$ is selected from among
  i) hydrogen,
  ii) —$NH_2$ and
  iii) —NH($C_{1-6}$alkyl), or
7b) m is 1, ----- is a single-bond,
  7b1) $R^{16}$ is =O;
  7b2) $R^{17}$ is selected from among
    i) —$NH_2$ and
    ii) —NH($C_{1-6}$alkyl) and
7c) independent of the value of m, $R^{15}$ is selected from among
  i) hydrogen,
  ii) halo,
  iii) cyano,
  iv) —C(O)$NH_2$,
  iv) $C_{1-6}$alkyl,
  vii) vinyl, and
  viii) ethynyl.

A twenty-sixth aspect of the third embodiment is directed to a compound or its stereoisomer or its salt or its metabolite or its deuteride thereof represented by formula I-3-13

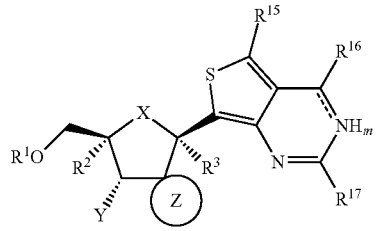

I-3-13 wherein
1) $R^1$ is selected from among:
  a) hydrogen,
  b) —P(O)(OH)$_2$,
  c) —P*(O)(O$R^{1a}$)(NHCH$R^{1b}$C(O)O$R^{1c}$),
    wherein
    $R^{1a}$ is
      i) hydrogen or
      ii) aryl,
    $R^{1b}$ is
      i) hydrogen or
      ii) $C_{1-6}$alkyl, and
    $R^{1c}$ is
      i) hydrogen
      ii) alkyl,
      iii) cycloalkyl, or
      iv) —$C_{1-3}$alkaryl,
  d) a 1,3,2-dioxaphosphinane-2-oxide,
  e) a 4H-benzo[d][1,3,2]dioxaphosphinine-2-oxide,
  f) —P*(O)(O$R^{1c}$)~, when Y is —O~, where $R^{1c}$ is defined above,
  g) —P(O)(OH)—O—P(O)(OH)$_2$,
  h) —P(O)(OH)—O—P(O)(OH)—O—P(O)(OH)$_2$,
  i) a $C_{2-7}$acyl,
  j) an aminoacyl,
  k) a $C_{1-6}$-alkylene-oxy-acyl, and
  l) a —C(O)—O—$C_{1-6}$alkyl, 2) $R^2$ is hydrogen;
3) $R^3$ is hydrogen or cyano;
4) Y is selected from among
  a) —OH,
  b) —O~, when $R^1$ is —P(O)(O$R^{1c}$)~, where $R^{1c}$ is defined above,
  c) —O($C_{2-7}$acyl),
  d) —O(aminoacyl), and
  e) —O($C_{1-6}$-alkylene-oxy$C_{2-7}$acyl);
5) X is —O—;

6) 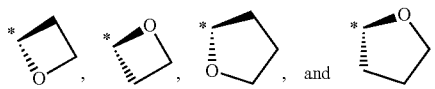 is selected from among where * represents the point of attachment to the 2'-carbon; and 7a) m is 0, ----- is a double-bond,
  7a1) $R^{16}$ is selected from among
    i) —$NH_2$,
    ii) —NH($C_{1-6}$alkyl),
    iii) —NH($C_{2-7}$acyl),
    iv) —O($C_{1-6}$alkyl),
    v) —O($C_{2-7}$acyl),
    vi) —O($C_{1-6}$alkyleneoxyacyl),
    vii) —O—C(O)—O—$C_{1-6}$alkyl,
    viii) —S($C_{1-6}$alkyl), and
    ix) —O$C_{1-3}$alkaryl,
  7a2) $R^{17}$ is selected from among
    i) hydrogen,
    ii) —$NH_2$ and
    iii) —NH($C_{1-6}$alkyl), or
7b) m is 1, ----- is a single-bond,
  7b1) $R^{16}$ is =O;
  7b2) $R^{17}$ is selected from among
    i) —$NH_2$ and
    ii) —NH($C_{1-6}$alkyl) and
7c) independent of the value of m, $R^{15}$ is selected from among
  i) hydrogen,
  ii) halo,
  iii) cyano,
  iv) —C(O)$NH_2$,
  iv) $C_{1-6}$alkyl,
  vii) vinyl, and
  viii) ethynyl.

Dosage, Administration, and Use

In the embodiments of this section, the expression "Compound I" is meant to encompass a compound or its stereoisomer or its salt or its metabolite or its deuteride thereof represented by formula I notwithstanding the excluded subject matter found in the Definitions.

A fourth embodiment is directed to a composition comprising compound I.

A first aspect of the fourth embodiment is directed to a composition for treating a subject infected with any one of hepatitis C virus, hepatitis B virus, Hepatitis A virus, West Nile virus, yellow fever virus, dengue virus, rhinovirus, polio virus, bovine viral diarrhea virus, Japanese encephalitis virus, or those viruses belonging to the groups of Pestiviruses, hepaciviruses, or flavaviruses, said composition comprising an effective amount of compound I.

A second aspect of the fourth embodiment is directed to a composition for treating a subject infected with a hepatitis C virus, which comprises an effective amount of compound I and optionally a pharmaceutically acceptable medium.

A third aspect of the fourth embodiment is directed to a composition for treating a subject infected with a dengue virus, which comprises an effective amount of compound I and optionally a pharmaceutically acceptable medium.

A fourth aspect of the fourth embodiment is directed to a composition for treating a subject infected with any one of a hepatitis B virus, a Hepatitis A virus, a West Nile virus, a yellow fever virus, a rhinovirus, polio virus, a bovine viral diarrhea virus, and a Japanese encephalitis virus, which comprises an effective amount of compound I and a pharmaceutically acceptable medium.

A fifth aspect of the fourth embodiment is directed to a composition for treating a subject infected with a hepatitis C virus, which comprises an effective amount of compound I and a pharmaceutically acceptable medium.

A sixth aspect of the fourth embodiment is directed to a composition for treating a subject infected with a dengue virus, which comprises an effective amount of compound I and a pharmaceutically acceptable medium.

A seventh aspect of the fourth embodiment is directed to a composition for treating a subject infected with a virus from any one of viruses belonging to the groups of Pestiviruses, hepaciviruses, or flavaviruses, which comprises an effective amount of compound I and a pharmaceutically acceptable medium.

Compound I may be independently formulated in a wide variety of oral administration dosage forms and carriers. Oral administration can be in the form of tablets, coated tablets, hard and soft gelatin capsules, solutions, emulsions, syrups, or suspensions. Compound I is efficacious when administered by suppository administration, among other routes of administration. The most convenient manner of administration is generally oral using a convenient daily dosing regimen which can be adjusted according to the severity of the disease and the patient's response to the antiviral medication.

Compound I together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w).

As noted above, the term "effective amount" as used herein means an amount required to reduce symptoms of the disease in a subject. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.3, 0.4, 0.5, 0.6, 0.7 0.75, 0.8, 0.9, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on knowledge, experience and the disclosures of this application, to ascertain a effective amount of the compound disclosed herein for a given disease and patient.

Compound I can be administered alone but will generally be administered in admixture with one or more suitable pharmaceutical excipients, diluents or carriers selected with regard to the intended route of administration and standard pharmaceutical practice.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; US 2002/0142050; US 2004/0224917; US 2005/0048116; US 2005/0058710; US 2006/0034937; US 2006/0057196; US 2006/0188570; US 2007/0026073; US 2007/0059360; US 2007/0077295; US 2007/0099902; US 2008/0014228; U.S. Pat. No. 6,267,985; U.S. Pat. No. 6,294,192; U.S. Pat. No. 6,383,471; U.S. Pat. No. 6,395,300; U.S. Pat. No. 6,569,463; U.S. Pat. No. 6,635,278; U.S. Pat. No. 6,645,528; U.S. Pat. No. 6,923,988; U.S. Pat. No. 6,932,983; U.S. Pat. No. 7,060,294; and U.S. Pat. No. 7,462,608.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

Compound I may be independently formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

Compound I may be independently formulated for vaginal administration. Pessaries, tampons, creams, gels, pastes, foams or sprays containing in addition to the active ingredient such carriers as are known in the art to be appropriate. Certain of these formulations may also be used in conjunction with a condom with or without a spermicidal agent.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering compositions containing the compounds contemplated herein unstable or compromising their therapeutic activity.

Additionally, compound I may be independently formulated in conjunction with liposomes, micelles, or complexed to or entrapped in a protein matrix, such as albumin. As to liposomes, it is contemplated that the compound I can be formulated in a manner as disclosed in U.S. Pat. Nos. 4,797,285; 5,013,556; 5,077,056; 5,077,057; 5,154,930; 5,192,549; 5,213,804; 5,225,212; 5,277,914; 5,316,771; 5,376,380; 5,549,910; 5,567,434; 5,736,155; 5,827,533; 5,882,679; 5,891,468; 6,060,080; 6,132,763; 6,143,321; 6,180,134; 6,200,598; 6,214,375; 6,224,903; 6,296,870; 6,653,455; 6,680,068; 6,726,925; 7,060,689; and 7,070,801. As to micelles, it is contemplated that compound I can be formulated in a manner as disclosed in U.S. Pat. Nos. 5,145,684 and 5,091,188. As to a protein matrix, it is contemplated that compound I can be complexed to or entrapped in a protein matrix as disclosed in any one of U.S. Pat. Nos. 5,439,686; 5,498,421; 6,096,331; 6,506,405; 6,537,579; 6,749,868; 6,753,006; and 7,820,788.

A fifth embodiment is directed to a use of compound I for the manufacture of a medicament for the treatment of any condition the result of an infection by any one of the following viral agents: hepatitis C virus, West Nile virus, yellow fever virus, dengue virus, rhinovirus, polio virus, hepatitis A virus, bovine viral diarrhea virus and Japanese encephalitis virus.

A first aspect of the fifth embodiment is directed to a use of compound I for the manufacture of a medicament for the treatment of a hepatitis C virus.

A second aspect of the fifth embodiment is directed to a use of compound I for the manufacture of a medicament for the treatment of a dengue virus.

A third aspect of the fifth embodiment is directed to a use of compound I for the manufacture of a medicament for the treatment of any condition the result of an infection by any one of the following viral agents: a West Nile virus, a yellow fever virus, a rhinovirus, a polio virus, a hepatitis A virus, a bovine viral diarrhea virus, and a Japanese encephalitis virus.

A fourth aspect of the fifth embodiment is directed to a use of compound I for the manufacture of a medicament for the treatment of any condition the result of an infection by a viral agent from any one of viruses belonging to the groups of Pestiviruses, hepaciviruses, or flavaviruses.

As noted above, the term "medicament" means a substance used in a method of treatment and/or prophylaxis of a subject in need thereof, wherein the substance includes, but is not limited to, a composition, a formulation, a dosage form, and the like, comprising compound I. It is contemplated that the use of any of compound I for the manufacture of a medicament for the treatment of any of the antiviral conditions disclosed herein, either alone or in combination with another compound disclosed herein. A medicament includes, but is not limited to, any one of the compositions contemplated by the fourth embodiment disclosed herein.

A sixth embodiment is directed to a method of treating a subject infected with any one of a hepatitis C virus, a West Nile virus, a yellow fever virus, a degue virus, a rhinovirus, a polio virus, a hepatitis A virus, a bovine viral diarrhea virus, a Japanese encephalitis virus or those viruses belonging to the groups of Pestiviruses, hepaciviruses, or flavaviruses, said method comprising administering an effective amount of compound I to the subject.

A first aspect of the sixth embodiment is directed to a method of treating a subject infected with a hepatitis C virus, said method comprising administering an effective amount of compound I to the subject.

A second aspect of the sixth embodiment is directed to a method of treating a subject infected with a dengue virus, said method comprising administering an effective amount of compound I to the subject. A third aspect of the sixth embodiment is directed to a method of treating a subject injected with any one of a West Nile virus, a yellow fever virus, a rhinovirus, a polio virus, a hepatitis A virus, a bovine viral diarrhea virus, a Japanese encephalitis virus or those viruses belonging to the groups of Pestiviruses, hepaciviruses, or flavaviruses, said method comprising administering an effective amount of compound I to the subject.

It is intended that a subject in need thereof is one that has any condition the result of an infection by any of the viral agents disclosed herein, which includes, but is not limited to, a hepatitis C virus, a West Nile virus, a yellow fever virus, a dengue virus, a rhinovirus, a polio virus, a hepatitis A virus, a bovine viral diarrhea virus or a Japanese encephalitis virus; flaviviridae viruses or pestiviruses or hepaciviruses or a viral agent causing symptoms equivalent or comparable to any of the above-listed viruses.

As noted above, the term "subject" means a mammal, which includes, but is not limited to, cattle, pigs, sheep, buffalo, llama, dogs, cats, mice, rats, monkeys, and humans, preferably the subject is a human. It is contemplated that in the method of treating a subject thereof of the ninth embodiment can be any of the compounds contemplated herein, either alone or in combination with another compound disclosed herein.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A fourth aspect of the sixth embodiment is directed to a method of treating a subject infected with hepatitis C virus or a subject infected with a dengue virus, said method comprising administering to the subject an effective amount of compound I and an effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours. It will be understood that the effective amount of compound I and the effective amount of another antiviral agent can be formulated in the same dosage form or formulated in separate dosage forms.

A fifth aspect of the sixth embodiment comprises adding to the 3'-terminus of an HCV RNA strand or a DENV RNA strand a radical or its salt thereof represented by

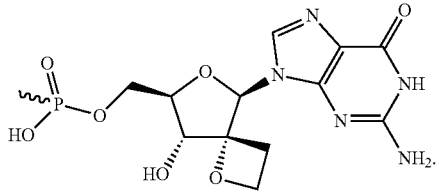

where ~~~~ is the point of attachment to the 3'-terminus. It is understood that addition of said compound to the nascent RNA strand will prevent or substantially increase the likelihood that propagation of the RNA strand having said compound added thereto will come to an end.

A seventh aspect of the sixth embodiment comprises increasing an intracellular concentration of a triphosphate ($P_3$) compound or its salt thereof represented by

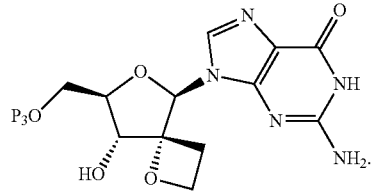

in a cell infected with HCV or DENV.

When compound I is administered in combination with another antiviral agent the activity may be increased over the activity exhibited for compound I alone. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions.

Examples of "another antiviral agent" include, but are not limited to: HCV NS3 protease inhibitors (see EP 1881001, US 2003/0187018, US 2005/0267018, US 2003/0119752, US 2003/0187018, US 2005/0090432, US 2009/0291902, US 2005/0267018, US 2005/0267018, US 2011/0237621, US 2009/0281141, US 2009/0105302, US 2009/0062311, US 2009/0281140, US 2007/0054842, US 2008/0108617, and US 2008/0108617); HCV NS5B Inhibitors (see US 2004/0229840, US 2005/0154056, US 2005/0098125, US 2006/0194749, US 2006/0241064, US 2006/0293306, US 2006/0040890, US 2006/0040927, US 2006/0166964, US 2007/0275947, U.S. Pat. No. 6,784,166, US 2007/0275930, US 2002/0147160, US 2002/0147160, US 2003/0176433, US 2004/0024190, US 2005/0043390, US 2005/0026160, US 2004/0171570, US 2005/0130923, US 2008/0146788, US 2007/0123484, US 2007/0024277, US 2007/0004669, US 2004/0142989, US 2004/0142993, US 2006/0004063, US 2006/0234962, US 2007/0231318, US 2007/0142380, WO 2004/096210, US 2007/0135363, WO 2005/103045, US 2008/0021047, US 2007/0265222, US 2006/0046983, US 2008/0280842, WO 2006065590, US 2006/0287300, WO 2007039142, WO 2007039145, US 2007/0232645, US 2007/0232627, WO 2007088148, WO 2007092000, and US 2010/0234316); HCV NS4 Inhibitors (see US 2005/0228013 and US 2007/0265262); HCV NS5A Inhibitors (see US 2006/0276511, US 2007/0155716, US 2008/0182863, US 2009/0156595, and US 2008/0182863); Toll-like receptor agonists (see US 2007/0197478); and other inhibitors (see US 2003/0207922, US 2006/0094706, US 2006/0122154, US 2005/0069522, US 2005/0096364, US 2005/0069522, US 2005/0096364, and US 2005/0215614); PSI-6130 (U.S. Pat. No. 7,429,572); RG7128 (U.S. Pat. No. 7,754,699); Compound A (disclosed in US 2010/0081628, see also compound 19a (PSI-938) and 19b disclosed in the same application, which are individual diastereomers of compound A); PSI-7977 (U.S. Pat. No. 7,964,580, claim 8) and PSI-7976 (disclosed in US 2010/0016251 and US 2010/0298257 (Ser. No. 12/783,680) (PSI-7977 (Sp-4) and PSI-7976 (Rp-4)); PSI-353661 (disclosed in US 2010/0279973, see compound II); telaprevir (also known as VX-950, which is disclosed in US 2010/0015090); boceprevir (disclosed in US 2006/0276405); BMS-790052 (disclosed in US 2008/0050336, see also US 2009/0041716); ITMN-191 (disclosed in US 2009/0269305 at Example 62-1); ANA-598 (shown below and identified as compound 31 in F. Ruebasam et al. Biorg. Med. Chem. Lett. (2008) 18:3616-3621; and TMC435 (formerly known as TMC435350).

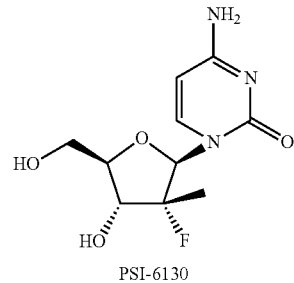
PSI-6130

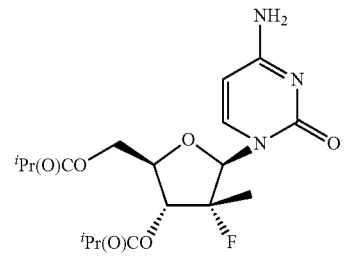
RG7128

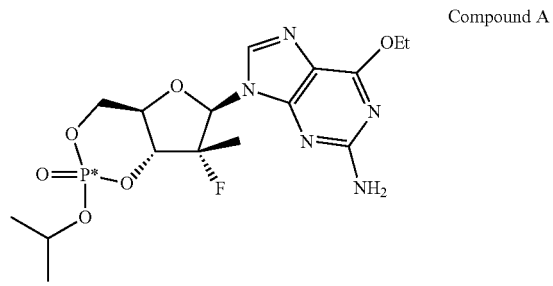
Compound A

-continued

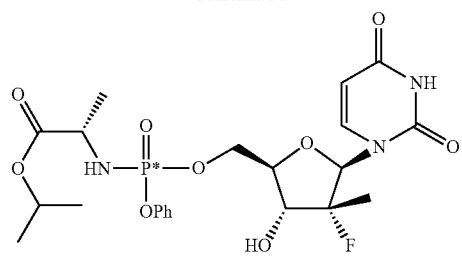

PSI-7977 (Sp-diastereomer)
PSI-7976 (Rp-diastereomer)

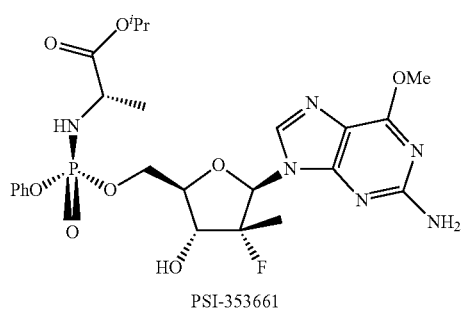

PSI-353661

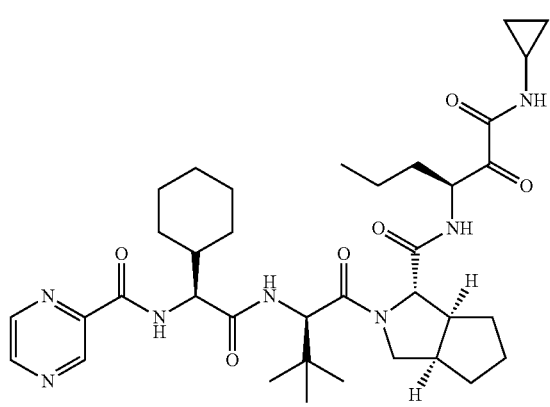

Telaprevir (VX-950)

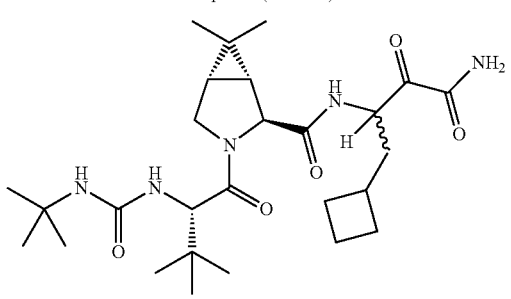

Boceprevir

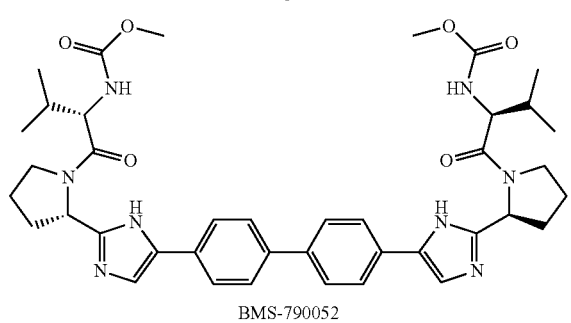

BMS-790052

-continued

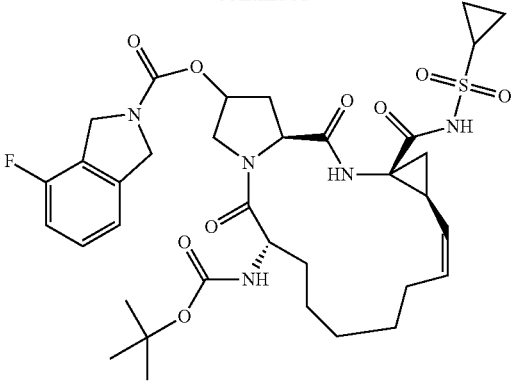

ITMN-191

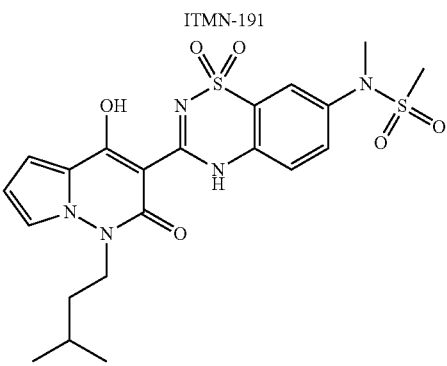

ANA-598

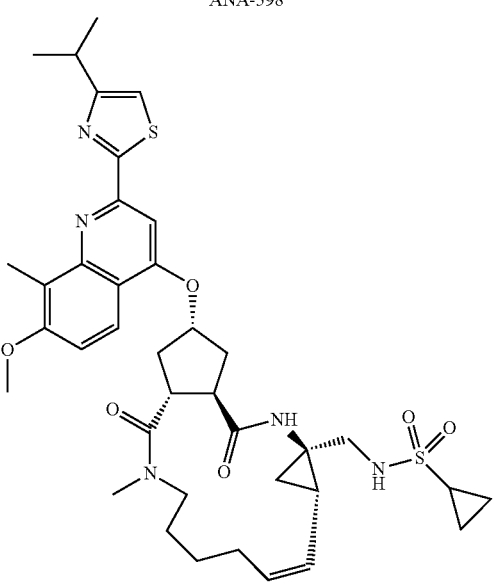

TCM435

The antiviral agents can be formulated in a manner known to one of ordinary skill. The respective patent documents provide guidance for the respective formulations. The preferred dosage forms of the antiviral agents are those that are approved by the FDA. However, not to be limited, contemplated dosage forms of the antiviral agents are contemplated as follows: RG7128 (500 mg, 1000 mg, or 1500 mg); Compound A (5 mg to 1000 mg and values inbetween); PSI-7977 (100 mg, 200 mg, or 400 mg); A dosage form for VX-950 is disclosed in McHutchison et al. N. Engl. J. Med. (2009) 360(18): 1827-1838; see also WO 2009/038663; Boceprevir (WO 2009/038663).

Additional examples of "another antiviral agent" and contemplated dosages are identified in the following table.

| Drug Name | Drug Category | Company | Clinical Phase | Dosage |
|---|---|---|---|---|
| RG7128 | Polymerase Inhibitor | Roche in collaboration with Pharmasset | Phase I | 500 mg BID, 100 mg BID |
| RG7227 | Protease Inhibitor | Roche in collaboration with Pharmasset | Phase I | 100 mg TID, 200 mg TID |
| Telaprevir (VX-950) | Protease Inhibitor | Vertex | Phase II | N/A |
| VX-222 | Polymerase Inhibitor | Vertex | Phase II | N/A |
| BMS 790052 | NS5a Inhibitor | Bristol-Myers Squibb | Phase II | 60 mg once a day or 600 mg twice a day |
| BMS 65032 | Protease Inhibitor | Bristol-Myers Squibb | Phase II | 60 mg once a day or 600 mg twice a day |
| BMS-824393 | NS5A Inhibitor | Bristol-Myers Squibb | Phase I | N/A |
| INX-189 | HCV Polymerase Inhibitor | Inhibitex | Phase I | from 3 mg to 100 mg, once a day |
| PSI-938 | Polymerase Inhibitor | Pharmasset | Phase I | 300 mg once a day |
| PPI-461 | NS5A Inhibitor | Presidio Pharmaceuticals | Phase I | four single doses followed by a 5-day, once-a-day dose |
| IDX375 | Polymerase Inhibitor | Idenix | Phase I | 25 mg once daily (QD), 50 mg QD, 100 mg QD, 200 mg QD, or 200 mg twice a day |
| ABT-072 | Polymerase Inhibitor | Abbott | Phase I | N/A |
| Clemizole | NS4B Inhibitor | Eiger BioPharmaceuticals | Phase I | N/A |
| MK-3281 | Polymerase Inhibitor | Merck | Phase I | N/A |
| PSI-7851 | Polymerase Inhibitor | Pharmasset | Phase I | 50 mg, 100 mg, 200 mg, or 400 mg |
| ABT-450 HCV | Protease Inhibitor | Abbott/Enanta | Phase I | N/A |
| VX-813 | Protease Inhibitor | Vertex | Phase I | N/A |
| PHX1766 | Protease Inhibitor | Phenomix | Phase I | 400 mg BID or 800 mg BID |
| ABT-333 | Polymerase Inhibitor | Abbott | Phase I | N/A |
| VX-916 | HCV Polymerase Inhibitor | Vertex | Phase I | N/A |
| RG7128 | Polymerase Inhibitor | Pharmasset/Genentech | Phase I | 500 or 100 mg BID |
| VX-500 | HCV Protease Inhibitor | Vertex | Phase I | N/A |
| Filibuvir (PF-00868554) | HCV Polymerase Inhibitor | Pfizer | Phase II | 200, 300, or 0500 mg BID (twice a day) |
| ACH-1625 | Protease Inhibitor | Achillion | Phase II | 200 or 600 mg |
| GS-9256 | Protease Inhibitor | Gilead | Phase II | N/A |
| BI 201335 | Protease Inhibitor | Boehringer Ingelheim Pharma | Phase II | 240 mg (once-a-day) or 240 mg (twice-a-day) |
| VX-222 | Polymerase Inhibitor | Vertex | Phase II | 250, 500, or 750 mg twice-a-day; 1500 mg once-a-day |
| RG7227 (Danoprevir) | Protease Inhibitor | InterMune/Genentech | Phase II | N/A |

-continued

| Drug Name | Drug Category | Company | Clinical Phase | Dosage |
|---|---|---|---|---|
| ANA598 | Polymerase Inhibitor | Anadys Pharmaceuticals | Phase II | First day 800 mg BID, followed by 200 or 400 mg twice daily |
| Vaniprevir (MK-7009) | HCV Protease Inhibitor | Merck | Phase II | 300 or 600 mg twice a day; 300 or 600 mg once-a-day |
| A-832 | NS5A Inhibitor | ArrowTherapeutics | Phase II | N/A |
| GS 9190 | Polymerase Inhibitor | Gilead | Phase II | N/A |
| VX-759 | Polymerase Inhibitor | Vertex | Phase II | 400 mg TID, 800 mg BID, or 800 mg TID |
| SCH900518 (Narlaprevir) | Protease Inhibitor | Schering/Merck | Phase II | N/A |
| BI 207127 | Polymerase Inhibitor | Boehringer Ingelheim Pharma | Phase II | N/A |
| PSI-7977 | Polymerase Inhibitor | Pharmasset | Phase IIa | 100, 200, or 400 mg once-a-day |
| TMC435 | Protease Inhibitor | Medivir/Tibotec | Phase IIa | N/A |
| BMS 791325 | Polymerase Inhibitor | Bristol-Myers Squibb | Phase IIa | N/A |
| BMS 650032 | Protease Inhibitor | Bristol-Myers Squibb | Phase IIa/b | N/A |
| BMS 790052 | NS5a Inhibitor | Bristol-Myers Squibb | Phase IIb | N/A |
| Boceprevir (SCH 503034) | Protease Inhibitor | Schering | Phase III | 800 mg three times a day |
| Telaprevir (VX 950) | Protease Inhibitor | Vertex | Phase III | 750 mg every 8 hours; 1125 mg dose every 12 hours; |
| BMS-824393 | Type Unknown | Bristol-Myers Squibb | Phase I | N/A |
| SCY-635 | Cyclophilin Inhibitor | SCYNEXIS | Phase I | up to 900 mg/day |
| ANA773 | TLR Agonist | Anadys Pharmaceuticals | Phase I | 800, 1200, 1600, or 200 mg every other day |
| CYT107 | Immunomodulator | Cytheris | Phase I | N/A |
| CF102 | A3AR Agonist | CAN-FITE | Phase I | N/A |
| IMO-2125 | TLR9 Agonist | Idera Pharmaceuticals | Phase I | N/A |
| Bavituximab (formerly Tarvacin) | Anti-Phospholipid Therapy | Peregrine | Phase I | N/A |
| NOV-205 | Immunomodulator | Novelos Therapeutics | Phase I | N/A |
| SD-101 | TLR9 Agonist | Dynavax | Phase Ib | N/A |
| Miravirsen Formerly (SPC3649-LNA-antimiR ™-122) | microRNA | Santaris Pharma | Phase II | up to 12 mg/kg |
| CTS-1027 | Anti-inflammatory | Conatus | Phase II | N/A |
| Oglufanide disodium | Immunomodulator | Implicit Bioscience | Phase II | N/A |
| Alinia (nitazoxanide) | Thiazolides | Romark | Phase II | 500 mg twice daily |
| SCV-07 | Broad Spectrum Immune Stimulator | SciClone | Phase II | N/A |
| MitoQ (mitoquinone) | Inflammation/ Fibrosis Inhibitor | Antipodean Pharmaceuticals | Phase II | N/A |
| Debio 025 | Cyclophilin Inhibitor | Debio | Phase II | 600 to 1000 mg/day |
| PF-03491390 (Formerly IDN-6556) | Pancaspase Inhibitor | Pfizer Pharmaceuticals | Phase II | 5 mg to 400 mg daily (given 1 to 3 times a day) |

According to the FDA-approved label dated Oct. 8, 2010, the recommended dose of COPEGUS (ribavirin) tablets depends on body weight and the HCV genotype to be treated, as shown in the following table.

| HCV Genotype | PEGASYS Dose* | COPEGUS Dose | Duration |
|---|---|---|---|
| Genotypes 1, 4 | 180 μg | <75 kg = 1000 mg | 48 weeks |
|  |  | ≥75 kg = 1200 mg | 48 weeks |
| Genotypes 2, 3 | 180 μg | 800 mg | 24 weeks |

Genotypes 2 and 3 showed no increased response to treatment beyond 24 weeks.
*See PEGASYS Package Insert for further details on PEGASYS dosing and administration.

The COPEGUS label further discloses that the recommended duration of treatment for patients previously untreated with ribavirin and interferon is 24 to 48 weeks. The daily dose of COPEGUS is 800 mg to 1200 mg administered orally in two divided doses. The dose should be individualized to the patient depending on baseline disease characteristics (e.g., genotype), response to therapy, and tolerability of the regimen.

An eighth embodiment is directed to a compound or a salt thereof represented by formula A,

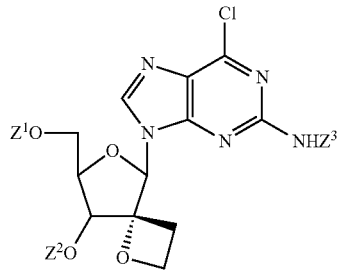

A wherein each one of $Z^1$, $Z^2$, and $Z^3$ is hydrogen or a protecting group (PG).

In a first aspect of the eighth embodiment, PG is selected from among —C(O)alkyl, —C(O)aryl, —C(O)O($C_{1-6}$alkyl), —C(O)O($C_{1-6}$alkylene)aryl, —C(O)Oaryl, —CH$_2$O-alkyl, —CH$_2$O-aryl, —SO$_2$-alkyl, —SO$_2$-aryl, and a silicon-containing protecting group. One of ordinary skill will appreciate that $Z^1$ and $Z^2$ can be the same, while $Z^3$ is different or that $Z^1$ and $Z^2$ are a part of the same radical, such as in the instance of ~Si($C_{1-6}$alkyl)$_2$OSi($C_{1-6}$alkyl)$_2$~, which would be derived from, for example, a 1,3-dihalo-1,1,3,3-tetra($C_{1-6}$alkyl)disiloxane.

In a second aspect of the eighth embodiment, PG is selected from among, benzoyl, acetyl, —C(O)OCH$_2$Ph, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl), 9-(p-methoxyphenyl)xanthine-9-yl (MOX), tert-butyldimethylsilyl, tert-butyldiphenylsilyl, and ~Si($C_{1-6}$alkyl)$_2$OSi($C_{1-6}$alkyl)$_2$OH, such as, —Si($^i$Pr)$_2$OSi($^i$Pr)$_2$OH or ~Si($^i$Pr)$_2$OSi($^i$Pr)$_2$~.

In a third aspect of the eighth embodiment, each of $Z^1$, $Z^2$, and $Z^3$ is hydrogen.

In a fourth aspect of the eighth embodiment, each of $Z^1$ and $Z^2$ is hydrogen and $Z^3$ is benzoyl.

In a fifth aspect of the eighth embodiment, $Z^1$ and $Z^2$ are comprised of ~Si($^i$Pr)$_2$OSi($^i$Pr)$_2$~ and $Z^3$ is hydrogen or benzoyl.

A ninth embodiment is directed to a process for preparing a compound represented by formula I-3-4'

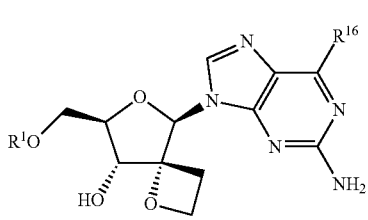

I-3-4' wherein $R^1$ is as defined for compound I-3-4
or
a compound represented by formula I-3-5',

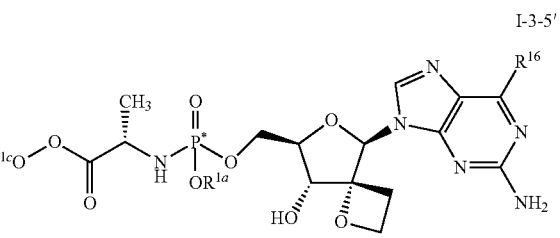

I-3-5' wherein $R^{1a}$, $R^{1c}$, are as defined for compound I-3-5
said process comprising
reacting compound A' with a nucleophile and optionally deprotecting to obtain compound B'

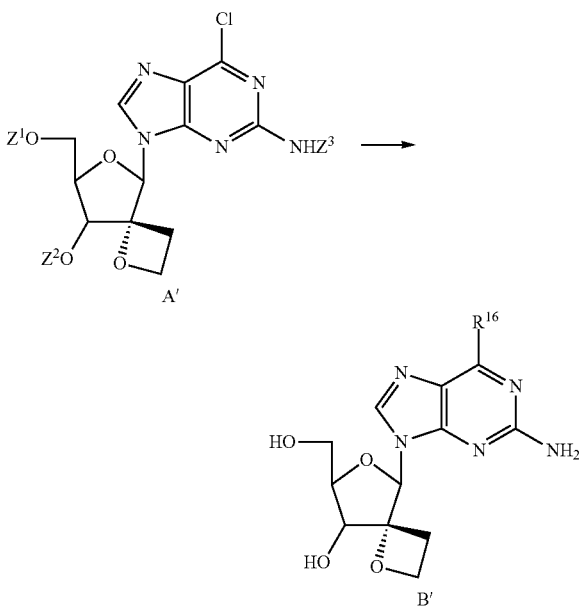

wherein the nucleophile is comprised of a radical selected from among —O($C_{1-6}$alkyl), —O$C_{1-3}$alkaryl, —S($C_{1-6}$alkyl), —NH($C_{1-6}$alkyl), and -cycloalkylamino, and wherein each one of $Z^1$, $Z^2$, and $Z^3$ is hydrogen or a protecting group (PG) and reacting B' with an appropriate reagent to obtain either I-3-4' or I-3-5'.

Conditions for converting B' to I-3-4' are as described herein. Conditions for converting B' to I-3-5' are as described herein, e.g., as described in the tenth embodiment.

In a first aspect of the ninth embodiment, the nucleophile is comprised of a $C_{1-6}$alkoxide. The $C_{1-6}$alkoxide is obtained from methanol, ethanol, propanol, i-propanol, n-butanol, i-butanol, s-butanol, t-butanol, n-pentanol, isopentanol, neopentanol, t-pentanol, and hexanol.

In a second aspect of the ninth embodiment, the nucleophile is comprised of a —$OC_{1-3}$alkaryl. The —$OC_{1-3}$alkaryl is obtained from the respective $C_{1-3}$alkaryl alcohol. For example, —$OCF_2Ph$ is obtained from benzylalcohol.

In a third aspect of the ninth embodiment, the nucleophile is comprised of a $C_{1-6}$alkylthiolate. The $C_{1-6}$alkyl thiolate is obtained from methylthiol, ethylthiol, propylthiol, i-propylthiol, n-butylthiol, i-butylthiol, s-butylthiol, t-butylthiol, n-pentylthiol, isopentylthiol, neopentylthiol, t-pentylthiol, and hexylthiol.

In a fourth aspect of the ninth embodiment, the nucleophile is comprised of a —$NH(C_{1-6}$alkyl). The —$NH(C_{1-6}$alkyl) is obtained from methylamine, ethylamine, propylamine, t-propylamine, n-butylamine, z-butylamine, s-butylamine, t-butylamine, n-pentylamine, isopentylamine, neopentylamine, t-pentylamine, and hexylamine.

In a fifth aspect of the ninth embodiment, the nucleophile is comprised of a -cycloalkylamino. The cycloalkylamino is derived from its respective cycloalkylamine.

In a sixth aspect of the ninth embodiment, the nucleophile is comprised of a —$C_{3-6}$cycloalkylamino. The —$C_{3-6}$cycloalkylamino is obtained from cyclopropylamine, 2-methyl-cyclopropylamine, cyclobutylamine, 2-methyl-cyclobutylamine, cyclopentylamine, 2-methyl-cyclopentylamine, cyclohexylamine, 2-methyl-cyclohexylamine, etc.

In solution or in the solid-state the nucleophile, i.e., the $C_{1-6}$alkoxide ($C_{1-6}$alkylO⁻), the $C_{1-3}$alkaryloxide (⁻$O(C_{1-3}$alkaryl), the $C_{1-6}$alkylthiolate ($C_{1-6}$alkylS⁻), the $C_{1-6}$alkylamide ($C_{1-6}$alkylNH⁻), and the cycloalkylamide (cycloalkylNH⁻) (or the $C_{3-6}$cycloalkylamide (⁻$NHC_{3-6}$cycloalkyl)), is associated with a cationic species, M. M is generally an alkali metal cation, such as $Li^+$, $Na^+$, $K^+$, etc. or a tetraalkylammonium, such as tetra-n-butyl-ammonium ("$Bu_4N^+$"). However, M can be other cationic species so long as the association with the nucleophile permits reaction with A.

In each of the first six aspects of the ninth embodiment, the nucleophile can be pre-formed or prepared in situ. A pre-formed nucleophile can be obtained commercially or prepared by procedures known to one of ordinary skill. The so-prepared pre-formed nucleophile can optionally be isolated as a solid or used directly in the reaction of the ninth embodiment. A nucleophile prepared in situ may occur in the presence or absence of compound A. In the instance of a pre-formed nucleophile or a nucleophile prepared in situ, the solvent used depends on the conditions of the reaction. In certain aspects a suitable solvent is a polar aprotic solvent. Examples of polar aprotic solvents include, but are not limited to, DMSO, HMPA, DMF, THF, 2-methyl-THF, dioxane, cyclopentylmethylether, t-butyl-methylether, etc. In other aspects the nucleophile is obtained directly from the solvent. For example, the solvent for the solvent for the first aspect of the ninth embodiment could be an $C_{1-6}$alcohol (e.g., methanol, ethanol, etc.), in which the $C_{1-6}$alkoxide can be obtained according to conventional procedures. Solvents for the second and third aspects of the ninth embodiment include polar aprotic solvent, as well as an alcoholic solvent. The solvent for the fourth aspect of the ninth embodiment could be a $C_{1-6}$alkylamine (e.g., methylamine, ethylamine, etc.), in which the $C_{1-6}$alkylamide is obtained by adding a base having sufficient basicity to obtain the desired nucleophile. Likewise, the solvent for the fifth and sixth aspects of the ninth embodiment could be a cycloalkylamine or a $C_{3-6}$cycloalkylamine (e.g., cyclopropylamine, cyclobutylamine, etc.), in which the cycloalkylamide or the $C_{3-6}$cycloalkylamide is obtained by adding a base having sufficient basicity to obtain the desired nucleophile. The optional deprotection step is done by conventional means.

A seventh aspect of the ninth embodiment is directed to a process for preparing a compound represented by formula I-3-5', which comprises reacting compound A' with a nucleophile to obtain compound B', wherein the nucleophile is comprised of a radical selected from among a —$O(C_{1-6}$alkyl), a —$OC_{1-3}$alkaryl, a —$NH(C_{1-6}$alkyl), and a $C_{3-6}$cycloalkylamino, and wherein for compound I-3-5', $R^{1a}$ and $R^{1c}$ are as defined, and $R^{16}$ is a —$O(C_{1-6}$alkyl). a —$OC_{1-3}$alkaryl, a —$NH(C_{1-6}$alkyl), and a $C_{3-6}$cycloalkylamino.

An eighth aspect of the ninth embodiment is directed to a process for preparing a compound represented by formula I-3-5', which comprises reacting compound A' with a nucleophile to obtain compound B', wherein the nucleophile is comprised of a radical selected from among a —$O(C_{1-6}$alkyl) and a —$OC_{1-3}$alkaryl, and wherein for compound I-3-5', $R^{1a}$ are $R^{1c}$ are as defined, and $R^{16}$ is a —$O(C_{1-6}$alkyl) or a —$OC_{1-3}$alkaryl.

A ninth aspect of the ninth embodiment is directed to a process for preparing a compound represented by formula I-3-5', which comprises reacting compound A' with a nucleophile to obtain compound B', wherein the nucleophile is comprised of a —$O(C_{1-6}$alkyl), and wherein for compound I-3-5', $R^{1a}$ and $R^{1c}$ are as defined, and $R^{16}$ is a —$O(C_{1-6}$alkyl).

A tenth aspect of the ninth embodiment is directed to a process for preparing a compound represented by formula I-3-5', which comprises reacting compound A' with a nucleophile to obtain compound B', wherein the nucleophile is comprised of a —$OC_{1-3}$alkaryl, and wherein for compound I-3-5', $R^{1a}$ and $R^{1c}$ are as defined, and $R^{16}$ is a —$OC_{1-3}$alkaryl.

In an eleventh aspect of the ninth embodiment, PG is selected from among —C(O)alkyl, —C(O)aryl, —C(O)O($C_{1-6}$alkyl), —C(O)O($C_{1-6}$alkylene)aryl, —C(O)Oaryl, —$CH_2O$-alkyl, —$CH_2O$-aryl, —$SO_2$-alkyl, —$SO_2$-aryl, and a silicon-containing protecting group. One of ordinary skill will appreciate that $Z^1$ and $Z^2$ can be the same, while $Z^3$ is different or that $Z^1$ and $Z^2$ are a part of the same radical, such as in the instance of ~$Si(C_{1-6}$alkyl$)_2OSi(C_{1-6}$alkyl$)_2$~, which would be derived from, for example, a 1,3-dihalo-1,1,3,3-tetra($C_{1-6}$alkyl)disiloxane.

In a twelfth aspect of the ninth embodiment, PG is selected from among, benzoyl, acetyl, —$C(O)OCH_2Ph$, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl), 9-(p-methoxyphenyl)xanthine-9-yl (MOX), tert-butyldimethylsilyl, tert-butyldiphenylsilyl, and ~$Si(C_{1-6}$alkyl$)_2OSi(C_{1-6}$alkyl$)_2OH$, such as, —$Si(^iPr)_2OSi(^iPr)_2OH$ or ~$Si(^iPr)_2OSi(^iPr)_2$~.

In a thirteenth aspect of the ninth embodiment, each of $Z^1$, $Z^2$, and $Z^3$ is hydrogen.

In a fourteenth aspect of the ninth embodiment, each of $Z^1$ and $Z^2$ is hydrogen and $Z^3$ is benzoyl.

In a fifteenth aspect of the ninth embodiment, $Z^1$ and $Z^2$ are comprised of ~$Si(^iPr)_2OSi(^iPr)_2$~ and $Z^3$ is hydrogen or benzoyl.

A tenth embodiment is directed to a process for preparing a compound represented by formula I-3-5",

I-3-5″

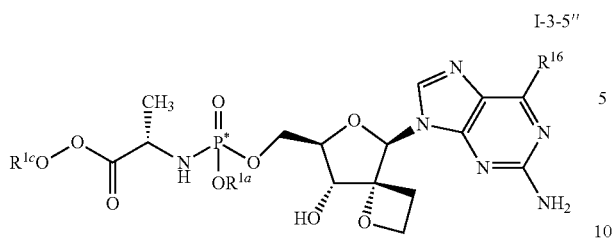

wherein $R^{1a}$ is phenyl or naphthyl;

$R^{1c}$ is hydrogen, $C_{1-6}$alkyl, $C_{3-6}$cycloalkyl, or $C_{1-3}$alkaryl; and $R^{16}$ is —O($C_{1-6}$alkyl), —O$C_{1-3}$alkaryl, —S($C_{1-6}$alkyl), —NH($C_{1-6}$alkyl), or -cycloalkylamino;

said process comprising:

reacting compound A″ with a nucleophile and optionally deprotecting to obtain compound B″,

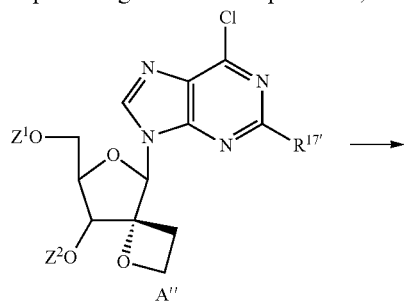

A″

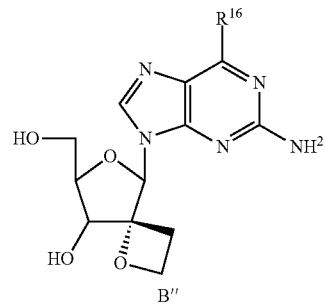

B″ wherein $R^{17'}$ is —NHZ$^3$, wherein each one of $Z^1$, $Z^2$, and $Z^3$ is hydrogen or a protecting group (PG);

the nucleophile is comprised of a radical selected from among, —O($C_{1-6}$alkyl), —O$C_{1-3}$alkaryl, —S($C_{1-6}$alkyl), —NH($C_{1-6}$alkyl), and -cycloalkylamino; and reacting B″ with a phosphoramidate represented by formula C to obtain I-3-5″

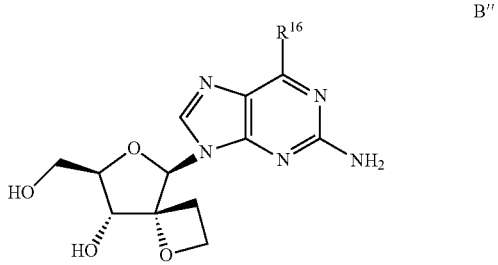

B‴

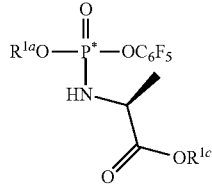

C wherein the phosphoramidate is comprised of a mixture of the $S_P$- and $R_P$-diastereomers.

The optional deprotection step is done by conventional means.

In a first aspect of the tenth embodiment, $R^{16}$ is —O($C_{1-6}$ alkyl), —O$C_{1-3}$alkaryl, —S($C_{1-6}$alkyl), —NH($C_{1-6}$alkyl), or —NH$C_{3-6}$cycloalkyl.

In a second aspect of the tenth embodiment, $R^{16}$ is —O($C_{1-6}$ alkyl).

In a third aspect of the tenth embodiment, $R^{16}$ is —O$C_{1-3}$ alkaryl.

In a fourth aspect of the tenth embodiment, $R^{16}$ is —S($C_{1-6}$ alkyl).

In a fifth aspect of the tenth embodiment, $R^{16}$ is —NH($C_{1-6}$ alkyl).

In a sixth aspect of the tenth embodiment, $R^{16}$ is —NH$C_{3-6}$ cycloalkyl.

In a seventh aspect of the tenth embodiment, the mole ratio of the $S_P$-diastereomer to the $R_P$-diastereomer ranges from about 2 to about 99.99 and all values in between, including 2, 5, 10, 15, 20, 25, 30, 35, 40, 45, 50, 55, 60, 65, 70, 75, 80, 85, 90, 95, 97, 98, 99, 99.9, and 99.99.

In an eighth aspect of the tenth embodiment, the mole ratio of the $R_P$-diastereomer to the $S_P$-diastereomer ranges from about 2 to about 99.99 and all values in between, including 2, 5, 10, 15, 20, 25, 30, 35, 40, 45, 50, 55, 60, 65, 70, 75, 80, 85, 90, 95, 97, 98, 99, 99.9, and 99.99.

In a ninth aspect of the tenth embodiment, the meanings of the protecting group for A″ is as described for A in the eighth embodiment.

An eleventh embodiment is directed to a process for preparing a compound represented by formula I-3-5‴

I-3-5‴

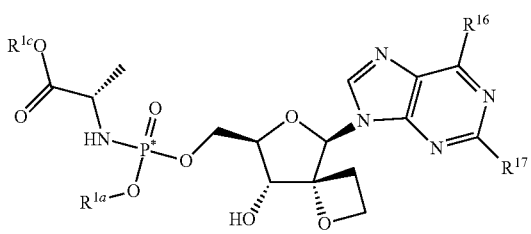

wherein $R^{1a}$ is phenyl or naphthyl; $R^{1c}$ is hydrogen, $C_{1-6}$alkyl, $C_{3-6}$cycloalkyl, or $C_{1-3}$alkaryl; $R^{16}$ is —O($C_{1-6}$ alkyl), —O$C_{1-3}$alkaryl, —S($C_{1-6}$alkyl), —NH($C_{1-6}$alkyl), or -cycloalkylamino; and $R^{17}$ is —H or —NH$_2$ said process comprising reacting a compound represented by formula B‴ with a phosphoramidate represented by formula C to obtain I-3-5‴

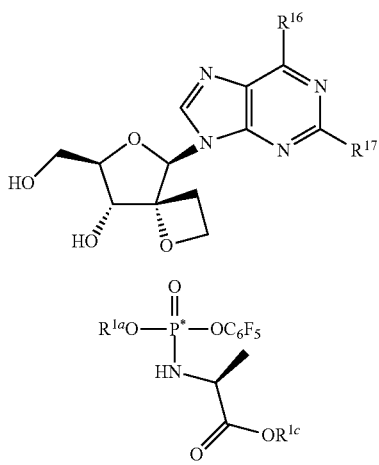

wherein the phosphoramidate is comprised of a mixture of the $S_P$- and $R_P$-diastereomers.

In a first aspect of the eleventh embodiment, $R^{16}$ is —O($C_{1-6}$ alkyl), —O$C_{1-3}$alkaryl, —S($C_{1-6}$alkyl), —NH($C_{1-6}$ alkyl), or —NH$C_{3-6}$cycloalkyl and $R^{17}$ is H or $NH_2$.

In a second aspect of the eleventh embodiment, the mole ratio of the $S_P$-diastereomer to the $R_P$-diastereomer ranges from about 2 to about 99.99 and all values in between, including 2, 5, 10, 15, 20, 25, 30, 35, 40, 45, 50, 55, 60, 65, 70, 75, 80, 85, 90, 95, 97, 98, 99, 99.9, and 99.99.

In a third aspect of the eleventh embodiment, the mole ratio of the $R_P$-diastereomer to the $S_P$-diastereomer ranges from about 2 to about 99.99 and all values in between, including 2, 5, 10, 15, 20, 25, 30, 35, 40, 45, 50, 55, 60, 65, 70, 75, 80, 85, 90, 95, 97, 98, 99, 99.9, and 99.99.

Preparation

Schemes 1-2 provide general procedures for preparing 2'-spiro-ara and 2'-spiro-ribo-nucleosides.

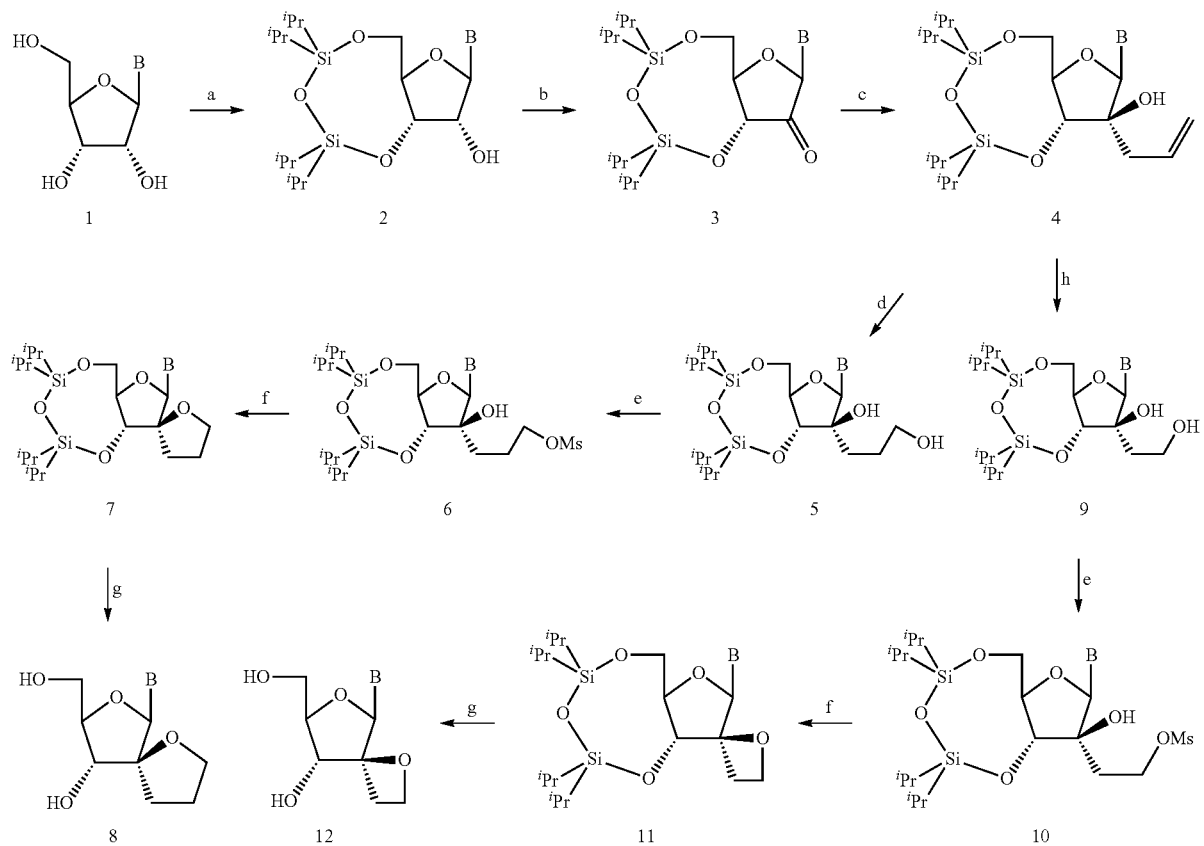

The disclosed reagents are meant to be exemplary only and should not be meant to narrow the scope of the embodiments disclosed below.

A seventh embodiment is directed to a process for preparing a compound or its stereoisomer or its salt or its metabolite or its deuteride represented by formula I, by any of the processes disclosed herein.

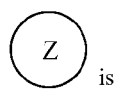 is

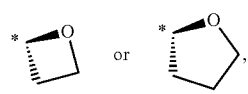

A first aspect of the seventh embodiment is directed to a process for preparing a compound or its stereoisomer or its salt or its metabolite or its deuteride thereof wherein PG said process comprising any one of the following reaction steps a'-h'

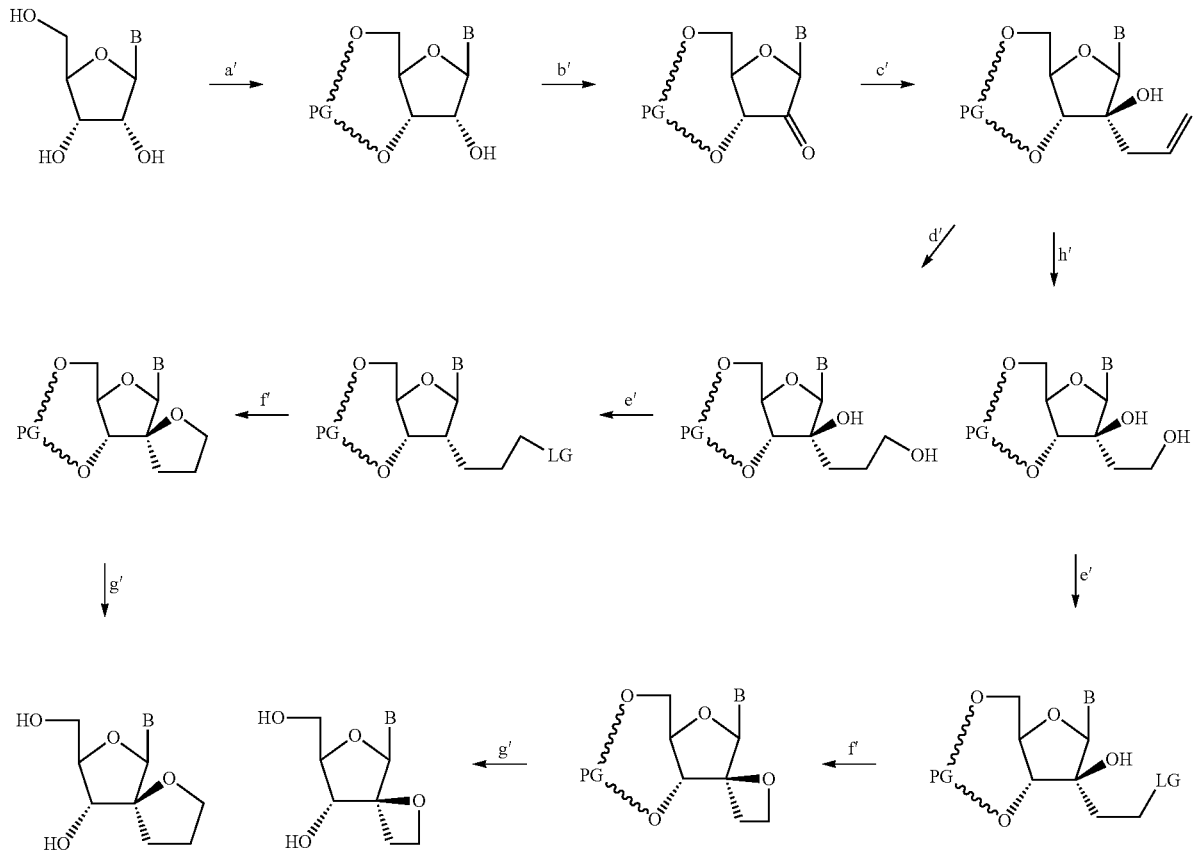

wherein B is defined above, PG is a protecting group, and LG is a leaving group.

Scheme 2. General Synthesis of 2'-Spiro-ribo-nucleosides

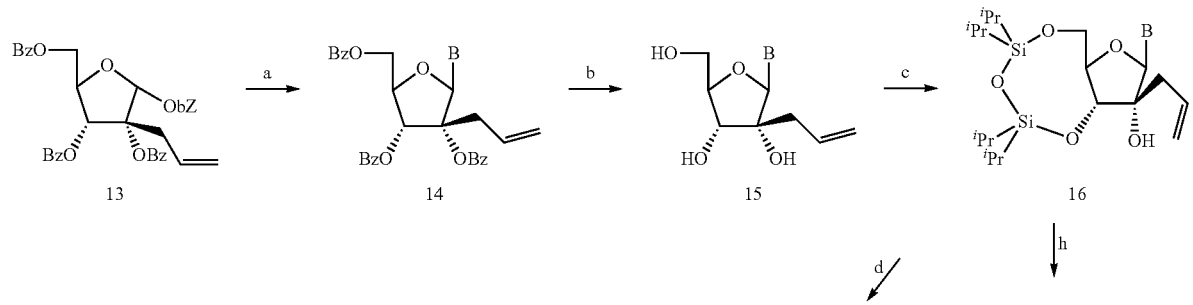

-continued

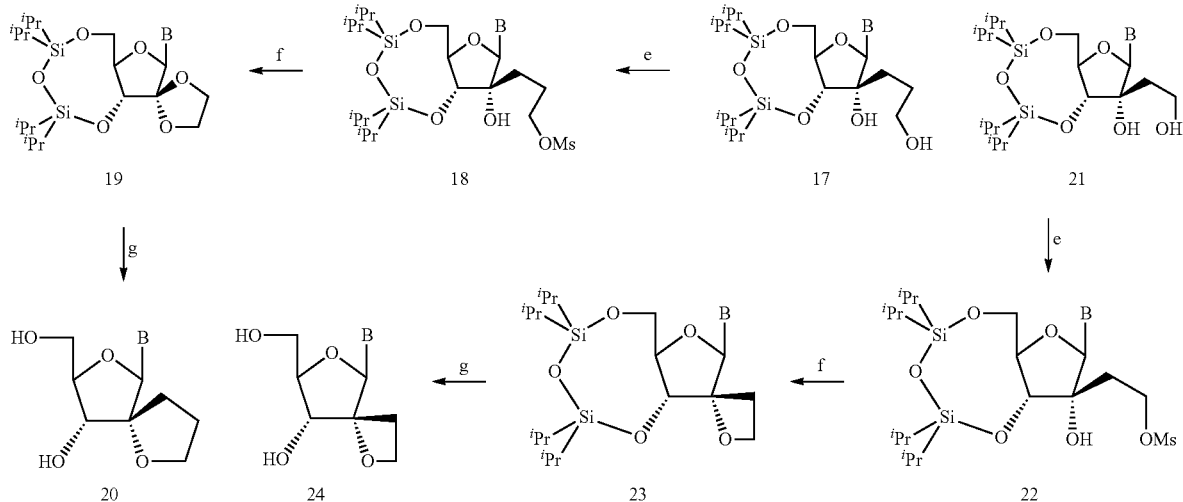

Reagents and conditions: a) Silylated base/TMSOT or Sn Cl₄ or base/TMSOTf/DBU; b) NH₃MeOH; c) TIPSCl/Pyr.; d) BH₃/H₂O; e) MsCl/Pyr; f) NaH; g) NH₄F; h) 1. OsO₄/NMO, 2. NaIO₄, 3. NaBH₄.

A second aspect of the seventh embodiment is directed to a process for preparing a compound or its stereoisomer or its salt or its metabolite thereof represented by formula I, wherein 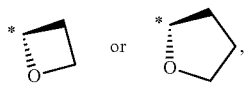 is said process comprising any one of the following reaction steps a'-h' wherein B is as defined above, PG and PG' are independent of one another leaving groups, and LG is a leaving group.

Scheme 3-6 provide general procedures for preparing additional compounds of formula I. In these schemes, Pg, represents a protecting group, which is defined herein. R is a substituent that provides for or is defined by the substituent "Y" as defined herein. As described above, examples of protecting groups are defined herein and disclosed in Protective Groups in Organic Synthesis, 3$^{rd}$ ed. T. W. Greene and P. G. M. Wuts, John Wiley & Sons, New York, N.Y., 1999. One of ordinary skill will appreciate the conditions available to protect and deprotect a given synthetic intermediate. Additionally, it is contemplated that one of ordinary skill would employ known procedures for the deoxygenation steps disclosed below.

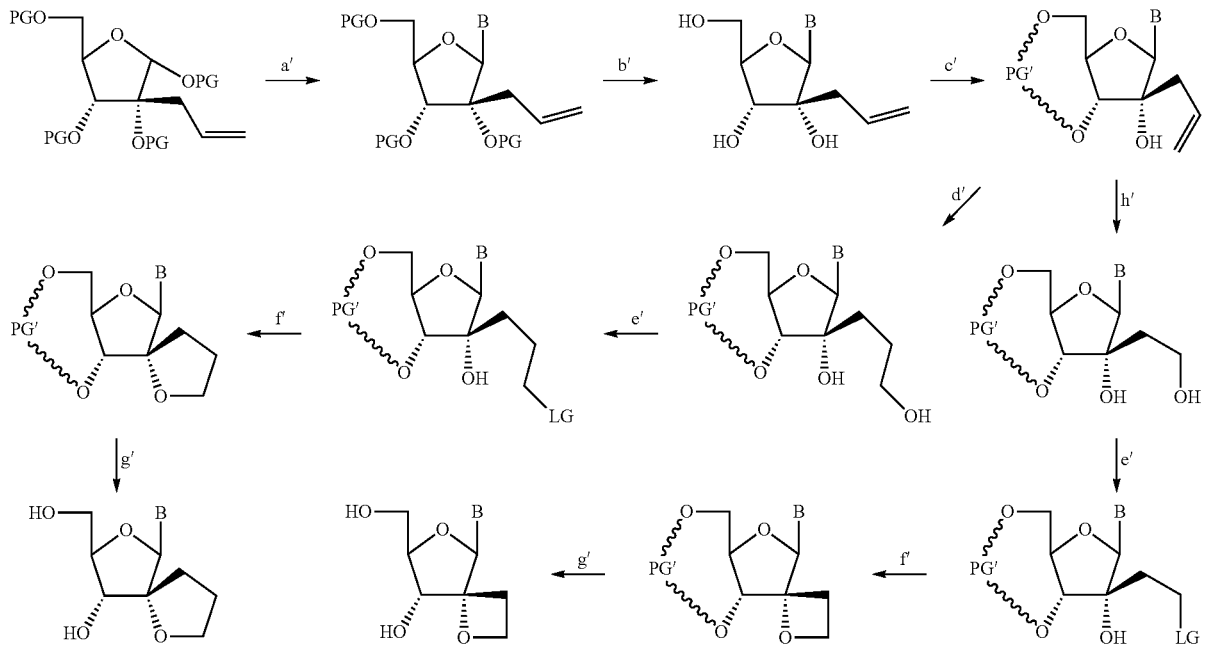

Scheme 3. General Procedure for preparing 2'-spiro-(1,3-dioxolan-5-yl) Nucleosides

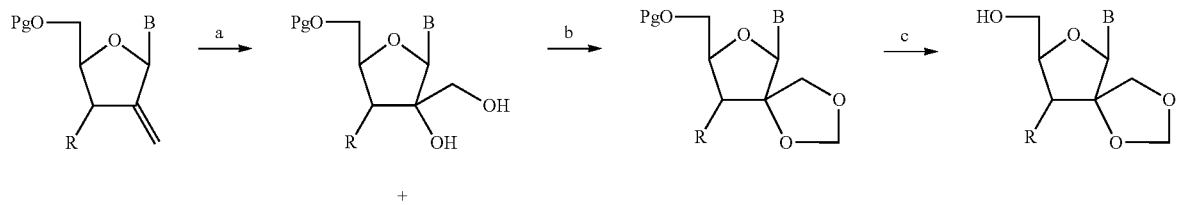

Scheme 3: Reagents: a) OsO4/NMO; b) HCHO/acid; c) deprotection

Scheme 4. General Procedure for Preparing 2'-spiro-(oxetan-3-yl) Nucleosides

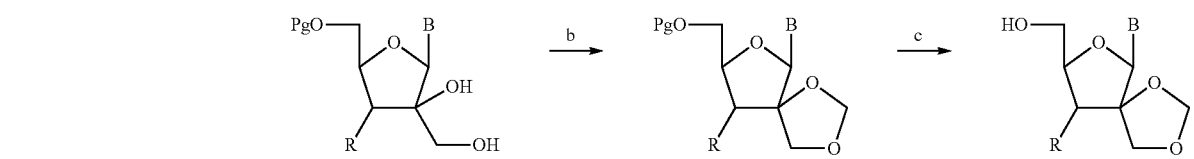

-continued

Scheme 4: Reagents: a) 1. HCHO/NaOH, 2. NaBH4; b) Mitsunobu reagents; c) deprotection.

Scheme 5. General Procedure for preparing 2'-spiro-(disubstituted-cyclopentano) and 2'-spiro-(disubstituted-cyclopenteno) Nucleosides

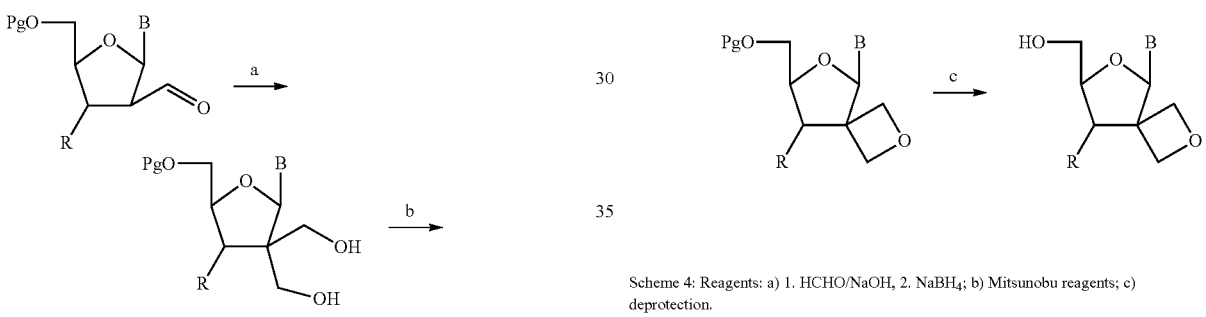

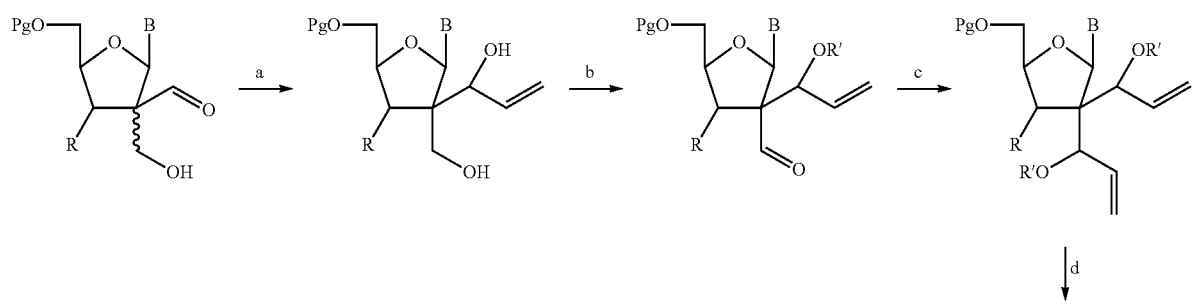

Scheme 5. Reagents: a) vinylMgBr, b) 1. Selective O-protection, 2. CrO3; c) 1. vinylMgBr, 2. selective O-protection; d) Grubbs' ring closure; e) deprotection; Pd/H2. Hydroxyl group or spiro-ring can be removed by general deoxygenation method.

Scheme 6. General Procedure for Preparing 2'-spiro-(mono-substituted-cyclopentano) and 2'-spiro-(mono-substituted-cyclopenteno) Nucleosides

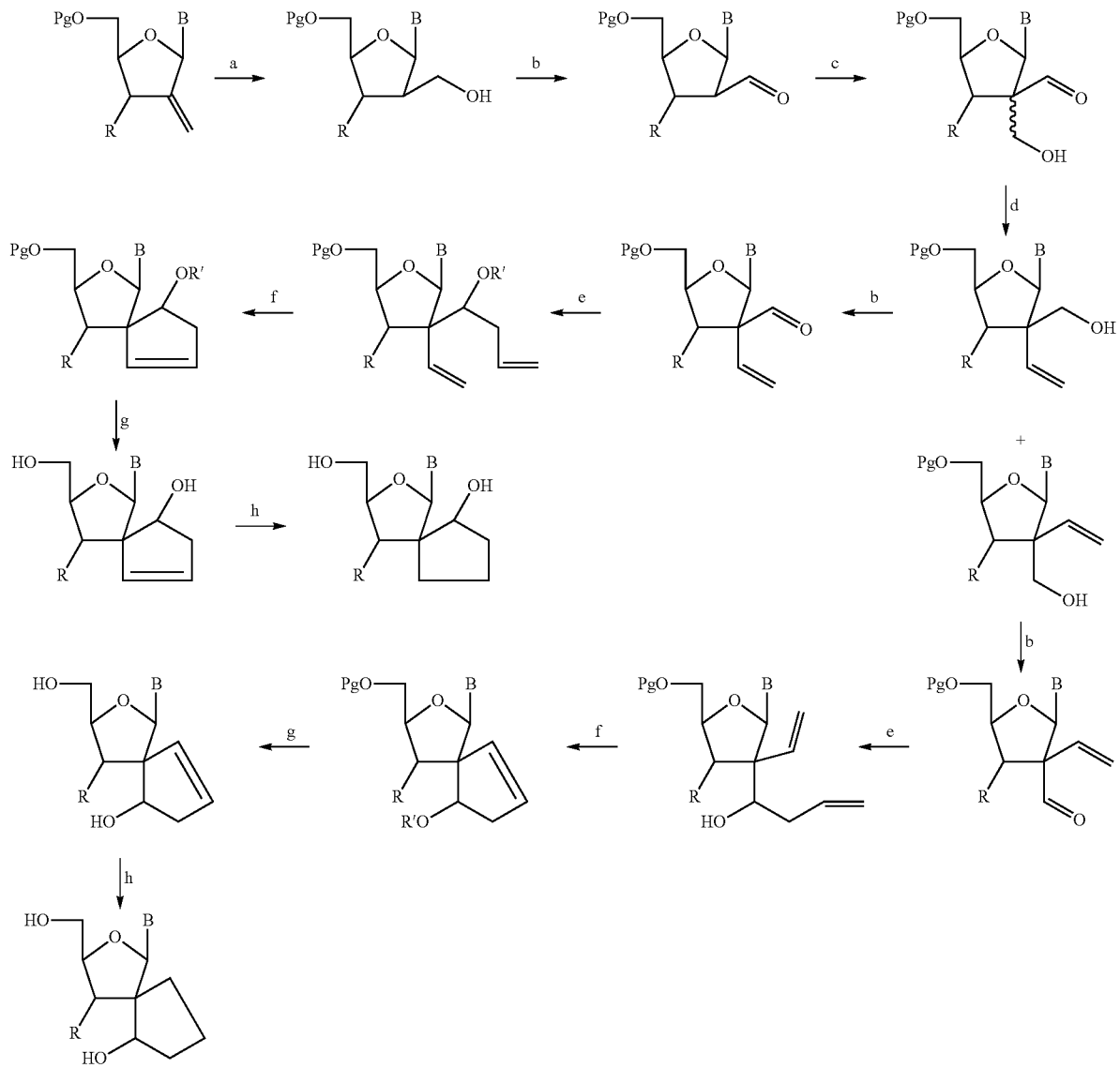

Scheme 6. Reagents: a) 1. BH$_3$, 2. H$_2$O$_2$/NaOH; b) CrO$_3$; c) HCHO/NaOH; d)CH$_2$═PPh$_3$; e) allylMgBr; f) Grubb's ring closure; g) deprotection; g) Pd/H$_2$. Hydroxyl group on spiro-ring can be removed by general deoxygenation methods.

See, e.g., Kim C. M. F. Tjen, et al Chem. Commun., 2000, 699-700.

One of ordinary skill will appreciate that other methods of preparing a compound of formula I are possible.

Procedures for introducing substituents at the 1' or 4' positions are disclosed in WO 2009/132135, as well as US 2009/0318380.

Procedures for preparing nucleosides and nucleotides of the "B" of Compound I-2 are disclosed in U.S. Pat. Nos. 3,798,209, 4,138,547, 4,458,016, 7,285,659, and 7,285,660.

Procedures for preparing nucleosides and nucleotides containing the "B" of Compound I-3-1 are disclosed in any one of WO 2010/075517, WO 2010/075549, and WO 2010/075554.

Procedures for preparing nucleosides and nucleotides containing the "B6" of Compound I-3-7 (or I-3-9) are disclosed in any one of WO 2010/002877 and WO 2009/132135.

Procedures for preparing nucleosides and nucleotides containing the "B7" of Compound I-3-7 (or I-3-10) are disclosed in any one of WO 2010/036407, WO 2009/132135, and WO 2009/132123.

Procedures for preparing nucleosides and nucleotides containing the "B8" of Compound I-3-7 (or I-3-11) are disclosed in WO 2009/132123.

Procedures for preparing nucleosides and nucleotides containing the "B9" of Compound I-3-7 (or I-3-12) are disclosed in WO 2010/036407.

Procedures for preparing nucleosides and nucleotides containing the "B10" of Compound I-3-7 (or I-3-13) are disclosed in WO 2010/093608.

Procedures for preparing deuterides are known to one of ordinary skill and reference can be made to US 2010/0279973 and procedures disclosed therein.

Procedures for preparing compound I-3-5''' are disclosed herein. Additional procedures for preparing and isolating compound C are disclosed in U.S. Ser. No. 13/076,552 (US 2011/0251152), filed on Mar. 31, 2011 and U.S. Ser. No. 13/076,842 (US 2011/0245484), filed on Mar. 31, 2011. To the extent necessary, the subject matter of U.S. Ser. No. 13/076,552 and U.S. Ser. No. 13/076,842 is hereby incorporated by reference.

EXAMPLES

Not to be limited by way of example, the following examples serve to facilitate a better understanding of the disclosure.

In the examples that follow, certain abbreviations have been used. The following table provides a selected number of abbreviations. It is believed that one of ordinary skill would know or be able to readily deduce the meaning of any abbreviations not specifically identified here.

| Abbreviation | Meaning |
| --- | --- |
| TMSCl | Trimethylsilylchloride |
| TIPSCl | 1,3-dichloro-1,1,3,3-tetraisopropyldisiloxane |
| EtOAc | Ethtyl Acetate |
| Pyr | pyridine |
| Ac2O | Acetic Anhydride |
| THF | Tetrahydrofuran |
| DCM | (=CH$_2$Cl$_2$) Dichloromethane |
| MsCl | Mesylchloride |
| HMDS | Hexamethyldisilazane |
| MeCN | Acetonitrile |
| NMO | N-Methylmorpholine-N-oxide |
| p-TsOH | para-toluene-sulfonic acid |
| MOPS | 3-(N-morpholino)propanesulfonic acid |
| HCHO | formaldehyde |
| NaHMDS | Sodium bis(trimethylsilyl)amide |
| NMI | N-methylimidazole |
| DTP | 1,3-dimethyl-3,4,5,6-tetrahydro-2(1H)-pyrimidinone |

I. Preparation of 2'-Spiro-ara-uracil and 2'-Spiro-ribo-uracil Analogs

A. Preparation 2'-spiro-ara-uridines

The following scheme describes a possible synthetic route for the preparation of 2'-spiro-ara-uracil analogs, 32 and 36. A synthetic intermediate common to compounds 32 and 36 is compound 28, which is obtained by protecting uridine 25 with 1,3-dichloro-1,1,3,3-tetraisopropyldisiloxane (TIPSCl) followed by oxidation of the 2'-carbon to form compound 27. Compound 28 is prepared by reacting compound 27 with an appropriate allyl-containing reagent.

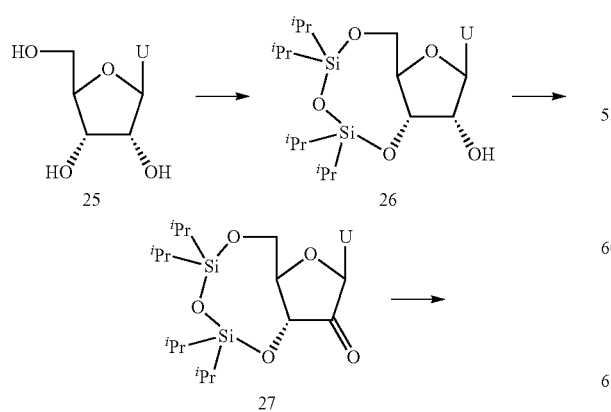

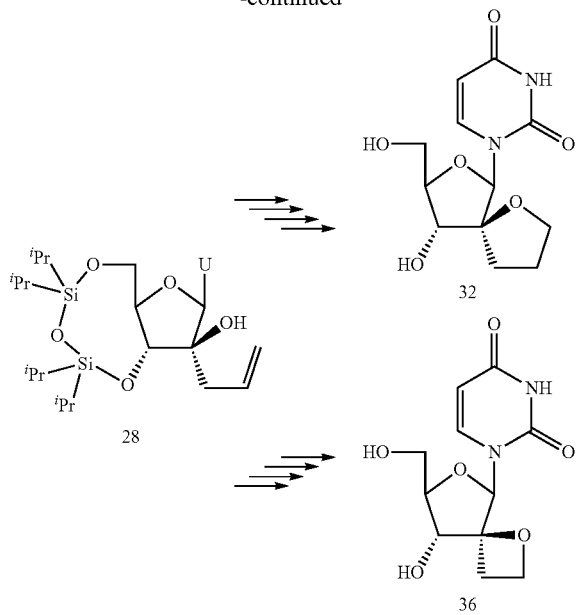

Example 1

Preparation of 1-((6aR,8R,9S,9aR)-9-allyl-9-hydroxy-2,2,4,4-tetraisopropyltetrahydro-6H-furo[3,2-f][1,3,5,2,4]trioxadisilocin-8-yl)pyrimidine-2,4(1H,3H)-dione, 28

Step 1. Preparation of Compound 26.

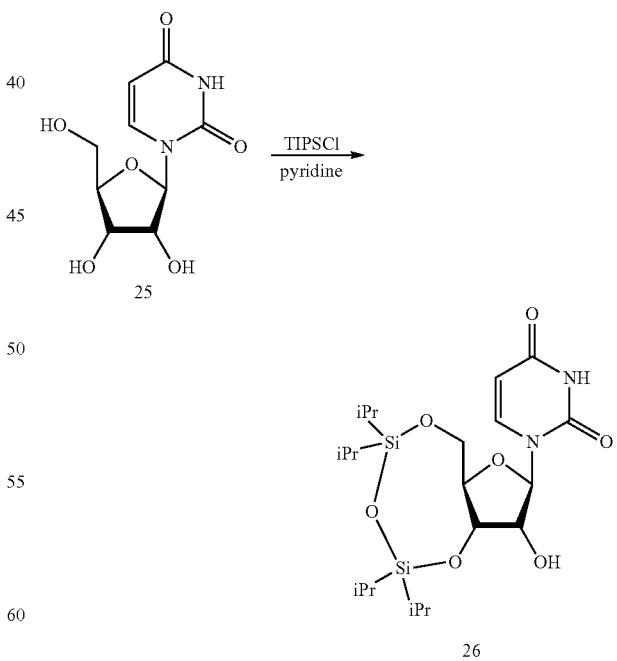

To a solution of compound 25 (20.0 g, 82.58 mmol) in anhydrous pyridine (150 mL) was added 1,3-dichloro-1,1,3, 3-tetraisopropyldisiloxane (TIPSCl, 27.35 g, 86.71 mmol) at room temperature. The mixture was stirred at room temperature for 20 h. The solvent was evaporated under reduced pressure and the residue was dissolved in EtOAc (200 mL). The organic solution was washed with H₂O and the solvent was evaporated to give a crude product 26 which was used for next step without further purification. ¹H NMR (400 MHz, CDCl₃): δ=10.11 (s, 1H), 7.78 (d, J=8.4 Hz, 1H), 5.73 (s, 1H), 5.68 (d, J=8.0 Hz, 1H), 4.07-4.38 (m, 4H), 3.96-4.00 (m, 2H), 0.91-1.21 (m, 28H).

Step 2. Preparation of Compound 27

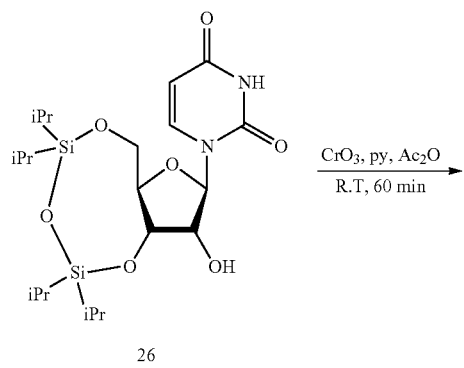

To a stirred solution of CrO₃ (13.0 g, 130.0 mmol), anhydrous pyridine (22 mL) and Ac₂O (13 mL) was added a solution of compound 26 (20.0 g, 41.28 mmol) in CH₂Cl₂ (50 mL). The mixture was stirred 60 min. The solution was filtered through to a short silica gel column. The solvent was evaporated and the residue was purified by silica gel column chromatography (hexane:EtOAc=2:1) to give the compound 27 (9.0 g, 45%). ¹H NMR (400 MHz, CDCl₃): δ=8.63 (s, 1H), 7.15 (d, J=8.0 Hz, 1H), 5.72-5.74 (m, 1H), 5.05 (d, J=8.8 Hz, 1H), 4.99 (s, 1H), 4.09-4.17 (m, 2H), 3.86-3.91 (m, 1H), 1.00-1.21 (m, 28H).

Step 3. Preparation of Compound 28.

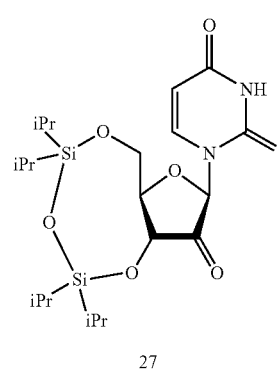

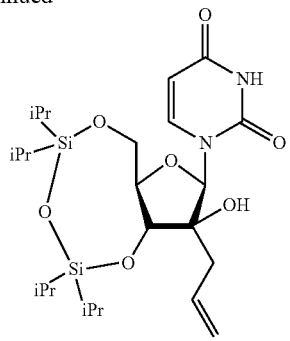

To a solution of compound 27 (5.0 g, 10.32 mmol) in THF (200 mL) was added a solution of allylmagnesium bromide (20.63 mL, 20.63 mmol) at −78° C. and the mixture was stirred at the same temperature for 2 h. Then the temperature was raised to −10° C. and the reaction was quenched with H₂O. The mixture was extracted with CH₂Cl₂ and the organic solution was dried with Na₂SO₄ and the solvent was evaporated under reduced pressure. The residue was purified by silica gel column chromatography (Hexanes:EtOAc=3:1) to give the compound 28 (4.0 g, 74%). ¹H NMR (400 MHz, CDCl₃): δ=8.82 (s, 1H), 7.82 (d, J=8.0 Hz, 1H), 6.04-56.14 (m, 1H), 5.89 (s, 1H), 5.68 (d, J=8.0 Hz, 1H), 5.28-5.37 (m, 2H), 4.24 (d, J=9.2 Hz, 1H), 4.15 (d, J=9.2 Hz, 1H), 3.97-4.01 (m, 1H), 3.78-3.80 (m, 1H), 2.69-2.75 (m, 1H), 2.48-2.53 (m, 1H), 2.44 (s, 1H), 1.04-1.09 (m, 28H).

Example 2

Preparation of 1-((5S,6R,8R,9R)-9-hydroxy-8-(hydroxymethyl)-1,7-dioxaspiro[4.4]nonan-6-yl)pyrimidine-2,4(1H,3H)-dione, 32 (2'-spiro-THF-ara-uracil)

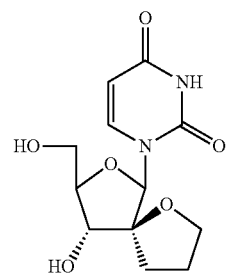 [SMILES: O=c1ccn(C2OC(CO)[C@@H](O)[C@@]23CCCO3)c(=O)[nH]1]

Step 1. Preparation of Compound 29.

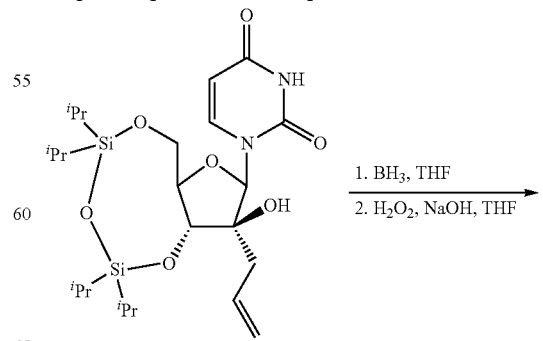

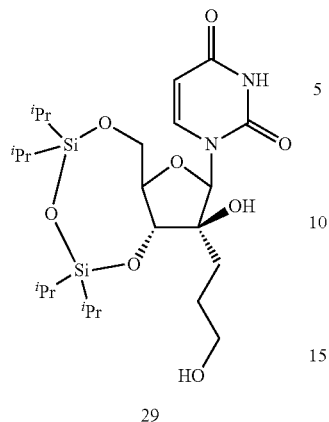

29

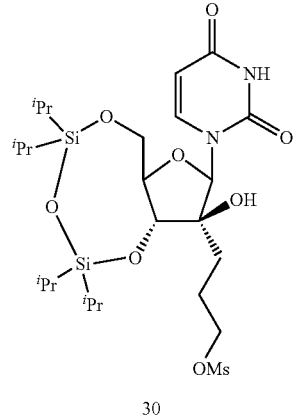

30

To a solution of compound 28 (2.0 g, 3.80 mmol) in THF (200 mL) was added BH$_3$ (0.57 mL, 5.7 mmol) at room temperature and the mixture was stirred at room temperature for 3 hr. The reaction mixture was cooled to 0° C. and 2 M aqueous NaOH (3.8 mL, 7.6 mmol) and 30% aqueous H$_2$O$_2$ (1.72 mL, 15.21 mmol) was added slowly. The mixture was allowed to warm to room temperature, stirred for 2 h and then poured into a mixture of diethyl ether (150 mL) and H$_2$O (150 mL). The aqueous phase was extracted with diethyl ether (50 mL) and the combined organic solution was washed with saturated aqueous NaHCO$_3$ (2×40 mL), and H$_2$O (2×40 mL), successively. The solution was dried (MgSO$_4$), filtered and evaporated to dryness under reduced pressure. The residue was purified by silica gel column chromatography (hexanes: EtOAc=1:1) to give the compound 29. (1.1 g, 53%). $^1$H NMR (400 MHz, CDCl$_3$): δ=10.39 (s, 1H), 8.00 (d, J=8.0 Hz, 1H), 5.86 (s, 1H), 5.70 (d, J=8.0 Hz, 1H), 4.14-4.17 (m, 2H), 3.96-3.99 (m, 2H), 3.70-3.73 (m, 1H), 3.47-3.52 (m, 1H), 2.02-2.17 (m, 2H), 1.97-2.00 (m, 1H), 1.89-1.90 (m, 1H), 0.99-1.11 (m, 28H).

A solution of MsCl (0.28 g, 2.42 mmol) in anhydrous CH$_2$Cl$_2$ (1.0 mL) was added to a solution of nucleoside 29 (1.1 g, 2.02 mmol) in anhydrous pyridine (2.0 mL) drop-wise at room temperature. After stirring for 12 h at room temperature, methanol (0.1 mL) was added and the resulting mixture was evaporated to dryness under reduced pressure. The residue was co-evaporated with anhydrous toluene (2×5 mL) and then dissolved in CH$_2$Cl$_2$ (50 mL). The solution was washed with saturated aqueous NaHCO$_3$ (2×25 mL). The combined aqueous phase was extracted with CH$_2$Cl$_2$ (50 mL). The combined organic solution was dried (Na$_2$SO$_4$), filtered and evaporated to dryness under reduced pressure. The residue was purified by silica gel column chromatography (hexanes: EtOAc=2:1) to give compound 30 (0.94 g, 74.6%).

Step 3. Preparation of Compound 31.

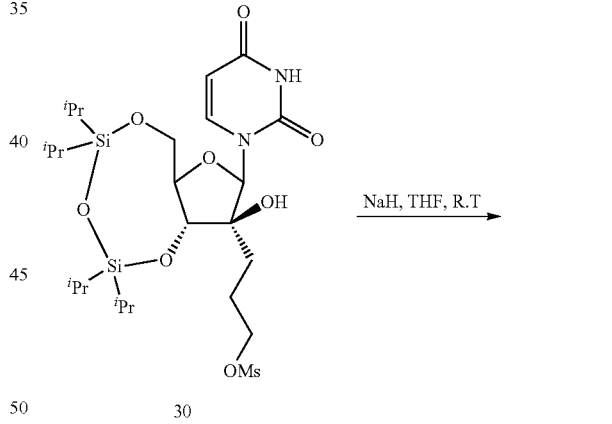

Step 2. Preparation of Compound 30.

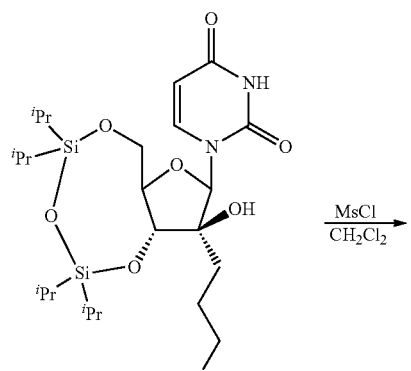

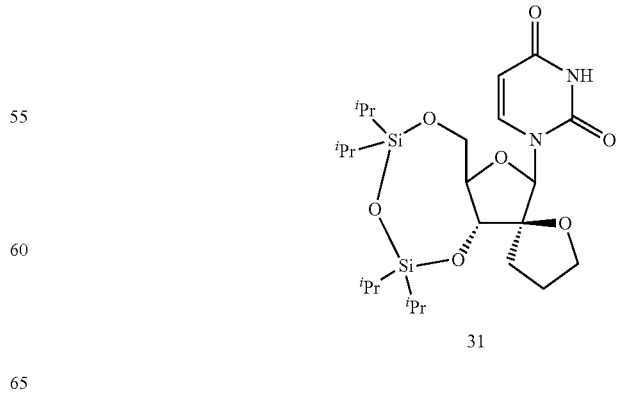

To a stirred suspension of NaH (108.8 mg, 4.53 mmol) in anhydrous THF (20 mL) was added a solution of compound 30 (0.94 g, 1.51 mmol) in THF drop-wise at 0° C. and the mixture was stirred for 2 h at room temperature. Ice-cold H₂O (10 mL) was slowly added followed by addition of CH₂Cl₂ (20 mL). The organic phase was washed with saturated aqueous NaHCO₃ (2×20 mL) and dried (Na₂SO₄). Solvent was evaporated to dryness under reduced pressure and the residue was purified by silica gel column chromatography (Hexanes: EtOAc=2:1) to provide compound 31 (0.43 g, 54.02%).

Step 4. Preparation of Compound 32.

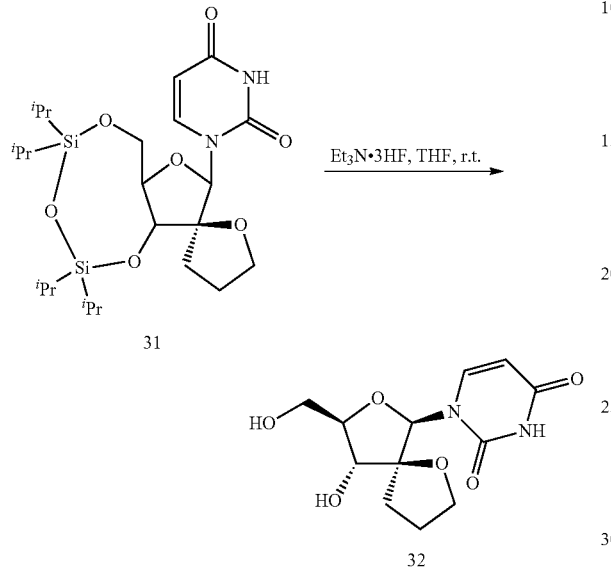

To a solution of compound 31 (150 mg, 0.285 mmol) in anhydrous THF (10 mL) was added Et₃N.3HF (0.3 mL) and the mixture was stirred at room temperature for 2 h. The mixture was then evaporated to dryness under reduced pressure and the residue was purified by silica gel column chromatography (0-15% MeOH in CH₂Cl₂) to give compound 32 (51.37 mg, 63.5%). $^1$H NMR (400 MHz, DMSO-d6): δ=11.32 (s, 1H), 7.80 (d, J=8.0 Hz, 1H), 5.83 (s, 1H), 5.63 (d, J=4.2 Hz, 1H), 5.59 (d, J=8.0 Hz, 1H), 5.03-5.05 (m, 1H), 3.83-3.86 (m, 1H), 3.64-3.70 (m, 3H), 3.47-3.60 (m, 2H), 2.27-2.29 (m, 1H), 1.74-1.81 (m, 3H). HRMS (TOF-ESI): Calc. For $C_{12}H_{17}N_2O_6$, 285.1087. found 285.1070.

Example 3

Preparation of 1-((4S,5R,7R,8R)-8-hydroxy-7-(hydroxymethyl)-1,6-dioxaspiro[3.4]octan-5-yl)pyrimidine-2,4(1H,3H)-dione, 36 (2'-spiro-oxetane-arauracil)

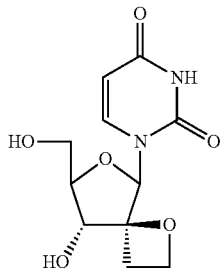

36

Step 1. Preparation of Compound 33.

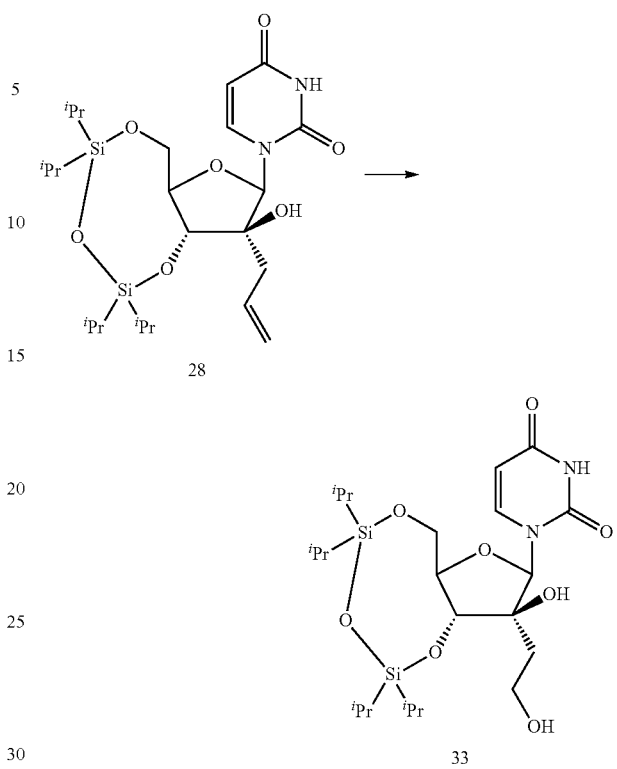

To a solution of compound 28 (4.8 g, 9.12 mmol) in DCM (200 mL) was bubbled with O₃ and the solution was stirred at −78° C. for 3 h. To the solution were added Me₂S (1 mL) and NaBH₄ (1.73 g, 45.60 mmol) at room temperature and the mixture was stirred overnight. The resulting solution was washed with H₂O and the solvent was evaporated. The residue was purified by silica gel column chromatography (hexanes:EtOAc=1:1) to give compound 33 (1.2 g, 25.7%). $^1$H NMR (400 MHz, CDCl₃): δ 11.16 (s, 1H), 7.92 (d, J=8.0 Hz, 1H), 6.01 (s, 1H), 5.69-5.72 (m, 1H), 5.64 (s, 1H), 4.58-4.63 (m, 2H), 3.94-4.17 (m, 4H), 3.65-3.68 (m, 1H), 2.49-2.53 (m, 1H), 1.58-1.61 (m, 1H), 1.01-1.11 (m, 28H).

Step 2. Preparation of Compound 34.

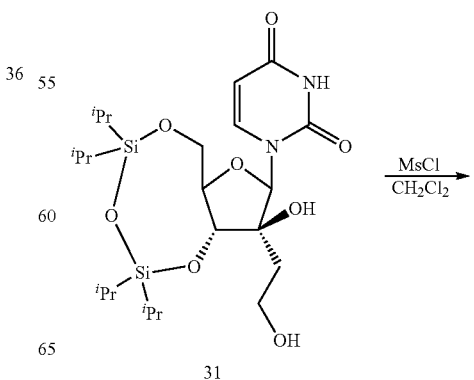

31

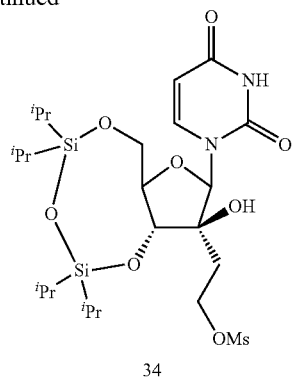

34

A solution of MsCl (0.31 g, 2.72 mmol) in anhydrous CH₂Cl₂ (10 mL) was added to a solution of nucleoside 33 (1.2 g, 2.26 mmol) in anhydrous pyridine (2.0 mL) drop-wise at room temperature and the solution was stirred at room temperature for 12 h. Methanol (5.0 mL) was added and the resulting mixture was evaporated to dryness under reduced pressure. The residue was co-evaporated with anhydrous toluene (2×5 mL) and purified by silica gel column chromatography (hexanes:EtOAc=2:1) to provide compound 34 (1.0 g, 73.0%).

Step 3. Preparation of Compound 35.

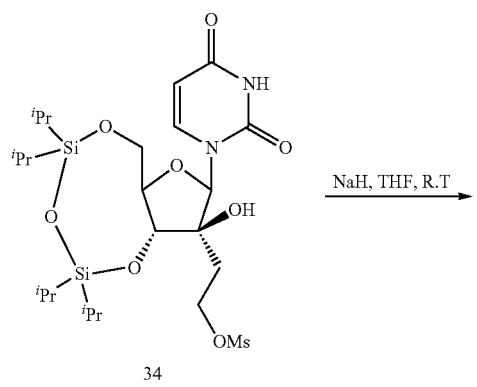

34 reduced pressure and the residue was purified by silica gel column chromatography (hexanse:EtOAc=2:1) to give compound 35. (0.5 g, 59.25%).

Step 4. Preparation of Compound 36.

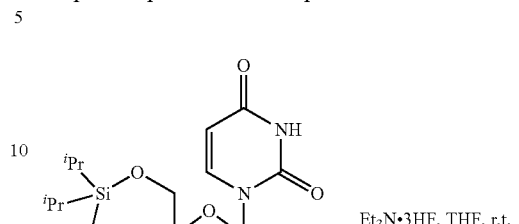

35

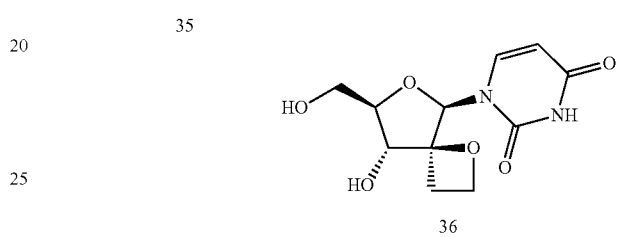

36

To a solution of compound 35 (300 mg, 0.585 mmol) in anhydrous THF (10 ml) was added Et₃N.3HF (0.15 mL) and the mixture was stirred at room temperature for 2 h. The mixture was then evaporated to dryness under reduced pressure and the residue was purified by silica gel column chromatography (0-15% MeOH in CH₂Cl₂) to give compound 36 (61.26 mg, 38.78%). $^1$H NMR (400 MHz, DMSO-d₆): δ 11.42 (s, 1H), 7.68 (d, J=8.0 Hz, 1H), 6.08 (s, 1H), 5.87 (d, J=5.2 Hz, 1H), 5.60 (d, J=8.0 Hz, 1H), 5.04-5.06 (m, 1H), 4.30-4.35 (m, 1H), 4.19-4.24 (m, 1H), 3.95-3.98 (m, 1H), 3.50-3.61 (m, 3H), 3.01-3.08 (m, 1H), 2.39-2.45 (m, 1H). HRMS (TOF-ESI): Calc. for $C_{11}H_{15}N_2O_6$, 271.0925. found 271.0917.

B. Preparation of 2'-Spiro-Ribo-Uracil Analogs

The following scheme shows that 2'-spiro-ribo-uracil analogs can be prepared from a common synthetic intermediate, compound 40.

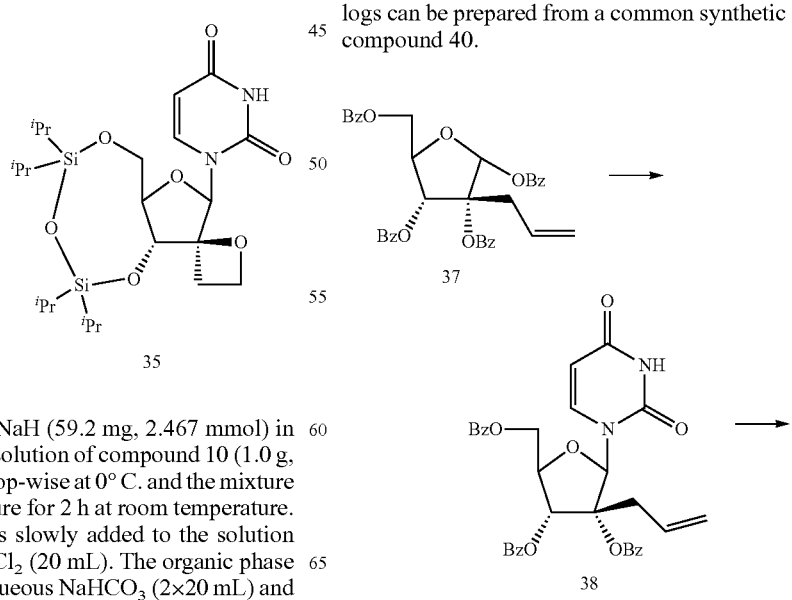

35

To a stirred suspension of NaH (59.2 mg, 2.467 mmol) in anhydrous THF was added a solution of compound 10 (1.0 g, 1.65 mmol) in THF (3 mL) drop-wise at 0° C. and the mixture was stirred at room temperature for 2 h at room temperature. Ice-cooled H₂O (10 mL) was slowly added to the solution followed by addition of CH₂Cl₂ (20 mL). The organic phase was washed with saturated aqueous NaHCO₃ (2×20 mL) and dried (Na₂SO₄). Solvent was evaporated to dryness under

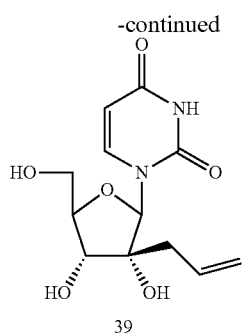

Example 4

Preparation of 1-((6aR,8R,9R,9aR)-9-allyl-9-hydroxy-2,2,4,4-tetraisopropyltetrahydro-6H-furo[3,2-f][1,3,5,2,4]trioxadisilocin-8-yl)pyrimidine-2,4(1H,3H)-dione, 40

Steps 1-2. Compound 39

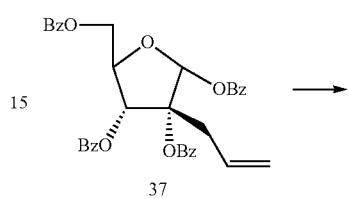

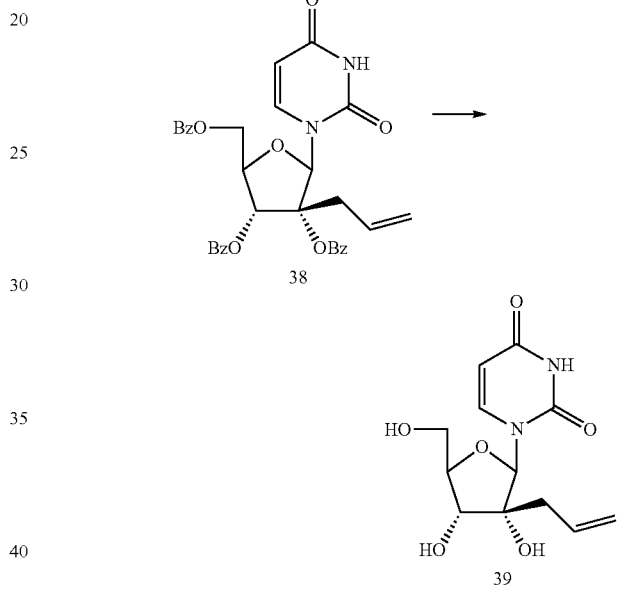

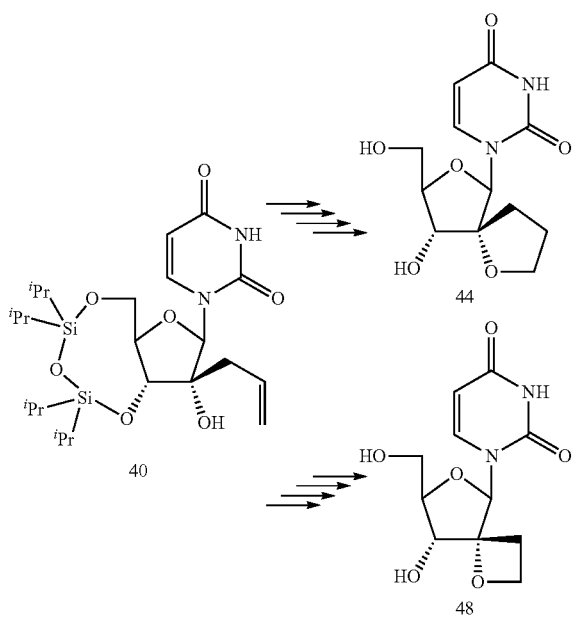

Preparation of compound 39 was accomplished according to literature method (Babu, B et al. Org Biomol. Chem. (2003) 1:3514-3526). A mixture of uracil (0.74 g, 6.59 mmol) and $(NH_4)_2SO_4$ (20 mg) in HMDS was refluxed for 4 h and the clear solution was concentrated to dryness under reduced pressure. The residue was dissolved in MeCN (60 mL). To the solution was added a solution of compound 37 (2.0 g, 3.3 mmol) followed by $SnCl_4$ (1 M in $CH_2Cl_2$ (8.24 mmol, 8.24 mL) at room temperature and the solution was heated at 65° C. for 3 h. The solution was poured into ice-water containing excess $NaHCO_3$ and EtOAc (200 mL). Organic solution was washed with brine and dried over $Na_2SO_4$. Solvent was evaporated and the residue was purified by silica gel column chromatography (19-60% EtOAc in hexanes) to give compound 38 (1.50 g, 76%) as white foam.

A suspension of compound 38 (2.5 g, 4.19 mmol) in 7N methanolic ammonia (40 mL) was stirred at room temperature for 16 h and the solution was evaporated to dryness. The residue was purified by silica gel column chromatography (0-20% MeOH in $CH_2Cl_2$) to give compound 39 (1.0 g, 83%).
$^1$H NMR (400 MHz, $CD_3OD$) δ: 7.96 (d, J=8.0 Hz, 1H), 6.01 (s, 1H), 5.89 (m, 1H), 5.68 (d, J=8.0 Hz, 1H), 4.99 (m, 2H), 3.89 (m, 4H), 2.43 (m, 1H), 2.23 (m, 1H).

Step 3. Preparation of Compound 40.

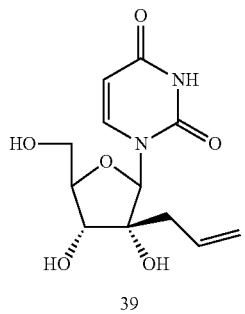

39

Step 1. Preparation of compound 41.

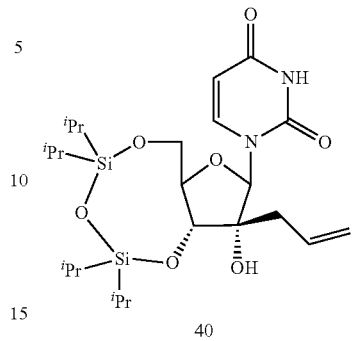

40

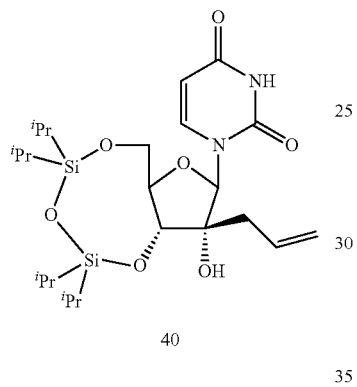

40

To a solution of 39 (0.60 g, 2.11 mmol) in pyridine (10 mL) and CH$_2$Cl$_2$ (20 mL) was added TIPSCl at 0° C. within 10 min. The solution was stirred at room temperature for 24 h. Solvent was evaporated and the residue was dissolved in EtOAc (100 mL). The solution was washed with brine and dried over Na$_2$SO$_4$. Solvent was evaporated and the residue was purified by silica gel column chromatography (0-5% MeOH in CH$_2$Cl$_2$) to give product 40 (1.00 g, 90%) as a syrup.

Example 5

Preparation of 1-((5R,6R,8R,9R)-9-hydroxy-8-(hydroxymethyl)-1,7-dioxaspiro[4.4]nonan-6-yl)pyrimidine-2,4(1H,3H)-dione, 44 (2'-spiro-THF-ribo-uracil)

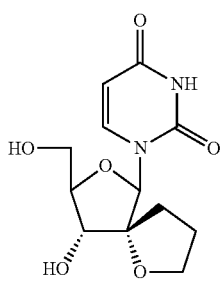

44

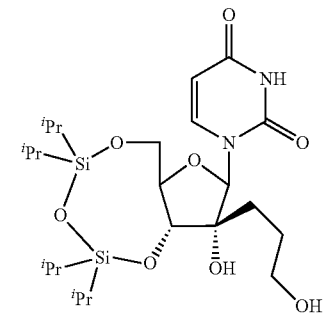

41

To a solution of 40 (1.0 g, 1.9 mmol) in THF (50 mL) was added borane-dimethylsulfide (2.85 mmol, 0.22 g) and the solution was stirred at 0° C. for 3 h. To the cooled solution was added 2N NaOH (1.9 mL, 3.8 mmol) and the mixture was stirred at room temperature for 2 h. EtOAc (100 mL) was added and the solution was washed with brine and dried over Na$_2$SO$_4$. Solvent was evaporated and the residue was purified by silica gel column chromatography (0-8% MeOH in CH$_2$Cl$_2$) to give product 41 (0.45 g, 44%). $^1$H NMR (400 MHz, CD$_3$OD) δ: 8.11 (s, 1H), 7.61 (D, J=8.0 Hz, 1H), 6.05 (s, 1H), 5.71 (d, J=8.0 Hz, 1H), 4.07 (m, 4H), 3.60 (m, 3H), 3.21 (s, 1H), 1.70 (m, 4H), 1.10 (m, 28H). LC-MS (ESI): 545 [M+H]$^+$.

Steps 2-3. Preparation of Compound 43.

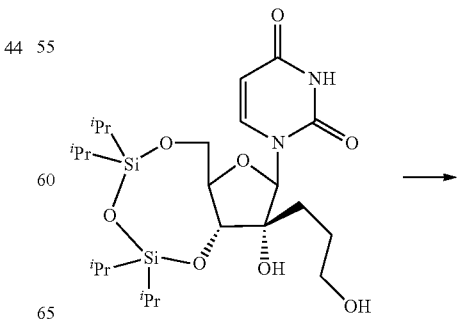

41

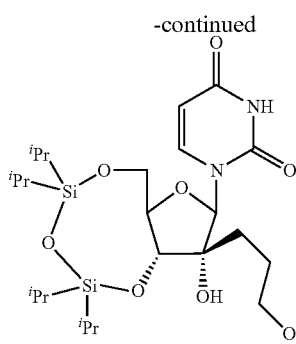

42

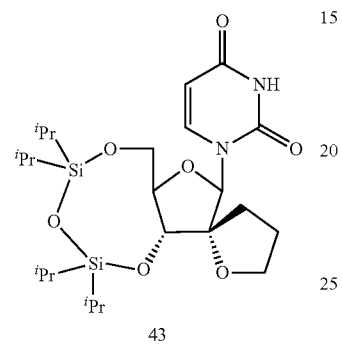

43

To a solution of 41 (0.30 g, 0.55 mmol) in CH$_2$Cl$_2$ (10 mL) and pyridine (2 mL) was added a solution of MsCl (0.09 g, 0.83 mmol) in CH$_2$Cl$_2$ (1 mL) and the solution was stirred at room temperature for 3 h. Water (5 mL) was added and the mixture was washed with brine and dried over Na$_2$SO$_4$. Solvent was evaporated to dryness and the residue was purified by silica gel column chromatography (0-5% MeOH in CH$_2$Cl$_2$) to give intermediate 42 (0.30 g, 87%). To THF (20 mL) was added NaH (60% in mineral oil, 0.05 g, 2.01 mmol) and the mixture was stirred at room temperature for 10 min. To the mixture was added a solution of 42 (0.25 g, 0.40 mmol) in THF (10 mL) and the mixture was stirred at room temperature for 1 h. Water (1 mL) was added followed by addition of EtOAc (100 mL). The mixture was washed with brine and dried over Na$_2$SO$_4$. Solvent was removed and the residue was purified by silica gel column chromatography (0-50% EtOAc in hexanes) to give compound 43 (0.17 g, 80%). $^1$H NMR (400 MHz, CD$_3$OD) δ: 8.17 (s, 1H), 7.90 (d, J=8.4 Hz, 1H), 5.88 (s, 1H), 5.68 (dd, J=2.4, 8.4 Hz, 1H), 4.26 (d, J=13.2 Hz, 1H), 4.01 (m, 5H), 1.90 (m, 4H), 1.05 (m, 12H). LC-MS (ESI): 527 [M+H]$^+$.

Step 4. Preparation of Compound 44.

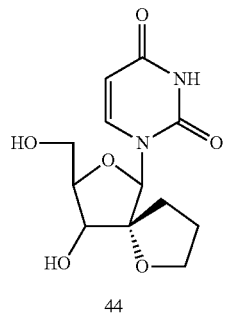

44

A mixture of 43 (0.05 g, 0.09 mmol) and NH$_4$F (100 mg) and catalytic TBAF in MeOH (10 mL) was refluxed for 5 h and the solvent was evaporated to dryness. The residue was purified by silica gel column chromatography (0-10% MeOH in CH$_2$Cl$_2$) to give compound 44 (0.02 g, 93%) as white solid. $^1$H NMR (400 MHz, CD$_3$OD) δ: 8.09 (d, J=8.4 Hz, 1H), 5.91 (s, 1H), 5.68 (d, J=8.4 Hz, 1H), 3.90 (m, 6H), 1.95 (m, 4H). LC-MS (ESI): 284 [M+H]$^+$.

Example 6

Preparation of 1-((4R,5R,7R,8R)-8-hydroxy-7-(hydroxymethyl)-1,6-dioxaspiro[3.4]octan-5-yl)pyrimidine-2,4(1H,3H)-dione, 48 (2'-spiro-oxetane-ribouracil)

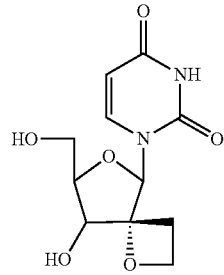

48

Step 1. Preparation of Compound 45.

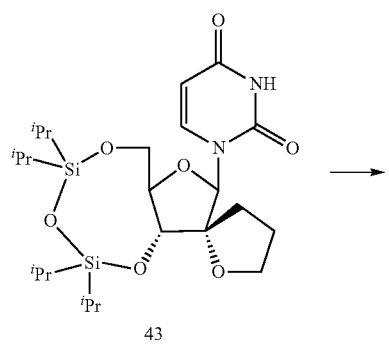

43

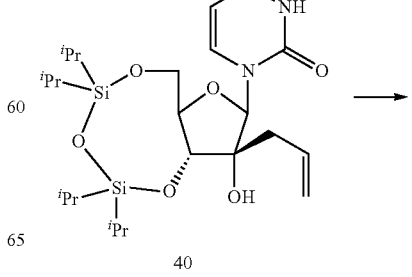

40

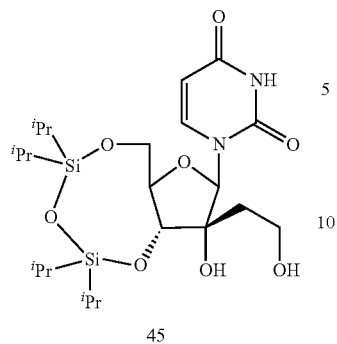

45

To a solution of 40 (0.25 g, 0.47 mmol) in THF (5 mL), t-BuOH (50 mL) and water (0.8 mL) was added OsO₄ (0.5 mL, 2.5% in t-BuOH) followed by addition of NMO (0.5 mL, 50% in water) and the mixture was stirred at room temperature for 3 h. Solvent was evaporated and the residue was co-evaporated with EtOH (20 mL) twice. The residue was dissolved in THF (8 mL) and water (2 mL). To the mixture was added NaIO₄ (0.29 g, 1.34 mmol) and the mixture was stirred at room temperature for 2 h. To the mixture was added MeOH (10 mL). To the mixture was added NaBH₄ (3 mol eq) and the mixture was stirred at room temperature for 1 h. EtOAc (10 mL) was added and the mixture was stirred at room temperature for 20 min. Solid was filtered off. Solvent was evaporated and the residue was purified by silica gel column chromatography (0-5% MeOH in CH₂Cl₂) to give compound 45 (0.16 g, 69%). ¹H NMR (400 MHz, CDCl₃) δ: 9.35 (s, 1H), 7.68 (d, J=8.0 Hz, 1H), 6.05 (s, 1H), 5.71 (d, J=8.0 Hz, 1H), 4.00 (m, 8H), 1.80 (m, 2H), 1.00 (m, 12H). LC-MS (ESI): 531 [M+H]⁺.

Steps 2-3. Preparation of Compound 47.

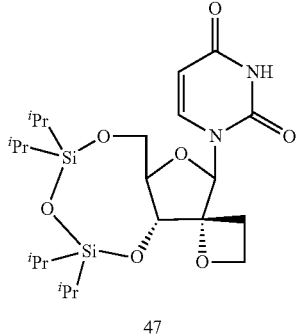

47

To a solution of 45 (0.25 g, 0.47 mmol) in CH₂Cl₂ (20 mL) and pyridine (2 mL) was added MsCl (0.10 g, 0.94 mmol) and the solution was stirred at room temperature for 3 h. Water (2 mL) was added and the solution was evaporated to dryness. EtOAc (100 mL) was added and the organic solution was washed with water, brine and dried over Na₂SO₄. Solvent was evaporated and the residue was purified by silica gel column chromatography (0.80% EtOAc in hexanes) to give intermediate 46 which was dissolved in THF (10 mL). The solution was added into a mixture of NaH (130 mg, 60% mineral oil) in THF (10 mL). The resulting mixture was stirred at room temperature for 2 h and poured into EtOAc (100 mL). The organic solution was washed with water, brine and dried over Na₂SO₄. Solvent was evaporated and the residue was purified by silica gel column chromatography (0-80% EtOAc in hexanes) to give compound 47 (0.054 g, 64%). δ$_H$ (CDCl₃): 8.87 (s, 1H), 7.79 (d, J=8.4 Hz, 1H), 6.22 (s, 1H), 5.68 (d, J=8.4 Hz, 1H), 4.60 (m, 2H), 4.21 (d, J=13.6 Hz. 1H), 4.00 (m, 2H), 3.90 (m, 1H), 2.62 (m, 2H), 1.10 (m, 12H). LC-MS (ESI): 513 [M+H]⁺.

Step 4. Preparation of Compound 48.

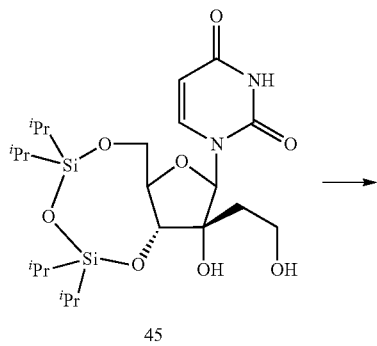

45

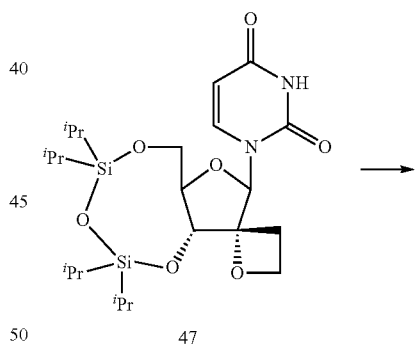

47

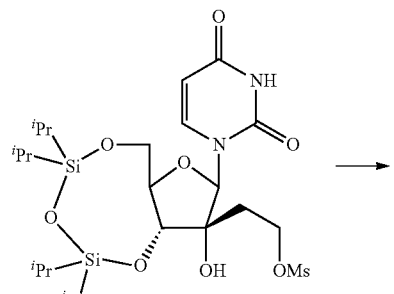

46

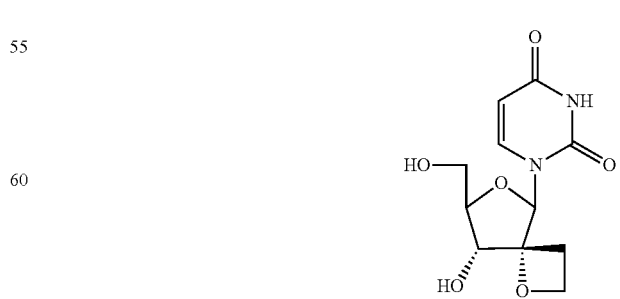

48

To a solution of 47 (0.07 g, 0.14 mmol) in MeOH (10 mL) was added NH$_4$F (100 mg) and the mixture was refluxed for 3 h. Solvent was evaporated and the residue was purified by silica gel column chromatography (0-12% MeOH in CH$_2$Cl$_2$) to give compound 48. $^1$H NMR (400 MHz, CD$_3$OD) δ: 7.93 (d, J=8.0 Hz, 1H), 6.17 (s, 1H), 5.67 (d, J=8.0 Hz, 1H), 4.53 (m, 2H), 3.95 (m, 2H), 3.72 (m, 2H), 2.60 (m, 2H). LC-MS (ESI): 270 [M+H]$^+$.

II. Preparation of 2'-Spiro-Cytosine Analogs

Examples 7-10 describe procedures for converting a protected 3'-5'-2'-spiro-uracil derivative to its corresponding cytidine derivative, as shown by the following equation.

| Ex | Starting Material | Z | Product |
|---|---|---|---|
| 12 | 43 |  | 49 |
| 13 | 31 | | 50 |
| 14 | 35 | | 51 |
| 15 | 47 | | 52 |

Example 7

Preparation of 4-amino-1-((5R,6R,8R,9R)-9-hydroxy-8-(hydroxymethyl)-1,7-dioxaspiro[4.4]nonan-6-yl)pyrimidin-2(1H)-one, 49. (2'-spiro-THF-ribo-cytidine)

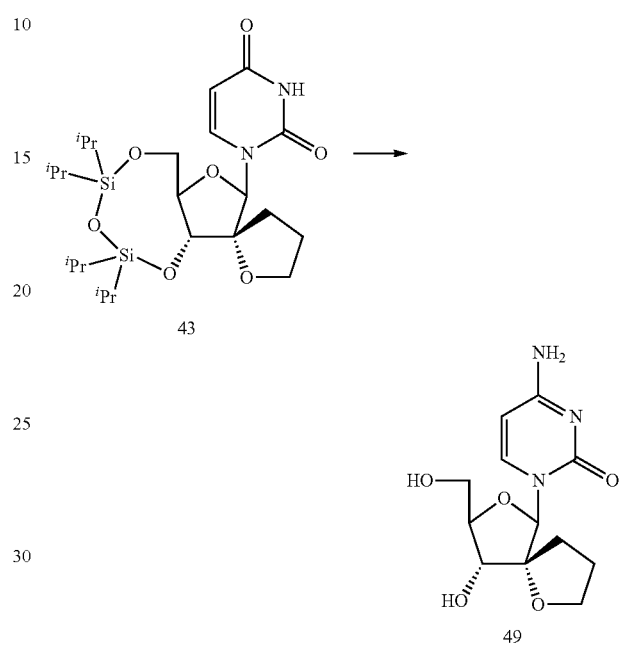

To a solution of compound 43 (0.08 g, 0.14 mmol) in MeCN (10 mL) was added DMAP (0.02 g, 0.14 mmol) and Et$_3$N (0.07 g, 0.71 mmol) followed by addition of TsCl (0.08 g, 0.43 mmol) and the solution was stirred at room temperature for 1 h. To the solution was added NH$_4$OH (30%, 2 mL) and the mixture was stirred at room temperature for 1 h. Solvent was evaporated to dryness and the residue was co-evaporated with toluene twice to give crude cytosine analog which was dissolved in CH$_2$Cl$_2$ (10 mL) and pyridine (1 mL). To the solution was added BzCl (0.1 mL, 0.86 mmol) and the solution was stirred at room temperature for 2 h. Water (5 mL) was added and the mixture was evaporated to dryness under reduced pressure. The residue was dissolved in EtOAc (100 mL) and the solution was washed with water, brine and dried over Na$_2$SO$_4$. Solvent was evaporated and the residue was purified by silica gel column chromatography (0-60% EtOAc in hexanes) to give N-benzoylcytosine analog which was dissolved in THF (10 mL). To the solution was added TBAF (0.12 g, 0.48 mmol) and the solution was stirred at room temperature for 1 h. Solvent was evaporated and the residue was purified by silica gel column (0-8% MeOH in CH$_2$Cl$_2$) to give N-benzoyl nucleoside which was dissolved in 7N NH$_3$ in MeOH (8 mL) and the solution was stirred at room temperature for 20 h. Solvent was evaporated and the residue was purified by silica gel column (0-30% MeOH in CH$_2$Cl$_2$) to give product 49 (0.09 g, 56% from 43). $^1$H NMR (400 MHz, CD$_3$OD) δ: 8.09 (d, J=7.6 Hz, 1H), 5.99 (s, 1H), 5.87 (d, J=7.6 Hz, 1H), 3.95 (m, 6H), 2.80 (m, 4H). LC-MS (ESI): 284 [M+H]$^+$.

Example 8

Preparation of 4-amino-1-((5S,6R,8R,9R)-9-hydroxy-8-(hydroxymethyl)-1,7-dioxaspiro[4.4]nonan-6-yl)pyrimidin-2(1H)-one, 50 (2'-spiro-THF-cytidine)

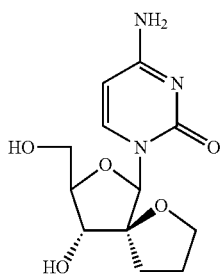

Compound 50 is prepared from compound 31 using a procedure that is analogous to that described in Example 7.

Data for 50: $^1$H NMR (400 MHz, DMSO-$J_6$): δ=7.65 (d, J=7.2 Hz, 1H), 7.05-7.19 (m, 2H), 5.98 (s, 1H), 5.68 (d, J=12 Hz, 1H), 5.57 (d, J=5.6 Hz, 1H), 4.86-4.92 (m, 1H), 3.74-3.77 (m, 1H), 3.54-3.70 (m, 4H), 3.35-3.38 (m, 1H), 2.17-2.24 (m, 1H), 1.66-1.85 (m, 3H). LC-MS (ESI): m/z 283.9 [M+1]$^+$. HRMS (TOF-ESI): Calc. For $C_{12}H_{18}N_3O_5$, 284.1241. found 285.1235.

Example 9

Preparation of 4-amino-1-((4S,5R,7R,8R)-8-hydroxy-7-(hydroxymethyl)-1,6-dioxaspiro[3.4]octan-5-yl)pyrimidin-2(1H)-one, 51 (2'-spiro-oxetane-ara-cytidine)

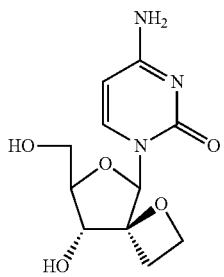

Compound 51 is prepared from compound 35 using a procedure that is analogous to that described in Example 7.

Data for 51: $^1$H NMR (400 MHz, DMSO-$d_6$): δ 7.55 (d, J=12 Hz, 1H), 7.12-7.20 (m, 2H), 6.16 (s, 1H), 5.76 (d, J=5.2 Hz, 1H), 5.68 (d, J=8.0 Hz, 1H), 4.91-4.94 (m, 1H), 4.24-4.29 (m, 1H), 4.06-4.11 (m, 1H), 3.93-3.96 (m, 1H), 3.46-3.63 (m, 3H), 2.87-2.94 (m, 1H), 2.42-2.47 (m, 1H). LC-MS (ESI): m/z 269.9 [M+1]$^+$. HRMS (TOF-ESI): Calc. For $C_{11}H_{16}N_3O_5$, 270.1084. found 270.1081.

Example 10

Preparation of 4-amino-1-((4R,5R,7R,8R)-8-hydroxy-7-(hydroxymethyl)-1,6-dioxaspiro[3.4]octan-5-yl)pyrimidin-2(1H)-one, 52 (2'-spiro-oxetane-THF-cytidine)

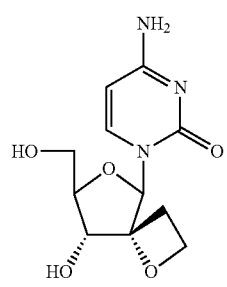

Compound 52 is prepared from compound 47 using a procedure that is analogous to that described in Example 7.

Data for 52: $^1$H NMR (400 MHz, CD$_3$OD) δ: 8.09 7.98 (d, J=7.6 Hz, 1H), 6.26 (s, 1H), 5.87 (d, J=7.6 Hz, 1H), 4.55 (m, 2H), 3.96 (m, 2H), 3.74 (m, 2H), 2.54 (m, 2H). LC-MS (ESI): 270 [M+H]$^+$.

III. Preparation of 2'-Spiro-Ara- and 2'-Spiro-Ribo Guanosine Analogs

A. Preparation of 2'-Spiro-Ara-Guanosine Analogs

Example 11

Preparation of (5S,6R,8R,9R)-6-(2-amino-6-methoxy-9H-purin-9-yl)-8-(hydroxymethyl)-1,7-dioxaspiro[4.4]nonan-9-ol, 62(2'-spiro-THF-ara-(2-amino-6-methoxy-purine) analogs)

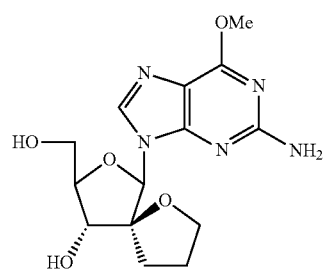 [SMILES: COc1nc(N)nc2c1ncn2C1OC(CO)[C@@H](O)[C@@]12CCCO2]

Step 1. Preparation of Compound 54.

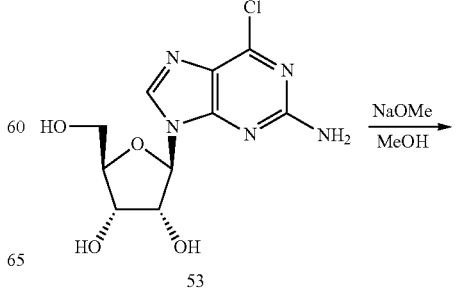

-continued

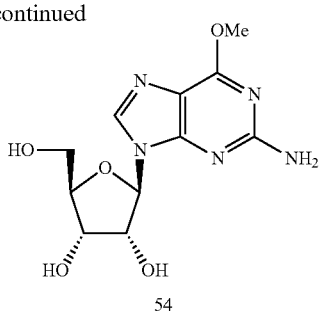
54

Step 3. Preparation of Compound 56.

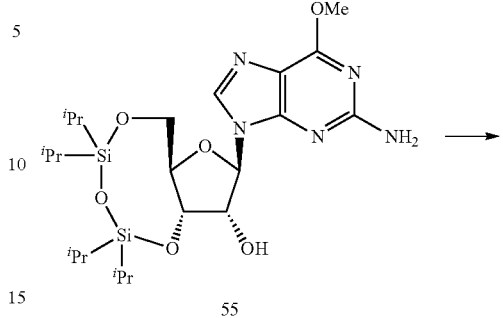
55

To a solution of compound 53 (20.0 g, 66.29 mmol) in anhydrous methanol (400 mL) was added NaOMe (3.58 g, 66.29 mmol) at room temperature. The mixture was heated to reflux for 12 h. The solution was filtered and the filtrate was evaporated to give a crude compound 54. (18.0 g, 91.14%). $^1$H NMR (400 MHz, DMSO-$d_6$): δ=8.09 (s, 1H), 5.75 (d, J=5.6 Hz, 1H), 4.41-4.44 (m, 1H), 4.02-4.09 (m, 1H), 3.96 (s, 3H), 3.86-3.89 (m, 1H), 3.62 (dd, J=12.0 Hz, 4.0 Hz, 1H), 3.52 (dd, J=12.0 Hz, 4.0 Hz, 1H).

Step 2. Preparation of Compound 55.

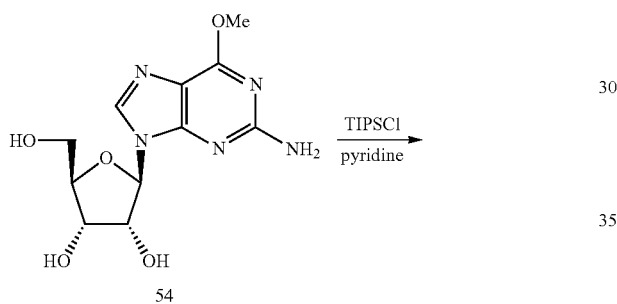
54

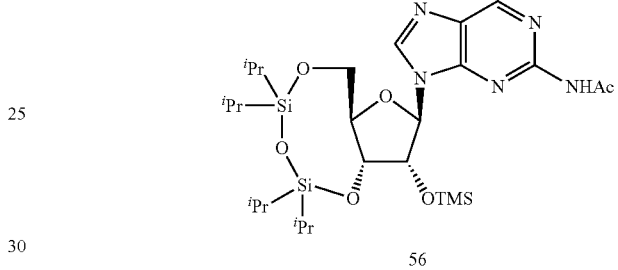
56

To a solution of compound 55 (16.6 g, 30.8 mmol) in anhydrous CH$_2$Cl$_2$ (200 mL) was added Et$_3$N (6.45 mL, 46.2 mmol) and TMSCl (4.99 g, 46.2 mmol) at 0° C. The mixture was stirred room temperature for 10 h and the solution was washed with H$_2$O, dried over Na$_2$SO$_4$ and the solvent was evaporated. The residue was purified by silica gel column chromatography (hexanes:EtOAc=5:1) to give intermediate (16.5 g, 87.53%) which was dissolved in pyridine (150 mL). To the solution was added solution of CH$_3$COCl (1.92 ml, 26.96 mmol) in CH$_2$Cl$_2$ (5 mL) at 0° C. and the solution was stirred overnight at room temperature. The solvent was evaporated and the residue was dissolved in CH$_2$Cl$_2$ (200 mL). The organic solution was washed with H$_2$O, dried with Na$_2$SO$_4$ and evaporated under reduced pressure. The residue was purified by silica gel column chromatography (hexanes: EtOAc=5:1) to give the compound 56 (11.0 g, 62.5%).

Step 4. Preparation of Compound 57.

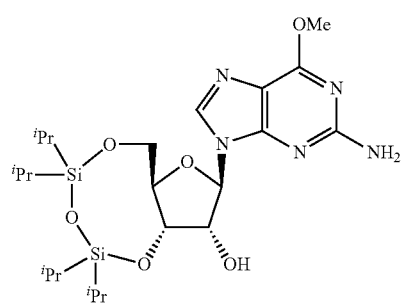
55

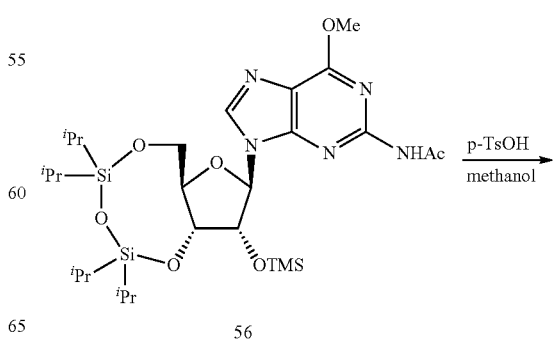
56

To a solution of compound 54 (18.0 g, 60.55 mmol) in anhydrous pyridine (200 mL) was added TIPSCl (22.9 g, 72.66 mmol) at room temperature. The mixture was stirred at room temperature for 20 h. Solvent was evaporated under reduced pressure and the residue was dissolved in EtOAc (200 mL). The solution was washed with H$_2$O, dried over Na$_2$SO$_4$ and evaporated to give a crude 55 which was used for next step without further purification. (16.6 g, 50.8%). $^1$H NMR (400 MHz, DMSO-$d_6$): δ=7.94 (s, 1H), 6.47 (s, 1H), 5.76 (s, 1H), 5.63 (d, J=5.2 Hz, 1H), 4.38-4.41 (m, 1H), 4.32-4.35 (m, 1H), 4.00-4.09 (m, 2H), 3.98 (s, 3H), 3.91-3.97 (m, 1H), 0.94-1.04 (m, 28H).

-continued

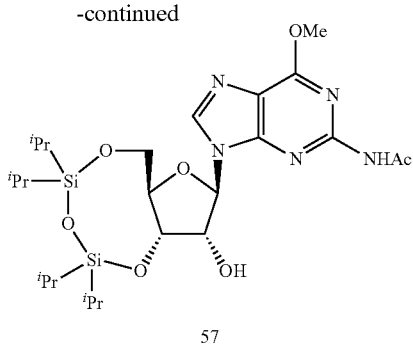

57

To a solution of compound 56 (11.0 g, 17.65 mmol) in methanol (100 mL) was added p-TsOH (1.1 g, 6.39 mmol) and the resulting solution was stirred overnight at room temperature. Solvent was evaporated and the residue was dissolved in EtOAc (200 mL). The solution was washed with H$_2$O and dried with Na$_2$SO$_4$. Solvent was evaporated under reduced pressure and the residue was purified by silica gel column chromatography (hexanse:EtOAc=5:1) to give compound 57 (8.0 g, 77.9%). $^1$H NMR (400 MHz, DMSO-d$_6$): δ=10.39 (s, 1H), 8.28 (s, 1H), 5.87 (s, 1H), 5.61 (d, J=4.4 Hz, 1H), 4.49-4.51 (m, 2H), 4.07-4.11 (m, 1H), 4.03 (s, 3H), 4.00-4.02 (m, 1H), 3.91-3.94 (m, 1H), 2.22 (s, 3H), 0.94-1.04 (m, 28H).

Step 5. Preparation of Compound 58.

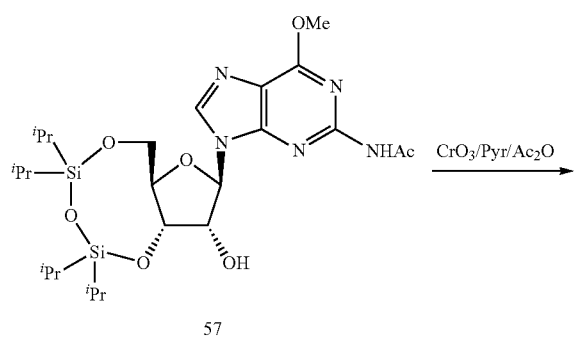

To a stirred solution of CrO$_3$ (2.58 g, 25.8 mmol), anhydrous pyridine (4.18 mL, 51.6 mmol) and Ac$_2$O (2.47 mL, 25.8 mmol) was added a solution of compound 57 (5.0 g, 8.61 mmol) in CH$_2$Cl$_2$ (100 mL). The mixture was stirred 60 min and filtered through a short silica gel column. The filtrate was evaporated and the residue was purified by silica gel column chromatography (hexanes:EtOAc=3:1) to give compound 58 (3.0 g, 60.0%)

Step 6. Preparation of Compound 59.

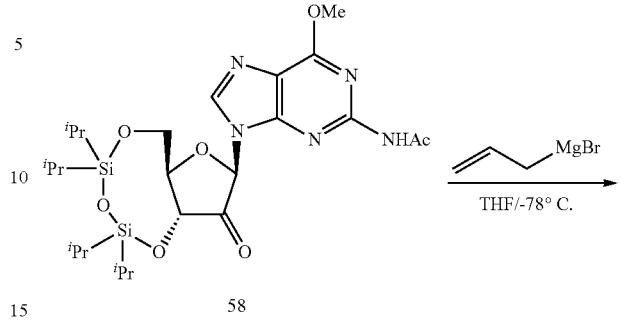

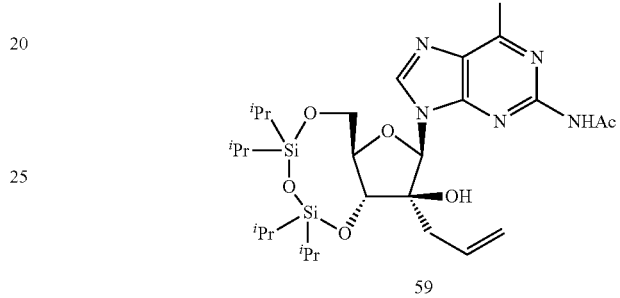

To a solution of compound 58 (3.0 g, 5.18 mmol) in THF (100 mL) was added solution of allylmagnesium bromide (10.36 mL, 10.36 mmol) at −78° C. and the mixture was stirred for 2 h at the same temperature. Then the temperature was raised to −10° C. and the reaction was quenched with H$_2$O. The mixture was extracted with DCM. The organic solution was dried with Na$_2$SO$_4$ and evaporated under reduced pressure. The residue was purified by silica gel column chromatography (hexanes:EtOAc=3:1) to give compound 59 (2.0 g, 62.5%). $^1$H NMR (400 MHz, DMSO-J$_6$): δ=10.36 (s, 1H), 8.17 (s, 1H), 5.99 (s, 1H), 5.82-5.90 (m, 1H), 5.49 (s, 1H), 5.01-5.20 (m, 2H), 4.46 (d, J=7.2 Hz, 1H), 4.07 (s, 3H), 3.97-4.06 (m, 3H), 2.48-2.58 (m, 2H), 2.26 (s, 3H), 0.94-1.04 (m, 28H).

Step 7. Preparation of Compound 60.

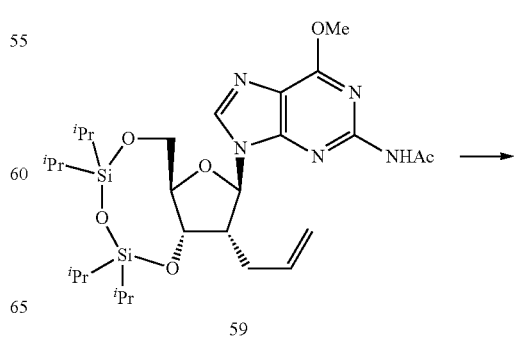

-continued

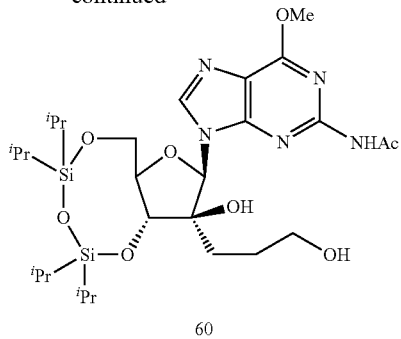

60

To a solution of 59 (1.20 g, 2.07 mmol) in THF (60 mL) was added BH$_3$·SMe$_2$ (0.5 mL, excess) and the solution was stirred at 0° C. for 1 h. To the solution was added an additional BH$_3$·SMe$_2$ (0.5 mL, excess) and the solution was stirred at 0° C. for 2 h. To the resulting solution was added 2N NaOH (2 mL) followed by the addition of H$_2$O$_2$ (30%, 2 mL) and the mixture was stirred at room temperature for 1 h. To the mixture was added additional 2N NaOH (2 mL) followed by the addition of H$_2$O$_2$ (30%, 2 mL) and the mixture was stirred at room temperature for 2 h. EtOAc (200 mL) was added and the mixture was washed with brine and dried over Na$_2$SO$_4$. Solvent was evaporated and the residue was purified by silica gel column (0-80% EtOAc in hexanes) to give product 60 (0.28 g, 22.7%) as foam. $^1$H NMR (400 MHz CDCl$_3$): 8.48 (s, 1H), 8.07 (s, 1H), 6.41 (br s, 1H), 6.15 (s. 1H), 5.00 (br s, 1H), 4.48 (d, J=9.2 Hz, 1H), 4.21 (d, J=13.6 Hz, 1H), 4.13-4.03 (m, 2H), 4.00 (s, 3H), 3.81 (J=8.4 Hz, 1H), 3.47 (m, 1H), 2.28-1.98 (m, 7H), 1.08 (m, 28H). LC-MS (ESI): 640 [M+H]$^+$.

Step 8. Preparation of Compound 61.

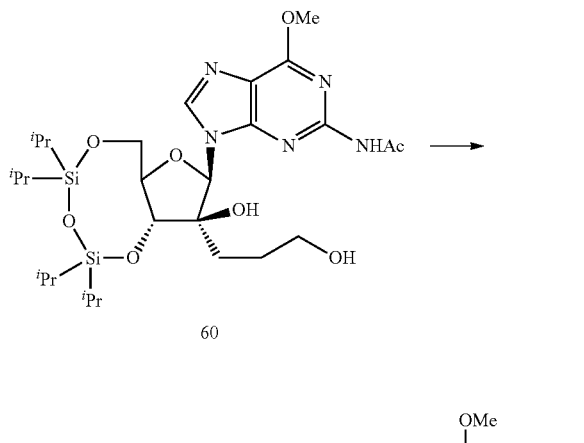

To a solution of compound 60 (0.28 g, 0.44 mmol) in CH$_2$Cl$_2$ (20 mL) and pyridine (1 mL) was added MsCl (0.3 mL, 3.88 mmol), and the solution was stirred at room temperature for 3 h. Water (10 mL) was added and the mixture was extracted with EtOAc (100 mL). The organic solution was washed with brine and dried over Na$_2$SO$_4$. Solvent was removed and the residue was used for the next reaction without purification.

To a solution of the mesylate obtained above in THF (30 mL) was added NaH (60% in mineral oil, 0.3 g, 7.5 mmol) and the mixture was stirred at room temperature for 2 h. Water (10 mL) was added slowly. The mixture was extracted with EtOAc (100 mL). The organic solution was washed with brine and dried over Na$_2$SO$_4$. Solvent was evaporated and the residue was dissolved in MeOH (10 mL). To the solution was added NH$_4$F (0.20 g, 5.40 mmol) and the mixture was heated at reflux for 5 h. Solvent was evaporated and the residue was purified by silica gel column (0-10% MeOH in CH$_2$Cl$_2$) to give product 61. (0.20 g, 47.8%). $^1$NMR (400 MHz CD$_3$OD): 8.8.46 (s, 1H), 6.26 (s, 1H), 4.20 (m, 4H), 3.90 (m, 1H), 3.85 (m, 2H), 3.71 (m, 1H), 3.34 (m, 1H), 2.41 (m, 1H), 2.34 (s, 3H), 1.86 (m, 3H). LC-MS (ESI): 380 [M+H]$^+$.

Step 9. Preparation of Compound 62.

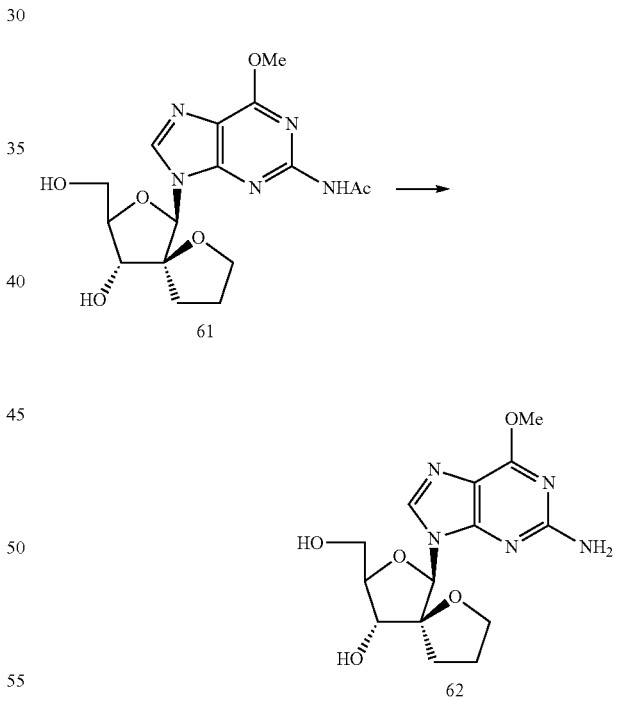

To a solution of compound 61 (0.08 g, 0.21 mmol) in MeOH (5 mL) was added NaOMe (4.8 M, 0.4 mL) and the solution was stirred at room temperature for 24 h. Solvent was evaporated and the residue was purified by silica gel column chromatography (0-15% MeOH in CH$_2$Cl$_2$) to give a solid which was recrystallized from MeOH in EtOAc to product 62 as white solid (0.04 g, 56%). $^1$NMR (400 MHz CD$_3$OD): 8.05 (s, 1H), 6.07 (s, 1H), 4.08 (m, 1H), 4.91 (m, 1H), 3.83 (m, 2H), 3.75 (m, 1H), 3.35 (m, 1H), 3.30 (s, 3H), 2.40 (m, 1H), 1.86 (m, 2H), 1.61 (m, 1H). LC-MS (ESI): 338 [M+H]$^+$.

Example 12

Preparation of (4S,5R,7R,8R)-5-(2-amino-6-methoxy-9H-purin-9-yl)-7-(hydroxymethyl)-1,6-dioxaspiro[3.4]octan-8-ol, 66 (2'-spiro-oxtane-ara-(2-amino-6-methoxy-purine) analog)

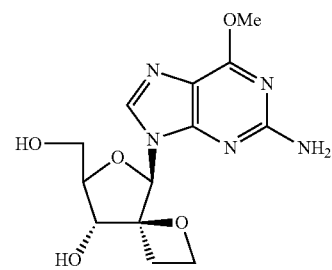

66

Step 1. Preparation of Compound 64.

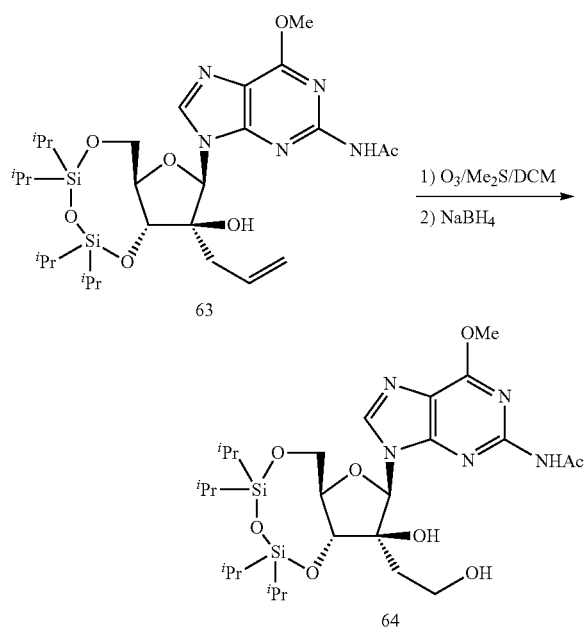

To a solution of compound 63 (1.7 g, 2.74 mmol) in DCM (250 mL) was bubbled with $O_3$ and the solution was stirred at −78° C. for 3 h. To the solution were added $Me_2S$ (1 mL) and $NaBH_4$ (0.104 g, 2.74 mmol) at room temperature. The mixture was stirred overnight and extracted with $CH_2Cl_2$. The organic solution was dried with $Na_2SO_4$. Solvent was evaporated and the residue was purified by silica gel column chromatography (hexanes:EtOAc=1:1) to give compound 64 (0.8 g, 47.06%).

Step 2. Preparation of Compound 65.

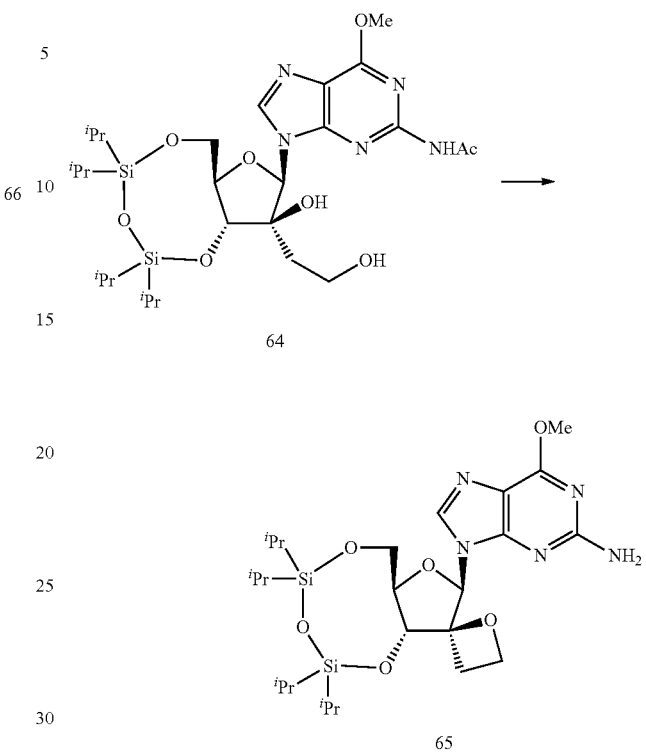

A solution of MsCl (0.22 g, 1.92 mmol) in anhydrous $CH_2Cl_2$ (3 mL) was added to a solution of 64 (0.80 g, 1.28 mmol) in anhydrous pyridine (5.0 ml) drop-wise at room temperature and the solution was stirred at room temperature for 12 h. Methanol (5.0 mL) was added and the resulting mixture was evaporated to dryness under reduced pressure. The residue was co-evaporated with anhydrous toluene (2×5 mL) and purified by silica gel column chromatography (hexanes:EtOAc=3:1) to give the mesylate (0.50 g, 55.6%). $^1$H NMR (400 MHz, $CDCl_3$): δ=8.15 (s, 1H), 8.09 (s, 1H), 5.95 (s, 1H), 4.66-4.69 (m, 2H), 4.51 (d, J=7.6 Hz, 1H), 4.10 (s, 3H), 4.05-4.11 (m, 2H), 3.81-3.87 (m, 1H), 2.97 (s, 3H), 2.50-2.58 (m, 1H), 2.38 (s, 3H), 2.19-2.24 (m, 1H), 0.94-1.04 (m, 28H).

To a stirred suspension of NaH (113.8 mg, 2.84 mmol) in anhydrous THF (10 mL) was added a solution of the mesylate (0.50 g, 0.71 mmol) in THF (5 mL) drop-wise at 0° C. and the mixture was stirred at room temperature for 2 h. The reaction was quenched by addition of ice-cold $H_2O$ (10 mL) slowly and the mixture was extracted with $CH_2Cl_2$. The organic phase was washed with saturated aqueous $NaHCO_3$ (2×20 mL), dried ($Na_2SO_4$), filtered and evaporated to dryness under reduced pressure to give 2'-oxetane-intermediate (0.4 g, 92.6%). $^1$H NMR (400 MHz, $CDCl_3$): δ=8.48 (s, 1H), 8.19 (s, 1H), 6.29 (s, 1H), 4.86 (d, J=6.8 Hz, 1H), 4.21-4.29 (m, 2H), 4.14 (s, 3H), 3.98-4.03 (m, 1H), 3.81-3.89 (m, 2H), 3.25-3.34 (m, 1H), 2.53 (s, 3H), 2.45-2.52 (m, 1H), 0.94-1.04 (m, 28H).

To a stirred solution of 2'-oxetane-intermediate (400 mg, 0.658 mmol) in anhydrous methanol (50 mL) was added NaOMe (71.28 mg, 1.32 mmol) and the solution was stirred at room temperature for 20 h. The solution was evaporated to give compound 65 (0.3 g, 92.6%).

125

Step 3. Preparation of Compound 66

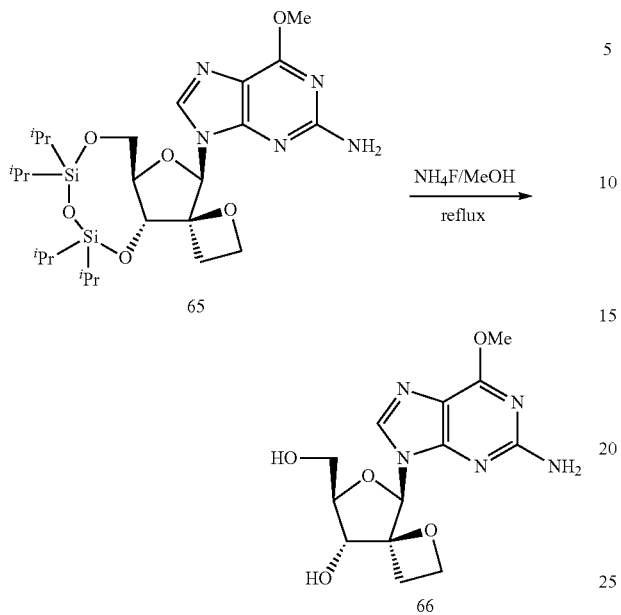

To a stirred solution of 65 (300 mg, 0.53 mmol) in anhydrous methanol (30 mL) was added NH₄F (39.28 mg, 1.06 mmol) at room temperature and the solution was heated to refluxed for 10 h. The solution was evaporated and the residue was purified by silica gel column chromatography (CH₂Cl₂: MeOH=20:1) to provide compound 66 (36.0 mg, 21.05%). ¹H NMR (400 MHz, DMSO-d₆): δ=7.94 (s, 1H), 6.52 (s, 2H), 6.09 (s, 1H), 5.92 (d, J=5.2 Hz, 1H), 5.02 (t, J=5.2 Hz, 1H), 4.28-4.30 (m, 1H), 4.17-4.19 (m, 1H), 3.97 (s, 3H), 3.94-3.97 (m, 1H), 3.69-3.73 (m, 1H), 3.53-3.59 (m, 2H), 2.95-2.98 (m, 1H), 2.35-2.37 (m, 1H). HRMS (TOF-ESI): Calc. For C₁₃H₁₇N₅O₅, 324.1308. found 324.1306.

B. Preparation of 2'-Spiro-Ribo-Guanosine Analogs

Example 13

Preparation of (5R,6R,8R,9R)-6-(2-amino-6-methoxy-9H-purin-9-yl)-8-(hydroxymethyl)-1,7-dioxaspiro[4.4]nonan-9-ol, 72 (2'-spiro-THF-ribo-(2-amino-6-methoxy-purine) analog)

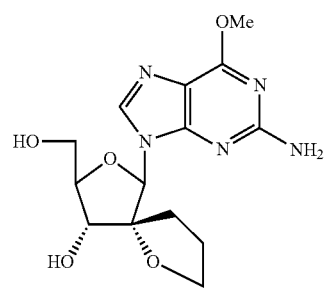

126

Step 1. Preparation of Compound 67.

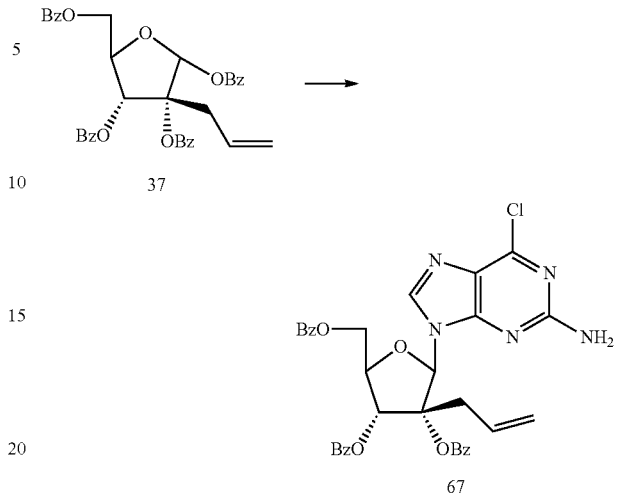

To a precooled (0° C.) solution of compound 37 (4.00 g, 6.59 mmol) and 6-chloroguanine (1.68 g, 9.89 mmol) in MeCN (80 mL) were added DBN (2.46 g, 19.78 mmol) then TMSOTf (5.86 g, 26.38 mmol), and the solution was heated at 65° C. for 5 h then room temperature for 16 h. The solution was cooled to room temperature and poured into a mixture of EtOAc (300 mL) and excess NaHCO₃ with ice. Organic solution was washed with NaHCO₃, brine and dried over Na₂SO₄. Solvent was evaporated and the residue was purified by silica gel column chromatography (5-60% EtOAc in hexanes) to give compound 67 (3.2 g, 74%). ¹NMR (400 MHz CD₃OD): δ: 8.18-7.25 (m, 16 Hz), 6.73 (s, 1H), 5.40 (m, 3H), 5.12 (m, 2H), 4.82 (m, 1H), 4.74 (m, 3H), 3.04 (m, 1H), 2.52 (m, 1H). LC-MS (ESI): 654 [M+H]⁺.

Step 2. Preparation of Compound 68.

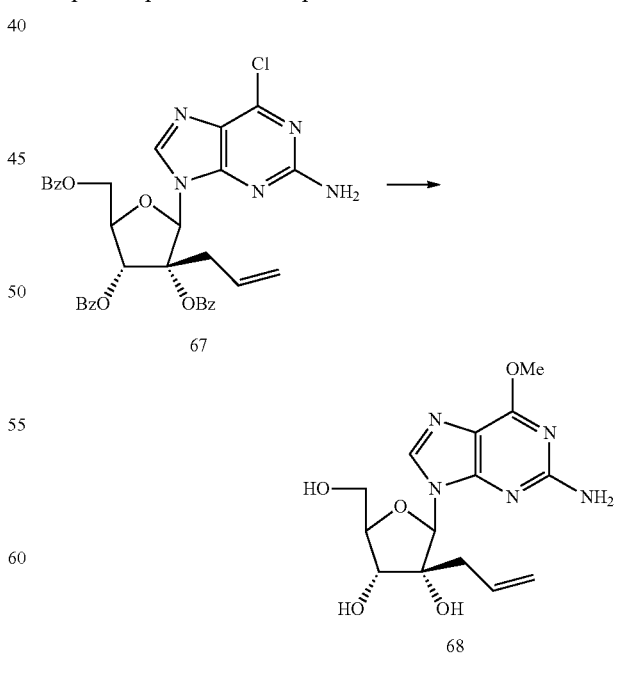

To a mixture of compound 67 (3.20 g, 4.89 mmol) in MeOH (80 mL) was added 25% NaOMe in MeOH 1.86 g, 48.92 mmol) and the solution was stirred at room temperature for 24 h. Solvent was evaporated and the residue was purified by silica gel column chromatography (0-15% MeOH in CH$_2$Cl$_2$) to give product 68 as white solid. $^1$NMR (400 MHz CD$_3$OD): δ: 8.13 (s, 1H), 5.97 (s, 1H), 5.67 (m, 1H), 4.77 (m, 1H), 4.56 (m, 1H), 4.45 (d, J=8.8 Hz, 1H), 4.13-3.83 (m, 6H), 2.25 (m, 1H), 2.05 (m, 1H). LC-MS (ESI): 338 [M+H]$^+$.

Step 3. Preparation of Compound 69.

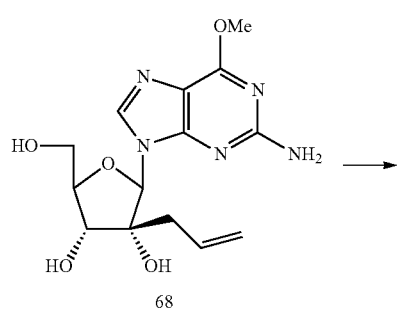

68

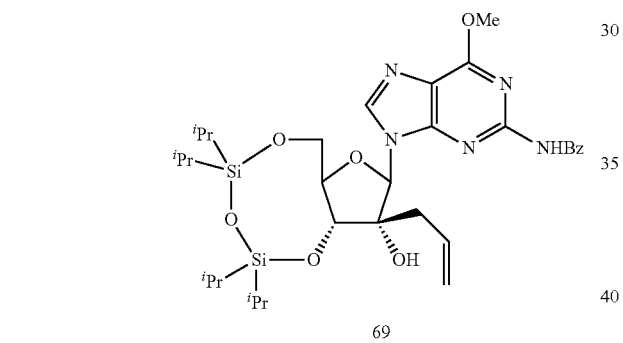

69

To a solution of compound 68 (1.33 g, 3.94 mmol) in pyridine (20 mL) was added TIPSCl (1.37 g, 4.34 mmol) and the solution was stirred at room temperature for 16 h. Solvent was evaporated and the residue re-dissolved in EtOAc (400 mL) and the solution was washed with brine and dried over Na$_2$SO$_4$. Solvent was evaporated and the residue purified by silica gel column chromatography (0-5% MeOH in CH$_2$Cl$_2$) to give intermediate (1.30 g, 57%). $^1$NMR (400 MHz CD$_3$OD): δ: 7.757 (s, 1H), 5.93 (s, 1H), 5.66 (m, 1H), 4.88 (m, 1H), 4.82 (s, 2H), 4.73 (d, J=7.6 Hz, 1H), 4.64 (m, 1H), 4.20 (m, 1H), 4.08 (m, 7H), 2.20 (m, 2H), 1.07 (m, 28H). LC-MS (ESI): 450 [M+H]$^+$. To a solution of the intermediate in pyridine (10 mL) and CH$_2$Cl$_2$ (20 mL) was added benzoyl chloride (0.63 g, 4.48 mmol) and the solution was stirred at room temperature for 5 h. Water (10 mL) was added and the solution was evaporated to give a residue which was dissolved in EtOAc (200 mL). Organic solution was washed with brine and dried over Na$_2$SO$_4$. Solvent was evaporated and the residue was purified by silica gel column chromatography (0-5% MeOH in CH$_2$Cl$_2$) to give compound 69 (1.50 g, 98%) as foam. δ$_H$ (CD$_3$OD): 8.46 (s, 1H), 7.78 (m, 6H), 5.98 (s, 1H), 5.72 (m, 1H), 5.00 (d, J=8.0 Hz, 1H), 4.83 (d, J=10.4 Hz, 1H), 4.50 (m, 1H), 4.35 (m, 1H), 4.10 (m, 5H), 2.32 (m, 1H), 2.20 (m, 1H), 1.05 (m, 28H). LC-MS (ESI): 684 [M+H]$^+$.

Step 4. Preparation of Compound 70.

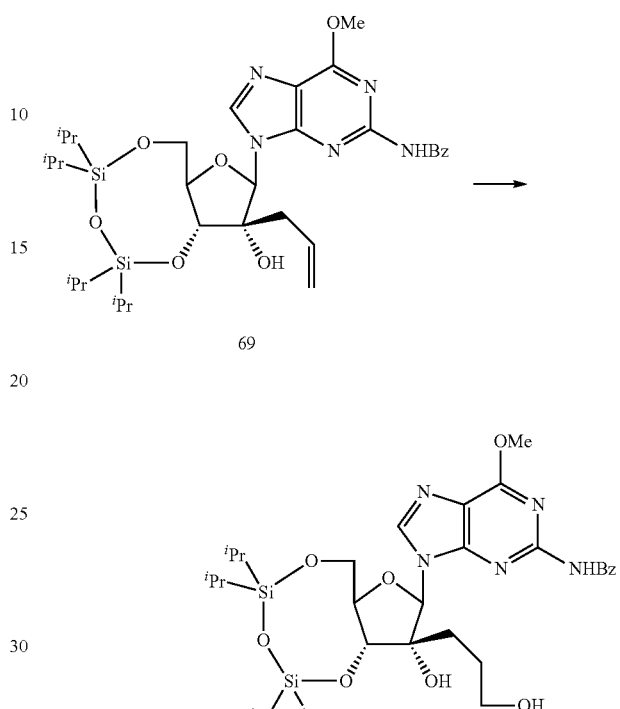

To a solution of compound 69 (0.20 g, 0.29 mmol) in THF (20 mL) was added BH$_3$.SMe$_2$ (0.15 g, 1.46 mmol) and the solution was stirred at 0° C. for 3 h. To the solution was added 2N NaOH (2N, 1 mL) then H$_2$O$_2$ (0.5 mL) at 0° C. The mixture was stirred at room temperature for 2 h. EtOAc (100 mL) was added and the solution was washed with brine and dried over Na$_2$SO$_4$. Solvent was evaporated and the residue was purified by silica gel column chromatography (0-100% EtOAc in hexanes) to give compound 70 (0.07 g, 33%). $^1$NMR (400 MHz CD$_3$OD): δ: 8.60 (s, 1H), 8.31 (s, 1H), 7.65 (m, 5H), 6.26 (s, 1H), 4.47 (d, J=8.8 Hz, 1H), 4.26 (m, 2H), 4.10 (m, 4H), 3.50 (m, 2H), 1.83 (m, 1H), 1.61 (m, 2H), 1.27 (m, 1H), 1.10 (m, 28H). LC-MS (ESI): 702 [M+H]$^+$.

Step 5. Preparation of Compound 71.

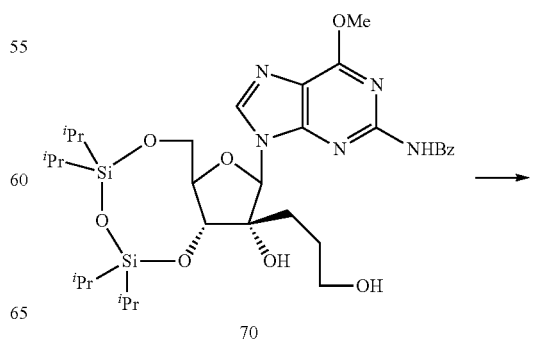

70

-continued

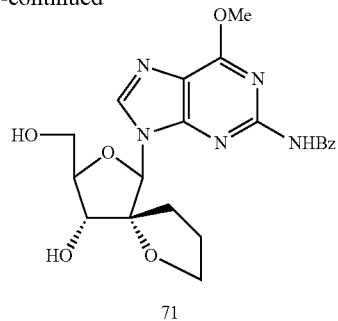

71

To a solution of compound 70 (0.05 g, 0.07 mmol) in CH$_2$Cl$_2$ (10 mL) and pyridine (0.5 mL) was added MsCl (0.1 mL g, excess) and the solution was stirred at room temperature for 2 h. EtOAc (100 mL) was added to the reaction. The mixture was washed with brine and dried over Na$_2$SO$_4$. Solvent was evaporated and the residue was co-evaporated with toluene twice to give mesylate. To a solution of the mesylate in THF (10 mL) was added NaH (60% in mineral oil, 0.06 g, 1.50 mmol) and the mixture was stirred at room temperature for 2 h. EtOAc (100 mL) was added and the organic solution was washed with brine and dried over Na$_2$SO$_4$. Solvent was evaporated and the residue was dissolved in MeOH (10 mL). To the solution was added NH$_4$F (0.10 g, 2.75 mmol) and the mixture was refluxed at 60° C. for 4 h. Solvent was evaporated and the residue was purified by silica gel column chromatography (0-10% MeOH in CH$_2$Cl$_2$) to give product 71 (0.023 g, 74% from 70) as white solid. $^1$NMR (400 MHz CD$_3$OD): δ: 8.63 (s, 1H), 7.80 (m, 5H), 6.20 (s, 1H), 4.59 (m, 1H), 4.00 (m, 9H), 1.94 (m, 3H), 1.36 (m, 1H). LC-MS (ESI): 440 [M+H]$^+$.

Step 6. Preparation of Compound 72.

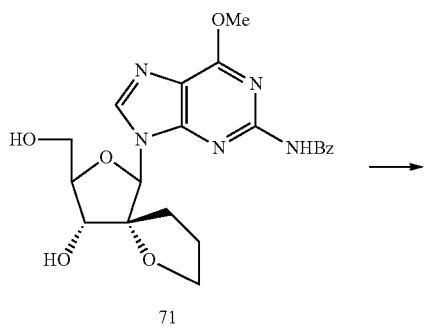

71

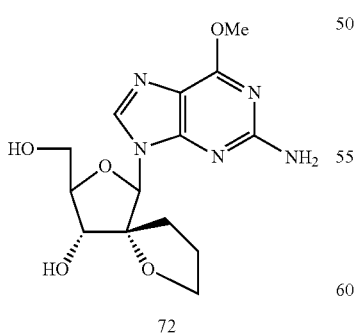

72

To a solution of 71 (0.03 g, 0.07 mmol) in MeOH (5 mL) was added NaOMe (0.11 g, 2.00 mmol) and the solution was stirred at room temperature for 2 days. Solvent was evaporated and the residue was purified by silica gel column chromatography (0-15% MeOH in CH$_2$Cl$_2$) to give nucleoside 72 (0.02 g, 87%) as white solid. $^1$NMR (400 MHz CD$_3$OD): δ: 8.24 (s, 1H), 5.97 (s, 1H), 4.36 (d, J=9.6 Hz, 1H), 4.00 (m, 8H), 1.94 (m, 2H), 1.80 (m, 1H), 1.34 (m, 1H). LC-MS (ESI): 338 [M+H]$^+$.

The corresponding guanosine derivative of 72 is prepared in a manner analogous to Example 15.

Example 14

Preparation of (4R,5R,7R,8R)-5-(2-amino-6-methoxy-9H-purin-9-yl)-7-(hydroxymethyl)-1,6-dioxaspiro[3.4]octan-8-ol, 76 (2'-spiro-oxetane-ribo-(2-amino-6-methoxy-purine) analog)

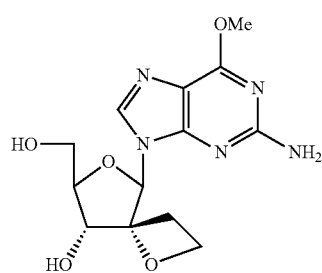

76

Step 1. Preparation of Compound 74.

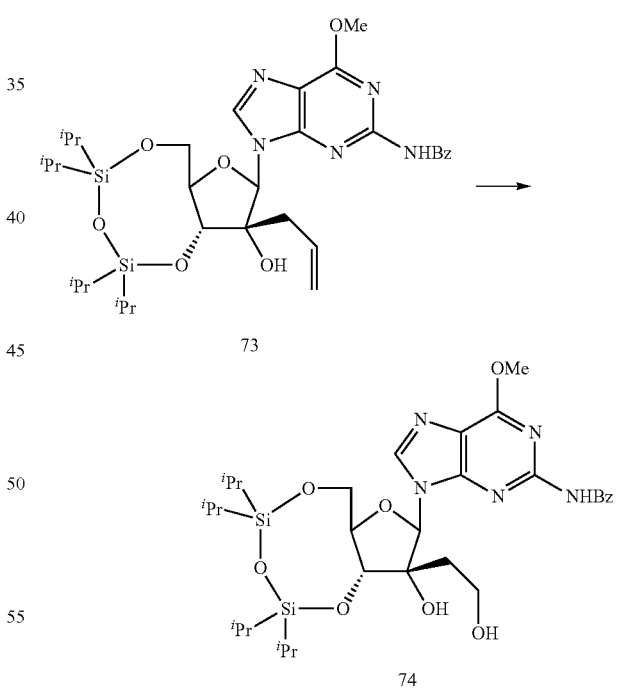

73

74

To a mixture of compound 73 (0.30 g. 0.44 mmol) in THF (6 mL), t-Butanol (6 mL) and water (1 mL) was added 0.25% OsO$_4$ in t-Butanol (0.5 mL) followed by addition of 50% NMO (0.2 mL, 0.85 mmol) and the mixture was stirred at room temperature for 16 h. Solvent was evaporated and the residue was co-evaporated with toluene twice to give diol as a mixture of diastereomers which was dissolved in THF (10 mL). To the solution was added water (1 mL) followed by addition of NaIO₄ (excess) portion-wise until starting material disappeared at room temperature for 3 h. EtOAc (100 mL) was added and the solution was washed with brine and dried over Na₂SO₄. Solvent was evaporated and the residue was dissolved in EtOAc (10 mL) and EtOH (10 mL). To the pre-cooled solution at 0° C. was added NaBH₄ (50.16 mg, 1.32 mmol) and the mixture was stirred at 0° C. for 1 h. EtOAc (100 mL) was added and the residue was purified by silica gel column chromatography (0-10% MeOH in CH₂Cl₂) to give compound 74 (0.14 g, 43% from 73). ¹NMR (400 MHz CDCl₃): δ: 8.57 (s, 1H), 8.48 (s, 1H), 7.70 (m, 5H), 6.26 (s, 1H), 4.15 (m, 9H), 1.28 (m, 2H), 1.15 (m, 28H). LC-MS (ESI): 688 [M+H]⁺.

Step 2. Preparation of Compound 75.

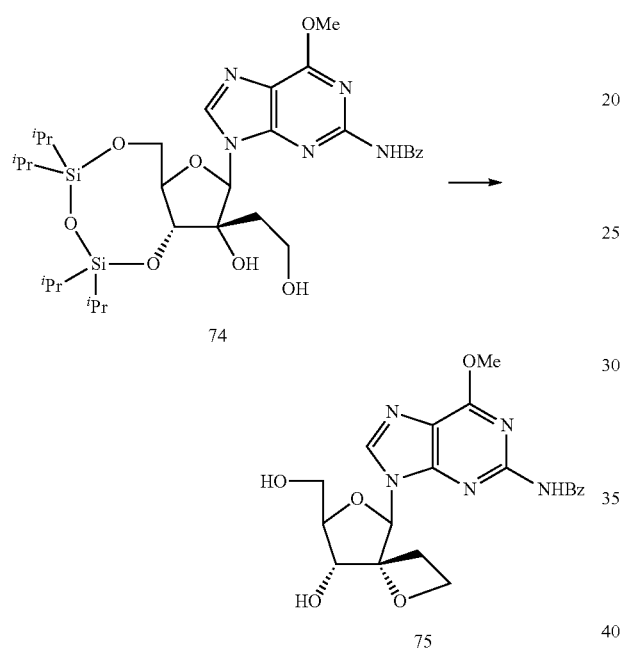

To a solution of compound 74 (0.33 g, 0.47 mmol) in CH₂Cl₂ (30 mL) and pyridine (3 mL) was added MsCl (0.11 g, 0.94 mmol) and the solution was stirred at room temperature for 3 h. Water (10 mL) was added and the mixture was extracted with EtOAc (100 mL). The solution was washed with brine and dried over Na₂SO₄. Solvent was evaporated and the residue was purified by silica gel column chromatography (0-100% EtOAc in hexanes) to give mesylate (0.30 g, 82%). δ_H (CDCl₃): 8.53 (s, 1H), 8.21 (s, 1H), 7.65 (m, 5), 6.14 (s, 1H), 4.80 (s, 1H), 4.54 (m, 2H), 4.33 (m, 1H), 4.16 (s, 3H), 4.10 (m, 3H), 2.95 (s, 3H), 2.05 (m, 2H), 1.05 (m, 28H). LC-MS (ESI): 766 [M+H]⁺. To a solution of mesylate (0.20 g, 0.26 mmol) in THF (10 mL) was added NaH (60% mineral oil, 110 mg, 2.75 mmol) and the mixture was stirred at room temperature for 1 h. The mixture was poured into EtOAc (100 mL) and the solution was washed with brine and dried over Na₂SO₄. Solvent was evaporated and the residue was purified by silica gel column chromatography (0-80% EtOAc in hexanes) to give oxetane-intermediate (0.15 g, 57%). ¹NMR (400 MHz CDCl₃): δ: 8.47 (s, 1H), 8.23 (s, 1H), 7.65 (m, 5H), 6.38 (s, 1H), 7.74 (m, 1H), 4.59 (m, 1H), 4.46 (, d, J=9.2 Hz, 1H), 4.26 (d, J=13.2 Hz, 1H), 4.15 (s, 3H), 4.00 (m, 2H), 2.56 (m, 2H), 1.09 (m, 28H). LC-MS (ESI): 686 [M+H]⁺.

To the solution of the oxetane-intermediate in MeOH (10 mL) was added NH₄F (1.3 mmol, 46.8 mg) and the mixture was heated at 60° C. for 5 h. Solvent was evaporated and the residue was purified by silica gel column chromatography (0-10% MeOH in CH₂Cl₂) to give compound 75 (0.05 g, 43% from 74) as white solid. LC-MS (ESI): 428[M+H]⁺.

Step 3. Preparation of Compound 76.

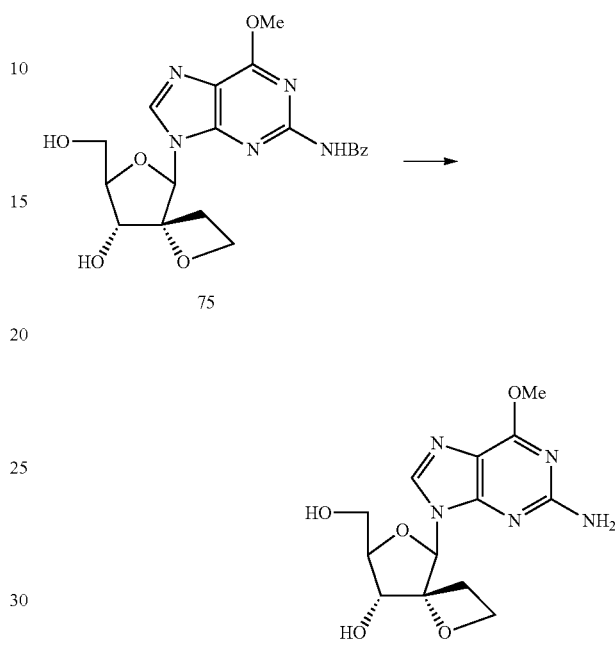

A solution of compound 75 (0.20 g, 0.45 mmol) in MeOH (10 mL) was added NaOMe (4.8 M, 0.8 mL) and the solution was stirred at room temperature for 20 h. Solvent was evaporated and the residue was purified by silica gel column chromatography (0-15% MeOH in CH₂Cl₂) to give compound 76 (0.10 g, 69%). ¹NMR (400 MHz CD₃OD): δ: 8.15 (s, 1H), 6.26 (s, 1H), 4.50 (m, 3H), 4.05 (s, 3H), 3.96 (m, 1H), 3.80 (m, 2H), 2.57 (m, 1H), 2.27 (m, 1H). LC-MS (ESI): 324 [M+H]⁺.

Example 15

Preparation of 2-amino-9-((4R,5R,7R,8R)-8-hydroxy-7-(hydroxymethyl)-1,6-dioxaspiro[3.4]octan-5-yl)-1H-purin-6(9H)-one, 77 (2'-spiro-oxetane-riboguanosine)

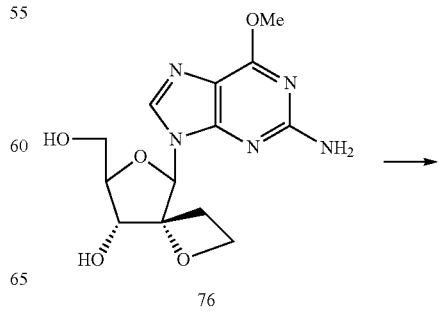

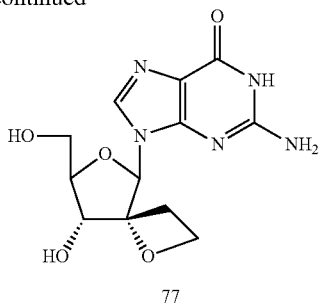

To a solution of compound 76 (0.04 g, 0.12 mmol) in MOPS buffer (0.1 M, 10 mL) was added adenosine deaminase (2.0 mg) and the solution was kept at 37° C. for 2 days. Solvent was evaporated and the residue was purified by silica gel column chromatography (0-30% MeOH in CH$_2$Cl$_2$) to give a crude compound 77 which was recrystallized from MeOH to remove crystalline of phosphate salt from buffer. The residue was re-dissolved in MeOH (50 mL) and formic acid (1 mL) was added. The solution was evaporated and the residue was co-evaporated with toluene twice. The resulting solid was purified by silica gel column chromatography (0-30% MeOH in CH$_2$Cl$_2$) to give product 77 as white solid (0.02 g, 65%). $^1$NMR (400 MHz CD$_3$OD): δ: 8.04 (s, 1H), 6.21 (s, 1H), 4.54 (m, 2H), 4.36 (d, J=8.8 Hz, 1H), 4.94 (m, 1H), 3.78 (m, 2H), 2.60 (m, 1H), 2.33 (m, 1H). LC-MS (ESI): 310 [M+H]$^+$.

IV. Preparation of 2'-Spiro-Ara- and 2'-Spiro-Ribo-Adenine Analogs

A. Preparation of 2'-Spiro-Ara-Adenine Analogs

Example 16

Preparation of (4S,5R,7R,8R)-5-(6-amino-9H-purin-9-yl)-7-(hydroxymethyl)-1,6-dioxaspiro[3.4]octan-8-ol, 87

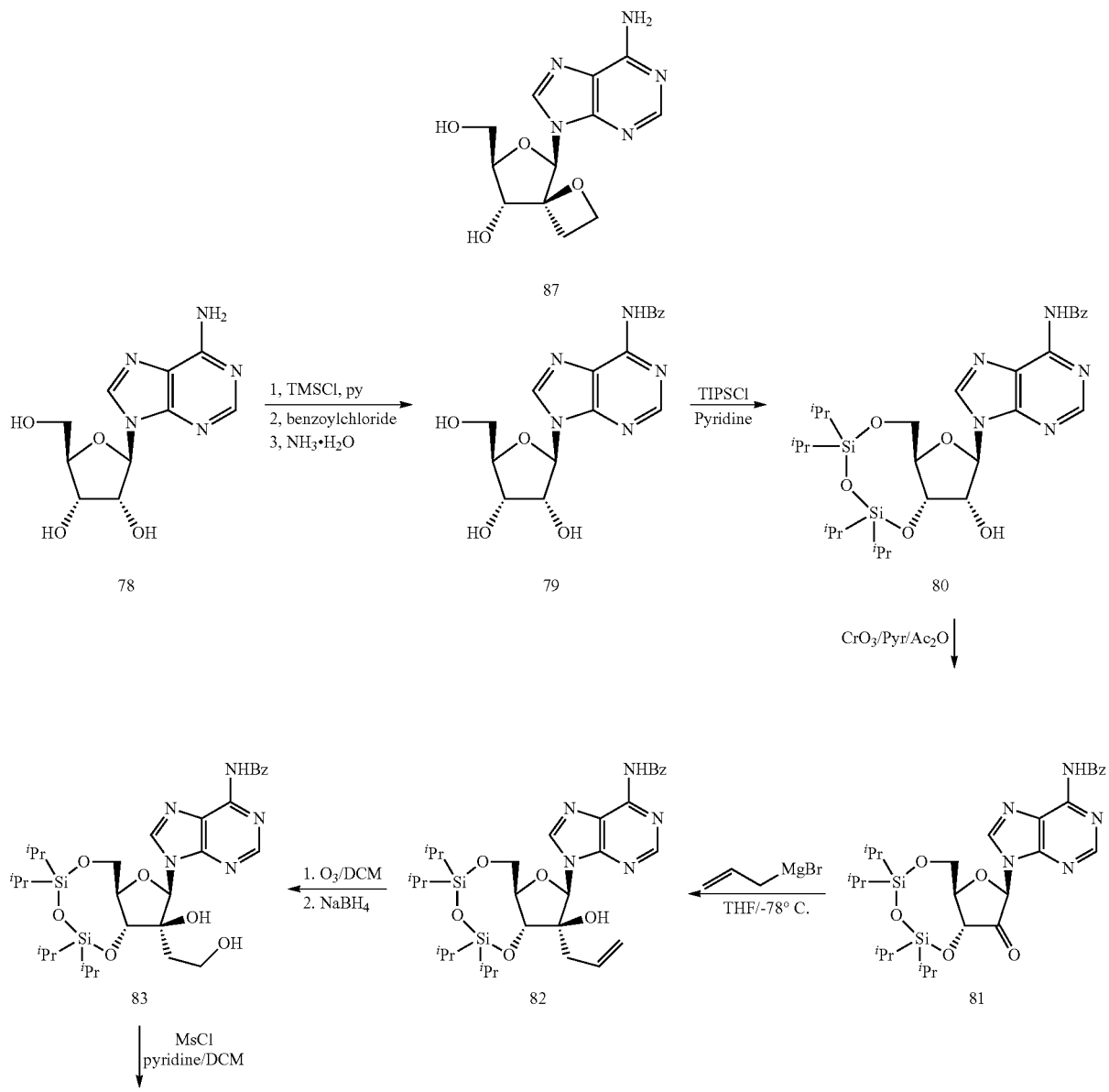

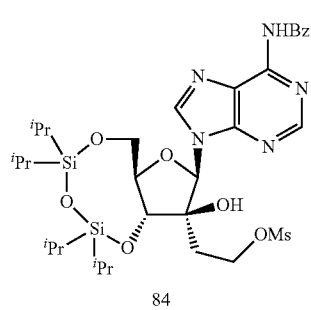
84

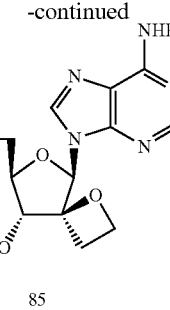
85

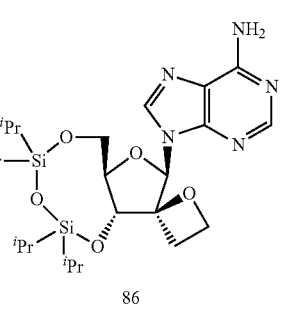
86

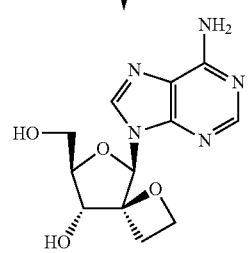
87

Compound 87 is prepared using an eight-step reaction sequence that begins with adenine (78).

Step 1: Preparation of Compound 79

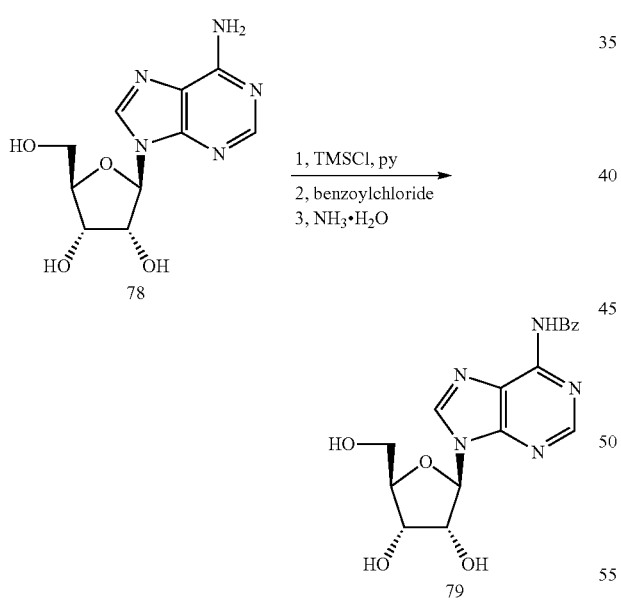

Compound 78 (30.0 g, 112.26 mmol) was dried by co-evaporation with anhydrous pyridine three times and dissolved in dry pyridine (400 mL). To the solution was added TMSCl (60.98 g, 561.3 mmol) and the solution was stirred for 1 h at 0° C. To the resulting solution was added benzoyl chloride (78.9 g, 561.3 mmol) dropwise and the mixture was stirred 3 h at room temperature. The mixture was cooled to 0° C. and H₂O (120 mL) was added, and the resulting mixture was stirred for 0.5 h. NH₃·H₂O (30%, 230 mL) was added and the mixture was stirred for 2 h. Solid was collected by filtration and washed with H₂O and EtOAc to give crude product 79. (38.0 g, 91.6%)

$^1$H NMR (400 MHz, DMSO-d$_6$) δ: 8.77 (s, 1H), 8.74 (s, 1H), 8.05 (d, J=12 Hz, 2H), 7.62-7.66 (m, 1H), 7.53-757 (m, 2H), 6.05 (d, J=6.0 Hz, 1H), 4.66 (t, J=5.8 Hz, 1H), 4.20 (t, J=4.8 Hz, 1H), 3.99 (dd, J=7.6 Hz, 3.6 Hz, 1H), 3.69 (dd, J=8.0 Hz, 4.0 Hz, 1H), 3.58 (dd, J=8.0 Hz, 4.0 Hz, 1H),

Step 2: Preparation of Compound 80

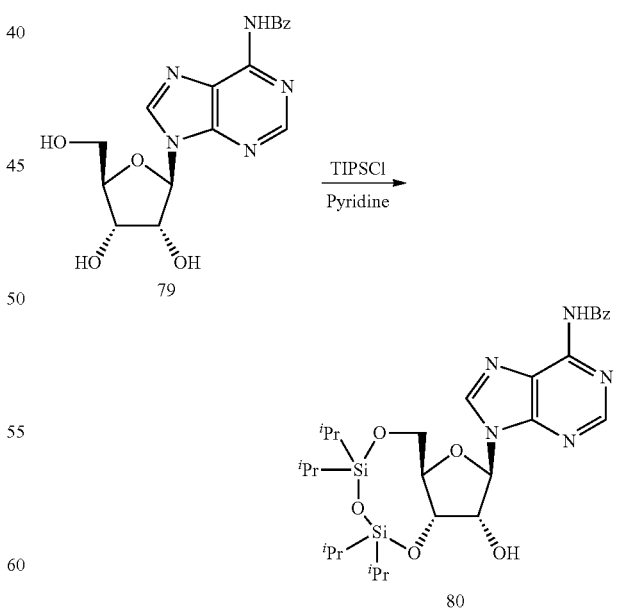

To a solution of compound 79 (38.0 g, 102.33 mmol) in anhydrous pyridine (200 mL) was added TIPSCl (38.7 g, 122.8 mmol) and the mixture was stirred for 20 h at room temperature. Solvent was removed under reduce pressure and the residue was dissolved in EtOAc (200 mL). The solution was washed with H₂O and the solvent was removed to give 80 which was used for next step without further purification. (45.0 g, 71.62%)

Step 3: Preparation of Compound 81

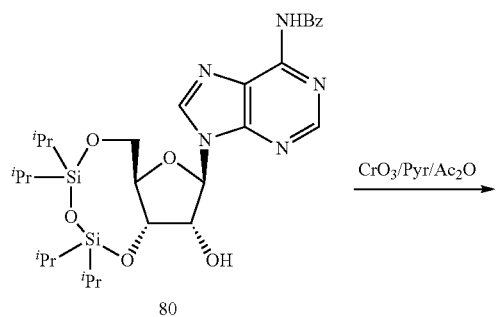

To a stirred solution of CrO₃ (20.0 g, 32.58 mmol), anhydrous pyridine (15.8 mL, 195.48 mmol) and Ac₂O (9.5 mL, 97.74 mmol) was added a solution of compound 80 (20.0 g, 32.58 mmol) in CH₂Cl₂. (100 mL). The mixture was stirred at room temperature for 60 min. The solution was passed through a short silica gel column. Solvent was removed and the residue was purified by silica gel column chromatography (hexane:EtOAc=3:1) to give compound 81 (4.0 g, 21.2%)

Step 4: Preparation of Compound 82

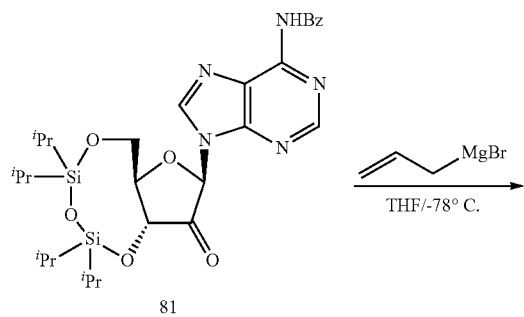

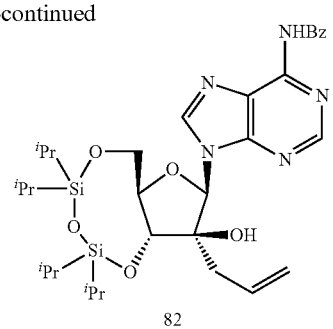

To a solution of compound 81 (4.0 g, 6.9 mmol) in THF (100 mL) was added a solution of allylmagnesium bromide (13.82 mL, 3.82 mmol) at −78° C. and the resulting mixture was stirred for 2 hours at the same temperature. Then the temperature was increased to −10° C. and the reaction mixture was quenched with H₂O and extracted with DCM. The organic layer was dried with Na₂SO₄ and solvent was removed under reduced pressure. The residue was purificated by silica gel column chromatography. (hexane:EtOAc=2:1) to give compound 82 (1.6 g, 35.5%). ¹H NMR (400 MHz, DMSO-d₆) δ: 11.20 (s, 1H), 8.73 (s, 1H), 8.39 (s, 1H), 8.04 (d, J=8.8 Hz, 2H), 7.53-7.65 (m, 3H), 6.17 (s, 1H), 5.82-5.95 (m, 1H), 5.55 (s, 1H), 515-5.23 (m, 1H), 5.02-5.10 (m, 1H), 4.60 (d, J=7.2 Hz, 1H), 3.85-4.10 (m, 3H), 2.55-2.60 (m, 2H), 0.94-1.04 (m, 28H), Step 5: Preparation of Compound 83

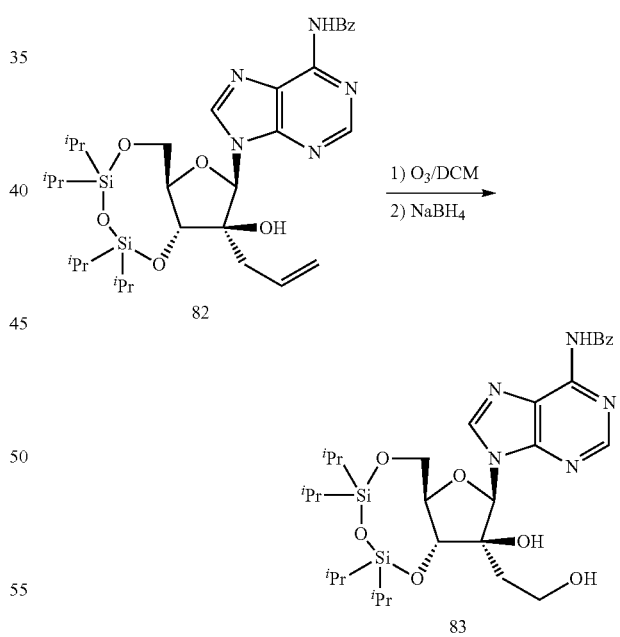

To a solution of compound 82 (1.6 g, 2.45 mmol) in DCM (100 mL) was bubbled with O₃ at −78° C. and the solution was stirred at the same temperature for 3 h. To the solution was added 1 ml of Me₂S followed by addition of NaBH₄ (92.5 mg, 2.45 mmol) at room temperature. The mixture was stirred overnight. The solution was washed with H₂O and the solvent was removed to give a crude product which was purified by silica gel column chromatography (hexane:EtOAc=1:1) to give compound 83 (1.0 g, 62.1%).

Step 6: Preparation of Compound 84

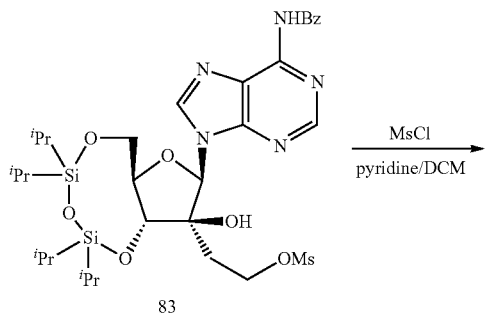

83

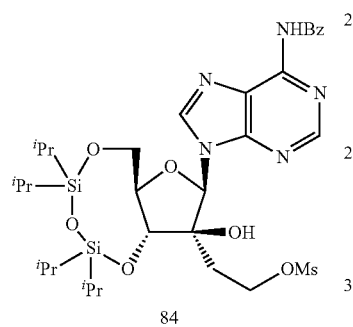

84

A solution of MsCl (0.349 g, 3.04 mmol) in anhydrous CH₂Cl₂ (3 mL) was added dropwise to a solution of nucleoside 83 (1.0 g, 1522 mmol) in anhydrous pyridine (5.0 mL) at room temperature. After stirring for 12 h, methanol (5.0 mL) was added and the resulting mixture was evaporated to dryness under reduced pressure. The residue was co-evaporated with anhydrous toluene (2×5 mL) then dissolved in CH₂Cl₂ (50 mL). The solution was washed with saturated aqueous NaHCO₃ (2×25 mL). The combined aqueous phase was extracted with CH₂Cl₂ (50 mL). The combined organic phase was dried (Na₂SO₄) and solvent was evaporated to dryness under reduced pressure to give compound 84 which was used for the next reaction without further purification.

Step 7: Preparation of Compound 85

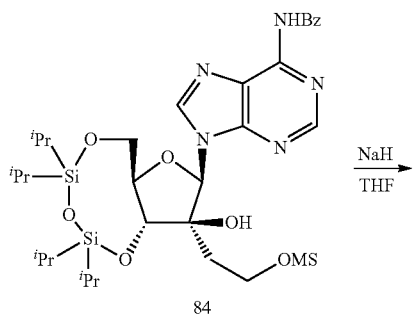

84

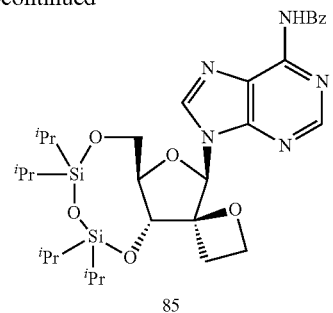

85

To a stirred suspension of NaH (180 mg, 4.50 mmol) in anhydrous THF (10 mL) was added a solution of compound 84 (1.0 g, 1.50 mmol) in THF (5 mL) at 0° C. After stirring at room temperature for 2 h, ice-water (10 mL) was slowly added. CH₂Cl₂ (50 mL) was added and the separated organic phase was washed with saturated aqueous NaHCO₃ (2×20 mL). The combined aqueous phase was extracted with CH₂Cl₂ (25 mL). The combined organic phase was dried (Na₂SC₄) and the solvent was evaporated to dryness under reduced pressure to provide 85 which was used for the next reaction without further purification.

Step 8: Preparation of Compound 86

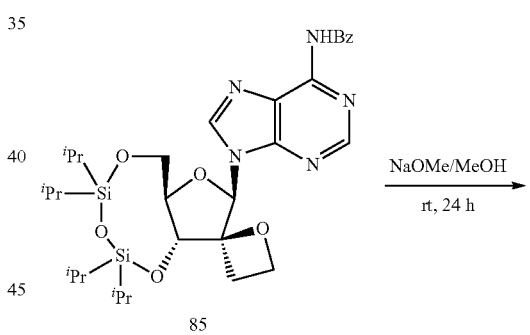

85

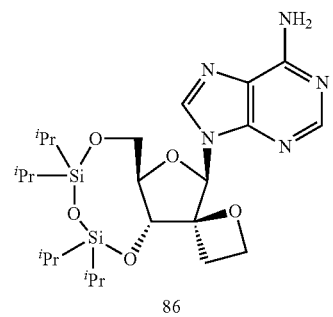

86

To a stirred solution of compound 85 (1.0 g, 1.55 mmol) in anhydrous methanol (50 mL) was added NaOMe (0.5 g, 9.26 mmol) and the solution was stirred at room temperature for 20 h. The solution was filtered and the filtrate was evaporated to give crude product 86.

Step 9: Preparation of Compound 87.

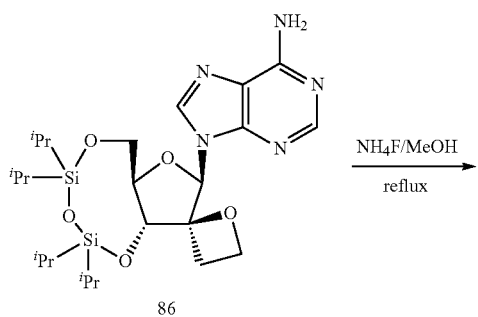

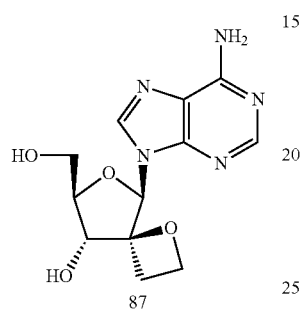

To a stirred solution of compound 86 (0.8 g, 1.49 mmol) in anhydrous methanol (30 mL) was added NH$_4$F (550 mg, 14.9 mmol) and the mixture was heated at reflux for 10 h. The mixture was filtered and the filtrate was evaporated to give a crude product which was purified by silica gel column chromatography (CH$_2$Cl$_2$:MeOH=20:1) to provide compound 87 (36.0 mg, 21.05%). $^1$H NMR (400 MHz, DMSO-d$_6$) δ: 8.21 (s, 1H), 8.17 (s, 1H), 7.29 (s, 2H), 6.26 (s, 1H), 5.90 (d, J=5.2 Hz, 1H), 5.04 (t, J=5.2 Hz, 1H), 4.08-4.30 (m, 2H), 3.92-3.97 (m, 1H), 3.70-374 (m, 1H), 3.55-3.66 (m, 2H), 2.98-3.05 (m, 1H), 2.41-2.49 (m, 1H). HRMS (TOF-ESI): Calc. For C$_{12}$H$_{16}$N$_5$O$_4$, 294.1197. found 294.1194.

Example 17

Preparation of (5S,6R,8R,9R)-6-(6-amino-9H-purin-9-yl)-8-(hydroxymethyl)-1,7-dioxaspiro[4.4]nonan-9-ol (94)

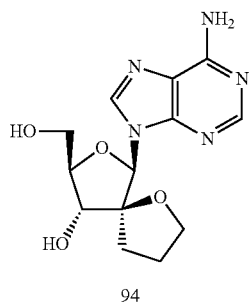

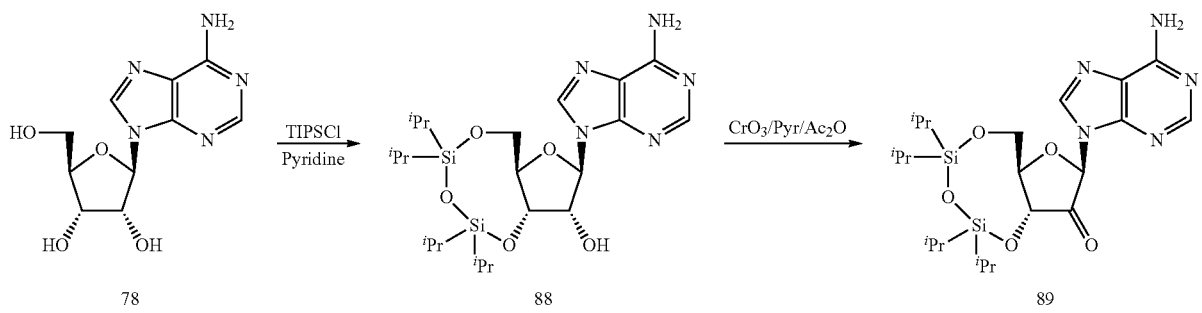

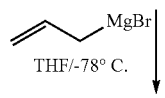

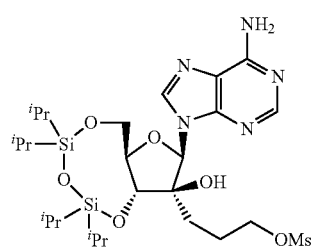
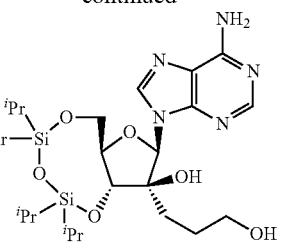
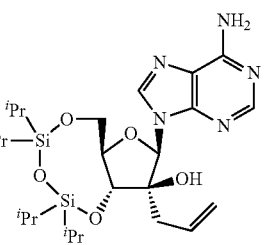

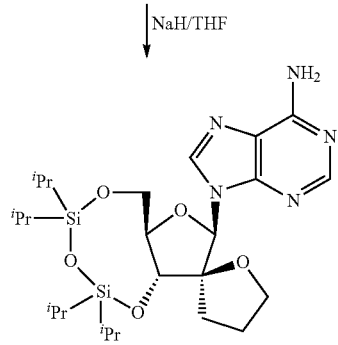
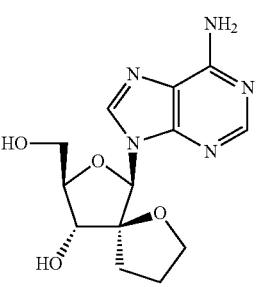

In the preparation of 94, it is possible to forego protection of the 6-amino-purine, which means that 94 can be prepared from adenine (78) using a seven-step sequence.

Step 1: Preparation of Compound 88

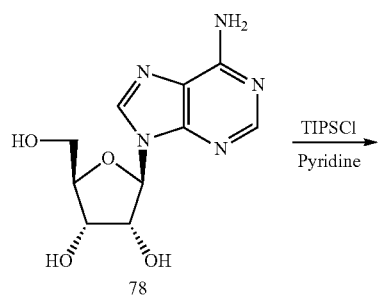

To a solution of compound 78 (30.0 g, 112.0 mmol) in anhydrous pyridine (200 mL) was added TIPSCl (342.5 g, 113.5 mmol) at 0° C. The mixture was stirred overnight and the solvent was removed under reduce pressure. The residue was dissolved in EtOAc (200 mL). The solution was washed with H₂O and the solvent was removed to give 88 which was used for next reaction without further purification.

Step 2: Preparation of Compound 89

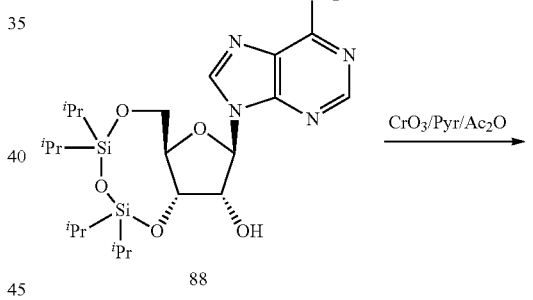

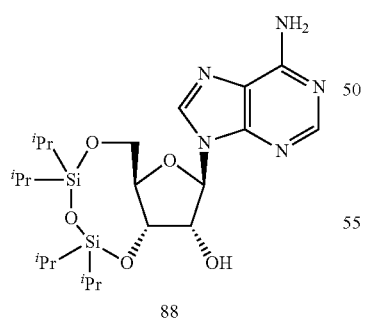

To a solution of CrO₃ (21.2 g, 212 mmol), anhydrous pyridine (32.42 mL, 414 mmol) and Ac₂O (20.3 ml, 212 mmol) was added compound 88 (54.0 g, 106 mmol) at 0° C. The mixture was stirred for 1 h and passed through a short silica gel column. The solvent was removed and the residue was co-evaporation with anhydrous toluene twice to give a crude compound 89 which was used for the next reaction without further purification.

Step 3: Preparation of Compound 90

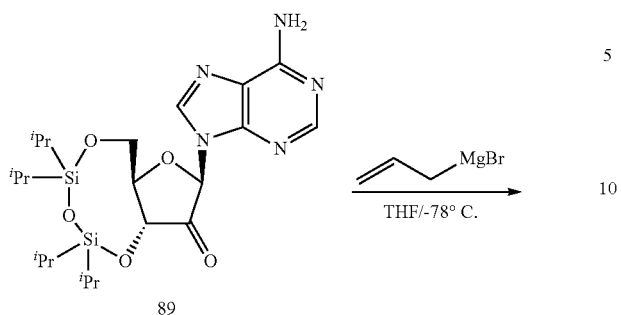

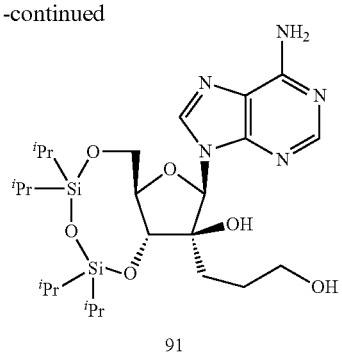

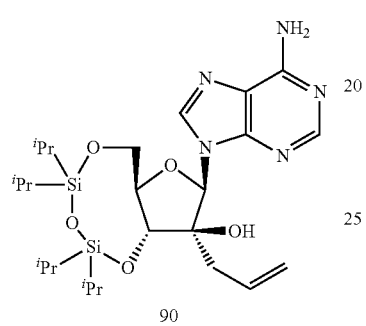

To a solution of compound 89 (31.0 g, 61.1 mmol) in THF (300 mL) was added a solution of allylmagnesium bromide (122 mL, 122 mmol) in THF (50 mL) at −78° C. and the solution was stirred for 2 h at the same temperature. The temperature was then raised to −10° C. and the reaction mixture was quenched by addition of NH$_4$Cl solution and the mixture was extracted with DCM. The organic layer was dried over Na$_2$SC$_4$ and the solvent was removed under reduced pressure. The residue was purificated by silica gel column chromatography (hexane:EtOAc=3:1) to give product 90 (8.0 g, 23.8%). $^1$H NMR (400 MHz, DMSO-d$_6$) δ: 8.12 (s, 1H), 8.10 (s, 1H), 7.28 (s, 2H), 5.99 (s, 1H), 5.82-5.92 (m, 1H), 5.44 (s, 1H), 5.12-5.19 (m, 1H), 5.01-5.08 (m, 1H), 4.56 (d, J=6.4 Hz, 1H), 3.96-4.04 (m, 1H), 3.90-3.96 (m, 1H), 3.82-3.89 (m, 1H), 2.46-2.55 (m, 2H), 0.94-1.04 (m, 28H), Step 4: Preparation of Compound 91

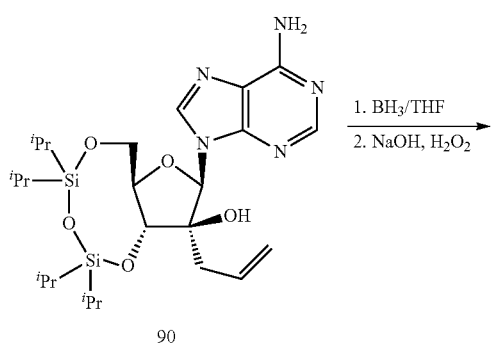

To a solution of compound 90 (2.0 g, 3.64 mmol) in THF (50 mL) was added a solution of BH$_3$ (1.82 mL, 18.2 mmol) at 0° C. and stirred for 2 h at the same temperature. To the solution was added a mixture of H$_2$O$_2$ (4.13 mL, 36.4 mmol) and NaOH (9.1 mL, 18.2 mmol). The resulting mixture was stirred at room temperature overnight and extracted with DCM. The solvent was removed and the residue was purified by silica gel column chromatography (hexane:EtOAc=1:1) to give product 91 (0.6 g, 29%). $^1$H NMR (400 MHz, DMSO-d$_6$) δ: 8.13 (s, 1H), 8.12 (s, 1H), 7.30 (s, 2H), 5.94 (s, 1H), 5.38 (s, 1H), 4.52-4.59 (m, 1H), 4.41-4.49 (m, 1H), 3.96-4.04 (m, 1H), 3.95-4.05 (m, 2H), 3.75-3.84 (m, 1H), 1.75-1.80 (m, 1H), 1.48-1.60 (m, 2H), 0.94-1.04 (m, 28H), Step 5: Preparation of Compound 92

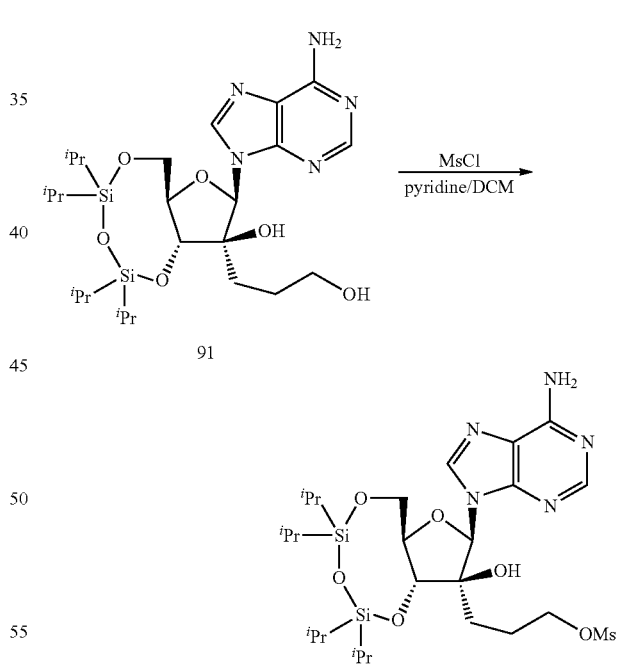

A solution of MsCl (0.058 g, 0.51 mmol) in anhydrous CH$_2$Cl$_2$ (5.0 mL) was added dropwise to a solution of nucleoside 91 (0.24 g, 0.42 mmol) in anhydrous pyridine (5.0 mL) at room temperature. After stirring for 12 h, methanol (5.0 mL) was added and the resulting mixture was evaporated to dryness under reduced pressure. The residue was co-evaporated with anhydrous toluene (2×5 mL). The residue was dissolved in CH$_2$Cl$_2$ (50 mL) and the solution was washed with saturated aqueous NaHCO₃ (2×25 mL). The combined aqueous phase was extracted with CH₂Cl₂ (50 mL). The combined organic phase was dried (Na₂SO₄) and the solvent was evaporated to dryness under reduced pressure to give crude product 92 which was used for the next reaction without further purification.

Step 6: Preparation of Compound 93

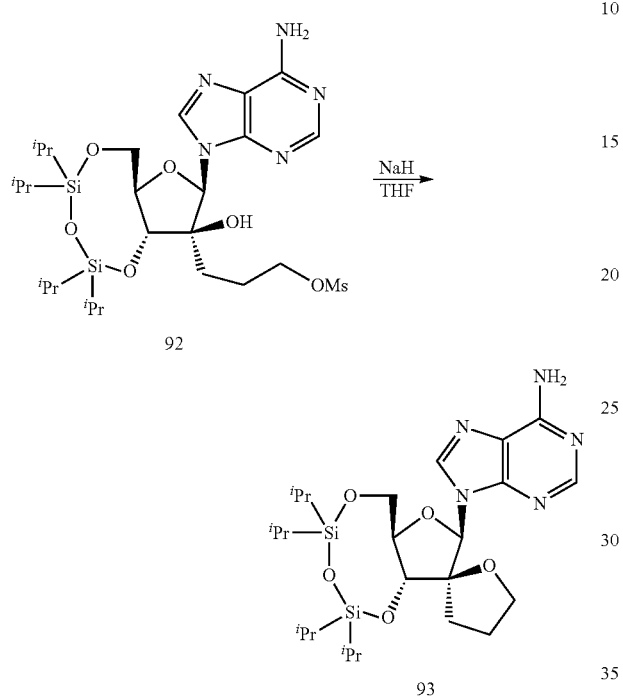

To a stirred suspension of NaH (112 mg, 2.79 mmol) in anhydrous THF was added a solution of compound 92 (0.45 g, 0.697 mmol) in THF dropwise at 0° C. After stirring at room temperature for 2 h, ice-water (10 mL) was slowly added and the mixture was diluted with CH₂Cl₂. The separated organic phase was washed with saturated aqueous NaHCO₃ (2×20 mL). The combined aqueous phase was extracted with CH₂Cl₂ (25 mL) and the combined organic phase was dried (Na₂SO₄) and the solvent was evaporated to dryness under reduced pressure to provide 93 (330 mg, 86.1%) for the next reaction without further purification.

Step 7: Preparation of Compound 94

To a stirred solution of compound 93 (0.25 g, 0.45 mmol) in anhydrous methanol (20 mL) was added NH₄F (200 mg, 5.4 mmol) and the mixture was heated at reflux for 10 h. The solvent was evaporated and the residue was purified by silica gel column chromatography (CH₂Cl₂:MeOH=20:1) to give 94 (53.4 mg, 38.7%). ¹H NMR (400 MHz, DMSO-d₆) δ: 8.26 (s, 1H), 8.14 (s, 1H), 7.28 (s, 2H), 6.02 (s, 1H), 5.69 (d, J=5.2 Hz, 1H), 5.07 (t, J=5.2 Hz, 1H), 4.09 (t, J=5.2 Hz, 1H), 3.72-3.79 (m, 1H), 3.60-3.69 (m, 3H), 3.18-3.24 (m, 1H), 2.29-2.34 (m, 1H), 1.74-1.82 (m, 2H), 1.62-1.64 (m, 1H). HRMS (TOF-ESI): Calc. For $C_{13}H_{18}N_5O_4^+$, 308.1359. found 308.1347.

B. Preparation of 2'-Spiro-Ribo-Adenine Analogs

Example 18

Preparation of (4R,5R,7R,8R)-5-(6-amino-9H-purin-9-yl)-7-(hydroxymethyl)-1,6-dioxaspiro[3.4]octan-8-ol (100)

Step 1. Preparation of Compound 95.

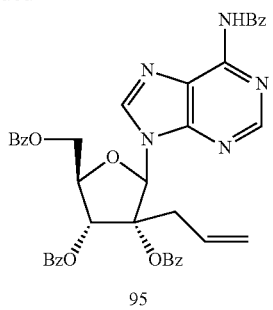

95

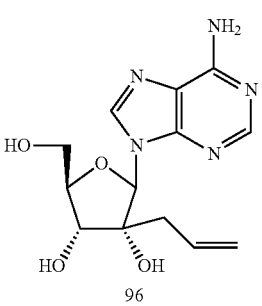

96

Step 3. Preparation of Compound 97.

A mixture of N⁶-benzoyladenine (3.14 g, 13.19 mmol) in HMDS (30 mL) with (NH₄)SO₄ (50 mg) was heated at 140° C. for 4 h. Solvent was removed and the residue was dissolved in MeCN (50 mL). To the solution was added a solution of sugar 37 in MeCN (30 mL). To the resulting solution was added SnCl₄ (39.57 mml, 1M, 39.57 mL) in CH₂Cl₂ at 0° C. and the solution was stirred at 60° C. for 4 h. The reaction solution was cooled to room temperature and poured into ice-water, excess NaHCO₃ and EtOAc (200 mL) with stirring. Organic solution was washed with brine and dried over Na₂SO₄. Solvent was removed and the residue was purified by silica gel column chromatography (10-70% EtOAc in hexane) to give compound 95 as foam (1.95 g, 41%). ¹H NMR (400 MHz, CDCl₃) δ: 9.04 (s, 1H), 8.89 (s, 1H), 8.26 (s, 1H), 7.35-8.20 (m, 20H), 6.53 (d, J=7.6 Hz, 1H), 5.29 (m, 1H), 4.68-5.00 (m, 4H), 2.99 (m, 1H), 2.65 (m, 1H). m/z: 724 (M+1).

Step 2. Preparation of Compound 96.

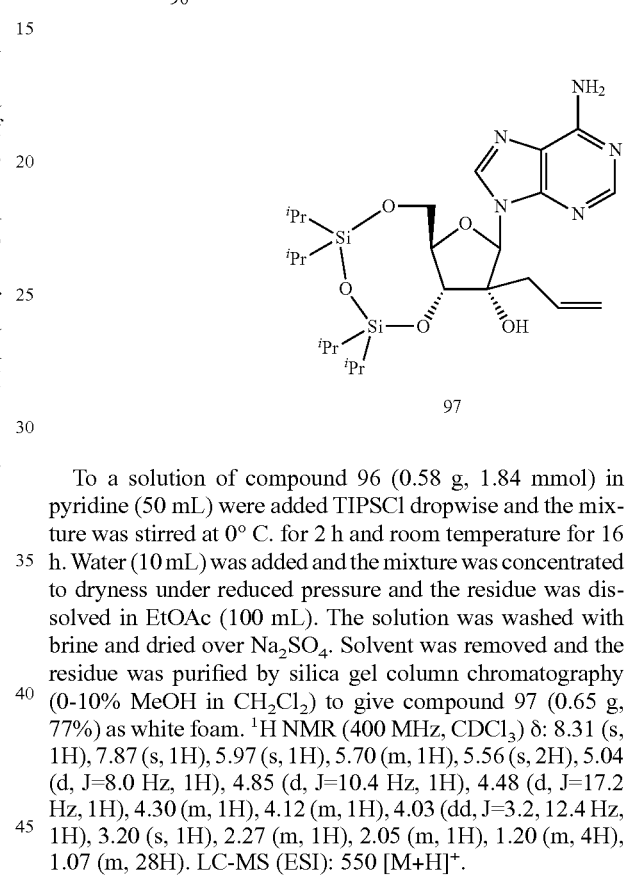

A solution of compound 95 (1.9 g, 2.63 mmol) in methanolic ammonia (7N, 50 mL) was stirred at room temperature for 24 h. Solvent was removed and the residue was purified by silica gel column chromatography (0-15% MeOH in CH₂Cl₂) to give compound 96 (0.47 g, 53%) as white solid. LC-MS (ESI): 308 [M+H]⁺.

To a solution of compound 96 (0.58 g, 1.84 mmol) in pyridine (50 mL) were added TIPSCl dropwise and the mixture was stirred at 0° C. for 2 h and room temperature for 16 h. Water (10 mL) was added and the mixture was concentrated to dryness under reduced pressure and the residue was dissolved in EtOAc (100 mL). The solution was washed with brine and dried over Na₂SO₄. Solvent was removed and the residue was purified by silica gel column chromatography (0-10% MeOH in CH₂Cl₂) to give compound 97 (0.65 g, 77%) as white foam. ¹H NMR (400 MHz, CDCl₃) δ: 8.31 (s, 1H), 7.87 (s, 1H), 5.97 (s, 1H), 5.70 (m, 1H), 5.56 (s, 2H), 5.04 (d, J=8.0 Hz, 1H), 4.85 (d, J=10.4 Hz, 1H), 4.48 (d, J=17.2 Hz, 1H), 4.30 (m, 1H), 4.12 (m, 1H), 4.03 (dd, J=3.2, 12.4 Hz, 1H), 3.20 (s, 1H), 2.27 (m, 1H), 2.05 (m, 1H), 1.20 (m, 4H), 1.07 (m, 28H). LC-MS (ESI): 550 [M+H]⁺.

Step 4. Preparation of Compound 98.

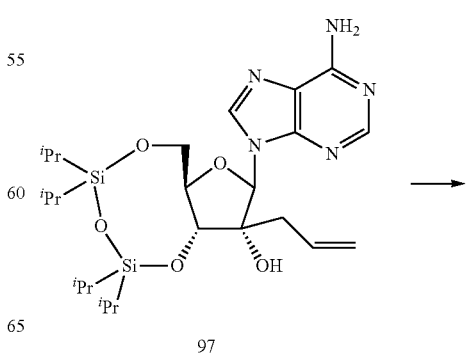

97

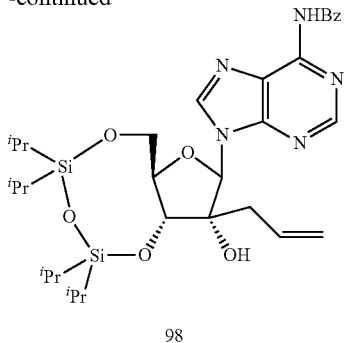

98

To a solution of compound 97 (0.25 g, 0.45 mmol) in CH$_2$Cl$_2$ (10 mL) and pyridine (1 mL) was added BzCl (3 eq) and the solution was stirred at 0° C. for 3 h and room temperature for 2 h. To the solution was added 30% NH$_4$OH (1 mL) slowly. The mixture was stirred at room temperature for 20 min. EtOAc (100 mL) was added and the solution was washed with brine and dried over Na$_2$SO$_4$. Solvent was evaporated and the residue was co-evaporated with toluene twice. The residue was purified by silica gel column chromatography (0-8% MeOH in CH$_2$Cl$_2$) to give compound 98 (0.10 g, 34%) as white solid. LC-MS (ESI): 654 [M+H]$^+$.

Step 5. Preparation of Compound 6.

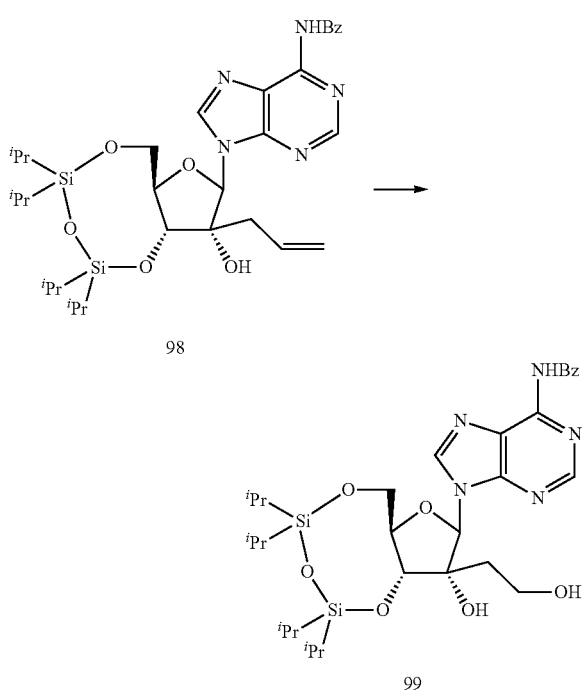

To a solution of compound 98 (0.12 g, 0.19 mmol) in THF (5 mL) and t-BuOH (5 mL) and water (1 mL) was added 0.025% OsO$_4$ in t-BuOH (0.5 mL) and NMO (50%, 0.3 mL). The solution was stirred at room temperature for 20 h. Solvent was evaporated and the residue was co-evaporated with EtOH twice. The residue was dissolved in THF (10 mL) and water (1 mL). To the solution was added NaIO$_4$ (10 eq) and the mixture was stirred at room temperature for 5 h. Solid was filtered and the filtrate was diluted with EtOAc (100 mL). The organic solution was washed with brine and dried over Na$_2$SO$_4$. The solvent was evaporated and the residue was dissolved in EtOAc (5 mL) and EtOH (5 mL). To the solution was added NaBH$_4$ (5 eq) and the mixture was stirred at 0° C. for 3 h. The mixture was poured into EtOAc (100 mL) and the solution was washed with brine and dried over Na$_2$SO$_4$. Solvent was evaporated and the residue was purified by silica gel column chromatograph (0.8% MeOH in CH$_2$Cl$_2$) to give compound 99 (0.10 g, 80%). $^1$H NMR (400 MHz, CDCl$_3$) δ: 9.12 (s, 1H), 8.79 (s, 1H), 8.35 (s, 1H), 7.48-8.04 (m, 5H), 6.18 (s, 1H), 4.85 (d, J=8.4 Hz, 1H), 4.32 (dd, J=4.4, 12.8 Hz, 1H), 4.24 (m, 1H), 4.07 (dd, J=2.8, 12.4 Hz, 1H), 3.74 (m, 2H), 3.65 (s, 1H), 3.28 (brs, 1H), 1.86 (m, 1H), 1.42 (m, 1H), 1.06-1.20 (m, 28H). LC-MS (ESI): 658 [M+H]$^+$.

Step 6. Preparation of Compound 100.

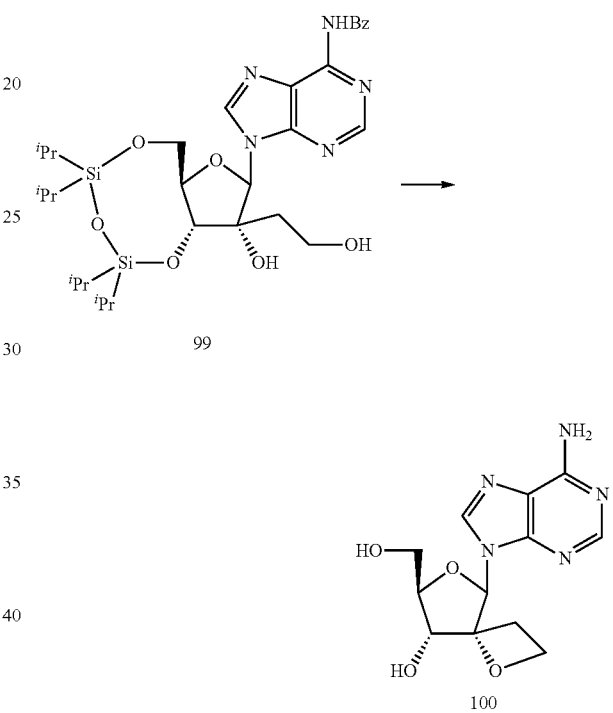

To a solution of compound 99 (0.20 g, 0.30 mmol) in CH$_2$Cl$_2$ (10 mL) and pyridine (1 mL) was added MsCl (0.1 mL) and the solution was stirred at 0° C. for 2 h. Water (5 mL) was added followed by addition of EtOAc (100 mL). The mixture was washed with brine and dried over Na$_2$SO$_4$. Solvent was removed and the residue was co-evaporated with toluene twice. The resulting mesylate was dissolved in dry THF (10 mL). To the solution was added NaH (100 mg, 2.5 mmol) and the mixture was stirred at room temperature for 3 h. EtOAc (100 mL) was added and the mixture was washed with brine and dried over Na$_2$SO$_4$. Solvent was removed and the residue was dissolved in MeOH (10 mL). To the solution was added butylamine (1 mL) and NH$_4$F (100 mg) and the mixture was refluxed for 5 h. Solvent was removed and the residue was purified by silica gel column chromatography (0-15% MeOH in CH$_2$Cl$_2$) to give compound 100 as white solid (0.04 g, 45.5%). $^1$H NMR (400 MHz, DMSO-d$_6$) δ: 8.37 (s, 1H), 8.18 (s, 1H), 7.35 (brs, 2H), 6.25 (s, 1H), 5.51 (d, J=8.0 Hz, 1H, OH), 5.14 (t, J=5.6 Hz, 1H, OH), 4.37 (m, 2H), 3.77 (m, 1H), 3.70 (m, 1H), 3.61 (m, 1H), 2.44 (m, 1H), 2.12 (m, 1H). LC-MS (ESI): 294 [M+H]$^+$

Example 19

Preparation of (5R,6R,8R,9R)-6-(6-amino-9H-purin-9-yl)-8-(hydroxymethyl)-1,7-dioxaspiro[4.4]nonan-9-ol (5)

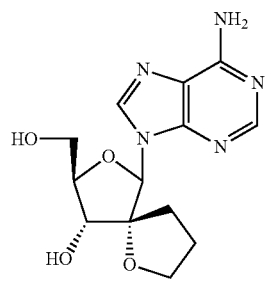

Step 1. Preparation of Compound 97.

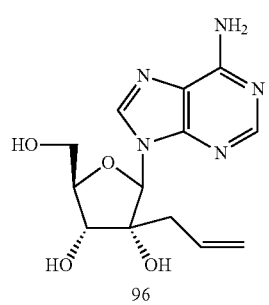

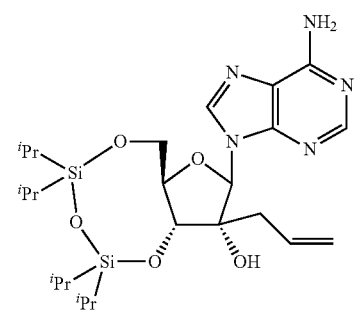

To a solution of compound 96 (0.58 g, 1.84 mmol) in pyridine (50 mL) were added TIPSCl dropwise and the mixture was stirred at 0° C. for 2 h and room temperature for 16 h. Water (10 mL) was added and the mixture was evaporated. The residue was dissolved in EtOAc (100 mL) and the solution was washed with brine and dried over Na₂SO₄. Solvent was removed and the residue was purified by silica gel column chromatography (0-10% MeOH in CH₂Cl₂) to give compound 97 as white foam. $^1$H NMR (400 MHz, CDCl₃) δ: 98.31 (s, 1H), 7.87 (s, 1H), 5.97 (s, 1H), 5.71 (m, 1H), 5.56 (brs, 2H), 5.045 (d, J=8.0 Hz, 1H), 4.85 (d, J=10.04 Hz, 1H), 4.47 (d, J=17.2 Hz, 1H), 4.30 (m, 1H), 4.12 (m, 1H), 4.03 (dd, J=3.2, 12.4 Hz, 1H), 3.22 (s, 1H), 2.30 (m, 1H), 2.07 (m, 1H), 1.00-1.25 (m, 28H). LC-MS (ESI): 550 [M+H]⁺.

Step 2. Preparation of Compound 101.

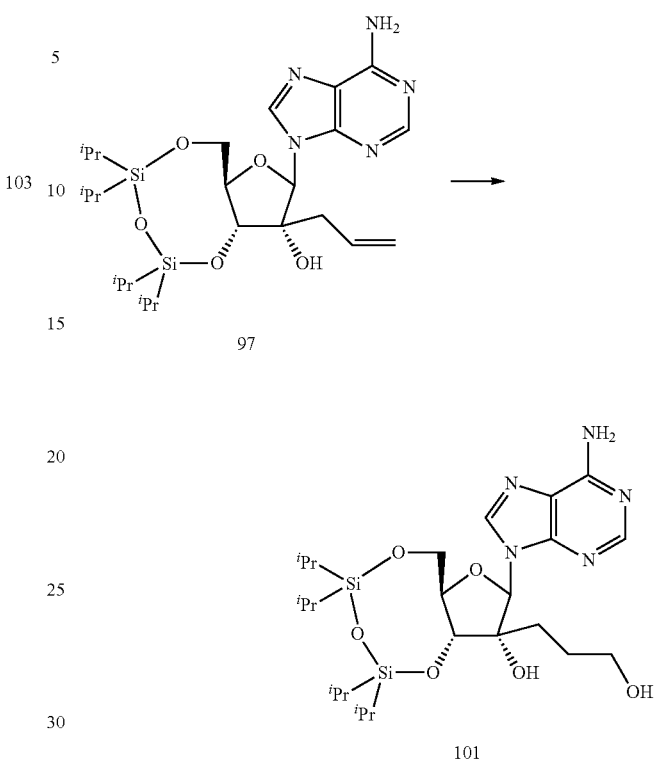

To a solution of compound 97 (0.10 g, 0.18 mmol) in THF (10 mL) was added BH₃—SMe₂ (0.3 mL) and the solution was stirred at 0° C. for 3 h. To the solution was added H₂O₂ (1 mL) then 2 N NaOH (1 mL) and the mixture was stirred at room temperature for 3 h. EtOAc (100 mL) was added and the organic solution was washed with brine and dried over Na₂SO₄. Solvent was removed and the residue was purified by silica gel column chromatography (0-10% MeOH in CH₂Cl₂) to give compound 101 (0.02 g, 24%). $^1$H NMR (400 MHz, CDCl₃) δ: 8.28 (s, 1H), 8.04 (s, 1H), 6.08 (s, 1H), 5.99 (brs, 2H), 4.81 (d, J=8.0 Hz, 1H), 4.26 (m, 1H), 4.15 (m, 1H), 4.05 (m, 1H), 3.72 (brs, 1H), 3.38 (m, 2H), 1.63 (m, 1H), 1.37 (m, 1H), 0.93-1.21 (m, 28H). LC-MS (ESI): 568 [M+H]⁺.

Step 3. Preparation of Compound 102.

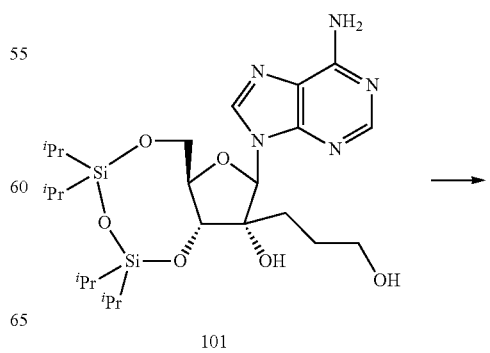

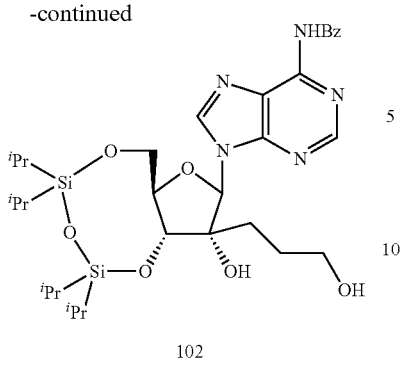

102

To a solution of compound 101 (0.09 g, 0.16 mmol) in CH$_2$Cl$_2$ (10 mL) and pyridine (1 mL) was added TMSCl (0.1 mL) and the solution was stirred at 0° C. for 1 h. To the solution was added BzCl (0.1 mL) and the resulting solution was stirred at 0° C. for 1 h and room temperature for 4 h. 30% NH$_4$OH (3 mL) was added and the solution was stirred at room temperature for 1 h. EtOAc (100 mL) was added and the solution was washed with brine and dried over Na$_2$SO$_4$. Solvent was removed and the residue was dissolved in MeOH (10 mL). To the solution was added 30% NH$_4$OH (1 mL) and the solution was stirred at room temperature for 1 h. Solvent was removed and the residue was purified by silica gel chromatography (0-10% MeOH in CH$_2$Cl$_2$) to give compound 102 (0.07 g, 62%) as foam. $^1$H NMR (400 MHz, CDCl$_3$) δ: 9.24 (s, 1H), 8.76 (s, 1H), 8.21 (s, 1H), 7.50-8.03 (m, 5H), 6.15 (s, 1H), 5.29 (s, 1H), 4.84 (d, J=7.6 Hz, 1H), 4.26 (dd, J=4.8, 12.4H, 1H), 4.16 (m, 1H), 4.04 (dd, 3.2, 12.4 Hz, 1H), 3.53 (brs, 1H), 5.37 (m, 2H), 1.63 (m, 1H), 1.31 (m, 1H), 0.98-1.21 (m, 28H). LC-MS (ESI): 672 [M+H]$^+$.

Step 4. Preparation of Compound 103.

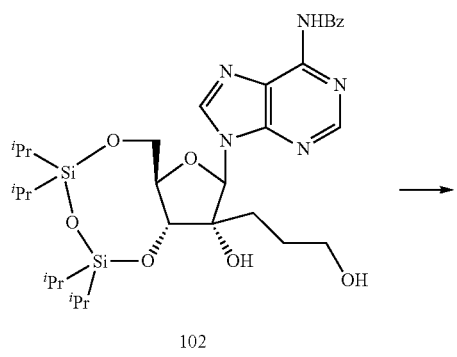

102

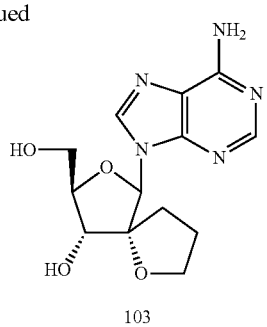

103

To a solution of compound 102 (0.07 g, 0.10 mmol) in CH$_2$Cl$_2$ (10 mL) and pyridine (1 mL) was added MsCl at 0° C. and the solution was stirred at room temperature for 3 h. To the solution was added water (10 mL) and the mixture was extracted with EtOAc (100 mL). Organic solution was dried over Na$_2$SO$_4$. Solvent was removed to give a crude mesylate which was dissolved in THF (10 mL). To the solution was added NaH (60% in mineral oil, 100 mg) and the mixture was stirred at room temperature for 2 h. Water (2 mL) was added slowly then the mixture was extracted with EtOAc (100 mL). The organic solution was washed with brine and dried over Na$_2$SO$_4$. Solvent was removed to give protected 2'-spiro-nucleoside which was dissolved in MeOH (10 mL). To the solution was added NH$_4$F (200 mg) and BuNH$_2$ (1 mL) and the mixture was refluxed for 5 h. Solvent was removed and the residue was purified by silica gel column chromatography (0-15% MeOH in CH$_2$Cl$_2$) to give compound 103 (20 mg, as white solid. $^1$H NMR (400 MHz, CD$_3$OD) δ: 8.55 (s, 1H), 8.19 (s, 1H), 6.08 (s, 1H), 4.38 (d, J=9.6 Hz, 1H), 3.84-4.12 (m, 5H), 1.90 (m, 2H), 1.78 (m, 1H), 1.30 (m, 1H). LC-MS (ESI): 308 [M+H]$^+$.

V. Preparation of 2'-Spiro-Ribo-(6-Substituted-Purine) Analogs

6-Substituted purine nucleosides can be prepared from common intermediate, 6-chloropurine analogs as shown in the following scheme.

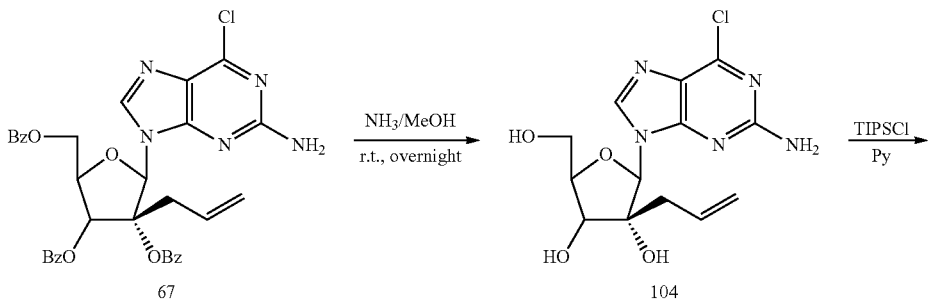

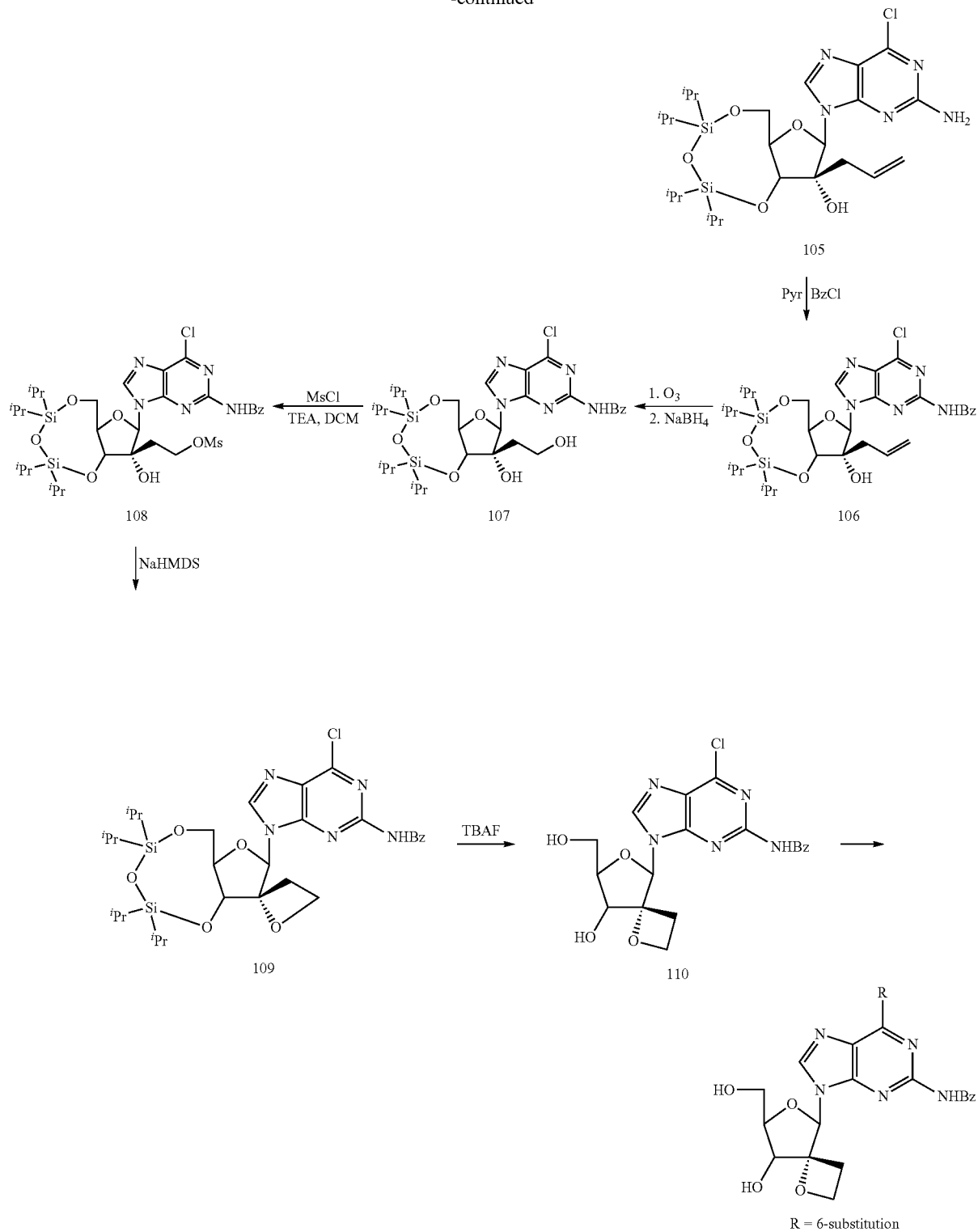

Treatment of compound 67 with methanolic ammonia gave free nucleoside 104. Selective protection of 3',5'-diol of nucleoside with TIPSCl followed by N-benzoylation provided intermediate 106. Ozonolysis of compound 106 followed by reduction of the resulting aldehyde gave compound 107. Selective mesylation of compound 108 followed by cyclization in the presence of base, such as NaH, or NaH-MDS, afforded 2'-oxetanyl compound 109. Treatment of compound 109 with TBAF provided the key intermediate for the 6-substitution. Treatment of 6-chloropurine intermediate with alcohol or amine or other nucleophile provided 6-substituted 2'-spironucleoside.

Example 20

Preparation of N-(6-chloro-9-((4R,5R,7R,8R)-8-hydroxy-7-(hydroxymethyl)-1,6-dioxaspiro[3.4]octan-5-yl)-9H-purin-2-yl)benzamide (110)

Step 1: Preparation of Compound 104

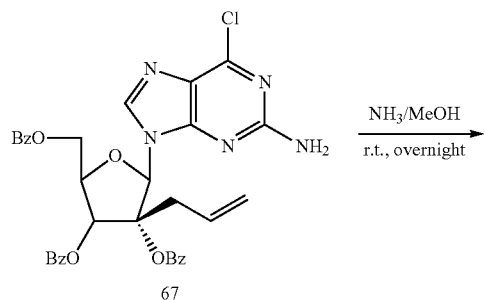

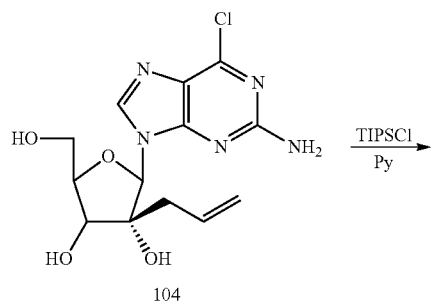

To a solution of compound 67 (6.5 g, 0.01 mol) in dry MeOH (50 mL) was added saturated NH$_3$/MeOH solution (50 mL). The mixture was stirred at room temperature overnight. The solvent was evaporated and the residue was recrystallized in MeOH/EtOAc to give the pure desired compound 104 (2.3 g, 67%).

$^1$H NMR (400 MHz, DMSO-d$_6$) δ 8.37 (s, 1H), 6.98 (s, 2H), 5.86 (s, 1H), 5.54-5.60 (m, 1H), 5.37 (d, J=6.4 Hz, 1H), 5.07 (t, J=5.2 Hz, 1H), 5.07 (s, 1H), 4.66 (dd, J=10.4 Hz, 2.0 Hz, 1H), 4.48 (d, J=17.2 Hz, 2.0 Hz, 1H), 4.20-4.24 (m, 1H), 3.85-3.88 (m, 1H), 3.76-3.79 (m, 1H), 3.64-3.69 (m, 1H), 2.21 (dd, J=14.8, 6.8 Hz, 1H), 1.95 (dd, J=4.8 Hz, 7.2 Hz, 1H). LC-MS (ESI): 341 [M+H]$^+$

Step 2: Preparation of Compound 105.

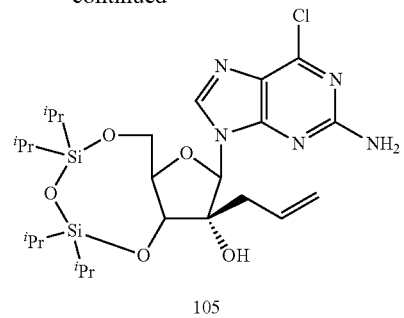

Compound 104 (0.5 g, 1.4 mmol) in anhydrous pyridine (10 mL) at 0° C. was stirred for 30 min until the solid was dissolved completely. To the solution was added TIPSCl (0.7 g, 2.2 mmol) dropwise and the stirring was continued at 0° C. for 3 h. Water (2 mL) was added and the solvent was removed under reduced pressure. The mixture was dissolved in EtOAc and the solution was washed with water, brine, and dried over MgSO$_4$. Solvent was evaporated to give crude compound 105 (0.75 g, yield: 88%). LC-MS (ESI): 584 [M+H]$^+$.

Step 3: Preparation of Compound 106

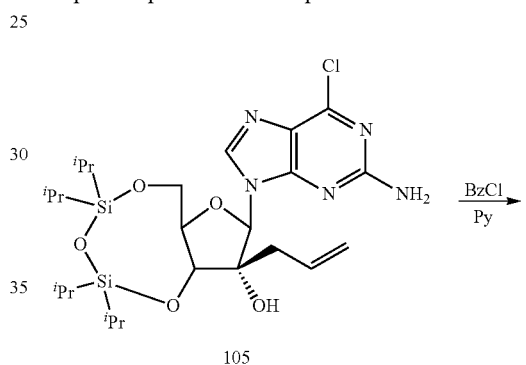

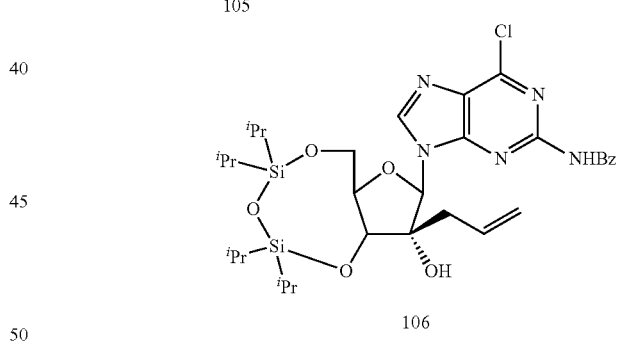

To a solution of compound 105 (0.75 g, 1.2 mmol) in a mixture of dry pyridine (15 mL) and CH$_2$Cl$_2$ (30 mL) was added BzCl (0.4 mL) and the solution was stirred at room temperature for 2 h. Water (10 mL) was added and the solution was evaporated. The residue was dissolved in EtOAc (200 mL) and the organic phase was washed with brine and dried over MgSO$_4$. Solvent was removed and the residue was purified by silica gel column chromatography (0-2% MeOH in CH$_2$Cl$_2$) to give compound 106 as foam (0.8 g, yield: 97%).
$^1$H NMR (400 MHz, CDCl$_3$): δ 8.79 (s, 1H), 8.05 (d, J=7.6 Hz, 2H), 7.51 (t, J=7.6 Hz, 1H), 7.45 (d, J=7.6 Hz, 2H), 7.10 (s, 1H), 5.95 (s, 1H), 5.62-5.73 (m, 1H), 5.00 (d, J=8.0 Hz, 1H), 4.77 (d, J=9.2 Hz, 1H), 4.30-4.35 (m, 2H), 4.05 (s, 1H), 3.93 (dd, J$_1$=12.4 Hz, J2=2.4 Hz, 1H), 3.30 (bs, 1H), 2.32-2.38 (m, 1H), 2.01-2.12 (m, 1H), 1.12-1.32 (m, 2H), 0.85-0.98 (m, 28H); LC-MS (ESI): 688 [M+H]$^+$.

Step 4: Preparation of Compound 107.

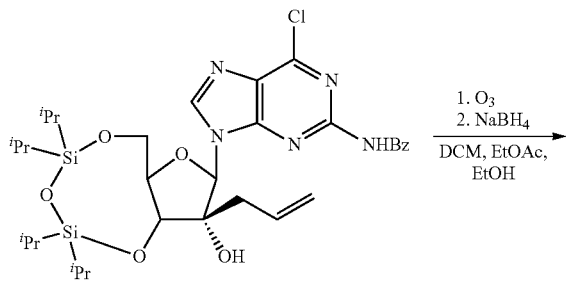

106

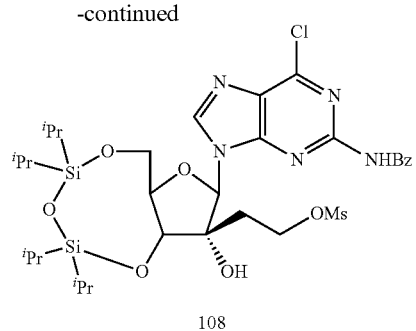

108

To a solution of compound 107 (3.2 g, 4.5 mmol) in DCM (50 mL) was added triethylamine (3 mL), then MsCl (1 g, 8.8 mmol) was added and the mixture was stirred at 0° C. for 2 h. DCM (150 mL) was added to the solution and the organic phase was washed with brine, water, and dried over MgSO$_4$. The solvent was evaporated and the residue was purified by silica gel column chromatography (02% MeOH in DCM) to give compound 108 as foam (3.3 g, yield: 94%). $^1$H NMR (400 MHz, CDCl$_3$): δ 8.76 (s, 1H), 8.36 (s, 1H), 7.90 (d, J=7.6 Hz, 2H), 7.61 (t, J=7.6 Hz, 1H), 7.50 (d, J=7.6 Hz, 2H), 6.15 (s, 1H), 4.90 (bs, 1H), 4.59 (d, J=7.6 Hz, 1H), 4.40 (bs, 1H), 4.34 (dd, J$_1$=12.8 Hz, J$_2$=4 Hz, 1H), 4.12-4.15 (m, 1H), 4.02 (dd, J$_1$=12.8 Hz, J$_2$=2.8 Hz, 1H), 3.28 (s, 1H), 2.98 (s, 3H), 2.03-2.09 (m, 1H), 1.56-1.66 (m, 1H), 1.02-1.21 (m, 28H). LC-MS (ESI): 770 [M+H]$^+$.

Step 6: Preparation of Compound 13

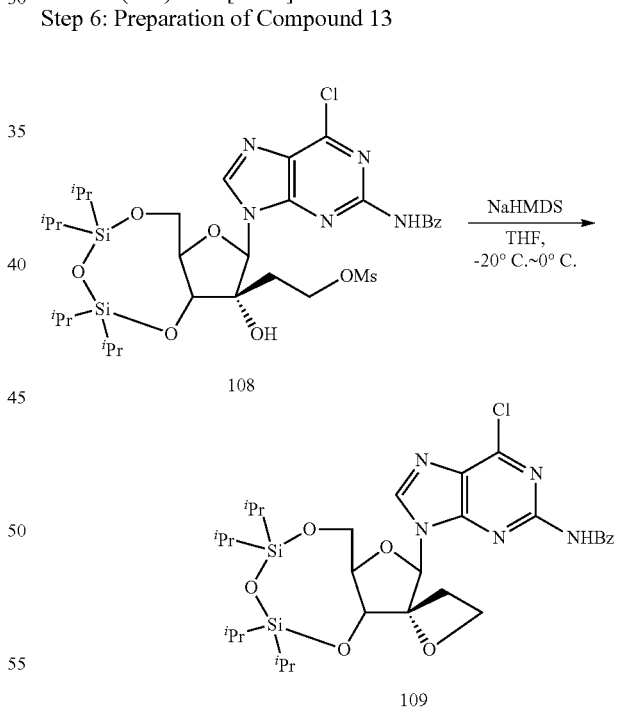

107

To a solution of compound 106 (0.8 g, 1.1 mmol) in DCM (100 mL) in a 250 mL three-neck flask was bubbled with O$_3$ at −78° C. After color of reaction solution became blue, the reaction mixture was stirred for additional 5 min. Excess O$_3$ was removed by bubbling N2 into the reaction mixture. EtOAc (30 mL) and ethanol (30 mL) was added. To the resulting solution was added NaBH$_4$ (300 mg) and the mixture was stirred at room temperature for additional 2 h. Additional EtOAc (300 mL) was added and the solution was washed with brine, water, and dried over MgSO$_4$. The solvent was evaporated and the residue was purified by silica gel column chromatography (02% MeOH in DCM) to give compound 107 (0.40 g, 50%) as foam. $^1$H NMR (400 MHz, CDCl$_3$): δ 8.76 (s, 1H), 8.60 (s, 1H), 7.93 (d, J=7.6 Hz, 2H), 7.61 (t, J=7.6 Hz, 1H), 7.50 (d, J=7.6 Hz, 2H), 6.25 (s, 1H), 4.56 (d, J=7.6 Hz, 2H), 4.40 (s, 1H), 4.10-4.31 (m, 3H), 4.02-4.12 (m, 2H), 3.75-3.85 (m, 2H), 2.01-2.12 (m, 1H), 1.35-1.42 (m, 1H), 1.02-1.21 (m, 28H). LC-MS (ESI): 692 [M+H]$^+$.

Step 5: Preparation of Compound 108.

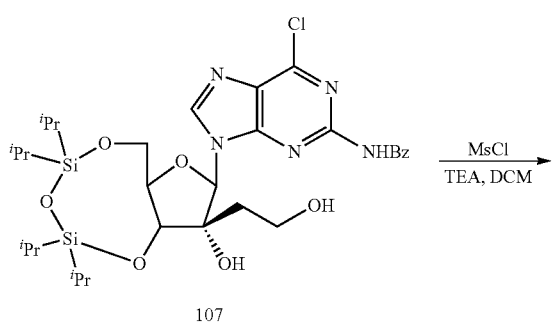

107

To a solution of compound 108 (2.8 g, 3.6 mmol) in THF (20 mL) was added 2M NaHMDS (5 mL, 10 mmol) in one portion at −20° C. The reaction mixture was stirred for 2 h, during which the temperature rose to 0° C. gradually. The reaction mixture was diluted with EtOAc (200 mL) and washed with a solution of ammonium chloride three times. The solution was concentrated in vacuo to give crude compound 109 which was used for the next reaction without further purification. LC-MS (ESI): 692 [M+H]$^+$.

Step 7: Preparation of 110

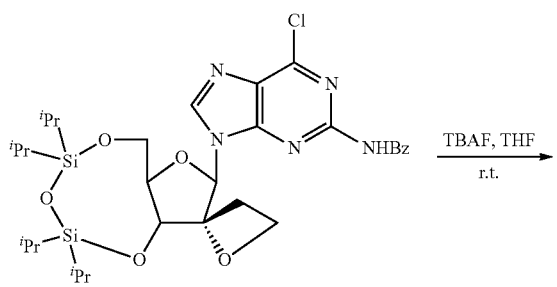
109

TBAF, THF
r.t.

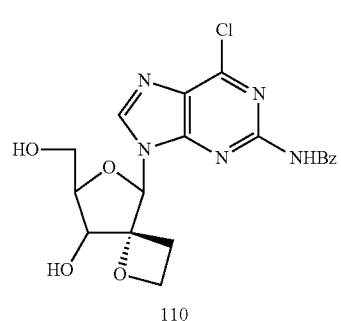
110

To a solution of compound 109 (2.4 g, 3.6 mmol) in THF (40 mL) was added TBAF (1.2 g, 4.5 mmol) and the reaction mixture was stirred at room temperature for 2 h. The solvent was evaporated and the residue was purified by silica gel column chromatography (DCM/MeOH=60/1) to give compound 110 (1.3 g, 87%). $^1$H NMR (400 MHz, DMSO-d$_6$): δ 11.35 (s, 1H), 8.78 (s, 1H), 7.98 (d, J=7.6 Hz, 2H), 7.58 (t, J=7.6 Hz, 1H), 7.50 (d, J=7.6 Hz, 2H), 6.28 (s, 1H), 5.45 (bs, 1H), 5.01 (bs, 1H), 4.41-4.45 (m, 3H), 3.55-3.75 (m, 3H), 3.12-3.15 (m, 1H), 2.29-2.31 (m, 1H), 2.25-2.28 (m, 1H)). LC-MS (ESI): 432 [M+H]$^+$.

Example 21

Preparation of (4R,5R,7R,8R)-5-(2-amino-6-(cyclopropylamino)-9H-purin-9-yl)-7-(hydroxymethyl)-1,6-dioxaspiro[3.4]octan-8-ol (111)

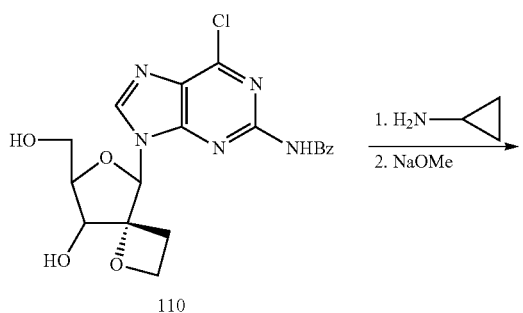
110

1. H$_2$N—△
2. NaOMe

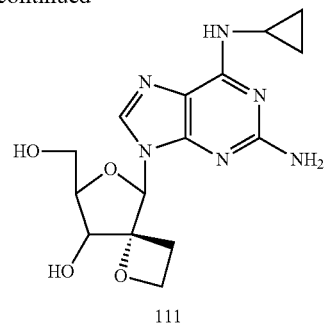
111

110 (800 mg, 1.85 mmol) in cyclopropylamine (10 mL) was stirred at room temperature for 24 h. To the solution were added MeOH (10 mL) and 5.4 M NaOMe (1.71 mL, 9.26 mmol) and the resulting mixture was stirred at room temperature for 15 h. The mixture was concentrated in vacuo, and the residue was purified by silica gel column chromatography (0 to 20% MeOH in CH$_2$Cl$_2$) to give 6-cyclopropylamino-nucleoside 111 (500 mg, 76%) as a white solid. $^1$H NMR (400 MHz, CD$_3$OD) δ: 8.02 (s, 1H), 6.21 (s, 1H), 4.53 (m, 2H), 4.43 (d, 1H, J=8.8 Hz), 3.96 (m, 1H), 3.82-3.77 (m, 2H), 2.91 (m, 1H), 2.56 (m, 1H), 2.27 (m, 1H), 0.83 (m, 2H), 0.60 (m, 2H). LCMS (ESI): 349 (M+H)$^+$.

Example 22

(4R,5R,7R,8R)-5-(2-amino-6-(azetidin-1-yl)-9H-purin-9-yl)-7-(hydroxymethyl)-1,6-dioxaspiro[3.4]octan-8-ol (112) was prepared.

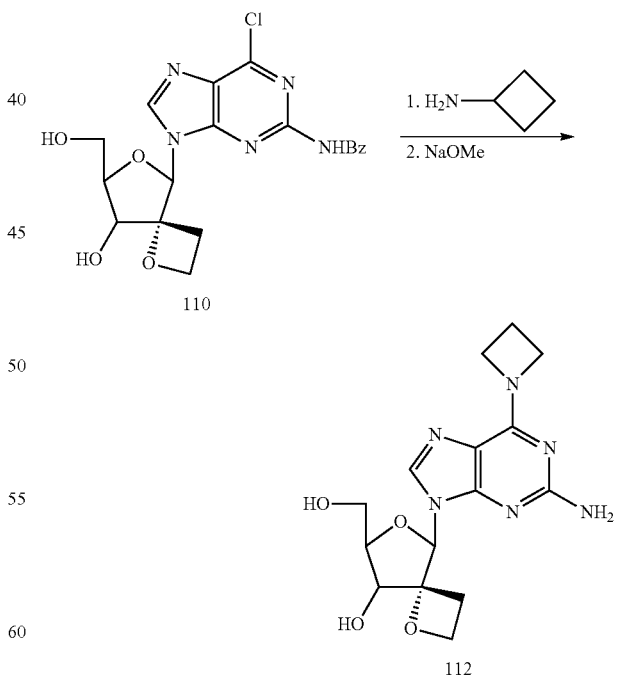

$^1$H NMR (400 MHz, CD$_3$OD) δ: 8.06 (s, 1H), 6.22 (s, 2H), 4.54 (m, 4H), 4.41 (m, 2H), 3.97 (m, 1H), 3.82 (m, 2H), 2.54 (m, 1H), 2.50 (m, 2H), 2.28 (m, 1H). LCMS (ESI): 349 (M+H)$^+$.

VI. Preparation of 2'-Spiro-Phosphoramidate Analogs

Examples 23-27 describe procedures for converting a corresponding -2'-spironucleoside to its corresponding phosphoramidate, as shown by the following equation.

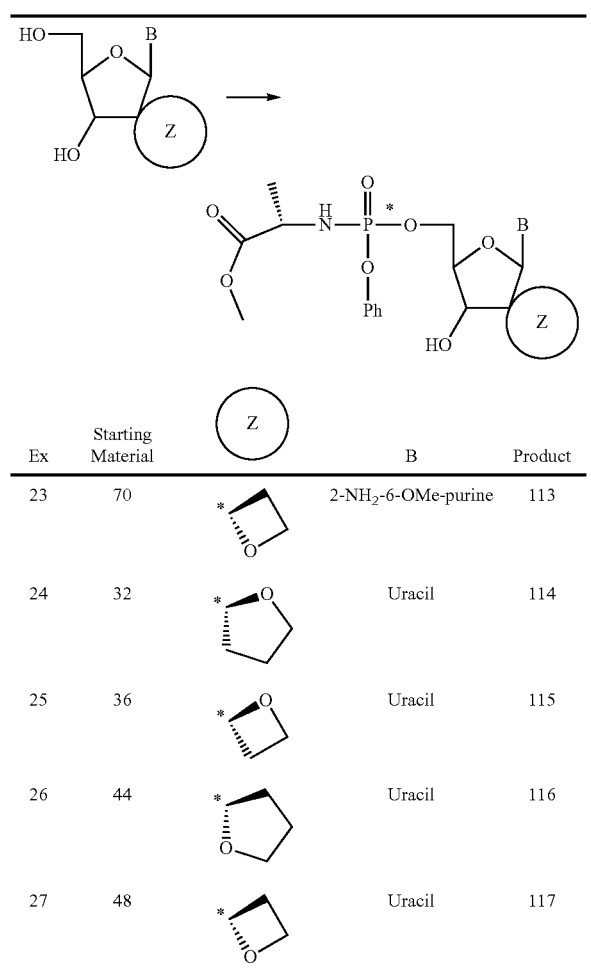

| Ex | Starting Material | B | Product |
|---|---|---|---|
| 23 | 70 | 2-NH$_2$-6-OMe-purine | 113 |
| 24 | 32 | Uracil | 114 |
| 25 | 36 | Uracil | 115 |
| 26 | 44 | Uracil | 116 |
| 27 | 48 | Uracil | 117 |

Example 23

Preparation of (2S)-methyl 2-(((((4R,5R,7R,8R)-5-(2-amino-6-methoxy-9H-purin-9-yl)-8-hydroxy-1,6-dioxaspiro[3.4]octan-7-yl)methoxy)(phenoxy)phosphoryl)amino)propanoate, 113

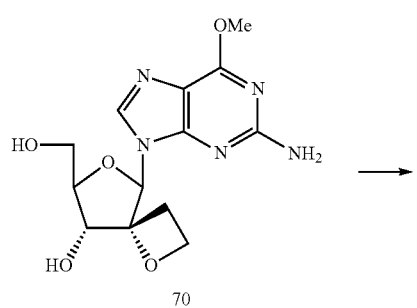

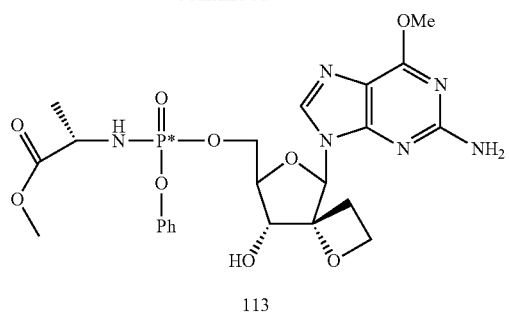

To a pre-cooled solution of phenyl dichlorophosphate (2.1 g, 9.96 mmol) in CH$_2$Cl$_2$ (40 mL) was added L-alanine methyl ester hydrochloride (1.39 g, 9.96 mmol) followed by addition of Et$_3$N (2.02 g, 19.92 mmol) in CH$_2$Cl$_2$ (5 mL) slowly and the mixture was stirred at −78° C. for 1 h then at room temperature for 16 h. Solvent was evaporated and the residue was filtered with Et$_2$O (20 mL). Solvent was evaporated to give chlorophosphate reagent which was dissolved in CH$_2$Cl$_2$ (10 mL) for the next reaction. To a mixture of compound 70 (0.02 g, 0.06 mmol) in CH$_2$Cl$_2$ (15 mL) were added N-methylimidazole (0.2 mL) and a solution of above reagent (0.5 mL, 0.5 mmol), and the resulting mixture was stirred at room temperature for 3 h. EtOAc (100 mL) was added and the mixture was washed with water, 1N HCl, aqueous NaHCO$_3$ and brine, sequentially. Organic solution was dried over Na$_2$SO$_4$ and evaporated, and the residue was purified by silica gel column chromatography (0-8% MeOH in CH$_2$Cl$_2$) to give compound 113 (0.01 g, 41%). $^1$H NMR (400 MHz, CDCl$_3$) δ: 7.69, 7.61 (ss, 1H), 7.25 (m, 5H), 6.18 (ss, 1H), 5.08 (ss, 2H), 4.60 (m, 3H), 4.35 (m, 1H), 4.06 (ss, 3H), 3.90 (m, 3H), 3.60 (ss, 3H), 3.35 (m, 1H), 2.66 (m, 1H), 2.18 (m, 1H), 1.32 (m, 3H). LC-MS (ESI): 565 [M+H]$^+$.

Example 24

Preparation of (2S)-methyl 2-(((((5S,6R,8R,9R)-6-(2,4-dioxo-3,4-dihydropyrimidin-1(2H)-yl)-9-hydroxy-1,7-dioxaspiro[4.4]nonan-8-yl)methoxy)(phenoxy)phosphoryl)amino)propanoate, 114

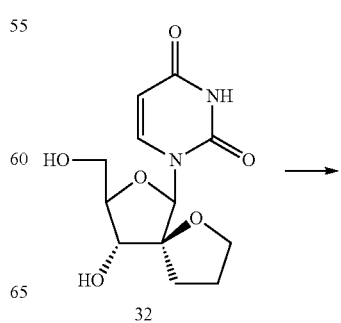

-continued

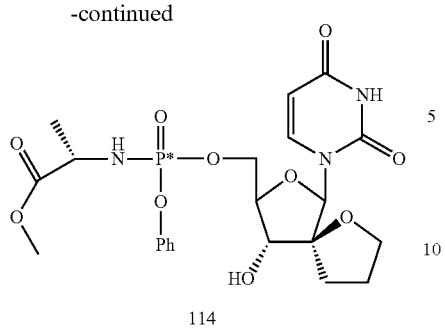

114

Compound 114 is prepared from 32 using a procedure analogous to Example 23. Data for 114: ¹H NMR (400 MHz, CDCl₃) δ: 8.75 (s, 1H), 7.60, 7.52 (dd, J=8.0 Hz, 1H), 7.24 (m, 5H), 6.05, 6.04 (ss, 1H), 5.65, 5.58 (d, J=8.0, 1H), 4.35 (m, 2H), 4.00 (m, 4H), 3.80 (m, 4H), 3.72, 3.70 (ss, 3H), 2.39 (m, 1H), 1.90 (m, 2H), 1.72 (m, 1H), 1.36 (m, 3H). LC-MS (ESI): 525 [M+H]⁺.

Example 25

Preparation of (2S)-methyl 2-(((((4S,5R,7R,8R)-5-(2,4-dioxo-3,4-dihydropyrimidin-1(2H)-yl)-8-hydroxy-1,6-dioxaspiro[3.4]octan-7-yl)methoxy)(phenoxy)phosphoryl)amino)propanoate, 115

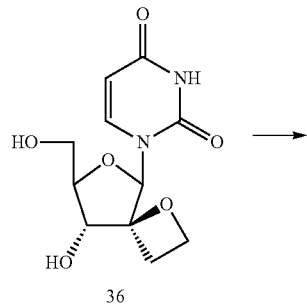

36

→

115

Compound 115 is prepared from 36 using a procedure analogous to Example 23.

Data for 115: ¹H NMR (400 MHz, CDCl₃) δ: 8.18 (s, 1H), 7.30 (m, 6H), 6.12 (ss, 1H), 5.62 (m, 1H), 4.07, 4.11 3.80 (m, 8H), 3.74, 3.72 (ss, 3H), 3.17 (m, 1H), 2.60 (m, 1H), 1.37 (d, J=7.2 Hz, 3H). LC-MS (ESI): 512 [M+H]⁺.

Example 26

Preparation of (2S)-methyl 2-((((((5R,6R,8R,9R)-6-(2,4-dioxo-3,4-dihydropyrimidin-1(2H)-yl)-9-hydroxy-1,7-dioxaspiro[4.4]nonan-8-yl)methoxy)(phenoxy)phosphoryl)amino)propanoate, 116

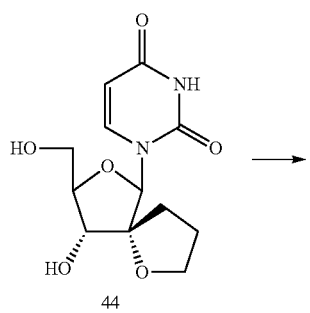

44

→

116

Compound 116 is prepared from 44 using a procedure analogous to Example 23. Data for 116: ¹H NMR (400 MHz, CDCl₃) δ: 8.51, 8.40 (ss, 1H), 7.48, 7.42 (d, 8.0 Hz, 1H), 7.29 (m, 5H), 5.98 (s, 1H), 5.62 (m, 1H), 4.48 (m, 2H), 3.95 (m, 6H), 3.73, 3.72 (ss, 3H), 2.83 (m, 1H), 1.95 (m, 2H), 1.69 (m, 1H), 1.37 (m, 3H). LC-MS (ESI): 526 [M+H]⁺.

Example 27

Preparation of (2S)-methyl 2-(((((4R,5R,7R,8R)-5-(2,4-dioxo-3,4-dihydropyrimidin-1(2H)-yl)-8-hydroxy-1,6-dioxaspiro[3.4]octan-7-yl)methoxy)(phenoxy)phosphoryl)amino)propanoate, 117

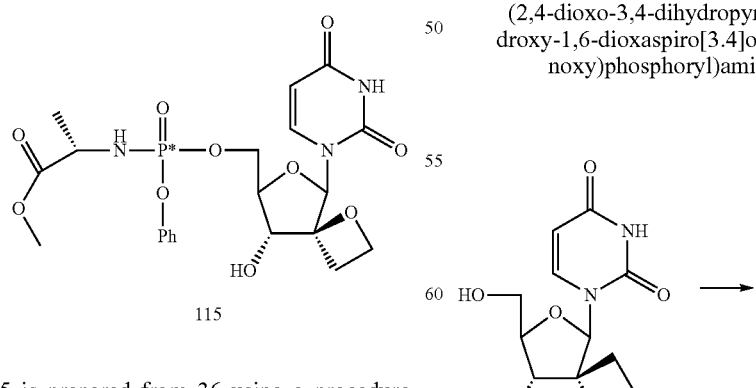

48

→

-continued

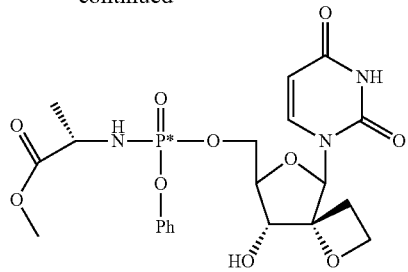

117

Compound 117 is prepared from 48 using a procedure analogous to Example 23.

Data for 117: $^1$H NMR (400 MHz, CDCl$_3$) δ: 9.15, 9.07 (ss, 1H), 7.26 (m, 7H), 6.19, 6.15 (ss, 1H), 5.65 (m, 1H), 4.50 (m, 4H), 3.95 (m, 4H), 3.72, 3.70 (ss, 3H), 3.42 (s, 1H), 2.75 (m, 1H), 2.46 (m, 1H), 1.35 (m, 3H). LC-MS (ESI): 512 [M+H]$^+$.

VII. General Synthesis of Chiral Phosphoramidates

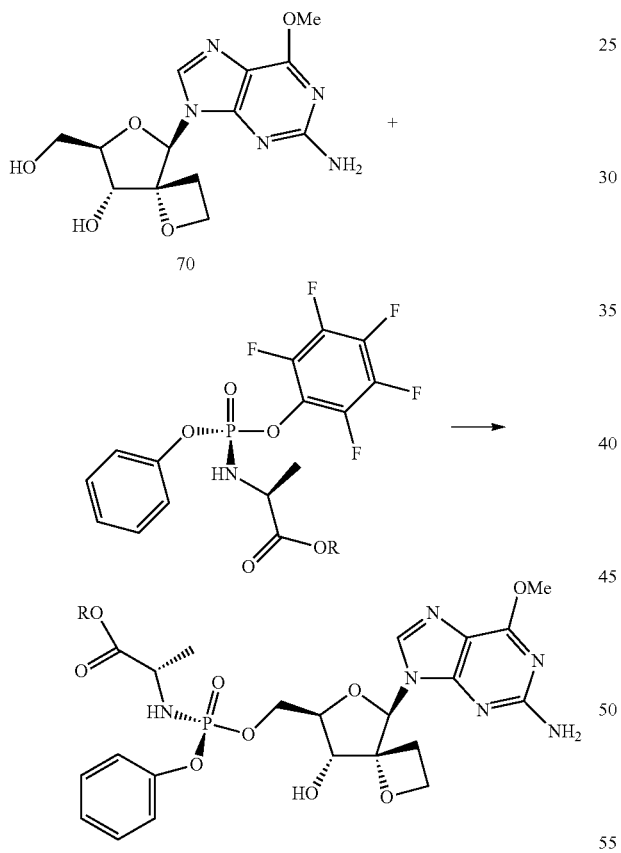

Example 29

General Procedure for preparation of chiral 2'-oxetanyl nucleoside phosphoramidates To a solution of the oxetanyl nucleoside 70 (360 mg, 1.11 mmol) in anhydrous THF (15 mL) was added 1.7 M t-butylmagnesium chloride in THF (1.31 mmol) dropwise under ice-water bath. The resulting suspension was stirred at room temperature for 30 min and the chiral pentafluorophenyl phosphoramidate reagent (R=neopentyl ($^{neo}$Pen), 1.67 mmol) in THF (10 mL) was added over 10 min by which time, the mixture became a clear solution. The mixture was stirred at room temperature for 4 h and diluted with EtOAc, (200 mL). The solution was washed with NH$_4$Cl solution (30 mL×3), and dried with sodium sulfate. Solvent was evaporated and the residue was purified by silica gel column chromatography (0 to 3% MeOH in CH$_2$Cl$_2$) to give the oxetanyl nucleoside phosphoramidate (79%, R=neopentyl) as a white solid.

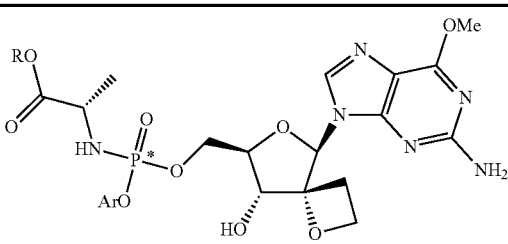

| Compound No. | P-Chirality ($R_P/S_P$) | Ar | R | Analytical data |
|---|---|---|---|---|
| 118 | $S_P$ | Ph | $^iPr^a$ | $^1$H NMR (400 MHz, CDCl$_3$) δ (ppm) 7.69 (s, 1H), 7.32-7.12 (m, 5H), 6.16 (s, 1H), 5.09 (s, 2H), 4.96 (m, 1H), 4.73 (dd, 1H, J = 8.8, 10.4 Hz), 4.61-4.53 (m, 3H), 4.33 (m, 1H), 4.06 (s, 3H), 3.98-3.90 (m, 2H), 3.70 (dd, 1H, J = 9.2, 11.2 Hz), 3.24 (d, 1H, J = 10.0 Hz), 2.68 (m, 1H), 2.17 (m, 1H), 1.30 (d, 3H, J = 7.2 Hz), 1.18 (2d, 6H, J = 6.4 Hz). $^{31}$P NMR (162 MHz) δ (ppm) 4.16. LC-MS (ESI): 593 [M + H]$^+$. |
| 119 | $R_P$ | Ph | $^iPr^a$ | $^1$H NMR (400 MHz, CDCl$_3$) δ (ppm) 7.62 (s, 1H), 7.32-7.12 (m, 5H), 6.20 (s, 1H), 5.11 (s, 2H), 4.97 (m, 1H), 4.6-4.53 (m, 4H), 4.38 (m, 1H), 4.07 (s, 3H), 3.99-3.92 (m, 2H), 3.85 (t, 1H, J = 11.2 Hz), 3.61 (bs, 1H), 2.62 (m, 1H), 2.15 (m, 1H), 1.98 (bs, 1H), 1.29 (d, 3H, J = 6.8 Hz), 1.20 (t, 3H, J = 6.4 Hz). $^{31}$P NMR (162 MHz) δ (ppm) 4.74. LC-MS (ESI): 593 (M + H)$^+$ |
| 120 | $S_P$ | Ph | $^{neo}$Pen$^b$ | $^1$H NMR (400 MHz, CDCl$_3$) δ (ppm) 7.69 (s, 1H), 7.32-7.12 (m, 5H), 6.16 (s, 1H), 5.07 (s, 2H), 4.72 (t, 1H, J = 10.0 Hz), 4.60-4.52 (m, 3H), 4.34 (m, 1H), 4.07-4.01 (m, 4H), 3.92 (m, 1H), 3.82 (d, 1H, J = 10.4 Hz), 3.70 (m, 1H), 3.15 (d, 1H, J = 10.0 Hz), 2.68 (m, 1H), 2.17 (m, 1H), 1.35 (d, 3H, J = 6.8 Hz), 0.89 (s, 9H). $^{31}$P NMR (162 MHz) δ (ppm) 4.11. LC-MS (ESI): 621 [M + H]$^+$. |
| 121 | $R_P$ | Ph | $^{neo}$Pen$^b$ | $^1$H NMR (400 MHz, CDCl$_3$) δ (ppm) 7.62 (s, 1H), 7.34-7.13 (m, 5H), 6.19 (s, 1H), 5.07 (s, 2H), 4.66-4.52 (m, 4H), 4.38 (m, 1H), 4.11-4.03 (m, 4H), 3.93 (m, 1H), 3.85-3.72 (m, 3H), 3.42 (bs, 1H), 2.63 (m, 1H), 2.15 (m, 1H), 1.34 (d, 3H, J = 7.2 Hz), 0.91 (s, 9H). $^{31}$P NMR (162 MHz) δ (ppm) 4.76. LC-MS (ESI): 621 [M + H]$^+$. |
| 122 | $S_P$ | Ph | ethyl | $^1$H NMR (400 MHz, CDCl$_3$) δ (ppm) 7.70 (s, 1H), 7.32-7.14 (m, 5H), 6.17 (s, 1H), 5.10 (s, 2m), 4.72 (t, 1H, J = 9.2 Hz), 4.59-4.54 (m, 3H), 4.35 (m, 1H), 4.15-4.09 (m, 5H), 4.00-3.91 (m, 2H), 3.77 (dd, 1H, J = 9.6, 11.2 Hz), 3.36 (d, 1H, |

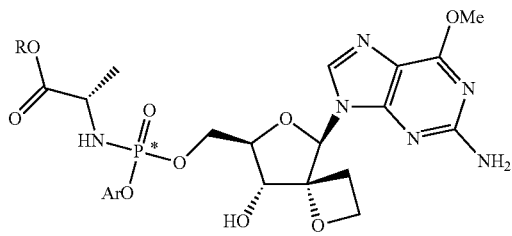

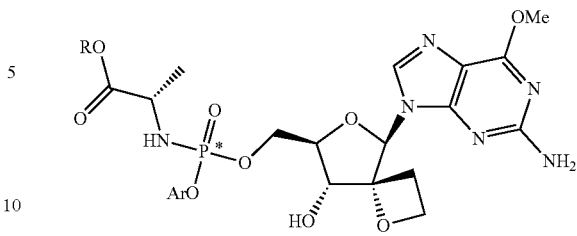

| Compound No. | P-Chirality ($R_P/S_P$) | Ar | R | Analytical data |
|---|---|---|---|---|
| | | | | J = 10.4 Hz), 2.67 (m, 1H), 2.18 (m, 1H), 1.31 (d, 3H, J = 7.2 Hz), 1.20 (t, 3H, J = 7.2 Hz). $^{31}$P NMR (162 MHz) δ (ppm) 4.08. LC-MS (ESI): 579 [M + H]$^+$. |
| 123 | $S_P/R_P$ | Np | $^{neo}$Pen$^b$ | $^1$H NMR (400 MHz, CDCl$_3$) δ (ppm) 8.10 (m, 1H), 7.82 (m, 1H), 7.69-7.63 (m, 2H), 7.49 (m, 3H), 7.36 (m, 1H), 6.15 (ds, 1H), 5.08 and 5.04 (s, 2H), 4.84-4.60 (m, 2H), 4.54 (t, 2H, J = 7.6 Hz), 4.40 (m, 1H), 4.11 (m, 1H), 4.04 (s, 3H), 3.93 (m, 2H), 3.79 (dd, 1H, J = 1.6, 10.8 Hz), 3.64 (dd, 1H, J = 6.4, 10.0 Hz), 3.37 (broad ds, 1H), 2.66 (m, 1H), 2.16 (m, 1H), 1.31 and 1.28 (s, 3H), 0.86 (s, 9H). $^{31}$P NMR (162 MHz) δ (ppm) 5.041, 4.47. LC-MS (ESI): 671 [M + H]$^+$. |
| 124 | $S_P$ | Ph | $^i$Bu$^c$ | $^1$H NMR (400 MHz, CDCl$_3$) δ (ppm) 7.71 (s, 1H), 7.31-7.12 (m, 5H), 6.18 (s, 1H), 5.14 (s, 2H), 4.7 (t, 1H, J = 8.8 Hz), 4.60-4.53 (m, 3H), 4.35 (m, 1H), 4.05 (s, 3H), 4.05-3.85 (m, 4H), 3.78 (dd, 1H, J = 6.8, 10.4 Hz), 3.53 (d, 1H, J = 9.6 Hz), 2.66 (m, 1H), 2.17 (m, 1H), 1.87 (m, 1H), 1.33 (d, 3H, J = 6.8 Hz), 0.88 and 0.86 (d, 6H, J = 1.6 Hz). $^{31}$P NMR (162 MHz) δ (ppm) 4.15. LC-MS (ESI): 607 [M + H]$^+$. |
| 125 | $R_P$ | Ph | $^i$Bu$^c$ | $^1$H NMR (400 MHz, CDCl$_3$) δ (ppm) 7.61 (s, 1H), 7.34-7.13 (m, 5H), 6.19 (s, 1H), 5.05 (s, 2H), 4.68-4.52 (m, 4H), 4.37 (m, 1H), 4.09-3.98 (m, 4H), 3.93-3.82 (m, 3H), 3.74 (t, 1H, J = 9.2 Hz), 3.34 (d, 1H, J = 9.6 Hz), 2.62 (m, 1H), 2.15 (m, 1H), 1.90 (m, 1H), 1.32 (d, 3H, J = 7.2 Hz), 0.89 (d, 6H, J = 6.4 Hz). $^{31}$P NMR (162 MHz) δ (ppm) 4.74. LC-MS (ESI): 607 [M + H]$^+$. |
| 126 | $S_P$ | Ph | $^n$Bu$^d$ | $^1$H NMR (400 MHz, CDCl$_3$) δ (ppm) 7.70 (s, 1H), 7.32-7.12 (m, 5H), 6.17 (s, 1H), 5.11 (s, 2H), 4.71 (t, 1H, J = 6.8 Hz), 4.59-4.52 (m, 3H), 4.35 (m, 1H), 4.11-3.91 (m, 7H), 3.81 (dd, 1H, J = 9.6, 11.6 Hz), 3.41 (d, 1H, J = 10.0 Hz), 2.67 (m, 1H), 2.17 (m, 1H), 1.54 (m, 2H), 1.36-1.27 (m, 5H), 0.87 (t, 3H, J = 7.6 Hz). $^{31}$P NMR (162 MHz) δ (ppm) 4.12. LC-MS (ESI): 607 [M + H]$^+$. |
| 127 | $R_P$ | Ph | $^n$Bu$^d$ | $^1$H NMR (400 MHz, CDCl$_3$) δ (ppm) 7.62 (s, 1H), 7.33-7.13 (m, 5H), 6.20 (s, 1H), 5.07 (s, 2H), 4.65-4.52 (m, 4H), 4.37 (m, 1H), 4.12-3.88 (m, 6H), 3.93 (m, 1H), 3.79 (t, 1H, J = 11.2 Hz), 3.43 (bs, 1H), 2.63 (m, 1H), 2.15 (m, 1H), 1.57 (m, 2H), 1.38-1.29 (m, 5H), 0.96 (t, 3H, J = 7.2 Hz). $^{31}$P NMR (162 MHz) δ (ppm) 4.70. LC-MS (ESI): 607 [M + H]$^+$. |
| 128 | $S_P$ | Ph | $^c$Pen$^e$ | $^1$H NMR (400 MHz, CDCl$_3$) δ (ppm) 7.69 (s, 1H), 7.32-7.13 (m, 5H), 6.16 (s, 1H), 5.12 (m, 1H), 5.07 (s, 2H), 4.73 (m, 1H), 4.60-4.53 (m, 3H), 4.34 (m, 1H), 4.06 (s, 3H), 3.98-3.90 (m, 2H), 3.66 (dd, 1H, J = 9.6, 11.2 Hz), 3.17 (d, 1H), 2.68 (m, 1H), 2.17 (m, 1H), 1.80 (m, 2H), 1.68-1.52 (m, 6H), 1.29 (d, 3H, J = 6.8 Hz). $^{31}$P NMR (162 MHz) δ (ppm) 4.18. LC-MS (ESI): 619 [M + H]$^+$. |
| 129 | $R_P$ | Ph | $^c$Pen$^e$ | $^1$H NMR (400 MHz, CDCl$_3$) δ (ppm) 7.62 (s, 1H), 7.33-7.13 (m, 5H), 6.20 (s, 1H), 5.16-5.13 (m, 3H), 4.64-4.54 (m, 4H), 4.38 (m, 1H), 4.07 (s, 3H), 3.99-3.91 (m, 2H), 3.83 (dd, 1H, J = 9.6, 11.6 Hz), 2.63 (m, 1H), 2.15 (m, 1H), 1.80 (m, 2H), 1.71-1.55 (m, 6H), 1.28 (d, 3H, J = 6.8 Hz). $^{31}$P NMR (162 MHz) δ (ppm) 4.76. LC-MS (ESI): 619 [M + H]$^+$. |
| 130 | $S_P$ | Ph | Bn$^f$ | $^1$H NMR (400 MHz, CDCl$_3$) δ (ppm) 7.73 (s, 1H), 7.37-7.11 (m, 10H), 6.17 (s, 1H), 5.09 (s, 2H), 5.07 (s, 2H), 4.75 (m, 1H), 4.58 (m, 3H), 4.40 (m, 1H), 4.09-4.01 (m, 4H), 3.92 (m, 1H), 3.74 (t, 1H, J = 2.6 Hz), 3.36 (bs, 1H), 2.68 (m, 1H), 2.19 (m, 1H), 1.28 (d, 3H, J = 7.2 Hz). $^{31}$P NMR (162 MHz) δ (ppm) 4.27. LC-MS (ESI): 641 [M + H]$^+$. |
| 131 | $R_P$ | Ph | Bn$^f$ | $^1$H NMR (400 MHz, CDCl$_3$) δ (ppm) 7.60 (s, 1H), 7.36-7.12 (m, 10H), 6.17 (s, 1H), 5.10 (d, 2H, J = 1.2 Hz), 5.05 (s, 2H), 4.66 (m, 1H), 4.62-4.51 (m, 3H), 4.34 (m, 1H), 4.13-4.03 (m, 4H), 3.89 (m, 1H), 3.74 (t, 1H J = 11.2 Hz), 3.31 (d, 1H, J = 7.6 Hz), 2.63 (m, 1H), 2.14 (m, 1H), 1.31 (d, 3H, J = 7.2 Hz). $^{31}$P NMR (162 MHz) δ (ppm) 4.64. LC-MS (ESI): 641 [M + H]$^+$. |

Notes:
$^a$iso-propyl.
$^b$neo-pentyl.
$^c$iso-butyl.
$^d$n-butyl.
$^e$cyclopentyl.
$^f$benzyl.

VIII. Synthesis of Cyclophosphate Prodrugs

Example 30

Preparation of Compound 132

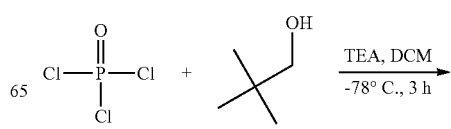

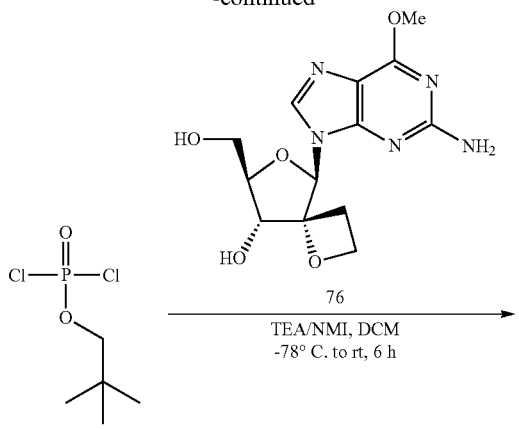

| Compound No. | P-chirality ($R_P/S_P$) | R | Analytical data |
|---|---|---|---|
| 132 | 1:1 mixture | neopentyl | $^1$H NMR (400 MHz, CDCl$_3$) δ (ppm) 7..71 (s, 1H), 6.21 and 6.20 (m, 1H), 5.11 and 5.09 (s, 2H), 4.73 (m, 1H), 4.63-4.48 (m, 3H), 4.29 (m, 1H), 4.07 and 4.06 (s, 3H), 3.91 (m, 1H), 3.70 (m, 2H), 2.69 (m, 1H), 2.19 (m, 1H), 0.93 and 0.91 (s, 9H). $^{31}$P NMR (162 MHz) δ (ppm) 1.71, 1.62. LC-MS (ESI): 488 [M + H]$^+$. |
| 133 | 3.7:1 mixture | isopropyl | $^1$H NMR (400 MHz, CDCl$_3$) δ (ppm) 7.63 and 7.62 (s, 1H), 6.06 and 6.02 (d, 1H, J = 0.8 Hz), 5.65 and 5.34 (2s, 1H, J = 10.4, 9.6 Hz), 5.00-4.79 (m, 3H), 4.67-4.32 (m, 4H), 4.13-4.04 (m, 4H), 2.81-2.65 (m, 1H), 2.41-2.31 (m, 1H), 1.51-1.42 (m, 6H). $^{31}$P NMR (162 MHz) δ (ppm) −2.58, −5.77. LC-MS (ESI): 428 [M + H]$^+$. |
| 134 | 4.7:1 mixture | cyclopentyl | $^1$H NMR (400 MHz, CDCl$_3$) δ (ppm) 7.64 (s, 1H), 6.07 and 6.03 (s, 1H), 5.66 and 5.24 (d, 1H, J = 9.6 Hz), 5.51-5.07 (m, 1H), 5.06 and 4.87 (s, 2H), 4.68-4.42 (m, 4H), 4.15-4.07 (m, 4H), 2.82-2.66 (m, 1H), 2.42-2.32 (m, 1H), 2.06-1.78 (m, 8H). $^{31}$P NMR (162 MHz) δ (ppm) −2.59, −5.74. LC-MS (ESI): 454 [M + H]$^+$. |

To a pre-cooled CH$_2$Cl$_2$ (2 mL) at −78° C. was added POCl$_3$ (0.07 mL, 0.74 mmol) and neopentyl alcohol (0.74 mmol)) to give a solution to which, Et$_3$N (0.12 mL, 0.87 mmol) was added dropwise. The resulting mixture was stirred at −78° C. for 3 h and the oxetanyl nucleoside 76 (70 mg, 0.22 mmol) in THF (2 mL) and then Et$_3$N (0.24 mL, 1.74 mmol) were added in one portion each. Then NMI (0.17 mL, 2.17 mmol) was added over 3 min. The resulting mixture was stirred for 6 h during which the temperature rose to room temperature. The mixture was cooled to −78° C., treated with concentrated HCl to pH 4, diluted with CH$_2$Cl$_2$ (10 mL). The organic solution was washed with dilute HCl solution, dried with sodium sulfate, and concentrated in vacuo. The residue was purified by silica gel column chromatography (0 to 3% MeOH in CH$_2$Cl$_2$) to give the oxetanyl nucleoside cyclophosphate 132 as a diastereomeric mixture (6.5 mg, 5.5%) as a syrup.

By the same fashion, the isopropyl cyclophosphate (133) was obtained as a diastereomeric mixture as a syrup (6.7 mg, from 100 mg of the oxetanyl nucleoside 76, 5%).

Cyclopentyl cyclophosphate 134 was also obtained as a diastereomeric mixture as a syrup (30 mg from 150 mg of the oxetanyl nucleoside, 14%).

IX. Preparation of 2'-Spiro-Analogs

Additional procedures (both non-stereo- and stereoselective) for preparing phosphoramidates are disclosed in U.S. patent application Ser. No. 12/783,680 (US 2010/0298257), filed May 20, 2010 and Ser. No. 13/076,552 (US 2011/0251152), filed on Mar. 31, 2011.

In addition of phosphoramidate analogs, cyclic phosphates are also contemplated. To that end, procedures for preparing cyclic phosphates are disclosed in U.S. patent application Ser. No. 12/479,075 (US 2010/0081628), filed on Jun. 5, 2009.

Procedures for preparing certain phosphorus-containing compounds are disclosed in U.S. Pat. No. 4,816,570.

Procedures for preparing a 1,3,2-dioxaphosphinane-2-oxide are disclosed in U.S. Pat. No. 6,752,981 and US 2009/0209481.

Procedures for preparing a 4H-benzo[d][1,3,2]dioxaphosphin-2-oxide are disclosed in U.S. Pat. No. 6,312,662.

Procedures for preparing certain 3',5'-diacyl derivatives are disclosed in U.S. Pat. No. 7,754,699, see also U.S. Pat. No. 5,246,937 for examples of diacyl derivatives.

Procedures for preparing aminoacyl derivatives are disclosed in U.S. Pat. Nos. 4,957,924 and 6,083,953.

Procedures for preparing a derivative comprised of —P(O)(O(CH$_2$)$_{1-3}$OC(O)(alkyl))$_2$ are disclosed in U.S. Pat. No. 5,663,159.

Procedures for preparing a derivative comprised of —P(O)(O(CH$_2$)$_{1-3}$OC(O)O(C$_{1-6}$alkyl))$_2$ are disclosed in U.S. Pat. Nos. 5,922,695; 5,977,089; and 6,043,230.

Procedures for preparing a derivative comprised of —P(O)(O(CH$_2$)$_{1-3}$SC(O)alkyl)$_2$ are disclosed in U.S. Pat. Nos. 5,770,725; 5,849,905; 6,020,482; and 7,105,499.

X. Preparation of 2'-Spiro-Nucleotides

| Starting Material | | B | Product |
|---|---|---|---|
| 32 | *⟁O | Uracil | 135 |
| 48 | *⟁O | Uracil | 136 |
| 49 | *⟁O | Cytosine | 137 |
| 50 | *⟁O | Cytosine | 138 |
| 51 | *⟁O | Cytosine | 139 |
| 52 | *⟁O | Cytosine | 140 |

The unprotected nucleoside (0.10 mmol) was dissolved in DTP and cooled to 0-5° C. while maintaining an inert atmosphere. To the stirred solution was added freshly distilled phosphorus oxychloride (0.30 mmol). After 1 h at 0-5° C., tributylamine (0.30 mmol) and freshly dried tributylammonium pyrophosphate (0.25 mmol) were added. The reaction was allowed to warm to ambient temperature for 1 h and then quenched by the addition 1.0 M aqueous triethylamine bicarbonate buffer (1 mL). The reaction solution was directly applied in portions to an ion-exchange HPLC semi-preparative column (Dionex DNA-PAC) and eluted with a gradient of 0.5 M aqueous triethylammonium bicarbonate in water. The product containing fractions were combined and concentrated to dryness. The residue was then dissolved in about 5 mL water and then subjected to lyophilization to yield ca 0.01-0.02 mmol of nucleoside triphosphate as its monotriethylamine salt.

XI. Biological Evaluation of Selected Analogs

HCV Replicon Assay.

HCV replicon assays using Clone A cells and ET-lunet cells were performed as described previously. L. J. Stuyver et al. *Antimicrob. Agents Chemother.* 2004, 48, 651-654. Briefly, Clone A cells and ET-lunet cells were seeded at a density of 1500 and 3000 cells per well in a 96-well plate, respectively. Test compounds serially diluted in culture medium without G418 were added to cells. Plates were incubated at 37° C. in a 5% CO$_2$ atmosphere for 4 days. Inhibition of HCV RNA replication was determined by quantitative real time PCR. See, e.g., L. J. Stuyver et al. *Antiviral Chem. Chemother.* 2006, 17, 79-87.

To express the antiviral effectiveness of a compound, the threshold RT-PCR cycle of the test compound was subtracted from the average threshold RT-PCR cycle of the no-drug control ($\Delta Ct_{HCV}$). A $\Delta Ct$ of 3.3 equals a 1-log 10 reduction (equal to the 90% effective concentration [EC$_{90}$]) in replicon RNA levels. The cytotoxicity of the test compound could also be expressed by calculating the $\Delta Ct_{rRNA}$ values. The $\Delta\Delta Ct$ specificity parameter could then be introduced ($\Delta Ct_{HCV}$-$\Delta Ct_{rRNA}$), in which the levels of HCV RNA are normalized for the rRNA levels and calibrated against the no-drug control.

Cell Cytotoxicity Assays.

Each compound (serially diluted from 100 µM) was added to Huh7 (2×10$^3$ cells/well), HepG2 (2×10$^3$ cells/well), BxPC3 (2×10$^3$ cells/well), or CEM (5×10$^3$ cells/well) cells and allowed to incubate for 8 days at 37° C. A medium only control was used to determine the minimum absorbance value and an untreated cell. At the end of the growth period, MTS dye from the CellTiter 96 Aqueous One Solution Cell Proliferation Assay kit (Promega) was added to each well and the plate was incubated for an additional 2 hours. The absorbance at 490 nm was read with a Victor3 plate reader (Perkin Elmer) using the medium only control wells as blanks. The 50% inhibition value (CC$_{50}$) was determined by comparing the absorbance in wells containing cells and test compound to untreated cell control wells.

The HCV NS5B reaction was performed in a 20 µL mixture containing varying concentrations of the test compound, 1 µM of all four natural ribonucleotides, [α-$^{32}$P]UTP, 20 ng/µL of genotype 1b (−) IRES RNA template, 1 unit/µL of SUPERase•In (Ambion, Austin, Tex.), 40 ng/µL of wild type or S282T NS5B Genotype 1b, 1 mM MgCl$_2$, 0.75 mM MnCl$_2$, and 2 mM DTT in 50 mM Hepes buffer (pH 7.5). The reaction was quenched by adding 80 µL of stop solution (12.5 mM EDTA, 2.25 M NaCl, and 225 mM sodium citrate) after incubating at 27° C. for 30 minutes. The radioactive RNA products were separated from unreacted substrates by passing the quenched reaction mixture through a Hybond N+ membrane (GE Healthcare, Piscataway, N.J.) using a dot-blot apparatus. The RNA products were retained on the membrane and the free nucleotides were washed out. The membrane was washed 4 times with a solution containing 0.6 M NaCl and 60 mM sodium citrate. After rinsing the membrane with water followed by ethanol, the membrane was exposed to a phosphorscreen and the products were visualized and quantified using a phosphorimager. The IC$_{50}$ values were calculated using GraFit program version 5 (Erithacus Software, Horley, Surrey, UK). All the reactions were done in duplicate and the results were reported as IC$_{50}$±standard error.

The biological activities of selected compounds are presented in Tables 1-5.

TABLE 1

Anti-HCV activity of selected nucleosides

| Ex. | Compound | EC$_{50}$ (μM) |
|---|---|---|
| 32 | (structure) | >100 |
| 50 | (structure) | >100 |
| 36 | (structure) | >100 |
| 51 | (structure) | >100 |
| 44 | (structure) | >100 |
| 49 | (structure) | >100 |
| 48 | (structure) | >100 |
| 52 | (structure) | >54.49 |
| 62 | (structure) | >20 |

TABLE 1-continued

Anti-HCV activity of selected nucleosides

| Ex. | Compound | EC$_{50}$ (μM) |
|---|---|---|
| 72 | (structure) | >20 |
| 76 | (structure) | >100 |
| 77 | (structure) | >20 |
| 66 | (structure) | >20 |

TABLE 2

Anti-HCV 1b activity of selected nucleoside phosphoramidates.

| Ex. | Compound | EC$_{50}$ | EC$_{90}$ | CC$_{50}$ |
|---|---|---|---|---|
| 114 | (structure) | 20.16 | 41.69 | >100 |
| 115 | (structure) | 28.5 | 71.09 | >100 |

TABLE 2-continued

Anti-HCV 1b activity of selected nucleoside phosphoramidates.

| Ex. | Compound | EC$_{50}$ | EC$_{90}$ | CC$_{50}$ |
|---|---|---|---|---|
| 116 | (structure) | 28.33 | 81.75 | >100 |
| 117 | (structure) | 16.71 | 49.20 | >100 |
| 113 | (structure) | 1.55 | 7.66 | >100 |

TABLE 3

Anti-HCV 1b activity of selected nucleoside phosphoramidates.

| Ex. | Compound | P*$^a$ | EC$_{50}$ (μM) | EC$_{90}$ (μM) | CC$_{50}$ (μM) |
|---|---|---|---|---|---|
| 118 | (structure) | S$_P$ | 1.49 | 3.44 | >20 |

TABLE 3-continued

Anti-HCV 1b activity of selected nucleoside phosphoramidates.

| Ex. | Compound | P*[a] | EC$_{50}$ (µM) | EC$_{90}$ (µM) | CC$_{50}$ (µM) |
|---|---|---|---|---|---|
| 119 | | R$_P$ | 4.52 | >20 | >20 |
| 120 | | S$_P$ | 0.39 | 0.676 | >20 |
| 121 | | R$_P$ | 9.31 | 18.5 | >20 |
| 122 | | S$_P$ | 0.857 | 3.0 | >20 |
| 123 | | S$_P$/R$_P$[b] | 0.31 | 0.853 | >20 |

TABLE 3-continued

Anti-HCV 1b activity of selected nucleoside phosphoramidates.

| Ex. | Compound | P*a | EC$_{50}$ (μM) | EC$_{90}$ (μM) | CC$_{50}$ (μM) |
|---|---|---|---|---|---|
| 124 | | S$_P$ | 0.566 | 1.81 | >20 |
| 125 | | R$_P$ | 4.42 | 8.45 | >20 |
| 126 | | S$_P$ | 0.274 | 0.7 | >20 |
| 127 | | R$_P$ | 3.1 | 6.45 | >20 |
| 128 | | S$_P$ | 0.45 | 1.09 | >20 |

TABLE 3-continued

Anti-HCV 1b activity of selected nucleoside phosphoramidates.

| Ex. | Compound | P*[a] | EC$_{50}$ (μM) | EC$_{90}$ (μM) | CC$_{50}$ (μM) |
| --- | --- | --- | --- | --- | --- |
| 129 | [structure with OMe-purine, cyclopentyl ester, Ph phosphoramidate, oxetane-spiro ribose] | R$_P$ | 0.67 | 1.97 | >20 |
| 130 | [structure with OMe-purine, benzyl ester, Ph phosphoramidate, oxetane-spiro ribose] | S$_P$ | 8.65 | 15.1 | >20 |
| 131 | [structure with OMe-purine, benzyl ester, Ph phosphoramidate, oxetane-spiro ribose] | R$_P$ | 11.7 | >20 | >20 |

[a]Chirality at Phosphorus (P*).
[b]S$_P$/R$_P$ = mixture of diastereomers.

TABLE 4

Anti-HCV 1b activity of selected nucleosides cyclic phosphates

| Example | Structure | P-chirality (R$_P$/S$_P$) | EC$_{50}$ (μM) | EC$_{90}$ (μM) | CC$_{50}$ (μM) |
| --- | --- | --- | --- | --- | --- |
| 132 (1:1) | [neopentyl cyclic phosphate, OMe-purine, oxetane-spiro ribose] | (1:1) | >20 | >20 | >20 |

TABLE 4-continued

Anti-HCV 1b activity of selected nucleosides cyclic phosphates

| Example | Structure | P-chirality ($R_P/S_P$) | $EC_{50}$ (μM) | $EC_{90}$ (μM) | $CC_{50}$ (μM) |
|---|---|---|---|---|---|
| 133 (3.7:1) | 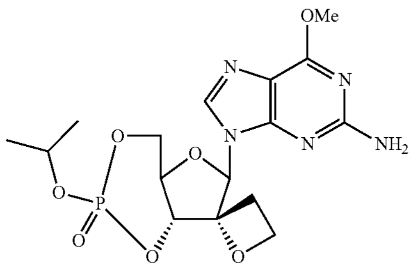 | (3.7:1) | >20 | >20 | >20 |
| 134 (4.7:1) | 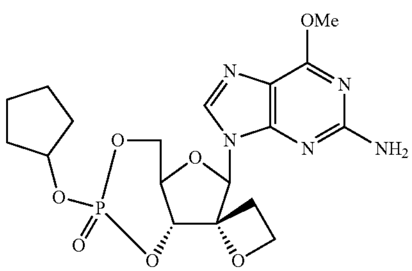 | (4.7:1) | 14.0 | >20 | >20 |

TABLE 5

Anti-HCV activity of selected nucleoside triphosphates against HCV polymerase wild-type and S282T mutant

| Ex | Compound | Wild-type $IC_{50}$ (μM) | S282T mutant $IC_{50}$ (μM) |
|---|---|---|---|
| 135 | | >100 | |
| 136 | | 39.4 | >100 |
| 137 | | >45.3 | >100 |
| 138 | | >100 | |

TABLE 5-continued

Anti-HCV activity of selected nucleoside triphosphates against HCV polymerase wild-type and S282T mutant

| Ex | Compound | Wild-type IC$_{50}$ (μM) | S282T mutant IC$_{50}$ (μM) |
|---|---|---|---|
| 139 | (cytosine nucleoside with spiro-oxetane sugar) | >100 | |
| 140 | (cytosine nucleoside with spiro-oxetane sugar) | >8.48 | 56.7 |

Dengue CPE Assay.

To measure cytopathic effect of Dengue virus 2, BHK-21 (Syrian Hamster Kidney, CCL-10 ATCC Manassas, Va.) cells were seeded at a density of 20,000 cells/well in a 96-well black/clear bottom plates (Becton Dickinson, Franklin Lakes, N.J.) one day prior to start of the assay and allowed to attach overnight in EMEM (ATCC Manassas, Va.)+10% FBS (Invitrogen, Carlsbad, Calif.) at 37° C. in a humidified 5% $CO_2$ atmosphere. The next day, the medium was removed and the cells were infected with Dengue 2 strain New Guinea C (VR-1584, ATCC Manassas, Va.) at an MOI of 0.08 pfu/cell for two hours in 50 μL EMEM+2% FBS. For both the single point and dose response assays, compounds (2× concentration) were diluted in EMEM+2% FBS and 50 μL was added to infected cells without removing virus. Cells were incubated for 3 days at 37° C. in a humidified 5% $CO_2$ atmosphere. The medium was aspirated and 50 μL of CellTiter-Glo (Promega™, Madison, Wis.) was added to each well and read for 0.1 seconds on a Perkin Elmer Victor3 (Waltham, Mass.) plate reader. Percent survival was determined by subtracting the average value of infected control wells and normalizing to the non-infected wells. The effective concentration was calculated from the dose response data by forecasting 50% cells surviving with drug treatment.

TABLE 6

Activity of selected nucleoside phosphoramidates against dengue virus.

| Ex. | Compound | P*[a] | EC$_{50}$ (μM) | CC$_{50}$ (μM) |
|---|---|---|---|---|
| 113 | (phosphoramidate nucleoside with OMe purine and spiro-oxetane sugar) | R$_P$/S$_P$[b] | 6.23 | >20 |
| 118 | (phosphoramidate nucleoside with OMe purine and spiro-oxetane sugar, isopropyl ester) | S$_P$ | 5.06 | >20 |

TABLE 6-continued

Activity of selected nucleoside phosphoramidates against dengue virus.

| Ex. | Compound | P*[a] | EC$_{50}$ (μM) | CC$_{50}$ (μM) |
|---|---|---|---|---|
| 119 | | R$_P$ | 8.64 | >20 |
| 120 | | S$_P$ | 1.88 | >20 |
| 121 | | R$_P$ | 2.26 | >20 |
| 122 | | S$_P$ | 5.84 | >20 |
| 123 | | S$_P$/R$_P$[b] | 1.74 | >20 |

TABLE 6-continued

Activity of selected nucleoside phosphoramidates against dengue virus.

| Ex. | Compound | P*a | EC$_{50}$ (μM) | CC$_{50}$ (μM) |
|---|---|---|---|---|
| 124 | | S$_P$ | 2.21 | >20 |
| 125 | | R$_P$ | 1.98 | >20 |
| 126 | | S$_P$ | 2.36 | >20 |
| 127 | | R$_P$ | 1.61 | >20 |
| 128 | | S$_P$ | 2.79 | >20 |

TABLE 6-continued

Activity of selected nucleoside phosphoramidates against dengue virus.

| Ex. | Compound | P*a | EC$_{50}$ (µM) | CC$_{50}$ (µM) |
|---|---|---|---|---|
| 129 | | R$_P$ | 2.36 | >20 |
| 130 | | S$_P$ | 3.84 | >20 |
| 131 | | R$_P$ | 1.49 | >20 |

<sup>a</sup>Chirality at Phosphorus (P*).
<sup>b</sup>S$_P$/R$_P$ = mixture of diastereomers.

Although a full and complete description is believed to be contained herein, certain patent and non-patent references may include certain essential subject matter. To the extent that these patent and non-patent references describe essential subject matter, these references are hereby incorporated by reference in their entirety. It is understood that the meanings of the incorporated subject matter are subservient to the meanings of the subject matter disclosed herein. The subject matter of U.S. 61/417,946, filed on Nov. 30, 2010 is hereby incorporated by reference in its entirety. The subject matter of U.S. Ser. No. 13/076,552 and U.S. Ser. No. 13/076,842, both filed on Mar. 31, 2011, is hereby incorporated by reference in its entirety.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:
1. A compound represented by formula I:

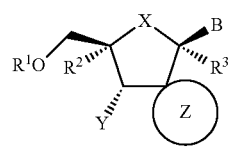

or a stereoisomer, a salt, a metabolite, or a deuteride thereof, wherein
1) R$^1$ is selected from the group consisting of
   a) hydrogen,
   b) —P(O)(OH)$_2$,
   c) —P(O)(O(CH$_2$)$_{1-3}$OC(O)O(alkyl))$_2$,
   d) —P(O)(O(CH$_2$)$_{1-3}$OC(O)(alkyl))$_2$,
   e) —P(O)(O(CH$_2$)$_{1-3}$SC(O)(alkyl))$_2$,
   f) —P(O)(O(CH$_2$)$_{1-3}$OCH$_2$(aryl))$_2$, g) —P(O)(O(CH$_2$)$_{1-3}$SCH$_2$(aryl))$_2$,
h) —P*(O)(OR$^{1a}$)(NHCHR$^{1b}$C(O)OR$^{1c}$),
where
R$^{1a}$ is
  i) hydrogen,
  ii) alkyl,
  iii) cycloalkyl, or
  iv) aryl,
R$^{1b}$ is
  i) hydrogen,
  ii) C$_{1-6}$alkyl,
  iii) cycloalkyl,
  iv) alkaryl, or
  v) alk(heteroaryl), and
R$^{1c}$ is
  i) hydrogen
  ii) alkyl,
  iii) cycloalkyl, or
  iv) alkaryl,
i) —P*(O)(NH(alkaryl)(O(CH$_2$)$_{1-3}$SC(O)(alkyl)),
j) a 1,3,2-dioxaphosphinane-2-oxide,
k) a 4H-benzo[d][1,3,2]dioxaphosphinine-2-oxide,
l) —P*(O)(OR$^{1c}$)~, when Y is —O~,
m) —P(O)(OH)—O—P(O)(OH)$_2$,
n) —P(O)(OH)—O—P(O)(OH)—O—P(O)(OH)$_2$,
o) an acyl,
p) a C$_{1-6}$-alkylene-oxy-acyl, and
q) a —C(O)—O-alkyl;
2) R$^2$ is selected from the group consisting of
  a) hydrogen,
  b) fluoro,
  c) azido,
  d) cyano,
  e) a C$_{1-6}$alkyl,
  f) a vinyl, and
  g) an ethynyl;
3) R$^3$ is selected from the group consisting of
  a) hydrogen,
  b) methyl, and
  c) cyano;
4) Y is selected from the group consisting of
  a) hydrogen,
  b) fluoro,
  c) —OH,
  d) —O~, when R$^1$ is —P(O)(OR$^{1c}$)~,
  e) —O(acyl),
  f) —O(C$_{1-6}$-alkylene-oxy-acyl),
  g) —O—C(O)—O-alkyl,
  h) —NH$_2$,
  i) —NH(acyl),
  j) —NH—C(O)—O-alkyl, and
  k) azido;
5) X is selected from the group consisting of
  a) —O—,
  b) —S—,
  c) —NH—,
  d) —CH$_2$—,
  e) >C=CH$_2$, and
  f) —NH—C(O)—O-alkyl;
6) Ⓩ is a four- or five-membered ring selected from the group consisting of radicals a-o represented by the following structures

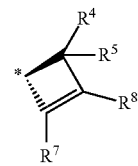 a

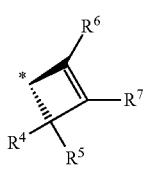 b

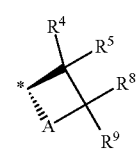 c

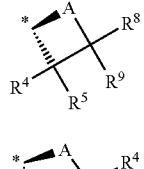 d

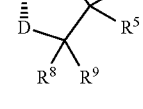 e

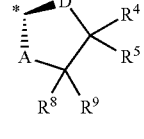 f

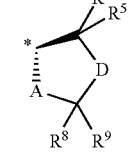 g

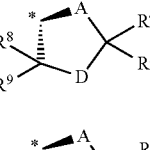 h

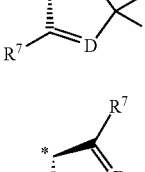 i

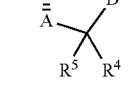 j

-continued

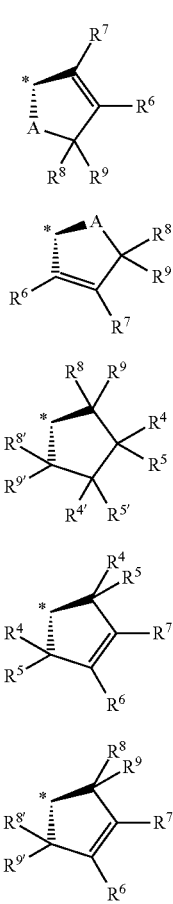

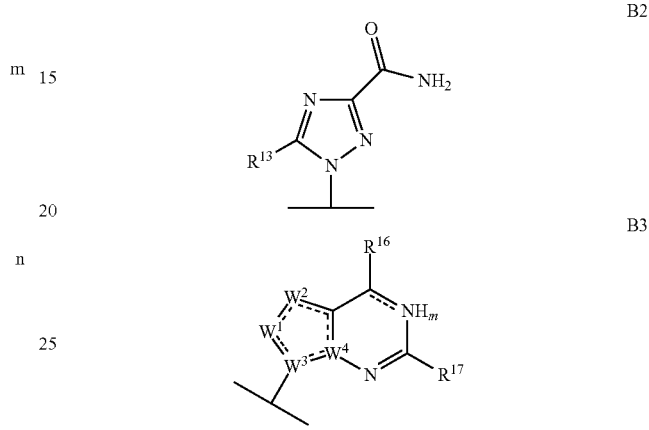

where * represents the point of attachment to the 2'-carbon and where
a) A is selected from the group consisting of
  i) —O—,
  ii) —S—,
  iii) —S(O)—,
  iv) —S(O)$_2$—, and
  v) —NH—,
b) D is selected from the group consisting of
  i) —O—,
  ii) —S— except for rings i and j,
  iii) —S(O)— except for rings i and j,
  iv) —S(O)$_2$— except for rings i and j,
  v) —NH— except for rings i and j,
  vi) —N—,
  vii) a methylene except for rings i and j,
  viii) a methine, and
  ix) a vinylidene except for rings i and j,
c) $R^4$, $R^{4'}$, $R^5$, $R^{5'}$, $R^6$, $R^7$, $R^8$, $R^{8'}$, $R^9$, and $R^{9'}$ are independently selected from the group consisting of
  i) hydrogen,
  ii) halo,
  iii) $C_{1-6}$alkyl,
  iv) hydroxy,
  v) alkoxy,
  vi) cycloalkoxy,
  vii) —O(acyl),
  viii) —O($C_{1-6}$-alkyleneoxyacyl),
  ix) —O—C(O)—O-alkyl,
  x) $C_{1-6}$alkylene-oxy(alkyl),
  xi) alkenyl,
  xii) ethynyl,
  xiii) —NH$_2$,
  xiv) —NH(alkyl),
  xv) —NH(cycloalkyl),
  xvi) heterocyclyl,
  xvii) aryl, and
  xviii) heteroaryl; and
7) B is selected from among B2, and B3 represented by the following structures:

where for B2,
  a) $R^{13}$ is selected from the group consisting of
    i) hydrogen,
    ii) halo,
    iii) cyano,
    iv) —C(O)NH$_2$,
    v) $C_{1-6}$alkyl,
    vi) vinyl, and
    vii) ethynyl,
  where for B3 m is 0 or 1, and ---- is a single or double bond
  a) when m is 0, ----- is a double-bond and $R^{16}$ and $R^{17}$ are independently selected from the group consisting of
    i) hydrogen,
    ii) —NH$_2$,
    iii) —NH(alkyl),
    iv) —NH(acyl),
    iv) —NH—C(O)—O-alkyl,
    v) -cycloheteroalkyl,
    vi) —O(alkyl),
    vii) —O(acyl),
    viii) —O($C_{1-6}$alkyleneoxyacyl),
    ix) —O—C(O)—O-alkyl, and
    x) —S(alkyl), or
  b) when m is 1, ----- is a single-bond
    b1) $R^{16}$ is selected from the group consisting of
      i) =O,
      ii) =NH, and
      iii) =N(alkyl), and
    b2) $R^{17}$ is selected from the group consisting of
      i) —NH$_2$,
      ii) —NH(alkyl),
      iii) —NH(acyl),
      iv) —NH—C(O)—O-alkyl, and
      v) -cycloheteroalkyl, and
  c) independent of the value of m, each bonding pair, $W^1$----$W^2$, $W^2$----C, C----$W^4$, $W^4$----$W^3$, and $W^3$----$W^1$, contained in the five-membered ring comprises a single or a double bond and i) $W^1$ is O, S, N, or $CR^{14}$,
ii) $W^2$ is N or $CR^{15}$,
iii) $W^3$ is C or N, and
iv) $W^4$ is C or N
and where $R^{14}$ and $R^{15}$, if present, are independently selected from the group consisting of
i) hydrogen,
ii) halo,
iii) cyano,
iv) —C(O)NH$_2$,
iv) $C_{1-6}$alkyl,
vii) vinyl, and
viii) ethynyl.

2. The compound according to claim 1, wherein B is B2 having the structure represented by formula I-2

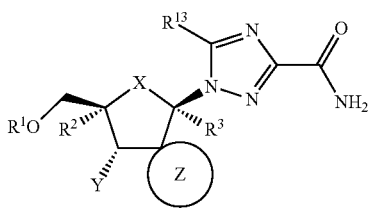

I-2 or a stereoisomer, a salt, a metabolite, or a deuteride thereof.

3. The compound or its stereoisomer or its salt or its metabolite or its deuteride thereof according to claim 2, wherein
1) $R^1$ is selected from the group consisting of
   a) hydrogen,
   b) —P(O)(OH)$_2$,
   c) —P(O)(O(CH$_2$)$_{1-3}$OC(O)O(C$_{1-6}$alkyl))$_2$,
   d) —P(O)(O(CH$_2$)$_{1-3}$OC(O)(C$_{1-6}$alkyl))$_2$,
   e) —P(O)(O(CH$_2$)$_{1-3}$SC(O)(C$_{1-6}$alkyl))$_2$,
   f) —P(O)(O(CH$_2$)$_{1-3}$OCH$_2$(aryl))$_2$,
   g) —P(O)(O(CH$_2$)$_{1-3}$SCH$_2$(aryl))$_2$,
   h) —P*(O)(OR$^{1a}$)(NHCHR$^{1b}$C(O)OR$^{1c}$),
   wherein
   $R^{1a}$ is
      i) hydrogen,
      ii) $C_{1-6}$alkyl,
      iii) $C_{3-6}$cycloalkyl, or
      iv) aryl,
   $R^{1b}$ is
      i) hydrogen,
      ii) $C_{1-6}$alkyl,
      iii) $C_{3-6}$cycloalkyl,
      iv) $C_{1-3}$alkaryl, or
      v) alk(heteroaryl), and
   $R^{1c}$ is
      i) hydrogen
      ii) $C_{1-6}$alkyl,
      iii) $C_{3-6}$cycloalkyl, or
      iv) $C_{1-3}$ alkaryl.
   i) —P*(O)(NH(alkaryl)(O(CH$_2$)$_{1-3}$SC(O)(alkyl)),
   j) a 1,3,2-dioxaphosphinane-2-oxide,
   k) a 4H-benzo[d][1,3,2]dioxaphosphinine-2-oxide,
   l) —P*(O)(OR$^{1c}$)~, when Y is —O~,
   m) —P(O)(OH)—O—P(O)(OH)$_2$,
   n) —P(O)(OH)—O—P(O)(OH)—O—P(O)(OH)$_2$,
   o) a $C_{2-7}$acyl,
   p) an aminoacyl,
   q) a $C_{1-6}$-alkylene-oxy-$C_{2-7}$acyl, and
   r) a —C(O)—O—$C_{1-6}$alkyl;

2) $R^2$ is selected from the group consisting of
   a) hydrogen,
   b) fluoro,
   c) azido, and
   d) cyano;
3) $R^3$ is selected from the group consisting of
   a) hydrogen,
   b) methyl, and
   c) cyano,
4) Y is selected from the group consisting of
   a) hydrogen,
   b) fluoro,
   c) —OH,
   d) —O~, when $R^1$ is —P(O)(OR$^{1c}$)~,
   e) —O(C$_{2-7}$acyl),
   f) —O(aminoacyl),
   g) —O(C$_{1-6}$-alkylene-oxy-acyl),
   h) —O—C(O)—O—C$_{1-6}$alkyl,
   i) —NH$_2$,
   j) —NH(C$_{2-7}$acyl),
   k) —NH(aminoacyl),
   l) —NH—C(O)—O—C$_{1-6}$alkyl, and
   m) azido;
5) X is selected from the group consisting of
   a) —O— and
   b) —S—;
6)

is a four- or five-membered ring selected from the group consisting of radicals c, d, e, f, g, and h, represented by the following structures

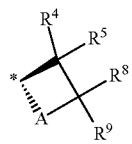

c

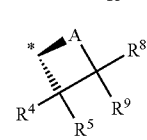

d

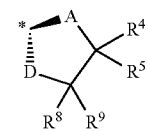

e

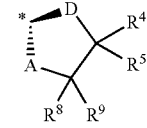

f

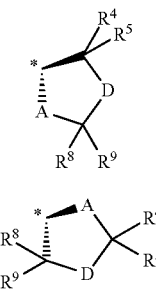

where * represents the point of attachment to the 2'-carbon and where
a) A is selected from the group consisting of
   i) —O—,
   ii) —S—,
   iii) —S(O)—,
   iv) —S(O)$_2$—, and
   v) —NH—,
b) D is selected from the group consisting of
   i) —O—,
   ii) —S—,
   iii) —S(O)—,
   iv) —S(O)$_2$—,
   v) —NH—,
   vi) a methylene, and
   vii) a vinylidene,
c) $R^4$, 1e, $R^8$, and $R^9$ are independently selected from the group consisting of
   i) hydrogen,
   ii) halo,
   iii) $C_{1-6}$alkyl
   iv) hydroxy,
   v) alkoxy,
   vi) cycloalkoxy,
   vii) —O(acyl),
   viii) —O($C_{1-6}$-alkyleneoxyacyl),
   ix) —O—C(O)—O-alkyl,
   x) $C_{1-6}$alkylene-oxy(alkyl),
   xi) alkenyl,
   xii) ethynyl,
   xiii) —NH$_2$,
   xiv) —NH(alkyl),
   xv) —NH(cycloalkyl),
   xvi) heterocyclyl,
   xvii) aryl, and
   xviii) heteroaryl; and
7) $R^{13}$ is hydrogen.

4. The compound or its stereoisomer or its salt or its metabolite or its deuteride thereof according to claim 2, wherein
1) $R^1$ is selected from the group consisting of
   a) hydrogen,
   b) —P(O)(OH)$_2$,
   c) —P(O)(O(CH$_2$)$_{1-3}$OC(O)O(C d) —P(O)(O(CH$_2$)$_{1-3}$OC(O)(C$_{1-6}$alkyl))$_2$,
   e) —P(O)(O(CH$_2$)$_{1-3}$SC(O)(C$_{1-6}$alkyl))$_2$,
   f) —P(O)(O(CH$_2$)$_{1-3}$OCH$_2$(aryl))$_2$,
   g) —P(O)(O(CH$_2$)$_{1-3}$SCH$_2$(aryl))$_2$,
   h) —P*(O)(OR$^{1a}$)(NHCHR$^{1b}$C(O)OR$^{1c}$),
   wherein
   $R^{1a}$ is
      i) hydrogen,
      ii) $C_{1-6}$alkyl,
      iii) $C_{3-6}$cycloalkyl, or
      iv) aryl,
   $R^{1b}$ is
      i) hydrogen,
      ii) $C_{1-6}$alkyl,
      iii) $C_{3-6}$cycloalkyl,
      iv) $C_{1-3}$alkaryl, or
      v) alk(heteroaryl), and
   $R^{1c}$ is
      i) hydrogen
      ii) $C_{1-6}$alkyl,
      iii) $C_{3-6}$cycloalkyl, or
      iv) $C_{1-3}$alkaryl,
   i) —P*(O)(NH(alkaryl))(O(CH$_2$)$_{1-3}$SC(O)(alkyl)),
   j) a 1,3,2-dioxaphosphinane-2-oxide,
   k) a 4H-benzo[d][1,3,2]dioxaphosphinine-2-oxide,
   l) —P*(O)(OR$^{1c}$)~, when Y is —O~,
   m) —P(O)(OH)—O—P(O)(OH)$_2$,
   n) —P(O)(OH)—O—P(O)(OH)—O—P(O)(OH)$_2$,
   o) a $C_{2-7}$acyl,
   p) an aminoacyl,
   q) a $C_{1-6}$-alkylene-oxy-$C_{2-7}$acyl, and
   r) a —C(O)—O—$C_{1-6}$alkyl;
2) $R^2$ is hydrogen;
3) $R^3$ is hydrogen;
4) Y is selected from the group consisting of
   a) —OH,
   b) —O~, when $R^1$ is —P(O)(OR$^{1c}$)~,
   c) —O($C_{2-7}$acyl),
   d) —O(aminoacyl),
   e) —O($C_{1-6}$-alkylene-oxy-acyl), and
   f) —O—C(O)—O—$C_{1-6}$alkyl;
5) X is —O—;
6)

is a four- or five-membered ring selected from the group consisting of radicals c, d, e, f, g, and h, represented by the following structures

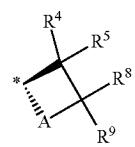

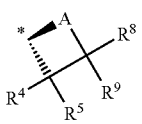

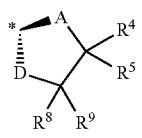

-continued

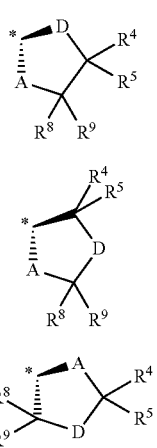

where * represents the point of attachment to the 2'-carbon and where
a) A is selected from the group consisting of
 i) —O—,
 ii) —S—,
 iii) —S(O)—,
 iv) —S(O)$_2$—, and
 v) —NH—,
b) D is selected from the group consisting of
 i) —O—,
 ii) —S—,
 iii) —S(O)—,
 iv) —S(O)$_2$—,
 v) —NH—,
 vi) a methylene, and
 vii) a vinylidene,
c) $R^4$, $R^5$, $R^8$, and $R^9$ are independently selected from the group consisting of
 i) hydrogen,
 ii) halo, and
 iii) $C_{1-6}$alkyl; and
7) $R^{13}$ is hydrogen.

5. The compound or its stereoisomer or its salt or its metabolite or its deuteride thereof according to claim 2, wherein
1) $R^1$ is selected from the group consisting of
 a) hydrogen,
 b) —P(O)(OH)$_2$,
 c) —P(O)(O(CH$_2$)$_{1-3}$OC(O)O(C$_{1-6}$alkyl))$_2$,
 d) —P(O)(O(CH$_2$)$_{1-3}$OC(O)(C$_{1-6}$alkyl))$_2$,
 e) —P(O)(O(CH$_2$)$_{1-3}$SC(O)(C$_{1-6}$alkyl))$_2$,
 f) —P(O)(O(CH$_2$)$_{1-3}$OCH$_2$(aryl))$_2$,
 g) —P(O)(O(CH$_2$)$_{1-3}$SCH$_2$(aryl))$_2$,
 h) —P*(O)(OR$^{1a}$)(NHCHR$^{1b}$C(O)OR$^{1c}$),
 wherein
 $R^{1a}$ is
  i) hydrogen,
  ii) $C_{1-6}$alkyl,
  iii) $C_{3-6}$cycloalkyl, or
  iv) aryl,
 $R^{1b}$ is
  i) hydrogen,
  ii) $C_{1-6}$alkyl,
  iii) $C_{3-6}$cycloalkyl,
  iv) $C_{1-3}$alkaryl, or
  v) alk(heteroaryl), and
 $R^{1c}$ is
  i) hydrogen
  ii) $C_{1-6}$alkyl,
  iii) $C_{3-6}$cycloalkyl, or
  iv) $C_{1-3}$ alkaryl,
 i) —P*(O)(NH(alkaryl)(O(CH$_2$)$_{1-3}$SC(O)(alkyl)),
 j) a 1,3,2-dioxaphosphinane-2-oxide,
 k) a 4H-benzo[d][1,3,2]dioxaphosphinine-2-oxide,
 l) —P*(O)(OR$^{1c}$)~, when Y is —O~,
 m) —P(O)(OH)—O—P(O)(OH)$_2$,
 n) —P(O)(OH)—O—P(O)(OH)—O—P(O)(OH)$_2$,
 o) a $C_{2-7}$acyl,
 p) an aminoacyl,
 q) a $C_{1-6}$-alkylene-oxy-$C_{2-7}$acyl, and
 r) a —C(O)—O—C$_{1-6}$alkyl;
2) $R^2$ is hydrogen;
3) $R^3$ is hydrogen;
4) Y is selected from the group consisting of
 a) —OH,
 b) —O~, when $R^1$ is —P(O)(OR$^{1c}$)~,
 c) —O(C$_{2-7}$acyl),
 d) —O(aminoacyl),
 e) —O(C$_{1-6}$-alkylene-oxy-acyl), and
 f) —O—C(O)—O—C$_{1-6}$alkyl;
5) X is —O—;
6)

is a four- or five-membered ring selected from the group consisting of radicals c, d, e, f, g, and h, represented by the following structures

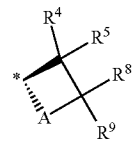
c

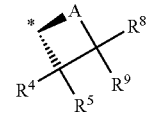
d

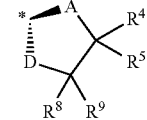
e

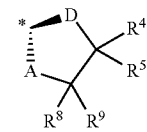
f

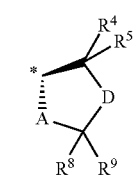
g

-continued

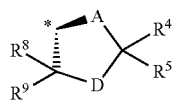
h where * represents the point of attachment to the 2'-carbon and where
a) A is —O—,
b) D is —O— or —CH$_2$—, and
c) R$^4$, R$^5$, R$^8$, and R$^9$ are each hydrogen; and
7) R$^{13}$ is hydrogen.

6. The compound or its stereoisomer or its salt or its metabolite or its deuteride thereof according to claim 2, wherein
1) R$^1$ is selected from the group consisting of
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$), wherein
  R$^{1a}$ is
    i) hydrogen or
    iv) aryl,
  R$^{1b}$ is
    i) hydrogen or
    ii) C$_{1-6}$alkyl, and
  R$^{1c}$ is
    i) hydrogen
    ii) C$_{1-6}$alkyl,
    iii) C$_{3-6}$cycloalkyl, or
    iv) C$_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~,
  m) —P(O)(OH)—O—P(O)(OH)$_2$,
  n) —P(O)(OH)—O—P(O)(OH)—O—P(O)(OH)$_2$,
  o) an C$_{2-7}$acyl,
  p) an aminoacyl,
  q) a C$_{1-6}$-alkylene-oxy-C$_{2-7}$acyl, and
  r) a —C(O)—O—C$_{1-6}$alkyl;
2) R$^2$ is hydrogen;
3) R$^3$ is hydrogen;
4) Y is selected from the group consisting of
  a) —OH,
  b) —O~, when R$^1$ is —P(O)(OR$^{1c}$)~,
  c) —O(C$_{2-7}$acyl), and
  d) —O(aminoacyl);
5) X is —O—;
6)

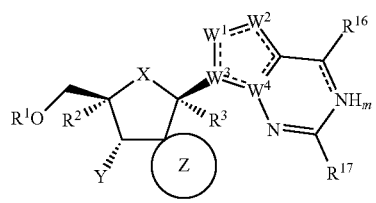

is a four- or five-membered ring selected from the group consisting of radicals c, d, e, and f represented by the following structures

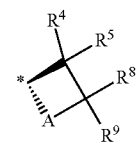
c

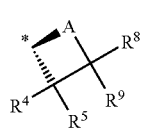
d

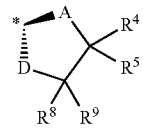
e

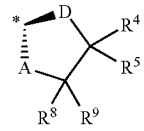
f where * represents the point of attachment to the 2'-carbon and where
a) A is —O—,
b) D is —O— or —CH$_2$—, and
c) R$^4$, R$^5$, R$^8$, and R$^9$ are each hydrogen; and
7) R$^{13}$ is hydrogen.

7. The compound according to claim 1, wherein B is B3 having the structure represented by formula I-3

I-3 or a stereoisomer, a salt, a metabolite, or a deuteride thereof.

8. The compound or its stereoisomer or its salt or its metabolite or its deuteride thereof according to claim 7, wherein
1) R$^1$ is selected from among the group consisting of
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$), wherein
  R$^{1a}$ is
    i) hydrogen,
    ii) C$_{1-6}$alkyl,
    iii) C$_{3-6}$cycloalkyl, or
    iv) aryl, $R^{1b}$ is
  i) hydrogen,
  ii) $C_{1-6}$alkyl,
  iii) $C_{3-6}$cycloalkyl,
  iv) $C_{1-3}$alkaryl, or
  v) alk(heteroaryl), and
$R^{1c}$ is
  i) hydrogen
  ii) $C_{1-6}$alkyl,
  iii) $C_{3-6}$cycloalkyl, or
  iv) $C_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~,
  m) —P(O)(OH)—O—P(O)(OH)$_2$,
  n) —P(O)(OH)—O—P(O)(OH)—O—P(O)(OH)$_2$,
  o) a $C_{2-7}$acyl,
  p) an aminoacyl,
  q) a $C_{1-6}$-alkylene-oxy-$C_{2-7}$acyl, and
  r) a —C(O)—O—$C_{1-6}$alkyl;
2) $R^2$ is selected from the group consisting of
  a) hydrogen,
  b) fluoro,
  c) azido, and
  d) cyano;
3) $R^3$ is selected from the group consisting of
  a) hydrogen,
  b) methyl, and
  c) cyano;
4) Y is selected from the group consisting of
  a) hydrogen,
  b) fluoro,
  c) —OH,
  d) —O~, when $R^1$ is —P(O)(OR$^{1c}$)~,
  e) —O($C_{2-7}$acyl),
  f) —O(aminoacyl),
  g) —O($C_{1-6}$-alkylene-oxy-acyl),
  h) —O—C(O)—O—$C_{1-6}$alkyl,
  i) —NH$_2$,
  j) —NH($C_{2-7}$acyl),
  k) —NH(aminoacyl),
  l) —NH—C(O)—O—$C_{1-6}$alkyl, and
  m) azido;
5) X is selected from the group consisting of
  a) —O— and
  b) —S—;
6)

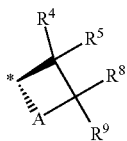

is a four- or five-membered ring selected from the group consisting of radicals c, d, e, f, g, and h, represented by the following structures c
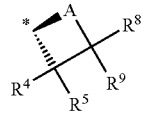

d
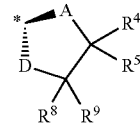

e
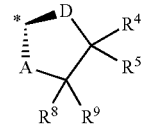

f
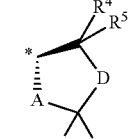

g
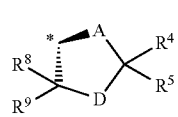

h where * represents the point of attachment to the 2'-carbon and where
  a) A is selected from the group consisting of
    i) —O—,
    ii) —S—,
    iii) —S(O)—,
    iv) —S(O)$_2$—, and
    v) —NH—,
  b) D is selected from the group consisting of
    i) —O—,
    ii) —S—,
    iii) —S(O)—,
    iv) —S(O)$_2$—,
    v) —NH—,
    vi) a methylene, and
    vii) a vinylidene, and
  c) $R^4$, $R^5$, $R^8$, and $R^9$ are independently selected from the group consisting of
    i) hydrogen,
    ii) halo,
    iii) $C_{1-6}$alkyl
    iv) hydroxy,
    v) alkoxy,
    vi) cycloalkoxy,
    vii) —O(acyl),
    viii) —O($C_{1-6}$-alkyleneoxyacyl),
    ix) —O—C(O)—O-alkyl,
    x) $C_{1-6}$alkylene-oxy(alkyl),
    xi) alkenyl,
    xii) ethynyl,
    xiii) —NH$_2$,
    xiv) —NH(alkyl),
    xv) —NH(cycloalkyl),
    xvi) heterocyclyl,
    xvii) aryl, and
    xviii) heteroaryl; and 7a) m is 0, ----- is a double-bond and $R^{16}$ and $R^{17}$ are independently selected from the group consisting of
  i) hydrogen,
  ii) —$NH_2$,
  iii) —$NH(C_{1-6}alkyl)$,
  iv) —$NH(C_{2-7}acyl)$,
  iv) —NH—C(O)—O—$C_{1-6}alkyl$,
  v) -cycloheteroalkyl,
  vi) —$O(C_{1-6}alkyl)$,
  vii) —$O(C_{2-7}acyl)$,
  viii) —$O(C_{1-6}alkyleneoxyacyl)$,
  ix) —O—C(O)—O—$C_{1-6}alkyl$,
  x) —$S(C_{1-6}alkyl)$, and
  xi) —$OC_{1-3}alkaryl$, or
7b) m is 1, ----- is a single-bond and
  b1) $R^{16}$ is selected from the group consisting of
    i) =O,
    ii) =NH, and
    iii) =$N(C_{1-6}alkyl)$, and
  b2) $R^{17}$ is selected from the group consisting of
    i) —$NH_2$,
    ii) —$NH(C_{1-6}alkyl)$,
    iii) —$NH(C_{2-7}acyl)$,
    iv) —NH—C(O)—O—$C_{1-6}alkyl$, and
    v) -cycloheteroalkyl, and
7c) independent of the value of m, each bonding pair, $W^1$----$W^2$, $W^2$----C, C----$W^4$, $W^4$----$W^3$, and $W^3$----$W^1$, contained in the five-membered ring comprises a single or a double bond and
  i) $W^1$ is O, S, N, or $CR^{14}$,
  ii) $W^2$ is N or $CR^{15}$,
  iii) $W^3$ is C or N, and
  iv) $W^4$ is C or N, and
where $R^{14}$ and $R^{15}$, if present, are independently selected from the group consisting of
  i) hydrogen,
  ii) halo,
  iii) cyano,
  iv) —$C(O)NH_2$,
  iv) $C_{1-6}alkyl$,
  vii) vinyl, and
  viii) ethynyl.

9. The compound or its stereoisomer or its salt or its metabolite or its deuteride thereof according to claim 7, wherein
1) $R^1$ is selected from the group consisting of
  a) hydrogen,
  b) —$P(O)(OH)_2$,
  c) —$P(O)(O(CH_2)_{1-3}OC(O)O(C_{1-6}alkyl))_2$,
  d) —$P(O)(O(CH_2)_{1-3}OC(O)(C_{1-6}alkyl))_2$,
  e) —$P(O)(O(CH_2)_{1-3}SC(O)(C_{1-6}alkyl))_2$,
  f) —$P(O)(O(CH_2)_{1-3}OCH_2(aryl))_2$,
  g) —$P(O)(O(CH_2)_{1-3}SCH_2(aryl))_2$,
  h) —$P*(O)(OR^{1a})(NHCHR^{1b}C(O)OR^{1c})$,
  wherein
  $R^{1a}$ is
    i) hydrogen,
    ii) $C_{1-6}alkyl$,
    iii) $C_{3-6}cycloalkyl$, or
    iv) aryl,
  $R^{1b}$ is
    i) hydrogen,
    ii) $C_{1-6}alkyl$,
    iii) $C_{3-6}cycloalkyl$,
    iv) $C_{1-3}alkaryl$, or
    v) alk(heteroaryl), and
  $R^{1c}$ is
    i) hydrogen
    ii) $C_{1-6}alkyl$,
    iii) $C_{3-6}cycloalkyl$, or
    iv) $C_{1-3}alkaryl$,
  i) —$P*(O)(NH(alkaryl)(O(CH_2)_{1-3}SC(O)(alkyl))$,
  j) a 1,3,2-dioxaphosphinane-2-oxide,
  k) a 4H-benzo[d][1,3,2]dioxaphosphinine-2-oxide,
  l) —$P*(O)(OR^{1c})$~, when Y is —O~,
  m) —P(O)(OH)—O—$P(O)(OH)_2$,
  n) —P(O)(OH)—O—P(O)(OH)—O—$P(O)(OH)_2$,
  o) a $C_{2-7}acyl$,
  p) an aminoacyl,
  q) a $C_{1-6}$-alkylene-oxy-$C_{2-7}acyl$, and
  r) a —C(O)—O—$C_{1-6}alkyl$;
2) $R^2$ is hydrogen;
3) $R^3$ is hydrogen;
4) Y is selected from the group consisting of
  a) —OH,
  b) —O~, when $R^1$ is —$P(O)(OR^{1c})$~,
  c) —$O(C_{2-7}acyl)$,
  d) —O(aminoacyl),
  e) —$O(C_{1-6}$-alkylene-oxy-acyl), and
  f) —O—C(O)—O—$C_{1-6}alkyl$;
5) X is —O—;
6)

is a four- or five-membered ring selected from the group consisting of radicals c, d, e, f, g, and h, represented by the following structures

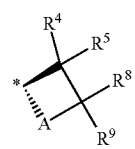

c

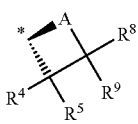

d

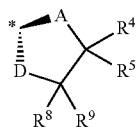

e

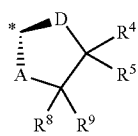

f

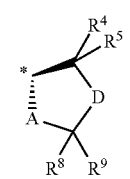

g

-continued h $$\begin{matrix} & * & A \\ R^8 & & R^4 \\ R^9 & D & R^5 \end{matrix}$$

where * represents the point of attachment to the 2'-carbon and where
  a) A is selected from the group consisting of
    i) —O—,
    ii) —S—,
    iii) —S(O)—,
    iv) —S(O)$_2$—, and
    v) —NH—,
  b) D is selected from the group consisting of
    i) —O—,
    ii) —S—,
    iii) —S(O)—,
    iv) —S(O)$_2$—,
    v) —NH—,
    vi) a methylene, and
    vii) a vinylidene,
  c) $R^4$, $R^5$, $R^8$, and $R^9$ are independently selected from the group consisting of
    i) hydrogen,
    ii) halo, and
    iii) $C_{1-6}$alkyl; and
7a) m is 0, ----- is a double-bond and $R^{16}$ and $R^{17}$ are independently selected from the group consisting of
    i) hydrogen,
    ii) —NH$_2$,
    iii) —NH($C_{1-6}$alkyl),
    iv) —NH($C_{2-7}$acyl),
    iv) —NH—C(O)—O—$C_{1-6}$alkyl,
    v) -cycloheteroalkyl,
    vi) —O($C_{1-6}$alkyl),
    vii) —O($C_{2-7}$acyl),
    viii) —O($C_{1-6}$alkyleneoxyacyl),
    ix) —O—C(O)—O—$C_{1-6}$alkyl,
    x) —S($C_{1-6}$alkyl), and
    xi) —O$C_{1-3}$alkaryl, or
7b) m is 1, ----- is a single-bond and
  b1) $R^{16}$ is selected from the group consisting of
    i) =O,
    ii) =NH, and
    iii) =N($C_{1-6}$alkyl), and
  b2) $R^{17}$ is selected from the group consisting of
    i) —NH$_2$,
    ii) —NH($C_{1-6}$alkyl),
    iii) —NH($C_{2-7}$acyl),
    iv) —NH—C(O)—O—$C_{1-6}$alkyl, and
    v) -cycloheteroalkyl, and
7c) independent of the value of m, each bonding pair, $W^1$----$W^2$, $W^2$----C, C----$W^4$, $W^4$----$W^3$, and $W^3$----$W^1$, contained in the five-membered ring comprises a single or a double bond and
    i) $W^1$ is O, S, N, or $CR^{14}$,
    ii) $W^2$ is N or $CR^{15}$,
    iii) $W^3$ is C or N, and
    iv) $W^4$ is C or N, and
  where $R^{14}$ and $R^{15}$, if present, are independently selected from the group consisting of
    i) hydrogen,
    ii) halo,
    iii) cyano,
    iv) —C(O)NH$_2$,
    iv) $C_{1-6}$alkyl,
    vii) vinyl, and
    viii) ethynyl.

10. The compound or its stereoisomer or its salt or its metabolite or its deuteride thereof according to claim 7, wherein
  1) $R^1$ is selected from the group consisting of
    a) hydrogen,
    b) —P(O)(OH)$_2$,
    c) —P(O)(O(CH$_2$)$_{1-3}$OC(O)O($C_{1-6}$alkyl))$_2$,
    d) —P(O)(O(CH$_2$)$_{1-3}$OC(O)($C_{1-6}$alkyl))$_2$,
    e) —P(O)(O(CH$_2$)$_{1-3}$SC(O)($C_{1-6}$alkyl))$_2$,
    f) —P(O)(O(CH$_2$)$_{1-3}$OCH$_2$(aryl))$_2$,
    g) —P(O)(O(CH$_2$)$_{1-3}$SCH$_2$(aryl))$_2$,
    h) —P*(O)(OR$^{1a}$)(NHCHR$^{1b}$C(O)OR$^{1c}$),
    wherein
    $R^{1a}$ is
      i) hydrogen,
      ii) $C_{1-6}$alkyl,
      iii) $C_{3-6}$cycloalkyl, or
      iv) aryl,
    $R^{1b}$ is
      i) hydrogen,
      ii) $C_{1-6}$alkyl,
      iii) $C_{3-6}$cycloalkyl,
      iv) $C_{1-3}$alkaryl, or
      v) alk(heteroaryl), and
    $R^{1c}$ is
      i) hydrogen
      ii) $C_{1-6}$alkyl,
      iii) $C_{3-6}$cycloalkyl, or
      iv) $C_{1-3}$alkaryl,
    i) —P*(O)(NH(alkaryl)(O(CH$_2$)$_{1-3}$ SC(O)(alkyl)),
    j) a 1,3,2-dioxaphosphinane-2-oxide,
    k) a 4H-benzo[d][1,3,2]dioxaphosphinine-2-oxide,
    l) —P*(O)(OR$^{1c}$)~, when Y is —O~,
    m) —P(O)(OH)—O—P(O)(OH)$_2$,
    n) —P(O)(OH)—O—P(O)(OH)—O—P(O)(OH)$_2$,
    o) a $C_{2-7}$acyl,
    p) an aminoacyl,
    p) a $C_{1-6}$-alkylene-oxy-$C_{2-7}$acyl, and
    q) a —C(O)—O—$C_{1-6}$alkyl;
  2) $R^2$, is hydrogen;
  3) $R^3$ is hydrogen;
  4) Y is selected from the group consisting of
    a) —OH,
    b) —O~, when $R^1$ is —P(O)(OR$^{1c}$)~,
    c) —O($C_{2-7}$acyl),
    d) —O(aminoacyl),
    e) —O($C_{1-6}$-alkylene-oxy-acyl), and
    f) —O—C(O)—O—$C_{1-6}$alkyl;
  5) X is —O~;
  6)

(Z)

is a four- or five-membered ring selected from the group consisting of radicals c, d, e, f, g, and h, represented by the following structures

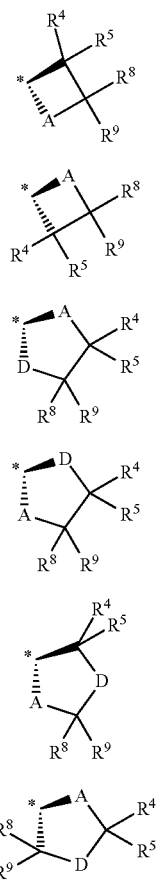

where * represents the point of attachment to the 2'-carbon and where
  a) A is —O—,
  b) D is —O— or —CH$_2$—,
  c) R$^4$, R$^5$, R$^8$, and R$^9$ are each hydrogen; and
7a) m is 0, ----- is a double-bond and R$^{16}$ and R$^{17}$ are independently selected from the group consisting of
  i) hydrogen,
  ii) —NH$_2$,
  iii) —NH(C$_{1-6}$alkyl),
  iv) —NH(C$_{2-7}$acyl),
  iv) —NH—C(O)—O—C$_{1-6}$alkyl,
  v) -cycloheteroalkyl,
  vi) —O(C$_{1-6}$alkyl),
  vii) —O(C$_{2-7}$acyl),
  viii) —O(C$_{1-6}$alkyleneoxyacyl),
  ix) —O—C(O)—O—C$_{1-6}$alkyl,
  x) —S(C$_{1-6}$alkyl), and
  xi) —OC$_{1-3}$alkaryl, or
7b) m is 1, ----- is a single-bond and
  b1) R$^{16}$ is selected from the group consisting of
    i) =O,
    ii) =NH, and
    iii) =N(C$_{1-6}$alkyl), and
  b2) R$^{17}$ is selected from the group consisting of
    i) —NH$_2$,
    ii) —NH(C$_{1-6}$alkyl),
    iii) —NH(C$_{2-7}$acyl),
    iv) —NH—C(O)—O—C$_{1-6}$alkyl, and
    v) -cycloheteroalkyl, and 7c) independent of the value of m, each bonding pair, W$^1$----W$^2$, W$^2$----C, C----W$^4$, W$^4$----W$^3$, and W$^3$----W$^1$, contained in the five-membered ring comprises a single or a double bond and
  i) W$^1$ is O, S, N, or CR$^{14}$,
  ii) W$^2$ is N or CR$^{15}$,
  iii) W$^3$ is C or N, and
  iv) W$^4$ is C or N, and
where R$^{14}$ and R$^{15}$, if present, are independently selected from the group consisting of
  i) hydrogen,
  ii) halo,
  iii) cyano,
  iv) —C(O)NH$_2$,
  iv) C$_{1-6}$alkyl,
  vii) vinyl, and
  viii) ethynyl.

11. The compound or its stereoisomer or its salt or its metabolite or its deuteride thereof according to claim 7, wherein
1) R$^1$ is selected from the group consisting of
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —P*(O)(OR$^{1a}$)(NHCHR$^{1b}$C(O)OR$^{1c}$),
  wherein
  R$^{1a}$ is
    i) hydrogen or
    iv) aryl,
  R$^{1b}$ is
    i) hydrogen or
    ii) C$_{1-6}$alkyl, and
  R$^{1c}$ is
    i) hydrogen
    ii) C$_{1-6}$alkyl,
    iii) C$_{3-6}$cycloalkyl, or
    iv) C$_{1-3}$alkaryl,
  i) —P*(O)(NH(alkaryl)(O(CH$_2$)$_{1-3}$SC(O)(alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~,
  m) —P(O)(OH)—O—P(O)(OH)$_2$,
  n) —P(O)(OH)—O—P(O)(OH)—O—P(O)(OH)$_2$,
  o) an C$_{2-7}$acyl,
  p) an aminoacyl,
  q) a C$_{1-6}$-alkylene-oxy-C$_{2-7}$acyl, and
  r) a —C(O)—O—C$_{1-6}$alkyl;
2) R$^2$ is hydrogen;
3) R$^3$ is hydrogen;
4) Y is selected from the group consisting of
  a) —OH,
  b) —O~, when R$^1$ is —P(O)(OR$^{1c}$)~,
  c) —O(C$_{2-7}$acyl), and
  d) —O(aminoacyl);
5) X is —O—;
6)

(z)

is a four- or five-membered ring selected from the group consisting of radicals c, d, e, and f represented by the following structures

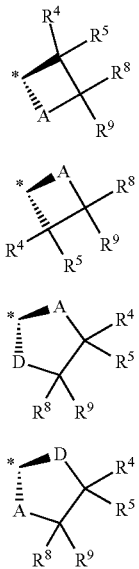

where * represents the point of attachment to the 2'-carbon and where
  a) A is —O—,
  b) D is —O— or —CH$_2$—,
  c) R$^4$, R$^5$, R$^8$, and R$^9$ are each hydrogen; and
7a) m is 0, ----- is a double-bond and R$^{16}$ and R$^{17}$ are independently selected from the group consisting of
  i) hydrogen,
  ii) —NH$_2$,
  iii) —NH(C$_{1-6}$alkyl),
  iv) —NH(C$_{2-7}$acyl),
  iv) —NH—C(O)—O—C$_{1-6}$alkyl,
  v) -cycloheteroalkyl,
  vi) —O(C$_{1-6}$alkyl),
  vii) —O(C$_{2-7}$acyl),
  viii) —O(C$_{1-6}$alkyleneoxyacyl),
  ix) —O—C(O)—O—C$_{1-6}$alkyl,
  x) —S(C$_{1-6}$alkyl), and
  xi) —OC$_{1-3}$alkaryl, or
7b) m is 1, ----- is a single-bond and
  b1) R$^{16}$ is selected from the group consisting of
    i) =O,
    ii) =NH, and
    iii) =N(C$_{1-6}$alkyl), and
  b2) R$^{17}$ is selected from the group consisting of
    i) —NH$_2$,
    ii) —NH(C$_{1-6}$alkyl),
    iii) —NH(C$_{2-7}$acyl),
    iv) —NH—C(O)—O—C$_{1-6}$alkyl, and
    v) -cycloheteroalkyl, and
7c) independent of the value of m, each bonding pair, W$^1$----W$^2$, W$^2$----C, C----W$^4$, W$^4$----W$^3$, and W$^3$----W$^1$, contained in the five-membered ring comprises a single or a double bond and
  i) W$^1$ is O, S, N, or CR$^{14}$,
  ii) W$^2$ is N or CR$^{15}$,
  iii) W$^3$ is C or N, and
  iv) W$^4$ is C or N, and where R$^{14}$ and R$^{15}$, if present, are independently selected from the group consisting of
  i) hydrogen,
  ii) halo,
  iii) cyano,
  iv) —C(O)NH$_2$,
  iv) C$_{1-6}$alkyl,
  vii) vinyl, and
  viii) ethynyl.

12. The compound according to claim 7, wherein W$^1$, W$^2$, W$^3$, and W$^4$ are as represented by formula I-3-1

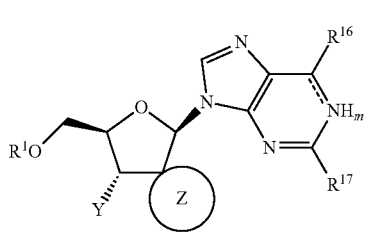

I-3-1 or a stereoisomer, a salt, a metabolite, or a deuteride thereof, wherein
  1) R$^1$ is selected from the group consisting of:
    a) hydrogen,
    b) —P(O)(OH)$_2$,
    c) —P*(O)(OR$^{1a}$)(NHCHR$^{1b}$C(O)OR$^{1c}$),
    wherein
    R$^{1a}$ is
      i) hydrogen or
      ii) aryl,
    R$^{1b}$ is
      i) hydrogen or
      ii) C$_{1-6}$alkyl, and
    R$^{1c}$ is
      i) hydrogen
      ii) C$_{1-6}$alkyl,
      iii) C$_{3-6}$cycloalkyl, or
      iv) C$_{1-3}$alkaryl,
    d) a 1,3,2-dioxaphosphinane-2-oxide,
    e) a 4H-benzo[d][1,3,2]dioxaphosphinine-2-oxide,
    f) —P*(O)(OR$^{1c}$)~, when Y is —O~,
    g) —P(O)(OH)—O—P(O)(OH)$_2$,
    h) —P(O)(OH)—O—P(O)(OH)—O—P(O)(OH)$_2$,
    i) a C$_{2-7}$acyl, and
    j) an aminoacyl;
  2) Y is selected from the group consisting of
    a) —OH,
    b) —O~, when R$^1$ is —P(O)(OR$^{1c}$)~,
    c) —O(C$_{2-7}$acyl), and
    d) —O(aminoacyl);
  3)

is selected from the group consisting of where * represents the point of attachment to the 2'-carbon; and 4a) in is 0, ----- is a double-bond
  4a1) $R^{16}$ is selected from the group consisting of
    i) —$NH_2$,
    ii) —$NH(C_{1-6}alkyl)$,
    iii) —$NH(C_{2-7}acyl)$,
    iv) -cycloalkylamino,
    v) —$O(C_{1-6}alkyl)$,
    vi) —$O(C_{2-7}acyl)$,
    vii) —$O(C_{1-6}alkyleneoxyacyl)$,
    viii) —O—C(O)—O—$C_{1-6}alkyl$,
    ix) —$S(C_{1-6}alkyl)$, and
    x) —$OC_{1-3}alkaryl$, and
  4a2) $R^{17}$ is selected from the group consisting of
    i) hydrogen,
    ii) —$NH_2$, and
    iii) —$NH(C_{1-6}alkyl)$, or
4b) m is 1, ----- is a single-bond
  4b1) $R^{16}$ is =O; and
  4b2) $R^{17}$ is selected from the group consisting of
    i) —$NH_2$ and
    ii) —$NH(C_{1-6}alkyl)$.

13. The compound or its stereoisomer or its salt or its metabolite or its deuteride thereof according to claim 12, wherein
1) $R^1$ is selected from the group consisting of:
  a) hydrogen,
  b) —$P(O)(OH)_2$,
  c) —$P*(O)(OR^{1a})(NHCHR^{1b}C(O)OR^{1c})$,
    wherein
    $R^{1a}$ is
      i) hydrogen,
      ii) phenyl,
      iii) p-fluorophenyl,
      iv) p-chlorophenyl,
      v) p-bromophenyl, or
      vi) naphthyl,
    $R^{1b}$ is
      i) hydrogen or
      ii) $C_{1-6}alkyl$, and
    $R^{1c}$ is
      i) hydrogen
      ii) $C_{1-6}alkyl$,
      iii) $C_{3-6}cycloalkyl$, or
      iv) $C_{1-3}$ alkaryl,
  d) —$P*(O)(OR^{1c})$~, when Y is —O~,
  e) —$P(O)(OH)$—O—$P(O)(OH)_2$,
  f) —$P(O)(OH)$—O—$P(O)(OH)$—O—$P(O)(OH)_2$,
  g) a $C_{2-7}acyl$, and
  h) an aminoacyl;
2) Y is selected from the group consisting of
  a) —OH,
  b) —O~, when $R^1$ is —$P(O)(OR^{1c})$~,
  c) —$O(C_{2-7}acyl)$, and
  d) —O(aminoacyl);

3)

(Z)

is selected from the group consisting of where * represents the point of attachment to the 2'-carbon; and 4a) m is 0, ----- is a double-bond
  4a1) $R^{16}$ is selected from the group consisting of
    i) —$NH_2$,
    ii) —$NH(C_{1-6}alkyl)$,
    iii) —$NH(C_{2-7}acyl)$,
    iv) -cycloalkylamino,
    v) —$O(C_{1-6}alkyl)$,
    vi) —$O(C_{2-7}acyl)$,
    vii) —$O(C_{1-6}alkyleneoxyacyl)$,
    viii) —O—C(O)—O—$C_{1-6}alkyl$,
    ix) —$S(C_{1-6}alkyl)$, and
    x) —$OC_{1-3}alkaryl$, and
  4a2) $R^{17}$ is selected from the group consisting of
    i) hydrogen,
    ii) —$NH_2$ and
    iii) —$NH(C_{1-6}alkyl)$, or
4b) m is 1, ----- is a single-bond
  4b1) $R^{16}$ is =O and
  4b2) $R^{17}$ is selected from the group consisting of
    i) —$NH_2$ and
    ii) —$NH(C_{1-6}alkyl)$.

14. The compound or its stereoisomer or its salt or its metabolite or its deuteride thereof according to claim 12, wherein
1) $R^1$ is selected from the group consisting of:
  a) hydrogen,
  b) —$P(O)(OH)_2$,
  c) —$P*(O)(OR^{1a})(NHCHR^{1b}C(O)OR^{1c})$,
    wherein
    $R^{1a}$ is
      i) hydrogen,
      ii) phenyl,
      iii) p-fluorophenyl,
      iv) p-chlorophenyl,
      v) p-bromophenyl, or
      vi) naphthyl,
    $R^{1b}$ is
      i) hydrogen or
      ii) $C_{1-6}alkyl$, and
    $R^{1c}$ is
      i) hydrogen
      ii) $C_{1-6}alkyl$,
      iii) $C_{3-6}cycloalkyl$, or
      iv) $C_{1-3}$ alkaryl,
  d) —$P*(O)(OR^{1c})$~, when Y is —O~,
  e) —$P(O)(OH)$—O—$P(O)(OH)_2$,
  f) —$P(O)(OH)$—O—$P(O)(OH)$—O—$P(O)(OH)_2$,
  g) a $C_{2-7}acyl$, and
  h) an aminoacyl;
2) Y is selected from the group consisting of
  a) —OH,
  b) —O~, when $R^1$ is —$P(O)(OR^{1c})$~, c) —O($C_{2-7}$acyl), and
d) —O(aminoacyl);
3) 

is selected from the group consisting of

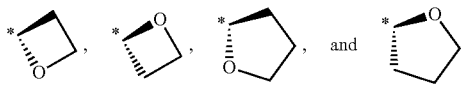

where * represents the point of attachment to the 2'-carbon; and 4a) m is 0, ----- is a double-bond
  4a1) $R^{16}$ is selected from the group consisting of
    i) —$NH_2$,
    ii) —NH($C_{1-6}$alkyl),
    iii) —NH($C_{2-7}$acyl),
    iv) -cycloalkylamino,
    v) —O($C_{1-6}$alkyl),
    vi) —O($C_{2-7}$acyl),
    vii) —S($C_{1-6}$alkyl), and
    viii) —O$C_{1-3}$alkaryl, and
  4a2) $R^{17}$ is selected from the group consisting of
    i) hydrogen,
    ii) —$NH_2$, and
    iii) —NH($C_{1-6}$alkyl), or
4b) m is 1, ----- is a single-bond
  4b1) $R^{16}$ is =O and
  4b2) $R^{17}$ is selected from the group consisting of
    i) —$NH_2$ and
    ii) —NH($C_{1-6}$alkyl).

15. The compound or its stereoisomer or its salt or its metabolite or its deuteride thereof according to claim 12, wherein 1) $R^1$ is selected from the group consisting of:
  a) hydrogen,
  b) —P(O)(OH)$_2$,
  c) —P*(O)(O$R^{1a}$)(NHCH$R^{1b}$C(O)O$R^{1c}$),
  wherein
    $R^{1a}$ is
      i) hydrogen,
      ii) phenyl,
      iii) p-fluorophenyl,
      iv) p-chlorophenyl,
      v) p-bromophenyl, or
      vi) naphtyl,
    $R^{1b}$ is
      i) hydrogen or
      ii) $C_{1-6}$alkyl, and
    $R^{1c}$ is
      i) hydrogen
      ii)
      iii) $C_{3-6}$cycloalkyl, or
      vi) $C_{1-3}$alkaryl,
  d) —P*(O)(O$R^{1c}$)~, when Y is —O~,
  e) —P(O)(OH)—O—P(O)(OH)$_2$,
  f) —P(O)(OH)—O—P(O)(OH)—O—P(O)(OH)$_2$,
  g) a $C_{2-7}$acyl, and
  h) an aminoacyl;

2) Y is selected from the group consisting of
  a) —OH,
  b) —O~, when $R^1$ is —P(O)(O$R^{1c}$)~,
  c) —O($C_{2-7}$acyl), and
  d) —O(aminoacyl);
3) 

is selected from the group consisting of

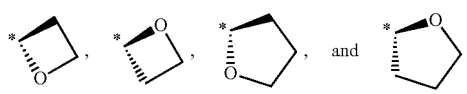

where * represents the point of attachment to the 2'-carbon; and 4a) m is 0, ----- is a double-bond
  4a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  4a2) $R^{17}$ is —$NH_2$ or —NH($C_{1-6}$alkyl), or
  4a3) $R^{16}$ is —$NH_2$, —O($C_{1-6}$alkyl), —O$C_{1-3}$alkaryl, —S($C_{1-6}$alkyl), —NH($C_{1-6}$alkyl), or -cycloalkylamino, and
  4a4) $R^{17}$ is hydrogen, or
4b) m is 1, ----- is a single-bond
  4b1) $R^{16}$ is =O and
  4b2) $R^{17}$ is —$NH_2$ or —NH($C_{1-6}$alkyl).

16. The compound according to claim 7, wherein Y, $W^1$, $W^2$, $W^3$, and $W^4$ are as represented by formula I-3-2

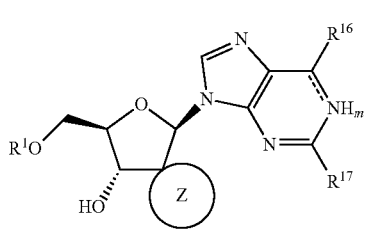

I-3-2 or a stereoisomer, a salt, a metabolite, or a deuteride thereof, wherein

1) $R^1$ is selected from the group consisting of:
  a) hydrogen,
  b) —P(O)(OH)$_2$,
  c) —P*(O)(O$R^{1a}$)(NHCH$R^{1b}$C(O)O$R^{1c}$),
  wherein
    $R^{1a}$ is
      i) hydrogen,
      ii) phenyl,
      iii) p-fluorophenyl,
      iv) p-chlorophenyl,
      v) p-bromophenyl, or
      vi) naphthyl,
    $R^{1b}$ is
      i) hydrogen or
      ii) $C_{1-6}$alkyl, and
    $R^{1c}$ is
      i) hydrogen
      ii) $C_{1-6}$alkyl, iii) $C_{3-6}$cycloalkyl, or
iv) $C_{1-3}$alkaryl,
d) —P(O)(OH)—O—P(O)(OH)$_2$,
e) —P(O)(OH)—O—P(O)(OH)—O—P(O)(OH)$_2$,
f) a $C_{2-7}$acyl, and
g) an aminoacyl;

2)

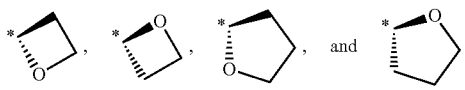

is selected from the group consisting of

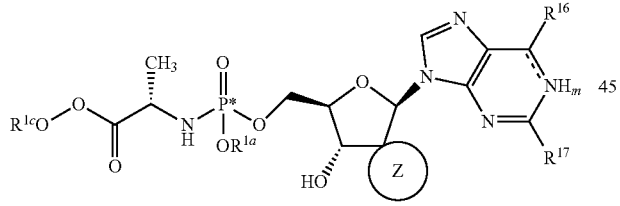

where * represents the point of attachment to the 2'-carbon; and 3a) m is 0, ----- is a double-bond
   3a1) $R^{16}$ is —O($C_{1-6}$alkyl), —O$C_{1-3}$alkaryl, —S($C_{1-6}$alkyl), —NH($C_{1-6}$alkyl), or cycloalkylamino and
   3a2) $R^{17}$ is —NH$_2$ or —NH($C_{1-6}$alkyl), or
   3a3) $R^{16}$ is —NH$_2$, —O($C_{1-6}$alkyl), —O$C_{1-3}$alkaryl, —S($C_{1-6}$alkyl), —NH($C_{1-6}$alkyl), or -cycloalkylamino and
   3a4) $R^{17}$ is hydrogen, or
3b) m is 1, ----- is a single-bond
   3b1) $R^{16}$ is =O and
   3b2) $R^{17}$ is —NH$_2$.

17. The compound according to claim 7, wherein $R^1$, Y, $W^1$, $W^2$, $W^3$, and $W^4$ are as represented by formula I-3-3

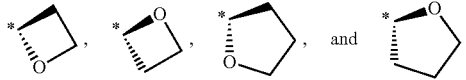

I-3-3 or a stereoisomer, a salt, a metabolite, or a deuteride thereof, wherein
1) $R^{1a}$ is selected from the group consisting of
   a) hydrogen,
   b) phenyl,
   c) p-fluorophenyl,
   d) p-chlorophenyl,
   e) p-bromophenyl, and
   f) naphthyl, and
2) $R^{1c}$ is selected from the group consisting of
   a) hydrogen
   b) $C_{1-6}$alkyl,
   c) $C_{3-6}$cycloalkyl, and
   d) $C_{1-3}$alkaryl;

3)

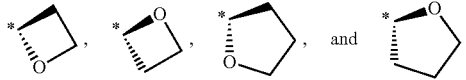

is selected from the group consisting of

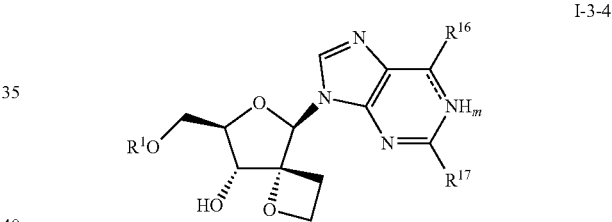

where * represents the point of attachment to the 2'-carbon; and 4a) m is 0, ----- is a double-bond
   4a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
   4a2) $R^{17}$ is —NH$_2$ or —NH($C_{1-6}$alkyl), or
   4a3) $R^{16}$ is —NH$_2$, —O($C_{1-6}$alkyl), —O$C_{1-3}$alkaryl, —S($C_{1-6}$alkyl), —NH($C_{1-6}$alkyl), or -cycloalkylamino, and
   4a4) $R^{17}$ is hydrogen, or
4b) m is 1, ----- is a single-bond
   4b1) $R^{16}$ is =O and
   4b2) $R^{17}$ is —NH$_2$ or —NH($C_{1-6}$alkyl).

18. The compound according to claim 7, wherein Y, Z, $W^1$, $W^2$, $W^3$, and $W^4$ are as represented by formula I-3-4

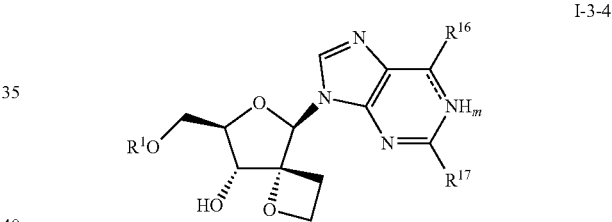

I-3-4 or a stereoisomer, a salt, a metabolite, or a deuteride thereof, wherein
1) $R^1$ is selected from the group consisting of:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
     i) hydrogen,
     ii) phenyl,
     iii) p-fluorophenyl,
     iv) p-chlorophenyl,
     v) p-bromophenyl, or
     vi) naphthyl,
   $R^{1b}$ is
     i) hydrogen or
     ii) $C_{1-6}$alkyl, and
   $R^{1c}$ is
     i) hydrogen
     ii) $C_{1-6}$alkyl,
     iii) $C_{3-6}$cycloalkyl, or
     iv) $C_{1-3}$alkaryl,
   d) —P(O)(OH)—O—P(O)(OH)$_2$,
   e) —P(O)(OH)—O—P(O)(OH)—O—P(O)(OH)$_2$,
   f) a $C_{2-7}$acyl, and
   g) an aminoacyl; and 2a) m is 0, ----- is a double-bond
  3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  3a2) $R^{17}$ is —$NH_2$ or —NH($C_{1-6}$alkyl), or
  3a3) $R^{16}$ is —$NH_2$, —O($C_{1-6}$alkyl), —O$C_{1-3}$alkaryl, —S($C_{1-6}$alkyl), —NH($C_{1-6}$alkyl), or -cycloalkylamino and
  3a4) $R^{17}$ is hydrogen, or
2b) m is 1, ----- is a single-bond
  3b1) $R^{16}$ is =O and
  3b2) $R^{17}$ is —$NH_2$ or —NH($C_{1-6}$alkyl).

19. The compound according to claim 7, wherein $R^1$, Y, Z, $W^1$, $W^2$, $W^3$, and $W^4$ are as represented by formula I-3-5

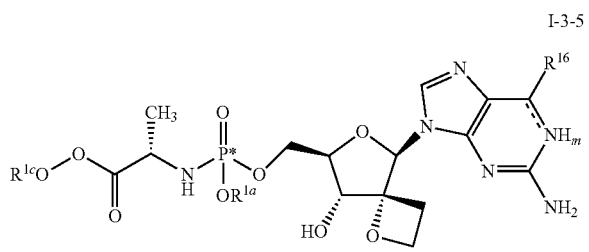

I-3-5 or a stereoisomer, a salt, a metabolite, or a deuteride thereof, wherein
1) $R^{1a}$ is
  a) hydrogen,
  b) phenyl, or
  c) naphthyl;
2) $R^{1c}$ is
  a) hydrogen
  b) $C_{1-6}$alkyl,
  c) $C_{3-6}$cycloalkyl, or
  d) $C_{1-3}$alkaryl; and
3a) m is 0, ----- is a double-bond
  3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  3a2) $R^{17}$ is —$NH_2$ or —NH($C_{1-6}$alkyl), or
  3a3) $R^{16}$ is —$NH_2$, —O($C_{1-6}$alkyl), —O$C_{1-3}$alkaryl, —S($C_{1-6}$alkyl), —NH($C_{1-6}$alkyl), or -cycloalkylamino, and
  3a4) $R^{17}$ is hydrogen, or
3b) m is 1, ----- is a single-bond
  3b1) $R^{16}$ is =O and
  3b2) $R^{17}$ is —$NH_2$ or —NH($C_{1-6}$alkyl).

20. The compound or its stereoisomer or its salt or its metabolite or its deuteride thereof according to claim 19, wherein
1) $R^{1a}$ is
  a) hydrogen,
  b) phenyl, or
  c) naphthyl;
2) $R^{1c}$ is
  a) hydrogen
  b) $C_{1-6}$alkyl,
  c) $C_{3-6}$cycloalkyl, or
  d) $C_{1-3}$alkaryl; and
3a) m is 0, ----- is a double-bond
  3a1) $R^{16}$ is —O($C_{1-6}$alkyl), —O$C_{1-3}$alkaryl, —S($C_{1-6}$alkyl), —NH($C_{1-6}$alkyl), or -cycloalkylamino, and
  3a2) $R^{17}$ is —$NH_2$, or
  3a3) $R^{16}$ is —$NH_2$, —O($C_{1-6}$alkyl), —O$C_{1-3}$alkaryl, —NH($C_{1-6}$alkyl), —S($C_{1-6}$alkyl), or -cycloalkylamino, and
  3a4) $R^{17}$ is hydrogen, or
3b) m is 1, ----- is a single-bond
  3b1) $R^{16}$ is =O and
  3b2) $R^{17}$ is —$NH_2$.

21. The compound or its stereoisomer or its salt or its metabolite or its deuteride thereof according to claim 19, wherein
1) $R^{1a}$ is
  a) hydrogen,
  b) phenyl, or
  c) naphthyl;
2) $R^{1c}$ is
  a) hydrogen
  b) $C_{1-6}$alkyl,
  c) $C_{3-6}$cycloalkyl, or
  d) $C_{1-3}$alkaryl; and
3a) m is 0, ----- is a double-bond
  3a1) $R^{16}$ is —O($C_{1-6}$alkyl) —O$C_{1-3}$alkaryl, and
  3a2) $R^{17}$ is —$NH_2$, or
  3a3) $R^{16}$ is —$NH_2$, and
  3a4) $R^{17}$ is hydrogen, or
3b) m is 1, ----- is a single-bond
  3b1) $R^{16}$ is =O and
  3b2) $R^{17}$ is —$NH_2$.

22. The compound according to claim 18, wherein m, $R^{16}$, and $R^{17}$ are as represented by formula I-3-6

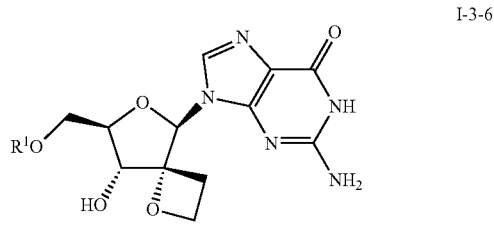

I-3-6 or a stereoisomer, a salt, a metabolite, or a deuteride thereof,
wherein
1) $R^1$ is hydrogen, —P(O)$(OH)_2$, —P(O)(OH)—O—P(O)$(OH)_2$, or —P(O)(OH)—O—P(O)(OH)—O—P(O)$(OH)_2$.

23. The compound according to claim 7, wherein $R^1$, Y, $W^1$, $W^2$, $W^3$, and $W^4$ are as represented by formula I-3-7

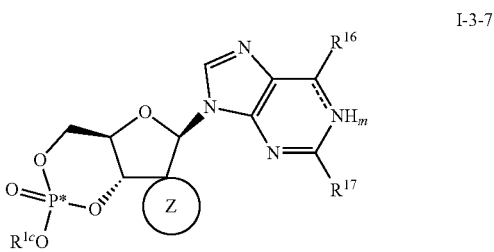

I-3-7 or a stereoisomer, a salt, a metabolite, or a deuteride thereof,
wherein
1) $R^{1c}$ is
  a) hydrogen
  b) $C_{1-6}$alkyl,
  c) $C_{3-6}$cycloalkyl, or
  d) $C_{1-3}$alkaryl;

2)

is selected from the group consisting of

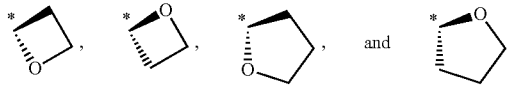

where * represents the point of attachment to the 2'-carbon; and 3a) m is 0, ----- is a double-bond
   3a1) $R^{16}$ is —O($C_{1-6}$alkyl), —O$C_{1-3}$alkaryl, —S($C_{1-6}$alkyl), —NH($C_{1-6}$alkyl), or cycloalkylamino, and
   3a2) $R^{17}$ is —NH$_2$, or
   3b1) $R^{16}$ is —NH$_2$, —O($C_{1-6}$alkyl), —O$C_{1-3}$alkaryl, —NH($C_{1-6}$alkyl), —S($C_{1-6}$alkyl), or -cycloalkylamino and
   3b2) $R^{17}$ is hydrogen, or
3b) m is 1, ----- is a single-bond
   3b1) $R^{16}$ is =O and
   3b2) $R^{17}$ is —NH$_2$ or —NH($C_{1-6}$alkyl).

24. The compound or its stereoisomer or its salt or its metabolite or its deuteride thereof according to claim 1, wherein B is selected from the group consisting of B5, B6, B7, B8, B9, and B10 represented by the following structures

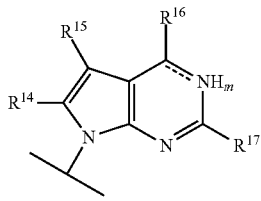
B5

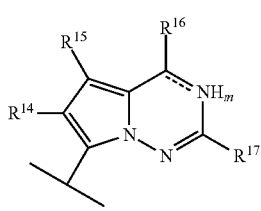
B6

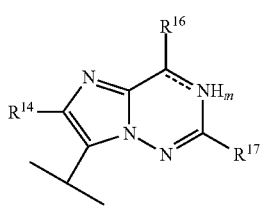
B7

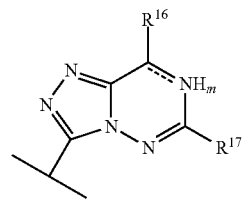
B8

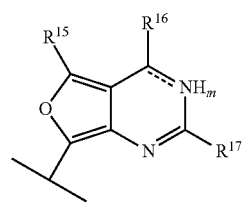
B9

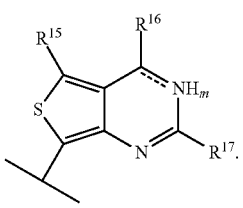
B10

25. The compound or its stereoisomer or its salt or its metabolite or its deuteride thereof according to claim 24, wherein
1) $R^1$ is selected from the group consisting of:
   a) hydrogen,
   b) —P(O)(OH)$_2$,
   c) —P(O)(O(CH$_2$)$_{1-3}$OC(O)O($C_{1-6}$alkyl))$_2$,
   d) —P(O)(O(CH$_2$)$_{1-3}$OC(O)($C_{1-6}$alkyl))$_2$,
   e) —P(O)(O(CH$_2$)$_{1-3}$SC(O)($C_{1-6}$alkyl))$_2$,
   f) —P(O)(O(CH$_2$)$_{1-3}$OCH$_2$(aryl))$_2$,
   g) —P(O)(O(CH$_2$)$_{1-3}$SCH$_2$(aryl))$_2$,
   h) —P*(O)(OR$^{1a}$)(NHCHR$^{1b}$C(O)OR$^{1c}$),
   wherein
   R$^{1a}$ is
      i) hydrogen or
      ii) aryl,
   R$^{1b}$ is
      i) hydrogen or
      ii) $C_{1-6}$alkyl, and
   R$^{1c}$ is
      i) hydrogen
      ii) alkyl,
      iii) cycloalkyl, or
      iv) —$C_{1-3}$alkaryl,
   i) —P*(O)(NH(alkaryl)(O(CH$_2$)$_{1-3}$SC(O)($C_{1-6}$alkyl)),
   j) a 1,3,2-dioxaphosphinane-2-oxide,
   k) a 4H-benzo[d][1,3,2]dioxaphosphinine-2-oxide,
   l) —P*(O)(OR$^{1c}$)~, when Y is —O~,
   m) —P(O)(OH)—O—P(O)(OH)$_2$,
   n) —P(O)(OH)—O—P(O)(OH)—O—P(O)(OH)$_2$,
   o) an $C_{2-7}$acyl,
   p) an aminoacyl,
   q) a $C_{1-6}$-alkylene-oxy-acyl, and
   r) a —C(O)—O—$C_{1-6}$alkyl;
2) $R^2$ is hydrogen;
3) $R^3$ is hydrogen or cyano;
4) Y is selected from the group consisting of
   a) —OH,
   b) —O, when $R^1$ is —P(O)(OR$^{1c}$)~, c) —O(acyl), and
d) —O(C$_{1-6}$-alkylene-oxyC$_{2-7}$acyl);
5) X is —O—;
6)

is selected from the group consisting of

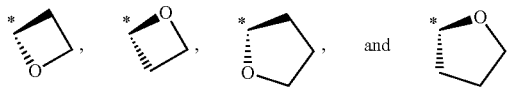

where * represents the point of attachment to the 2'-carbon; and 7a) m is 0, ----- is a double-bond and R$^{16}$ and R$^{17}$ are independently selected from the group consisting of
  i) hydrogen,
  ii) —NH$_2$,
  iii) —NH(alkyl),
  iv) —NH(acyl),
  iv) —NH—C(O)—O-alkyl,
  v) -cycloheteroalkyl,
  vi) —O(alkyl),
  vii) —O(acyl),
  viii) —O(C$_{1-6}$alkyleneoxyacyl),
  ix) —O—C(O)—O-alkyl,
  x) —S(C$_{1-6}$alkyl),
  xi) —OC$_{1-3}$alkaryl, or
7b) m is 1, ----- is a single-bond and
  b1) R$^{16}$ is selected from the group consisting of
    i) =O,
    ii)
    iii) =N(alkyl), and
  b2) R$^{17}$ is selected from the group consisting of
    i) —NH$_2$,
    ii) —NH(alkyl),
    iii) —NH(acyl),
    iv) —NH—C(O)—O-alkyl, and
    v) -cycloheteroalkyl, and
7c) independent of the value of m, R$^{14}$ and R$^{15}$, if present, are independently selected from the group consisting of
  i) hydrogen,
  ii) halo,
  iii) cyano,
  iv) —C(O)NH$_2$,
  iv) C$_{1-6}$alkyl,
  vii) vinyl, and
  viii) ethynyl.

26. The compound or its stereoisomer or its salt or its metabolite or its deuteride thereof according to claim 24, wherein
1) R$^1$ is selected from the group consisting of:
  a) hydrogen,
  b) —P(O)(OH)$_2$,
  c) —P(O)(O(CH$_2$)$_{1-3}$OC(O)O(C$_{1-6}$alkyl))$_2$,
  d) —P(O)(O(CH$_2$)$_{1-3}$OC(O)(C$_{1-6}$alkyl))$_2$,
  e) —P(O)(O(CH$_2$)$_{1-3}$SC(O)(C$_{1-6}$alkyl))$_2$,
  f) —P(O)(O(CH$_2$)$_{1-3}$OCH$_2$(aryl))$_2$,
  g) —P(O)(O(CH$_2$)$_{1-3}$SCH$_2$(aryl))$_2$,
  h) —Pt(O)(OR$^{1a}$)(NHCHR$^{1b}$C(O)OR$^{1c}$), wherein
R$^{1a}$ is
  i) hydrogen or
  ii) aryl,
R$^{1b}$ is
  i) hydrogen or
  ii) C$_{1-6}$alkyl, and
R$^{1c}$ is
  i) hydrogen,
  ii) alkyl,
  iii) cycloalkyl, or
  vi) —C$_{1-3}$alkaryl,
  i) —P*(O)(NH(alkaryl)(O(CH$_2$)$_{1-3}$SC(O)(C$_{1-6}$alkyl)),
  j) a 1,3,2-dioxaphosphinane-2-oxide,
  k) a 4H-benzo[d][1,3,2]dioxaphosphinine-2-oxide,
  l) —P*(O)(OR$^{1c}$)~, when Y is —O~,
  m) —P(O)(OH)—O—P(O)(OH)$_2$,
  n) —P(O)(OH)—O—P(O)(OH)—O—P(O)(OH)$_2$,
  o) an C$_{2-7}$acyl,
  p) an aminoacyl,
  q) a C$_{1-6}$-alkylene-oxy-acyl, and
  r) a —C(O)—O—C$_{1-6}$alkyl;
2) R$^2$ is hydrogen;
3) R$^3$ is hydrogen or cyano;
4) Y is selected from the group consisting of
  a) —OH,
  b) —O~, when R$^1$ is —P(O)(OR$^{1c}$)~,
  c) —O(acyl), and
  d) —O(C$_{1-6}$-alkylene-oxyC$_{2-7}$acyl);
5) X is —O—;
6)

is selected from the group consisting of

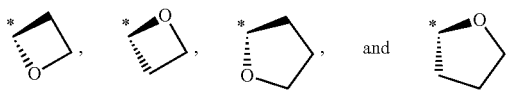

where * represents the point of attachment to the 2'-carbon; and 7a) m is 0, ----- is a double-bond,
  7a1) R$^{16}$ is selected from the group consisting of
    i) —NH$_2$,
    ii) —NH(C$_{1-6}$alkyl),
    iii) —NH(C$_{2-7}$acyl),
    iv) —NH—C(O)—O—C$_{1-6}$alkyl,
    v) -cycloheteroalkyl,
    vi) —O(C$_{1-6}$alkyl),
    vii) —O(C$_{2-7}$acyl),
    viii) —O(C$_{1-6}$alkyleneoxyacyl),
    ix) —O—C(O)—O—C$_{1-6}$alkyl,
    x) —S(C$_{1-6}$alkyl), and
    xi) —OC$_{1-3}$alkaryl, and
  7a2) R$^{17}$ is selected from the group consisting of
    i) hydrogen,
    ii) —NH$_2$,
    iii) —NH(C$_{1-6}$alkyl),
    iv) —NH(C$_{2-7}$acyl), and
    v) —NH—C(O)—O—C$_{1-6}$alkyl, or 7b) m is 1, ----- is a single-bond,
   7b1) $R^{16}$ is =O;
   7b2) $R^{17}$ is selected from the group consisting of
      i) —$NH_2$,
      ii) —$NH(C_{1-6}alkyl)$, and
      iii) —$NH(C_{2-7}acyl)$, and
7c) independent of the value of m, $R^{14}$ and $R^{15}$, if present, are independently selected from the group consisting of
   i) hydrogen,
   ii) halo,
   iii) cyano,
   iv) —$C(O)NH_2$,
   iv) $C_{1-6}$alkyl,
   vii) vinyl, and
   viii) ethynyl.

27. The compound or its stereoisomer or its salt or its metabolite or its deuteride thereof according to claim 24, wherein
   1) $R^1$ is selected from the group consisting of:
      a) hydrogen,
      b) —$P(O)(OH)_2$,
      c) —$P(O)(O(CH_2)_{1-3}OC(O)O(C_{1-6}alkyl))_2$,
      d) —$P(O)(O(CH_2)_{1-3}OC(O)(C_{1-6}alkyl))_2$,
      e) —$P(O)(O(CH_2)_{1-3}SC(O)(C_{1-6}alkyl))_2$,
      f) —$P(O)(O(CH_2)_{1-3}OCH_2(aryl))_2$,
      g) —$P(O)(O(CH_2)_{1-3}SCH_2(aryl))_2$,
      h) —$P^*(O)(OR^{1a})(NHCHR^{1b}C(O)OR^{1c})$, wherein
         $R^{1a}$ is
            i) hydrogen or
            ii) aryl,
         $R^{1b}$ is
            i) hydrogen or
            ii) $C_{1-6}$alkyl, and
         $R^{1c}$ is
            i) hydrogen
            ii) alkyl,
            iii) cycloalkyl, or
            vi) —$C_{1-3}$alkaryl,
      i) —$P^*(O)(NH(alkaryl)(O(CH_2)_{1-3}SC(O)(C_{1-6}alkyl))$,
      j) a 1,3,2-dioxaphosphinane-2-oxide,
      k) a 4H-benzo[d][1,3,2]dioxaphosphinine-2-oxide,
      l) —$P^*(O)(OR^{1c})$~, when Y is —O~,
      m) —$P(O)(OH)$—O—$P(O)(OH)_2$,
      n) —$P(O)(OH)$—O—$P(O)(OH)$—O—$P(O)(OH)_2$,
      o) a $C_{2-7}$acyl,
      p) an aminoacyl,
      q) a $C_{1-6}$-alkylene-oxy-acyl, and
      r) a —$C(O)$—O—$C_{1-6}$alkyl;
   2) $R^2$ is hydrogen;
   3) $R^3$ is hydrogen or cyano;
   4) Y is selected from the group consisting of
      a) —OH,
      b) —O~, when $R^1$ is —$P(O)(OR^{1c})$~,
      c) —$O(C_{2-7}acyl)$,
      d) —O(aminoacyl), and
      d) —$O(C_{1-6}$-alkylene-oxy$C_{2-7}$acyl);
   5) X is —O—;
   6)

(Z)

is selected from the group consisting of

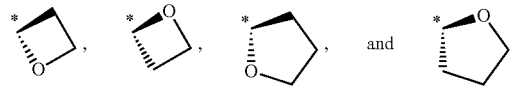

where * represents the point of attachment to the 2'-carbon; and
7a) m is 0, ----- is a double-bond,
   7a1) $R^{16}$ is selected from the group consisting of
      i) —$NH_2$,
      ii) —$NH(C_{1-6}alkyl)$,
      iii) —$NH(C_{2-7}acyl)$,
      iv) —$O(C_{1-6}alkyl)$,
      v) —$O(C_{2-7}acyl)$,
      vi) —$O(C_{1-6}alkyleneoxyacyl)$, and
      vii) —O—C(O)—O—$C_{1-6}alkyl$,
      viii) —$S(C_{1-6}alkyl)$, and
      ix) —$OC_{1-3}alkaryl$,
   7a2) $R^{17}$ is selected from the group consisting of
      i) hydrogen,
      ii) —$NH_2$,
      iii) —$NH(C_{1-6}alkyl)$,
      iv) —$NH(C_{2-7}acyl)$, and
      v) —NH—C(O)—O—$C_{1-6}$alkyl, or
7b) m is 1, ----- is a single-bond,
   7b1) $R^{16}$ is =O;
   7b2) $R^{17}$ is selected from the group consisting of
      i) —$NH_2$,
      ii) —$NH(C_{1-6}alkyl)$, and
      iii) —$NH(C_{2-7}acyl)$, and
7c) independent of the value of m, $R^{14}$ and $R^{15}$, if present, are independently selected from the group consisting of
   i) hydrogen,
   ii) halo,
   iii) cyano,
   iv) —$C(O)NH_2$,
   iv) $C_{1-6}$alkyl,
   vii) vinyl, and
   viii) ethynyl.

28. The compound or its stereoisomer or its salt or its metabolite or its deuteride thereof according to claim 24, wherein
   1) $R^1$ is selected from the group consisting of:
      a) hydrogen,
      b) —$P(O)(OH)_2$,
      c) —$P^*(O)(OR^{1a})(NHCHR^{1b}C(O)OR^{1c})$, wherein
         $R^{1a}$ is
            i) hydrogen or
            ii) aryl,
         $R^{1b}$ is
            i) hydrogen or
            ii) $C_{1-6}$alkyl, and
         $R^{1c}$ is
            i) hydrogen
            ii) alkyl,
            iii) cycloalkyl, or
            iv) —$C_{1-3}$alkaryl,
      d) a 1,3,2-dioxaphosphinane-2-oxide,
      e) a 4H-benzo[d][1,3,2]dioxaphosphinine-2-oxide,
      f) —$P^*(O)(OR^{1c})$~, when Y is —O~,
      g) —$P(O)(OH)$—O—$P(O)(OH)_2$,
      h) —$P(O)(OH)$—O—$P(O)(OH)$—O—$P(O)(OH)_2$,
      i) a $C_{2-7}$acyl,
      j) an aminoacyl,
      k) a $C_{1-6}$-alkylene-oxy-acyl, and
      l) a —$C(O)$—O—$C_{1-6}$alkyl;

2) $R^2$ is hydrogen;
3) $R^3$ is hydrogen or cyano;
4) Y is selected from the group consisting of
   a) —OH,
   b) —O~, when $R^1$ is —P(O)(OR$^{1c}$)~,
   c) —O(C$_{2-7}$acyl),
   d) —O(aminoacyl), and
   e) —O(C$_{1-6}$-alkylene-oxyC$_{2-7}$acyl);
5) X is —O—;
6)

is selected from the group consisting of

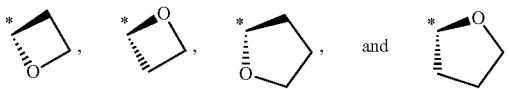

where * represents the point of attachment to the 2'-carbon; and 7a) m is 0, ----- is a double-bond,
   7a1) $R^{16}$ is selected from the group consisting of
      i) —NH$_2$,
      ii) —NH(C$_{1-6}$alkyl),
      iii) —NH(C$_{2-7}$acyl),
      iv) —O(C$_{1-6}$alkyl),
      v) —O(C$_{2-7}$acyl),
      vi) —O(C$_{1-6}$alkyleneoxyacyl), and
      vii) —O—C(O)—O—C$_{1-6}$alkyl,
      viii) —S(C$_{1-6}$alkyl), and
      ix) —OC$_{1-3}$alkaryl, and
   7a2) $R^{17}$ is selected from the group consisting of
      i) hydrogen,
      ii) —NH$_2$ and
      iii) —NH(C$_{1-6}$alkyl), or
7b) m is 1, ----- is a single-bond,
   7b1) $R^{16}$ is =O; and
   7b2) $R^{17}$ is selected from the group consisting of
      i) —NH$_2$ and
      ii) —NH(C$_{1-6}$alkyl) and
7c) independent of the value of m, $R^{14}$ and $R^{15}$, if present, are independently selected from the group consisting of
   i) hydrogen,
   ii) halo,
   iii) cyano,
   iv) —C(O)NH$_2$,
   iv) C$_{1-6}$alkyl,
   vii) vinyl, and
   viii) ethynyl.

29. The compound according to claim 24, wherein B' is B5 as represented by formula I-3-9

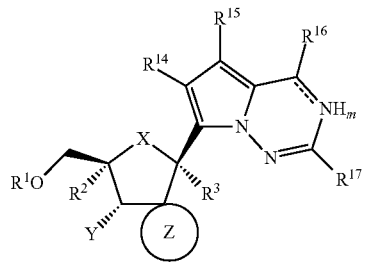

I-3-9 or a stereoisomer, a salt, a metabolite, or a deuteride thereof, wherein
1) $R^1$ is selected from the group consisting of:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
      i) hydrogen or
      ii) aryl,
   $R^{1b}$ is
      i) hydrogen or
      ii) C$_{1-6}$alkyl, and
   $R^{1c}$ is
      i) hydrogen
      ii) alkyl,
      iii) cycloalkyl, or
      iv) —C$_{1-3}$alkaryl,
   d) a 1,3,2-dioxaphosphinane-2-oxide,
   e) a 4H-benzo[d][1,3,2]dioxaphosphinine-2-oxide,
   f) —P*(O)(OR$^{1c}$)~, when Y is —O~,
   g) —P(O)(OH)—O—P(O)(OH)$_2$,
   h) —P(O)(OH)—O—P(O)(OH)—O—P(O)(OH)$_2$,
   i) a C$_{2-7}$acyl,
   j) an aminoacyl,
   k) a C$_{1-6}$-alkylene-oxy-acyl, and
   l) a —C(O)—O—C$_{1-6}$alkyl,
2) $R^2$ is hydrogen;
3) $R^3$ is hydrogen or cyano;
4) Y is selected from the group consisting of
   a) —OH,
   b) —O~, when $R^1$ is —P(O)(OR$^{1c}$)~,
   c) —O(C$_{2-7}$acyl),
   d) —O(aminoacyl), and
   d) —O(C$_{1-6}$-alkylene-oxyC$_{2-7}$acyl);
5) X is —O—;
6)

is selected from the group consisting of

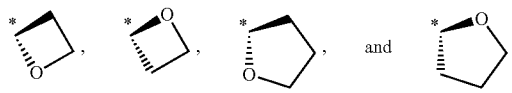

where * represents the point of attachment to the 2'-carbon; and 7a) m is 0, ----- is a double-bond,
  7a1) $R^{16}$ is selected from the group consisting of
    i) —$NH_2$,
    ii) —$NH(C_{1-6}alkyl)$,
    iii) —$NH(C_{2-7}acyl)$,
    iv) —$O(C_{1-6}alkyl)$,
    v) —$O(C_{2-7}acyl)$,
    vi) —$O(C_{1-6}alkyleneoxyacyl)$, and
    vii) —O—C(O)—O—$C_{1-6}alkyl$,
    viii) —$S(C_{1-6}alkyl)$, and
    ix) —$OC_{1-3}alkaryl$, and
  7a2) $R^{17}$ is selected from the group consisting of
    i) hydrogen,
    ii) —$NH_2$ and
    iii) —$NH(C_{1-6}alkyl)$, or
7b) m is 1, ----- is a single-bond,
  7b1) $R^{16}$ is =O; and
  7b2) $R^{17}$ is selected from the group consisting of
    i) —$NH_2$ and
    ii) —$NH(C_{1-6}alkyl)$ and
7c) independent of the value of m, $R^{14}$ and $R^{15}$ are independently selected from the group consisting of
  i) hydrogen,
  ii) halo,
  iii) cyano,
  iv) —$C(O)NH_2$,
  iv) $C_{1-6}alkyl$,
  vii) vinyl, and
  viii) ethynyl.

30. The compound according to claim 24, wherein B' is B7 as represented by formula I-3-10

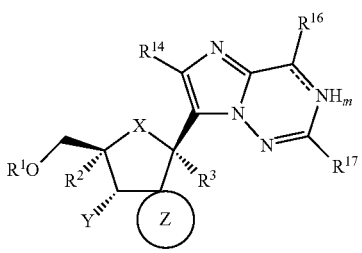

I-3-10 or a stereoisomer, a salt, a metabolite, or a deuteride thereof, wherein
1) $R^1$ is selected from the group consisting of:
  a) hydrogen,
  b) —$P(O)(OH)_2$,
  c) —$P^*(O)(OR^{1a})(NHCHR^{1b}C(O)OR^{1c})$, wherein
    $R^{1a}$ is
      i) hydrogen or
      ii) aryl,
    $R^{1b}$ is
      i) hydrogen or
      ii) $C_{1-6}alkyl$, and
    $R^{1c}$ is
      i) hydrogen
      ii) alkyl,
      iii) cycloalkyl, or
      iv) —$C_{1-3}alkaryl$,
  d) a 1,3,2-dioxaphosphinane-2-oxide,
  e) a 4H-benzo[d][1,3,2]dioxaphosphinine-2-oxide,
  f) —$P^*(O)(OR^{1c})$~, when Y is —O~,
  g) —P(O)(OH)—O—$P(O)(OH)_2$,
  h) —P(O)(OH)—O—P(O)(OH)—O—$P(O)(OH)_2$,
  i) a $C_{2-7}acyl$,
  j) an aminoacyl,
  k) a $C_{1-6}$-alkylene-oxy-acyl, and
  l) a —C(O)—O—$C_{1-6}alkyl$;
2) $R^2$ is hydrogen;
3) $R^3$ is hydrogen or cyano;
4) Y is selected from the group consisting of
  a) —OH,
  b) —O~, when $R^1$ is —$P(O)(OR^{1c})$~,
  c) —$O(C_{2-7}acyl)$,
  d) —O(aminoacyl), and
  e) —$O(C_{1-6}$-alkyl ene-oxy$C_{2-7}acyl)$;
5) X ic —O—;
6)

is selected from the group consisting of

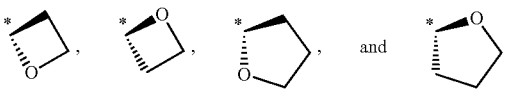

where * represents the point of attachment to the 2'-carbon; and
7a) m is 0, ----- is a double-bond,
  7a1) $R^{16}$ is selected from the group consisting of
    i) —$NH_2$,
    ii) —$NH(C_{1-6}alkyl)$,
    iii) —$NH(C_{2-7}acyl)$,
    iv) —$O(C_{1-6}alkyl)$,
    v) —$O(C_{2-7}acyl)$,
    vi) —$O(C_{1-6}alkyleneoxyacyl)$,
    vii) —O—C(O)—O—$C_{1-6}alkyl$,
    viii) —$S(C_{1-6}alkyl)$, and
    ix) —$OC_{1-3}alkaryl$, and
  7a2) $R^{17}$ is selected from the group consisting of
    i) hydrogen,
    ii) —$NH_2$ and
    iii) —$NH(C_{1-6}alkyl)$, or
7b) m is 1, ----- is a single-bond,
  7b1) $R^{16}$ is =O;
  7b2) $R^{17}$ is selected from the group consisting of
    i) —$NH_2$ and
    ii) —$NH(C_{1-6}alkyl)$ and
7c) independent of the value of m, $R^{14}$ is selected from the group consisting of
  i) hydrogen,
  ii) halo,
  iii) cyano,
  iv) —$C(O)NH_2$,
  iv) $C_{1-6}alkyl$,
  vii) vinyl, and
  viii) ethynyl.

31. The compound according to claim 24, wherein B' is B8 as represented by formula I-3-11

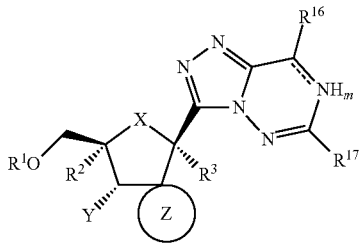

I-3-11 or a stereoisomer, a salt, a metabolite, or a deuteride thereof, wherein
1) $R^1$ is selected from the group consisting of:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
      i) hydrogen or
      ii) aryl,
   $R^{1b}$ is
      i) hydrogen or
      ii) $C_{1-6}$alkyl, and
   $R^{1c}$ is
      i) hydrogen
      ii) alkyl,
      iii) cycloalkyl, or
      iv) —$C_{1-3}$alkaryl,
   d) a 1,3,2-dioxaphosphinane-2-oxide,
   e) a 4H-benzo[d][1,3,2]dioxaphosphinine-2-oxide,
   f) —P*(O)(OR$^{1c}$)~, when Y is —O~,
   g) —P(O)(OH)—O—P(O)(OH)$_2$,
   h) —P(O)(OH)—O—P(O)(OH)—O—P(O)(OH)$_2$,
   i) a $C_{2-7}$acyl,
   j) an aminoacyl,
   k) a $C_{1-6}$-alkylene-oxy-acyl, and
   l) a —C(O)—O—$C_{1-6}$alkyl;
2) $R^2$ is hydrogen;
3) $R^3$ is hydrogen or cyano;
4) Y is selected from the group consisting of
   a) —OH,
   b) —O~, when $R^1$ is —P(O)(OR$^{1c}$)~,
   c) —O($C_{2-7}$acyl),
   d) —O(aminoacyl), and
   e) —O($C_{1-6}$-alkylene-oxy$C_{2-7}$acyl);
5) X is —O—;
6)

is selected from the group consisting of

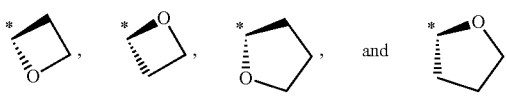

where * represents the point of attachment to the 2'-carbon; and
7a) m is 0, ----- is a double-bond,
   7a1) $R^{16}$ is selected from the group consisting of
      i) —NH$_2$,
      ii) —NH($C_{1-6}$alkyl),
      iii) —NH($C_{2-7}$acyl),
      iv) —O($C_{1-6}$alkyl),
      v) —O($C_{2-7}$acyl),
      vi) —O($C_{1-6}$alkyleneoxyacyl),
      vii) —O—C(O)—O—$C_{1-6}$alkyl,
      viii) —S($C_{1-6}$alkyl), and
      ix) —O$C_{1-3}$alkaryl, and
   7a2) $R^{17}$ is selected from the group consisting of
      i) hydrogen,
      ii) —NH$_2$ and
      iii) —NH($C_{1-6}$alkyl), or
7b) m is 1, ----- is a single-bond,
   7b1) $R^{16}$ is =O; and
   7b2) $R^{17}$ is selected from the group consisting of
      i) —NH$_2$ and
      ii) —NH($C_{1-6}$alkyl).

32. The compound according to claim 24, wherein B' is B9 as represented by formula I-3-12

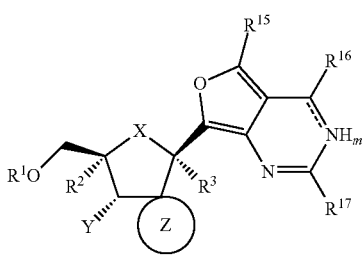

I-3-12 or a stereoisomer, a salt, a metabolite, or a deuteride thereof, wherein
1) $R^1$ is selected from the group consisting of:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
      i) hydrogen or
      ii) aryl,
   $R^{1b}$ is
      i) hydrogen or
      ii) $C_{1-6}$alkyl, and
   $R^{1c}$ is
      i) hydrogen
      ii) alkyl,
      iii) cycloalkyl, or
      iv) —$C_{1-3}$alkaryl,
   d) a 1,3,2-dioxaphosphinane-2-oxide,
   e) a 4H-benzo[d][1,3,2]dioxaphosphinine-2-oxide,
   f) —P*(O)(OR$^{1c}$)~, when Y is —O~,
   g) —P(O)(OH)—O—P(O)(OH)$_2$,
   h) —P(O)(OH)—O—P(O)(OH)—O—P(O)(OH)$_2$,
   i) a $C_{2-7}$acyl,
   j) an aminoacyl,
   k) a $C_{1-6}$-alkylene-oxy-acyl, and
   l) a —C(O)—O—$C_{1-6}$alkyl;
2) $R^2$ is hydrogen;
3) $R^3$ is hydrogen or cyano;

4) Y is selected from the group consisting of
   a) —OH,
   b) —O~, when $R^1$ is —P(O)(OR$^{1c}$)~,
   c) —O($C_{2-7}$acyl),
   d) —O(aminoacyl), and
   e) —O($C_{1-6}$-alkylene-oxy$C_{2-7}$acyl);
5) X is —O—;
6)

is selected from the group consisting of

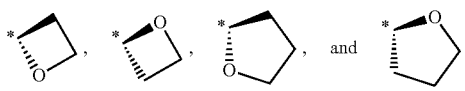

where * represents the point of attachment to the 2'-carbon; and 7a) m is 0, ----- is a double-bond,
  7a1) $R^{16}$ is selected from the group consisting of
   i) —NH$_2$,
   ii) —NH($C_{1-6}$alkyl),
   iii) —NH($C_{2-7}$acyl),
   iv) —O($C_{1-6}$alkyl),
   v) —O($C_{2-7}$acyl),
   vi) —O($C_{1-6}$alkyleneoxyacyl),
   vii) —O—C(O)—O—$C_{1-6}$alkyl,
   viii) —S($C_{1-6}$alkyl), and
   ix) —O$C_{1-3}$alkaryl, and
  7a2) $R^{17}$ is selected from the group consisting of
   i) hydrogen,
   ii) —NH$_2$ and
   iii) —NH($C_{1-6}$alkyl), or
7b) m is 1, ----- is a single-bond,
  7b1) $R^{16}$ is =O; and
  7b2) $R^{17}$ is selected from the group consisting of
   i) —NH$_2$ and
   ii) —NH($C_{1-6}$alkyl) and
7c) independent of the value of m, $R^{15}$ is selected from the group consisting of
   i) hydrogen,
   ii) halo,
   iii) cyano,
   iv) —C(O)NH$_2$,
   iv) $C_{1-6}$alkyl,
   vii) vinyl, and
   viii) ethynyl.

33. The compound according to claim 24, wherein B' is B10 as represented by formula I-3-13

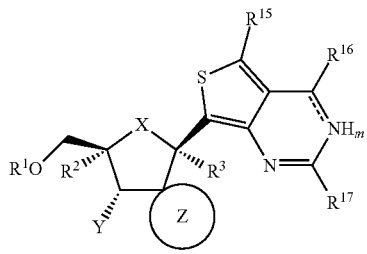

I-3-13 or a stereoisomer, a salt, a metabolite, or a deuteride thereof, wherein
1) $R^1$ is selected from the group consisting of:
   a) hydrogen,
   b) —P(O)(OH)$_2$,
   c) —P*(O)(OR$^{1a}$)(NHCHR$^{1b}$C(O)OR$^{1c}$),
   wherein
   $R^{1a}$ is
     i) hydrogen or
     ii) aryl,
   $R^{1b}$ is
     i) hydrogen or
     ii) $C_{1-6}$alkyl, and
   $R^{1c}$ is
     i) hydrogen
     ii) alkyl,
     iii) cycloalkyl, or
     iv) —$C_{1-3}$alkaryl,
   d) a 1,3,2-dioxaphosphinane-2-oxide,
   e) a 4H-benzo[d][1,3,2]dioxaphosphinine-2-oxide,
   f) —P*(O)(OR$^{1c}$)~, when Y is —O~,
   g) —P(O)(OH)—O—P(O)(OH)$_2$,
   h) —P(O)(OH)—O—P(O)(OH)—O—P(O)(OH)$_2$,
   i) a $C_{2-7}$acyl,
   j) an aminoacyl,
   k) a $C_{1-6}$-alkylene-oxy-acyl, and
   l) a —C(O)—O—$C_{1-6}$alkyl;
2) $R^2$ is hydrogen;
3) $R^3$ is hydrogen or cyano;
4) Y is selected from the group consisting of
   a) —OH,
   b) —O~, when $R^1$ is —P(O)(OR$^{1c}$)~,
   c) —O($C_{2-7}$acyl),
   d) —O(aminoacyl), and
   e) —O($C_{1-6}$-alkylene-oxy$C_{2-7}$acyl);
5) X is —O—;
6)

is selected from the group consisting of

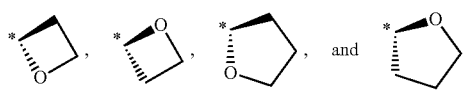

where * represents the point of attachment to the 2'-carbon; and 7a) m is 0, ----- is a double-bond,
  7a1) $R^{16}$ is selected from the group consisting of
    i) —$NH_2$,
    ii) —$NH(C_{1-6}alkyl)$,
    iii) —$NH(C_{2-7}acyl)$,
    iv) —$O(C_{1-6}alkyl)$,
    v) —$O(C_{2-7}acyl)$,
    vi) —$O(C_{1-6}alkyleneoxyacyl)$,
    vii) —O—C(O)—O—$C_{1-6}alkyl$,
    viii) —$S(C_{1-6}alkyl)$, and
    ix) —$OC_{1-3}alkaryl$, and
  7a2) $R^{17}$ is selected from the group consisting of
    i) hydrogen,
    ii) —$NH_2$ and
    iii) —$NH(C_{1-6}alkyl)$, or
7b) m is 1, ----- is a single-bond,
  7b1) $R^{16}$ is =O; and
  7b2) $R^{17}$ is selected from the group consisting of
    i) —$NH_2$ and
    ii) —$NH(C_{1-6}alkyl)$ and
7c) independent of the value of m, $R^{15}$ is selected from the group consisting of
  i) hydrogen,
  ii) halo,
  iii) cyano,
  iv) —$C(O)NH_2$,
  iv) $C_{1-6}alkyl$,
  vii) vinyl, and
  viii) ethynyl.

34. A composition comprising the compound or its stereoisomer or its salt or its metabolite or its deuteride thereof as claimed in claim 1 and a pharmaceutically acceptable medium.

35. A composition for treating a hepatitis C virus, which comprises an effective amount of the compound as claimed in any claim 1 or a stereoisomer, a salt, a metabolite, or a deuteride thereof and a pharmaceutically acceptable medium.

36. A composition for treating a dengue virus, which comprises an effective amount of the compound or its stereoisomer or its salt or its metabolite or its deuteride thereof as claimed in claim 1 and a pharmaceutically acceptable medium.

37. A method of treating a subject infected by a virus, which comprises:
  administering to the subject an effective amount of the compound or its stereoisomer or its salt or its metabolite or its deuteride thereof as claimed in claim 1;
  wherein the virus is selected from the group consisting of hepatitis C virus, West Nile virus, a yellow fever virus, a dengue virus, a rhinovirus, a polio virus, a hepatitis A virus, a bovine viral diarrhea virus, and a Japanese encephalitis virus.

38. A method of treating a hepatitis C virus infection in a subject in need thereof, which comprises:
  administering to the subject an effective amount of the compound or its stereoisomer or its salt or its metabolite or its deuteride thereof as claimed in claim 1.

39. A method of treating a dengue virus infection in a subject in need thereof, which comprises:
  administering to the subject an effective amount of the compound or its stereoisomer or its salt or its metabolite or its deuteride thereof as claimed in claim 1.

40. A method of treating a hepatitis C virus (HCV) or dengue (DENV) infection, which comprises adding to the 3'-terminus of an HCV or DENV RNA strand a radical or its salt thereof represented by

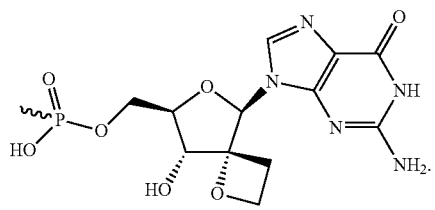

where ⁓⁓⁓ is the point of attachment to the 3'-terminus.

41. The method of claim 40, which comprises adding the radical or its salt thereof to the 3'-terminus of an HCV RNA.

42. The method of claim 40, which comprises adding the radical or its salt thereof to the 3'-terminus of a DENV RNA.

43. A method of treating a hepatitis C virus (HCV) or dengue (DENV) infection, which comprises increasing an intracellular concentration of a triphosphate ($P_3$) compound or its salt thereof or represented by

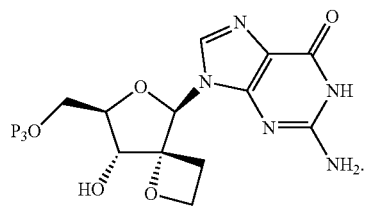

in a cell infected with HCV or DENV.

44. The method of claim 43, which comprises increasing the intracellular concentration of the triphosphate ($P_3$) compound in an HCV infected cell.

45. The method of claim 43, which comprises increasing the intracellular concentration of the triphosphate ($P_3$) compound in a DENV infected cell.

46. A compound or a salt thereof represented by formula A,

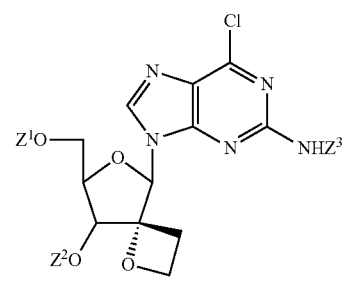

wherein each one of $Z^1$, $Z^2$, and $Z^3$ is hydrogen or a protecting group (PG).

47. A process for preparing a compound represented by formula I-3-4'

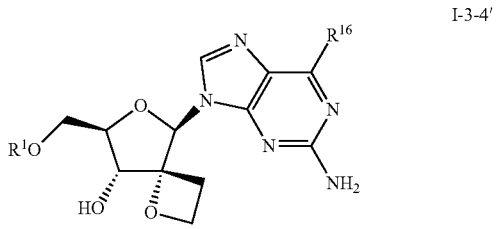

wherein
1) $R^1$ is selected from the group consisting of:
  a) hydrogen,
  b) —P(O)(OH)$_2$,
  c) —P*(O)(OR$^{1a}$)(NHCHR$^{1b}$C(O)OR$^{1c}$),
  wherein
  $R^{1a}$ is
    i) hydrogen,
    ii) phenyl,
    iii) p-fluorophenyl,
    iv) p-chlorophenyl,
    v) p-bromophenyl, or
    vi) naphthyl,
  $R^{1b}$ is
    i) hydrogen or
    ii) $C_{1-6}$alkyl, and
  $R^{1c}$ is
    i) hydrogen
    ii) $C_{1-6}$alkyl,
    iii) $C_{3-6}$cycloalkyl, or
    iv) $C_{1-3}$ alkaryl,
  d) —P(O)(OH)—O—P(O)(OH)$_2$,
  e) —P(O)(OH)—O—P(O)(OH)—O—P(O)(OH)$_2$,
  f) a $C_{2-7}$acyl, and
  g) an aminoacyl;
or
a compound represented by formula I-3-5',

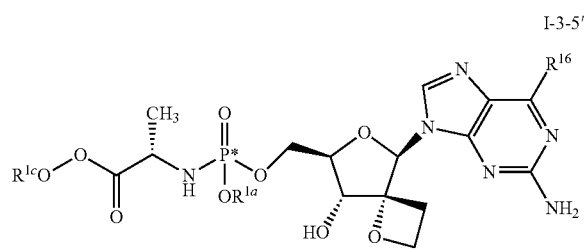

I-3-5' wherein
1) $R^{1a}$ is
  a) hydrogen,
  b) phenyl, or
  c) naphthyl, and
2) $R^{1c}$ is
  a) hydrogen
  b) $C_{1-6}$alkyl,
  c) $C_{3-6}$cycloalkyl, or
  d) $C_{1-3}$alkaryl; and
3) $R^{16}$ is
  a) —O($C_{1-6}$alkyl),
  b) —O$C_{1-3}$alkaryl,
  c) —S($C_{1-6}$alkyl),
  d) —NH($C_{1-6}$alkyl), or
  e) -cycloalkylamino,
said process comprising
reacting compound A' with a nucleophile and optionally deprotecting to obtain compound B'

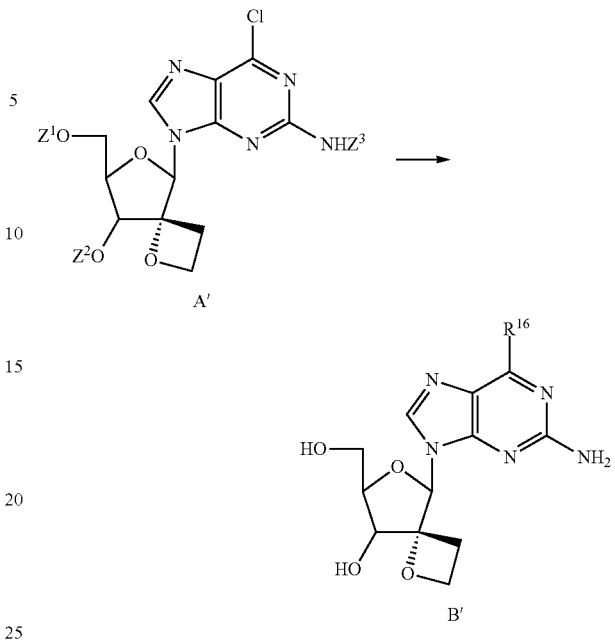

A'

B' wherein the nucleophile is comprised of a radical selected from the group consisting of —O($C_{1-6}$alkyl), —O$C_{1-3}$alkaryl, —NH($C_{1-6}$alkyl), and -cycloalkylamino, and
wherein PG is a protecting group, and wherein each one of $Z^1$, $Z^2$, and $Z^3$ is hydrogen or a protecting group (PG) and
reacting B' with an appropriate reagent to obtain either I-3-4' or I-3-5'.

48. The process according to claim 47 for preparing the compound represented by formula I-3-5', wherein $R^{16}$ is a —O($C_{1-6}$alkyl) a —O$C_{1-3}$alkaryl, a —NH($C_{1-6}$alkyl), and a $C_{3-6}$cycloalkylamino and wherein the nucleophile is comprised of a radical selected from the group consisting of a —O($C_{1-6}$alkyl), a —O$C_{1-3}$alkaryl, a —NH($C_{1-6}$alkyl), and a $C_{3-6}$cycloalkylamino.

49. The process according to claim 47 for preparing the compound represented by formula I-3-5', wherein $R^{16}$ is a —O($C_{1-6}$alkyl) or a —O$C_{1-3}$alkaryl, and wherein the nucleophile is comprised of a radical selected from the group consisting of a —O($C_{1-6}$alkyl) and a —O$C_{1-3}$alkaryl.

50. The process according to claim 47 for preparing the compound represented by formula I-3-5', wherein $R^{16}$ is a —O($C_{1-6}$alkyl), and wherein the nucleophile is comprised of a —O($C_{1-6}$alkyl).

51. The process according to claim 48 for preparing the compound represented by formula I-3-5', wherein $R^{16}$ is a —O$C_{1-3}$alkaryl, and wherein the nucleophile is comprised of a —O$C_{1-3}$alkaryl.

52. A process for preparing a compound represented by formula I-3-5",

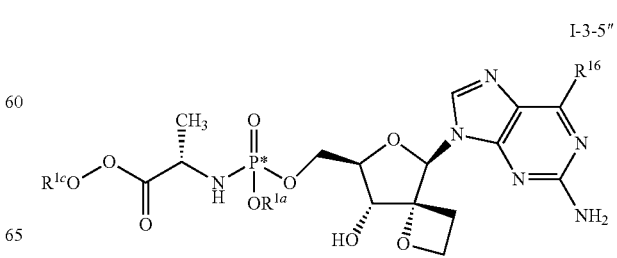

I-3-5"

wherein $R^{1a}$ is phenyl or naphthyl;

$R^{1c}$ is hydrogen, $C_{1-6}$alkyl, $C_{3-6}$cycloalkyl, or $C_{1-3}$alkaryl; and $R^{16}$ is —O($C_{1-6}$alkyl), —O$C_{1-3}$alkaryl, —S($C_{1-6}$alkyl), —NH($C_{1-6}$alkyl), or -cycloalkylamino;

said process comprising:

reacting compound A″ with a nucleophile and optionally deprotecting to obtain compound B″,

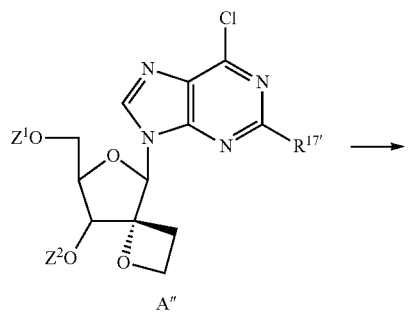

A″ wherein $R^{17'}$ is —NHZ$^3$, wherein each one of $Z^1$, $Z^2$, and $Z^3$ is hydrogen or a protecting group (PG);

the nucleophile is comprised of a radical selected from the group consisting of —O($C_{1-6}$alkyl), —O$C_{1-3}$alkaryl, —S($C_{1-6}$alkyl), —NH($C_{1-6}$alkyl), and -cycloalkylamino;

and reacting B″ with a phosphoramidate represented by formula C to obtain I-3-5″

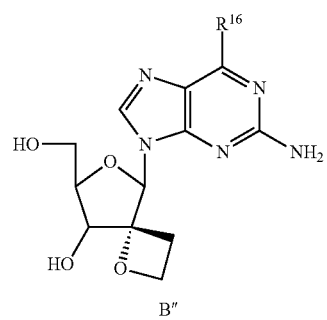

B″

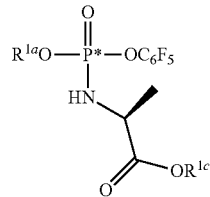

C wherein the phosphoramidate is comprised of a mixture of the $S_P$- and $R_P$-diastereomers.

53. The process according to claim 52, wherein $R^{16}$ is —O($C_{1-6}$alkyl), —S($C_{1-6}$alkyl), —NH($C_{1-6}$alkyl), or —NHC$_{3-6}$cycloalkyl.

54. The process according to claim 52, wherein the mole ratio of the $S_P$-diastereomer to the $R_P$-diastereomer is selected from the group consisting of 2, 5, 10, 15, 20, 25, 30, 35, 40, 45, 50, 55, 60, 65, 70, 75, 80, 85, 90, 95, 97, 98, 99, 99.9, and 99.99.

55. The process according to claim 52, wherein the mole ratio of the $R_P$-diastereomer to the $S_P$-diastereomer is selected from the group consisting of 2, 5, 10, 15, 20, 25, 30, 35, 40, 45, 50, 55, 60, 65, 70, 75, 80, 85, 90, 95, 97, 98, 99, 99.9, and 99.99.

56. A process for preparing a compound represented by formula I-3-5‴

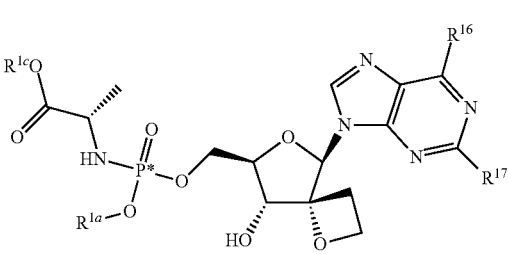

I-3-5‴ wherein $R^{1a}$ is phenyl or naphthyl; $R^{1c}$ is hydrogen, $C_{1-6}$alkyl, $C_{3-6}$cycloalkyl, or $C_{1-3}$alkaryl; $R^{16}$ is —O($C_{1-6}$ alkyl), —O$C_{1-3}$alkaryl, —S($C_{1-6}$alkyl), —NH($C_{1-6}$ alkyl), or -cycloalkylamino; and $R^{17}$ is —H or —NH$_2$ said process comprising reacting a compound represented by formula B‴ with a phosphoramidate represented by formula C to obtain I-3-5″

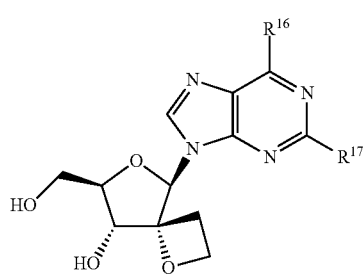

B‴

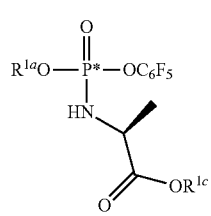
wherein the phosphoramidate is comprised of a mixture of the $S_P$- and $R_P$-diastereomers.
57. A compound that is selected from the group consisting of:
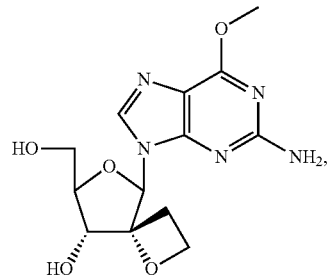
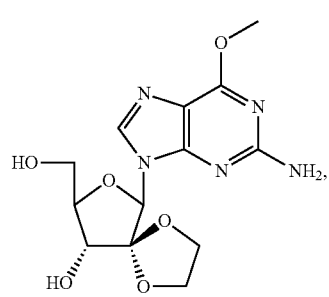
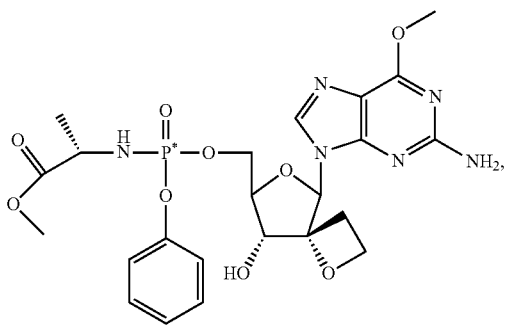
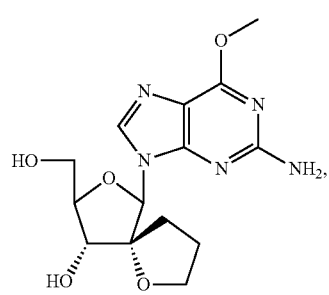
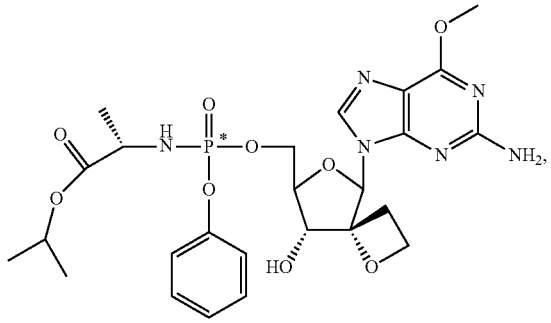
(Sp)
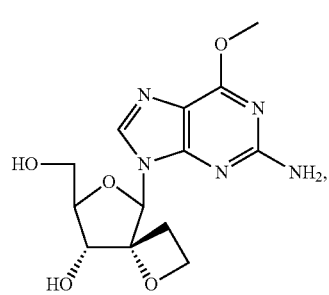
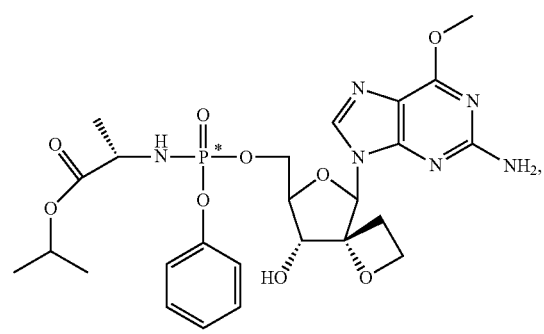
(Rp)
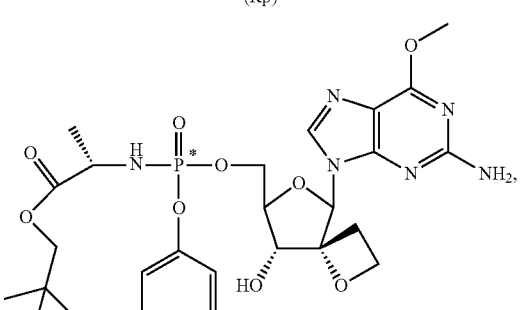
(Sp)

251
-continued
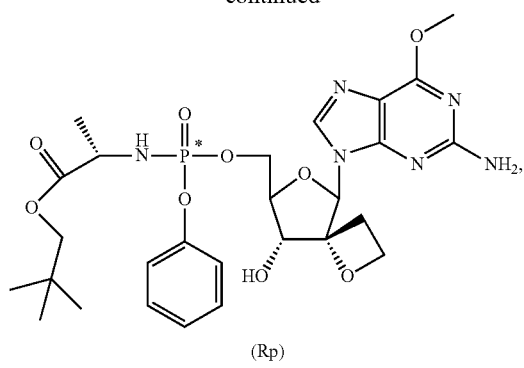
(Rp)
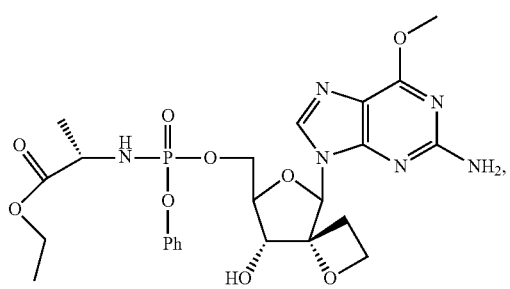
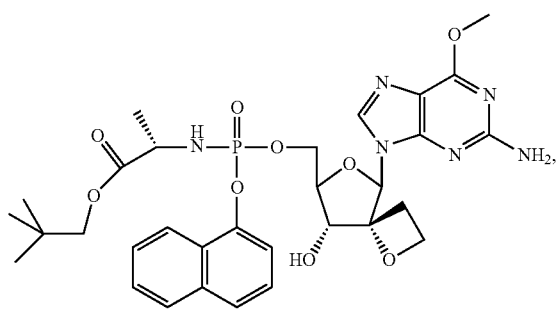
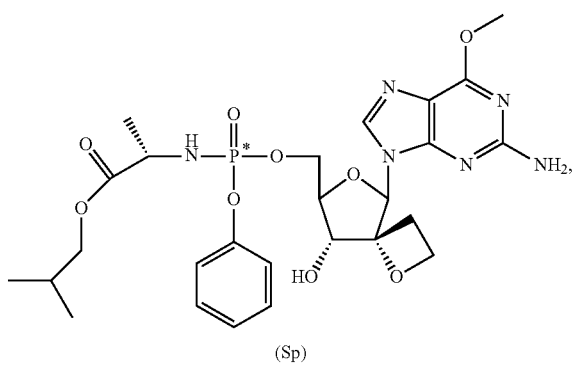
(Sp)
252
-continued
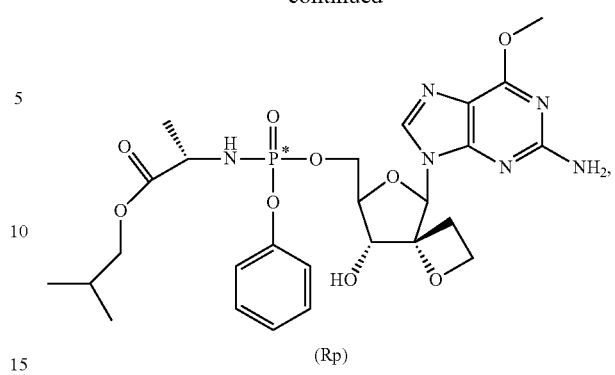
(Rp)
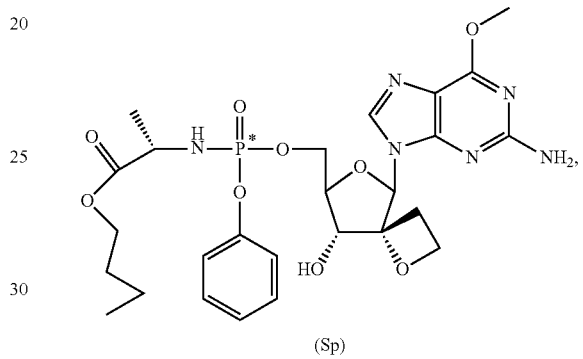
(Sp)
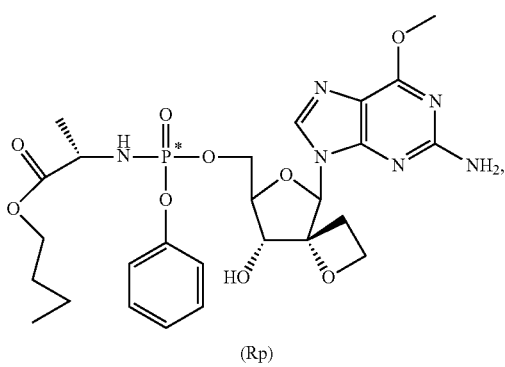
(Rp)
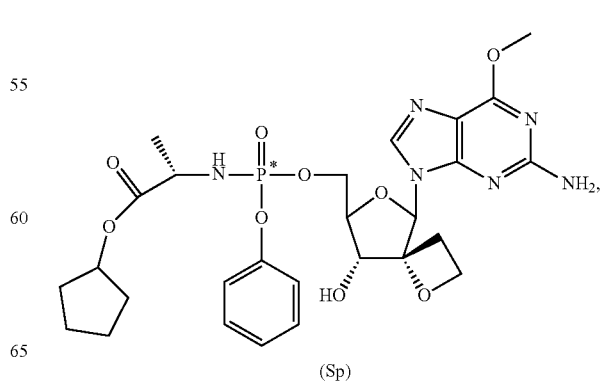
(Sp)

253
-continued
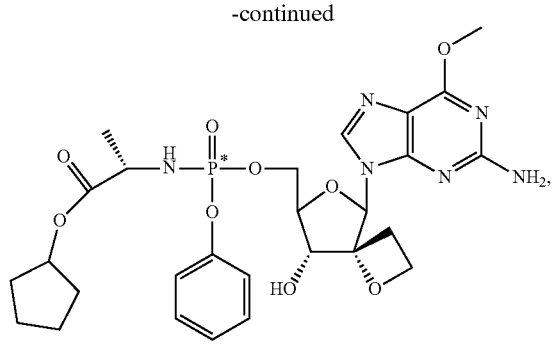
(Rp)
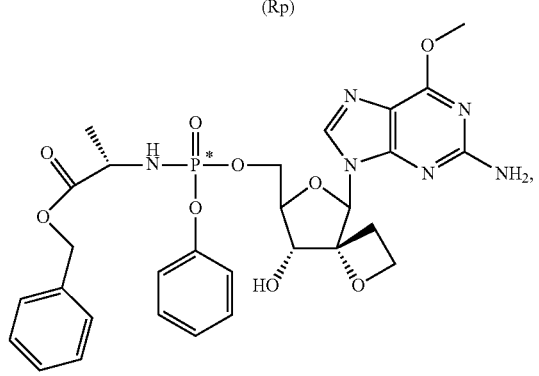
(Sp)
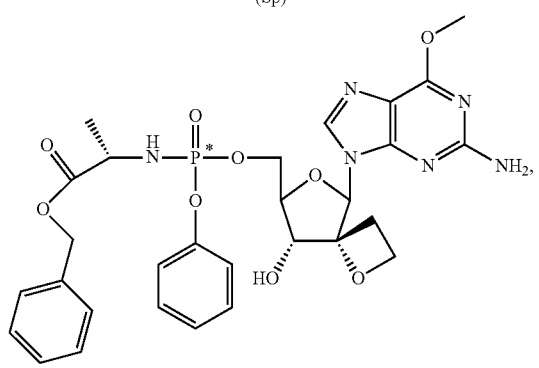
(Rp)
254
-continued
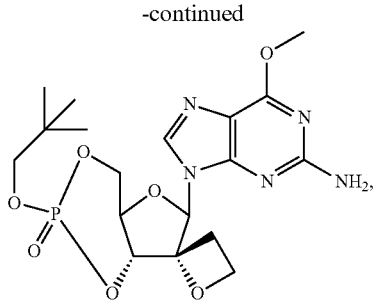
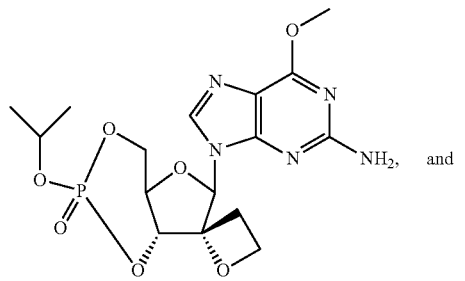
and
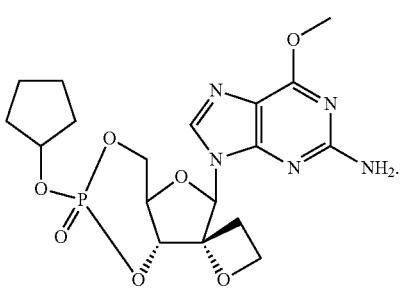
* * * * *